(12) United States Patent
Freyne et al.

(10) Patent No.: US 7,648,975 B2
(45) Date of Patent: Jan. 19, 2010

(54) MACROCYCLIC QUINAZOLINE DERIVATIVES AS ANTIPROLIFERATIVE AGENTS

(75) Inventors: Eddy Jean Edgard Freyne, Rumst (BE); Timothy Pietro Suren Perera, Geel (BE); Peter Jacobus Johannes Antonius Buijnsters, Etten-Leur (BE); Marc Willems, Oud-Turnhout (BE); Gaston Stanislas Marcella Diels, Ravels (BE); Werner Constant Johan Embrechts, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 300 days.

(21) Appl. No.: 10/558,007

(22) PCT Filed: May 25, 2004

(86) PCT No.: PCT/EP2004/005621

§ 371 (c)(1),
(2), (4) Date: Nov. 22, 2005

(87) PCT Pub. No.: WO2004/105765

PCT Pub. Date: Dec. 9, 2004

(65) Prior Publication Data

US 2006/0247237 A1    Nov. 2, 2006

(30) Foreign Application Priority Data

May 27, 2003  (WO) ................. PCT/EP03/05723
Sep. 15, 2003  (WO) ................. PCT/EP03/10266
Dec. 18, 2003  (WO) ................. PCT/EP03/51061

(51) Int. Cl.
*A01N 43/00*   (2006.01)
*A61K 31/33*   (2006.01)
*C07D 487/00*  (2006.01)
*C07D 491/00*  (2006.01)
*C07D 513/00*  (2006.01)

(52) U.S. Cl. .................................. 514/183; 540/468
(58) Field of Classification Search .................. None
See application file for complete search history.

(56) References Cited

U.S. PATENT DOCUMENTS

| 6,344,459 B1 | 2/2002 | Bridges et al. |
| 2002/0173646 A1 | 11/2002 | Thomas et al. |

FOREIGN PATENT DOCUMENTS

| GB | 807899 | 1/1959 |
| GB | 1465451 | 2/1977 |
| GB | 1542514 | 3/1979 |
| WO | WO 96/09294 | 3/1996 |
| WO | WO 96/33980 | 10/1996 |
| WO | WO 96/39145 | 12/1996 |

OTHER PUBLICATIONS

U.S. Appl. No. 11/720,693, filed Jun. 2007, Freyne.*
Expert Opinion on Therapeutic Patents, Ashley Publications, vol. 8, No. 4, pp. 475-478, 1998.
Hennequin et al., J. Med. Chem, vol. 45, No. 6, pp. 1300-1312, 2002.
Palmer et al., J. Med. Chem., vol. 40, No. 10, pp. 1519-1529, 1997.
Yang et al., Biochimica et Biophysica Acta, 1550, pp. 144-152, 2001.
Brown et al., "*High Throughput Screening*", 1997, editors: Devlin, John P., Publishers: Dekker, New York, N.Y., pp. 317-328.
Burke, Terrence R. Jr., "Protein-tyrosine Kinase Inhibitors", *Drugs of The Future*, 1992, pp. 119-131, vol. 17, No. 2.

(Continued)

*Primary Examiner*—James O Wilson
*Assistant Examiner*—Noble Jarrell

(57) ABSTRACT

The present invention concerns the compounds of formula (I) the N-oxide forms, the pharmaceutically acceptable addition salts and the stereochemically isomeric forms thereof, wherein Z represents O, $CH_2$, NH or S; in particular Z represents NH; Y represents —$C_{3-9}$alkyl-, —$C_{3-9}$alkenyl-, —$C_{3-9}$alkynyl-, —$C_{3-7}$alkyl-CO—NH— optionally substituted with amino, mono- or di($C_{1-4}$alkyl)amino or $C_{1-4}$ alkyloxycarbonylamino-, —$C_{3-7}$alkenyl-CO—NH— optionally substituted with amino, mono- or di($C_{1-4}$alkyl)amino or $C_{1-4}$alkyloxycarbonylamino-, $C_{1-5}$alkyl-oxy-$C_{1-5}$alkyl-, —$C_{1-5}$alkyl $NR^{13}$—, —$C_{1-5}$alkyl-, —$C_{1-5}$alkyl-$NR^{14}$—CO—$C_{1-5}$alkyl-, —$C_{1-5}$alkyl-CO $NR^{15}$—$C_{1-5}$alkyl-, —$C_{1-6}$alkyl-CO—NH—, —$C_{1-6}$alkyl-NH—CO—, —$C_{1-3}$alkyl-NH—CS-Het$^{20}$-, —$C_{1-3}$alkyl-NH—CO-Het$^{20}$, —$C_{1-2}$alkyl-CO-Het$^{21}$-CO—, -Het$^{22}$-$CH_2$—CO—NH—$C_{1-3}$alkyl-, —CO—NH—$C_{1-6}$alkyl-, —NH—CO—$C_{1-6}$alkyl-, —CO—$C_{1-7}$alkyl-, —$C_{1-7}$alkyl-CO—, —$C_{1-6}$alkyl-CO—$C_{1-6}$alkyl-, —$C_{1-2}$alkyl-NH—CO—$CR^{16}R^{17}$—NH—, —$C_{1-2}$alkyl-CO—NH—$CR^{18}R^{19}$—CO—, —$C_{1-2}$alkyl-CO—$NR^{20}$—$C_{1-3}$alkyl-CO—, $C_{1-2}$alkyl-$NR^{21}$—$CH_2$—CO—NH—$C_{1-3}$alkyl-, or $NR^{22}$—CO—$C_{1-3}$alkyl-NH—, $X^1$ represents a direct bond, O or —O—$C_{1-2}$alkyl-, CO, —CO—$C_{1-2}$alkyl-, $NR^{11}$, —$NR^{11}$—$C_{1-2}$alkyl-, —$CH_2$—, —O—N═CH— or —$C_{1-2}$alkyl-; $X^2$ represents a direct bond, O, —O—$C_{1-2}$alkyl-, CO, —CO—$C_{1-2}$alkyl-, $NR^{12}$, —$NR^{12}$—$C_{1-2}$alkyl-, —$CH_2$—, —O—N═CH— or —$C_{1-2}$alkyl-. The growth inhibitory effect anti-tumour activity of the present compounds has been demonstrated in vitro, in enzymatic on the receptor tyrosine kinase EGFR.

(I)

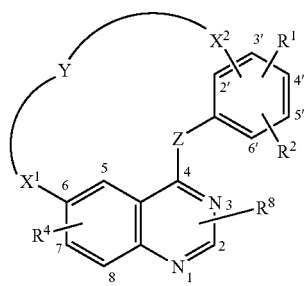

8 Claims, No Drawings

OTHER PUBLICATIONS

Davies et al., "Specificity and Mechanism of Action of Some Commonly Used Protein Kinase Inhibitors", *Biochemical Society*, 2000, pp. 95-105, vol. 351.

Delia, Thomas, "Fused Pyrimidines, Part Four, Miscellaneous Fused Pyrimidines: Chapter VI-Pyrimidotriazines.", *Heterocyclic Compounds*, John Wiley & Sons, Inc., Interscience Publications, pp. 261-304, 1992.

Druker et al., "Lessons Learned From The Development of An Abl Tyrosine Kinase Inhibitor For Chronic Myelogenous Leukemia", *The Journal of Clinical Investigation*, Jan. 2000, pp. 3-7, vol. 5, No. 1.

Elder et al., "Overexpression of transforming growth factor alpha in psoriatic epidermis", *Science*, 1989, pp. 811-814, vol. 243.

Furuta, K. et al., "Molecular Design of Glutathione-Derived Biochemical Probes Targeting the GS-X Pump", *Tetrahedron*, 1999, Elsevier Science Publishers, Amsterdam, NL., pp. 7529-7540, vol. 55, No. 24, , XP004167533.

Kawato, H.C. et al.: "Novel Peptidomimetrics of the Antifungal Cyclic Peptide Rhodopeptin: Synthesis of Mimetics and their Antifungal Activity", *Organic Letters*, 2001, pp. 3451-3454, vol. 3, No. 22, XP002300247.

March, J., "*Advanced Organic Chemistry*", 3$^{rd}$ edition, 1985, pp. 1036-1039.

Morin, Michael J., "From Oncogene to Drug: Development of Small Molecule Tyrosine Kinase Inhibitors as Anti-tumor and Anti-angiogenic Agents", *Oncogene*, 2000, pp. 6574-6583, vol. 19.

Nagamatsu et al., "Sytheses of 3-Substituted 1-Methyl-6-Phenylpyrimido[5,4-*e*]-1,2,4-triazine-5,7(1*H*,6*H*)-diones (6-Phenyl Analogs of Toxoflavin) and Their 4-Oxides, and Evaluation of Antimicrobial Activity of Toxoflavins and Their Analogs.", *Chem Pharm Bull.*, 1993, pp. 362-368, vol. 41, No. 2.

Nagamatsu et al., "General Syntheses of 1-Alkyltoxoflavin and 8-Alkylfervenulin Derivatives of Biological Significance By The Regioselective Alylation of Reumycin Derivatives And The Rates of Transalkylation From 1-Alkyltoxoflavins Into Nucleophiles.", *J. Chem. Soc. Perkin Trans. 1*, 2001, pp. 130-137.

"*Protective Groups in Organic Chemistry*", edited by J W F McOmie, 1973, Plenum Press.

Shawver et al., "Smart Drugs: Tyrosine Kinase Inhibitors In Cancer Therapy", *Cancer Cells*, Mar. 2002, pp. 117-123, vol. 1.

Wright et al., "Anilinoquinazoline Inhibitors of Fructose 1,6-Bisphosphate Bind at a Nove Allosteric Site: Synthesis, in vitro Characterizations, and X-ray Crystallography", *J. Med. Chem.*, 2002, pp. 3865-3877. vol. 45.

Database Beilstein, Beilstein Institute for Organic Chemistry, Frankfurt-Main, DE; 2001, XP002300248.

Database Beilstein, Beilstein Institute for Organic Chemistry, Frankfurt-Main, DE; 2000, XP002300249.

Database Beilstein, Beilstein Institute for Organic Chemistry, Frankfurt-Main, DE; 1994, 1, XP002300250.

PCT Intl. Search Report, PCT/EP2004/005621, Oct. 27, 2004.

* cited by examiner

MACROCYCLIC QUINAZOLINE DERIVATIVES AS ANTIPROLIFERATIVE AGENTS

CROSS REFERENCE TO RELATED APPLICATIONS

This application is the national stage of PCT Application No. PCT/EP2004/005621, filed 25 May 2004, which application claims priority from PCT Application No. PCT/EP2003/05723, filed 27 May 2003, PCT Application No. PCT/EP2003/10266, filed 15 Sep. 2003, and PCT Application No. PCT/EP2003/51061, filed 18 Dec. 2003.

This invention relates to quinazoline derived macrocycles that have been found to possess anti-proliferative activity, such as anti-cancer activity and are accordingly useful in methods of treatment of the human or animal body, for example in the manufacture of medicaments for use in hyper proliferative disorders such as atherosclerosis, restenosis and cancer. The invention also relates to processes for the manufacture of said quinazoline derivatives, to pharmaceutical compositions containing them and to their use in the manufacture of medicaments of use in the production of anti-proliferative effect.

In particular, the compounds of the present invention were found to inhibit tyrosine kinase enzymes, also called tyrosine kinases. Tyrosine kinases are a class of enzymes, which catalyse the transfer of the terminal phosphate of adenosine triphosphate to the phenolic hydroxyl group of a tyrosine residue present in the target protein. It is known, that several oncogenes; involved in the transformation of a cell into a malignant tumour cell, encode tyrosine kinase enzymes including certain growth factor receptors such as EGF, FGF, IGF-1R, IR, PDGF and VEGF. This family of receptor tyrosine kinases and in particular the EGF family of receptor tyrosine kinases are frequently present in common human cancers such as breast cancer, non-small cell lung cancers including adenocarcinomas and squamous cell cancer of the lung, bladder cancer, oesophageal cancer, gastrointestinal cancer such as colon, rectal or stomach cancer, cancer of the prostate, leukaemia and ovarian, bronchial or pancreatic cancer, which are examples of cell proliferation disorders.

Accordingly, it has been recognised that the selective inhibition of tyrosine kinases will be of value in the treatment of cell proliferation related disorders. Support for this view is provided by the development of Herceptin® (Trastuzumab) and Gleevec™ (imatinib mesylate) the first examples of target based cancer drugs. Herceptin® (Trastuzumab) is targeted against Her2/neu, a receptor tyrosine kinase found to be amplified up to 100-fold in about 30% of patients with invasive breast cancer. In clinical trials Herceptin® (Trastuzumab) proved to have anti-tumour activity against breast cancer (Review by L. K. Shawer et al, "Smart Drugs: Tyrosine kinase inhibitors in cancer therapy", 2002, Cancer Cell Vol. 1, 117), and accordingly provided the proof of principle for therapy targeted to receptor tyrosine kinases. The second example, Gleevec™ (imatinib mesylate), is targeted against the abelson tyrosine kinase (BcR-Abl), a constitutively active cytoplasmic tyrosine kinase present in virtually all patients with chronic myelogenous leukemia (CML) and 15% to 30% of adult patients with acute lymphoblastic leukaemia. In clinical trials Gleevec™ (imatinib mesylate) showed a spectacular efficacy with minimal side effects that led to an approval within 3 months of submission. The speed of passage of this agent through clinical trials and regulatory review has become a case study in rapid drug development (Drucker B. J. & Lydon N, "Lessons learned from the development of an Abl tyrosine kinase inhibitor for chronic myelogenous leukaemia.", 2000, J. Clin. Invest. 105, 3).

Further support is given by the demonstration that EGF receptor tyrosine kinase inhibitors, specifically attenuates the growth in athymic nude mice of transplanted carcinomas such as human mammary carcinoma or human squamous cell carcinoma (Review by T. R. Burke Jr., Drugs of the Future, 1992, 17, 119). As a consequence, there has been considerable interest in the development of drugs to treat different cancers that target the EGFR receptor. For example, several antibodies that bind to the extra-cellular domain of EGFR are undergoing clinical trials, including Erbitux™ (also called C225, Cetuximab), which was developed by Imclone Systems and is in Phase III clinical trials for the treatment of several cancers. Also, several promising orally active drugs that are potent and relatively specific inhibitors of the EGFR tyrosine kinase are now well advanced in clinical trials. The AstraZeneca compound ZD1839, which is now called IRESSA® and approved for the treatment of advanced non-small-cell lung cancer, and the OSI/Genentech/Roche compound OSI-774, which is now called Tarceva™ (erlotinib), have shown marked efficacy against several cancers in human clinical trials (Morin M. J., "From oncogene to drug: development of small molecule tyrosine kinase inhibitors as anti-tumour and anti-angiogenic agents, 2000, Oncogene 19, 6574).

In addition to the above, EGF receptor tyrosine kinases has been shown to be implicated in non-malignant proliferative disorders such as psoriasis (Elder et al., Science, 1989, 243; 811). It is therefore expected that inhibitors of EGF type receptor tyrosine kinases will be useful in the treatment of non-malignant diseases of excessive cellular proliferation such as psoriasis, benign prostatic hypertrophy, atherosclerosis and restenosis.

It is disclosed in International Patent Application WO96/33980 and in J. Med. Chem, 2002, 45, 3865 that certain 4 anilino substituted quinazoline derivatives may be useful as inhibitors of tyrosine kinase and in particular of the EGF type receptor tyrosine kinases. Unexpectedly it was found that Quinazoline derivatives of the present formula (I) that are different in structure, show to have tyrosine kinase inhibitory activity.

It is accordingly an object of the present invention to provide further tyrosine kinase inhibitors useful in the manufacture of medicaments in the treatment of cell proliferative related disorders.

This invention concerns compounds of formula (I)

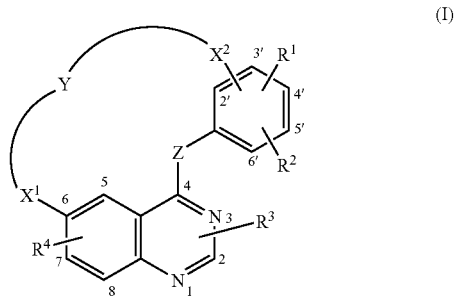

(I)

the N-oxide forms, the pharmaceutically acceptable addition salts and the stereochemically isomeric forms thereof, wherein Z represents O, $CH_2$, NH or S; in particular Z represents NH;

Y represents $—C_{3-9}$alkyl-, $—C_{3-9}$alkenyl-, $—C_{3-9}$alkynyl-,

—$C_{3-7}$alkyl-CO—NH— optionally substituted with amino, mono- or di($C_{1-4}$alkyl)amino or $C_{1-4}$alkyloxycarbonylamino-, —$C_{3-7}$alkenyl-CO—NH— optionally substituted with amino, mono- or di($C_{1-4}$alkyl)amino or $C_{1-4}$alkyloxycarbonylamino-, —$C_{3-7}$alkynyl-CO—NH— optionally substituted with amino, mono- or di($C_{1-4}$alkyl)amino or $C_{1-4}$alkyloxycarbonylamino-, —$C_{1-5}$alkyl-oxy-$C_{1-5}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-5}$alkyl-CO—$NR^{15}$—$C_{1-5}$alkyl-, —$C_{1-6}$alkyl-CO—NH—, —$C_{1-6}$alkyl-NH—CO—, —$C_{1-3}$alkyl-NH—CS-$Het^{20}$-, —$C_{1-3}$alkyl-NH—CO-$Het^{20}$-, —$C_{1-2}$alkyl-CO-$Het^{21}$-CO—, -$Het^{22}$-$CH_2$—CO—NH—$C_{1-3}$alkyl-, —CO—NH—$C_{1-6}$alkyl-, —NH—CO—$C_{1-6}$alkyl-, —CO—$C_{1-7}$alkyl-, —$C_{1-7}$alkyl-CO—, —$C_{1-6}$alkyl-CO—$C_{1-6}$alkyl-, —$C_{1-2}$alkyl-NH—CO—$CR^{16}R^{17}$—NH—, —$C_{1-2}$alkyl-CO—NH—$CR^{18}R^{19}$—CO—, —$C_{1-2}$alkyl-CO—$NR^{20}$—$C_{1-3}$alkyl-CO—, —$C_{1-2}$alkyl-$NR^{21}$—$CH_2$—CO—NH—$C_{1-3}$alkyl-, or —$NR^{22}$—CO—$C_{1-3}$alkyl-NH—;

$X^1$ represents a direct bond, O, —O—$C_{1-2}$alkyl-, CO, —CO—$C_{1-2}$alkyl-, $NR^{11}$, —$NR^{11}$—$C_{1-2}$alkyl-, —$CH_2$—, —O—N=CH— or —$C_{1-2}$alkyl-;

$X^2$ represents a direct bond, O, —O—$C_{1-2}$alkyl-, CO, —CO—$C_{1-2}$alkyl-, $NR^{12}$, —$NR^{12}$—$C_{1-2}$alkyl-, —$CH_2$—, —O—N=CH— or —$C_{1-2}$alkyl-;

$R^1$ represents hydrogen, cyano, halo, hydroxy, formyl, $C_{1-6}$alkoxy-, $C_{1-6}$alkyl-, halo-phenyl-carbonylamino-, $C_{1-6}$alkoxy- substituted with halo,
$C_{1-4}$alkyl substituted with one or where possible two or more substituents selected from hydroxy or halo;

$R^2$ represents hydrogen, cyano, halo, hydroxy, hydroxycarbonyl-, $Het^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, $Het^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, $Ar^5$, $Ar^1$-oxy-, dihydroxyborane, $C_{1-6}$alkoxy- substituted with halo,
$C_{1-4}$alkyl substituted with one or where possible two or more substituents selected from halo, hydroxy or $NR^5R^6$,
$C_{1-4}$alkylcarbonyl- wherein said $C_{1-4}$alkyl is optionally substituted with one or where possible two or more substituents selected from hydroxy or $C_{1-4}$alkyl-oxy-;

$R^3$ represents hydrogen, $C_{1-4}$alkyl, or $C_{1-4}$alkyl substituted with one or more substituents selected from halo, $C_{1-4}$alkyloxy-, amino-, mono- or di($C_{1-4}$alkyl)amino-, $C_{1-4}$alkylsulfonyl- or phenyl;

$R^4$ represents hydrogen, hydroxy, $Ar^3$-oxy, $Ar^4$—$C_{1-4}$alkyloxy-, $C_{1-4}$alkyloxy-, $C_{2-4}$alkenyloxy- optionally substituted with $Het^{12}$ or $R^4$ represents $C_{1-4}$alkyloxy substituted with one or where possible two or more substituents selected from $C_{1-4}$alkyloxy-, hydroxy, halo, $Het^2$-, —$NR^7R^8$, -carbonyl-$NR^9R^{10}$ or $Het^3$-carbonyl-;

$R^5$ and $R^6$ are each independently selected from hydrogen or $C_{1-4}$alkyl;

$R^7$ and $R^8$ are each independently selected from hydrogen, $C_{1-4}$alkyl, $Het^8$, aminosulfonyl-, mono- or di($C_{1-4}$alkyl)-aminosulfonyl, hydroxy-$C_{1-4}$alkyl-, $C_{1-4}$alkyl-oxy-$C_{1-4}$alkyl-, hydroxycarbonyl-$C_{1-4}$alkyl-, $C_{3-6}$cycloalkyl, $Het^9$-carbonyl-$C_{1-4}$alkyl-, $Het^{10}$-carbonyl-, polyhydroxy-$C_{1-4}$alkyl-, $Het^{11}$-$C_{1-4}$alkyl- or $Ar^2$—$C_{1-4}$alkyl-;

$R^9$ and $R^{10}$ are each independently selected from hydrogen, $C_{1-4}$alkyl $C_{3-6}$cycloalkyl, $Het^4$, hydroxy-$C_{1-4}$alkyl-, $C_{1-4}$alkyloxy$C_{1-4}$alkyl- or polyhydroxy-$C_{1-4}$alkyl-;

$R^{11}$ represents hydrogen, $C_{1-4}$alkyl, $Het^5$, $Het^6$-$C_{1-4}$alkyl-, $C_{2-4}$alkenylcarbonyl-optionally substituted with $Het^7$-$C_{1-4}$alkylaminocarbonyl, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{12}$ represents hydrogen, $C_{1-4}$alkyl, $C_{1-4}$alkyl-oxy-carbonyl-, $Het^{18}$-$C_{1-4}$alkyl-, phenyl-$C_{1-4}$alkyl-oxy-carbonyl-, $Het^{17}$, $C_{2-4}$alkenylcarbonyl- optionally substituted with $Het^{19}$-$C_{1-4}$alkylaminocarbonyl-, $C_{2-4}$alkenylsulfonyl-, $C_{1-4}$alkyloxy$C_{1-4}$alkyl- or $R^{12}$ represents phenyl optionally substituted with one or where possible two or more substituents selected from hydrogen, hydroxy, amino or $C_{1-4}$alkyloxy-;

$R^{13}$ represents hydrogen, $C_{1-4}$alkyl, $Het^{13}$, $Het^{14}$-$C_{1-4}$alkyl- or phenyl optionally substituted with one or where possible two or more substituents selected from hydrogen, hydroxy, amino or $C_{1-4}$alkyloxy-;

$R^{14}$ and $R^{15}$ are each independently selected from hydrogen, $C_{1-4}$alkyl, $Het^{15}$-$C_{1-4}$alkyl- or $C_{1-4}$alkyloxy$C_{1-4}$alkyl-;

$R^{16}$ and $R^{17}$ each independently represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino;

$R^{18}$ and $R^{19}$ each independently represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino;

$R^{20}$ and $R^{22}$ each independently represents hydrogen or $C_{1-4}$alkyl optionally substituted with hydroxy or $C_{1-4}$alkyloxy;

$R^{21}$ represents hydrogen, $C_{1-4}$alkyl, $Het^{23}$-$C_{1-4}$alkylcarbonyl- or $R^{21}$ represents mono- or di($C_{1-4}$alkyl)amino-$C_{1-4}$alkyl-carbonyl- optionally substituted with hydroxy, pyrimidinyl, dimethylamine or $C_{1-4}$alkyloxy;

$Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$alkyl)amino- or amino-carbonyl-;

$Het^2$ represents a heterocycle selected from morpholinyl, piperazinyl, piperidinyl, pyrrolidinyl, thiomorpholinyl or dithianyl wherein said $Het^2$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino-, mono- or di($C_{1-4}$alkyl)amino-$C_{1-4}$alkyl-, amino$C_{1-4}$alkyl-, mono- or di($C_{1-4}$alkyl)amino-sulfonyl-, aminosulfonyl-;

$Het^3$, $Het^4$ and $Het^8$ each independently represent a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said $Het^3$, $Het^4$ or $Het^8$ is optionally substituted with one or where possible two or more substituents selected from hydroxy-, amino-, $C_{1-4}$alkyl-, $C_{3-6}$cycloalkyl-$C_{1-4}$alkyl-7, aminosulfonyl-, mono- or di($C_{1-4}$alkyl)aminosulfonyl or amino-$C_{1-4}$alkyl-;

$Het^5$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^6$ and $Het^7$ each independently represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^9$ and $Het^{10}$ each independently represent a heterocycle selected from furanyl, piperidinyl, morpholinyl, piperazinyl, pyrazolyl, dioxolanyl, thiazolyl, oxazolyl, imidazolyl, isoxazolyl, oxadiazolyl, pyridinyl or pyrrolidinyl wherein said $Het^9$ or $Het^{10}$ is optionally substituted $C_{1-4}$alkyl, $C_{3-6}$cycloalkyl-$C_{1-4}$alkyl- or amino-$C_{1-4}$alkyl-;

$Het^{11}$ represents a heterocycle selected from indolyl or

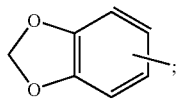

$Het^{12}$ represents a heterocycle selected from morpholinyl, piperazinyl, piperidinyl, pyrrolidinyl, thiomorpholinyl or dithianyl wherein said $Het^{12}$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino- or mono- or di($C_{1-4}$alkyl)amino-$C_{1-4}$alkyl-;

$Het^{13}$ represent a heterocycle selected from pyrrolidinyl optionally substituted with one or, where possible two or more substituents selected from $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-;

$Het^{14}$ represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Het^{17}$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{20}$, $Het^{21}$ and $Het^{22}$ each independently represent a heterocycle selected from pyrrolidinyl, 2-pyrrolidinonyl, piperazinyl or piperidinyl optionally substituted with one or where possible two or more substituents selected from hydroxy, $C_{1-4}$alkyl, hydroxy-$C_{1-4}$alkyl- or polyhydroxy-$C_{1-4}$alkyl-;

$Het^{23}$ represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Ar^1$, $Ar^2$, $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

As used in the foregoing definitions and hereinafter,
halo is generic to fluoro, chloro, bromo and iodo;
$C_{1-2}$alkyl defines methyl or ethyl;
$C_{1-3}$alkyl defines straight and branched chain saturated hydrocarbon radicals having from 1 to 3 carbon atoms such as, for example, methyl, ethyl, propyl and the like;
$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like;
$C_{1-5}$alkyl defines straight and branched chain saturated hydrocarbon radicals having from 1 to 5 carbon atoms such as, for example, methyl, ethyl, propyl, butyl, pentyl, 1-methylbutyl, 2,2-dimethylpropyl, 2,2-dimethylethyl and the like;
$C_{1-6}$alkyl is meant to include $C_{1-5}$alkyl and the higher homologues thereof having 6 carbon atoms such as, for example hexyl, 1,2-dimethylbutyl, 2-methylpentyl and the like;
$C_{1-7}$alkyl is meant to include-$C_{1-6}$alkyl and the higher homologues thereof having 7 carbon atoms such as, for example 1,2,3-dimethylbutyl, 1,2-methylpentyl and the like;
—$C_{3-9}$alkyl defines straight and branched chain saturated hydrocarbon radicals having from 3 to 9 carbon atoms such as propyl, butyl, pentyl, hexyl, heptyl, octyl, nonyl and the like;
$C_{2-4}$alkenyl defines straight and branched chain hydrocarbon radicals containing one double bond and having from 2 to 4 carbon atoms such as, for example vinyl, 2-propenyl, 3-butenyl, 2-butenyl and the like;
$C_{3-9}$alkenyl defines straight and branched chain hydrocarbon radicals containing one double bond and having from 3 to 9 carbon atoms such as, for example 2-propenyl, 3-butenyl, 2-butenyl, 2-pentenyl, 3-pentenyl, 3-methyl-2-butenyl, 3-hexenyl and the like;
$C_{2-6}$alkynyl defines straight and branched chain hydrocarbon radicals containing one triple bond and having from 2 to 6 carbon atoms such as, for example, 2-propynyl, 3-butynyl, 2-butynyl, 2-pentynyl, 3-pentynyl, 3-methyl-2-butynyl, 3-hexynyl and the like;
$C_{3-6}$cycloalkyl is generic to cyclopropyl, cyclobutyl, cyclopentyl and cyclohexyl;
$C_{1-4}$alkyloxy defines straight or branched saturated hydrocarbon radicals such as methoxy, ethoxy, propyloxy, butyloxy, 1-methylethyloxy, 2-methylpropyloxy and the like;
$C_{1-6}$alkyloxy is meant to include $C_{1-4}$alkyloxy and the higher homologues such as methoxy, ethoxy, propyloxy, butyloxy, 1-methylethyloxy, 2-methylpropyloxy and the like;
polyhydroxy-$C_{1-4}$alkyl is generic to a $C_{1-4}$alkyl as defined hereinbefore, having two, three or were possible more hydroxy-substituents, such as for example As used in the foregoing definitions and hereinafter, the term formyl refers to a radical of formula —CH(=O). When $X^1$ represent the divalent radical —O—N=CH—, said radical is attached with the carbon atom to the $R^3$, $R^4$ bearing cyclic moiety of the compounds of formula (I) and when $X^2$ represents the divalent radical —N=CH—, said radical is attached with the carbon atom to the $R^1$, $R^2$ bearing phenyl moiety of the compounds of formula (I).

The heterocycles as mentioned in the above definitions and hereinafter, are meant to include all possible isomeric forms thereof, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

Further, the heterocycles as mentioned in the above definitions and hereinafter may be attached to the remainder of the molecule of formula (I) through any ring carbon or heteroatom as appropriate. Thus, for example, when the heterocycle is imidazolyl, it may be a 1-imidazolyl, 2-imidazolyl, 3-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzothiazolyl, it may be 2-benzothiazolyl, 4-benzothiazolyl, 5-benzothiazolyl, 6-benzothiazolyl and 7-benzothiazolyl.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic pamoic and the like acids.

The pharmaceutically acceptable addition salts as mentioned hereinabove are meant to comprise the therapeutically active non-toxic base addition salt forms which the compounds of formula (I) are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide.

A first group of compounds according to the present invention consists of those compounds of formula (I) wherein one or more of the following restrictions apply;

Z represents O, NH or S;

Y represents —$C_{3-9}$alkyl-, —$C_{3-9}$alkenyl-, —$C_{1-5}$alkyl-oxy-$C_{1-5}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-5}$alkyl-CO—$NR^{15}$—$C_{1-5}$alkyl-, —$C_{1-6}$alkyl-CO—NH—, —$C_{1-6}$alkyl-NH—CO—, —CO—NH—$C_{1-6}$alkyl-, —NH—CO—$C_{1-6}$alkyl-, —CO—$C_{1-7}$alkyl-, $C_{1-7}$alkyl-CO—, —$C_{1-6}$alkyl-CO—$C_{1-6}$alkyl-, —$C_{1-2}$alkyl-NH—CO—$CHR^{16}$—NH—;

$X^1$ represents a direct bond, O, —O—$C_{1-2}$alkyl-, CO, —CO—$C_{1-7}$alkyl-, $NR^{11}$, —$NR^{11}$—$C_{1-2}$alkyl-; —$CH_2$—, —N=CH— or —$C_{1-2}$alkyl-;

$X^2$ represents a direct bond, O, —O—$C_{1-2}$alkyl-, CO, —CO—$C_{1-2}$alkyl-, $NR^{12}$, —$NR^{12}$—$C_{1-2}$alkyl-, —$CH_2$—O—N=CH— or —$C_{1-2}$alkyl-;

$R^1$ represents hydrogen, cyano, halo, hydroxy, formyl, $C_{1-6}$alkoxy-, $C_{1-6}$alkyl-, $C_{1-6}$alkoxy- substituted with halo, $C_{1-4}$alkyl substituted with one or where possible two or more substituents selected from hydroxy or halo;

$R^2$ represents hydrogen, cyano, halo; hydroxy, hydroxycarbonyl-, $Het^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, $Het^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, $Ar^5$, $Ar^1$-oxy-, dihydroxyborane, $C_{1-6}$alkoxy- substituted with halo, $C_{1-4}$alkyl substituted with one or where possible two or more substituents selected from halo, hydroxy or $NR^5R^6$, $C_{1-4}$alkylcarbonyl- wherein said $C_{1-4}$alkyl is optionally substituted with one or where possible two or more substituents selected from hydroxy or $C_{1-4}$alkyl-oxy-;

$R^3$ represents hydrogen, $C_{1-4}$alkyl, or $C_{1-4}$alkyl substituted with one or more substituents selected from halo, $C_{1-4}$alkyloxy-, amino-, mono- or di($C_{1-4}$alkyl)amino-, $C_{1-4}$alkyl-sulfonyl- or phenyl;

$R^4$ represents hydrogen, hydroxy, $Ar^3$-oxy, $Ar^4$—$C_{1-4}$alkyloxy-, $C_{1-4}$alkyloxy-, $C_{2-4}$alkenyloxy- optionally substituted with $Het^{12}$ or $R^4$ represents $C_{1-4}$alkyloxy substituted with one or where possible two or more substituents selected from $C_{1-4}$alkyloxy-, hydroxy, halo, $Het^2$-, —$NR^7R^8$, -carbonyl-$NR^9R^{10}$ or $Het^3$-carbonyl-;

$R^5$ and $R^6$ are each independently selected from hydrogen or $C_{1-4}$alkyl;

$R^7$ and $R^8$ are each independently selected from hydrogen, $C_{1-4}$alkyl, $Het^8$, aminosulfonyl-, mono- or di($C_{1-4}$alkyl)-aminosulfonyl, hydroxy-$C_{1-4}$alkyl-, $C_{1-4}$alkyl-oxy-$C_{1-4}$alkyl-, hydroxycarbonyl-$C_{1-4}$alkyl-, $C_{3-6}$cycloalkyl, $Het^9$-carbonyl-$C_{1-4}$alkyl-, $Het^{10}$-carbonyl-, polyhydroxy-$C_{1-4}$alkyl-, $Het^{11}$-$C_{1-4}$alkyl- or $Ar^2$—$C_{1-4}$alkyl-;

$R^9$ and $R^{10}$ are each independently selected from hydrogen, $C_{1-4}$alkyl, $C_{3-6}$cycloalkyl, $Het^4$, hydroxy-$C_{1-4}$alkyl, $C_{1-4}$-alkyloxy$C_{1-4}$alkyl- or polyhydroxy-$C_{1-4}$alkyl-;

$R^{11}$ represents hydrogen, $C_{1-4}$alkyl, $Het^5$, $Het^6$-$C_{1-4}$alkyl-, $C_{2-4}$alkenylcarbonyl-optionally substituted with $Het^7$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{12}$ represents hydrogen, $C_{1-4}$alkyl, $C_{1-4}$alkyl-oxy-carbonyl-, $Het^{17}$, $Het^{18}$-$C_{1-4}$alkyl-, $C_{2-4}$alkenylcarbonyl- optionally substituted with $Het^{19}$-$C_{1-4}$alkylaminocarbonyl-, $C_{2-4}$alkenylsulfonyl-, $C_{1-4}$alkyloxy$C_{1-4}$alkyl- or $R^{12}$ represents phenyl optionally substituted with one or where possible two or more substituents selected from hydrogen, hydroxy, amino or $C_{1-4}$alkyloxy-;

$R^{13}$ represents hydrogen, $C_{1-4}$alkyl, $Het^{13}$, $Het^{14}$-$C_{1-4}$alkyl- or phenyl optionally substituted with one or where possible two or more substituents selected from hydrogen, hydroxy, amino or $C_{1-4}$alkyloxy-;

$R^{14}$ and $R^{15}$ are each independently selected from hydrogen, $C_{1-4}$alkyl, $Het^{15}$-$C_{1-4}$alkyl- or $C_{1-4}$alkyloxy$C_{1-4}$alkyl-;

$R^{16}$ represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino;

$Het^1$ represents a heterocycle selected from piperidinyl, morpholinyl, piperazinyl, furanyl, pyrazolyl, dioxolanyl, thiazolyl, oxazolyl, imidazoyl, isoxazolyl, oxadiazolyl, pyridinyl or pyrrolidinyl wherein said $Het^1$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

$Het^2$ represents a heterocycle selected from morpholinyl, piperazinyl, piperidinyl, pyrrolidinyl, thiomorpholinyl or dithianyl wherein said $Het^2$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino-, mono- or di($C_{1-4}$alkyl)amino-$C_{1-4}$alkyl-, amino$C_{1-4}$alkyl-, mono- or di($C_{1-4}$alkyl)amino-sulfonyl-, aminosulfonyl-;

$Het^3$, $Het^4$ and $Het^8$ each independently represent a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said $Het^3$, $Het^4$ or $Het^8$ is optionally substituted with one or where possible two or more substituents selected from hydroxy-, amino-, $C_{1-4}$alkyl-, $C_{3-6}$cycloalkyl-$C_{1-4}$alkyl-, aminosulfonyl-, mono- or di($C_{1-4}$alkyl)aminosulfonyl $Het^5$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^6$ and $Het^7$ each independently represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^9$ and $Het^{10}$ each independently represent a heterocycle selected from furanyl, piperidinyl, morpholinyl, piperazinyl, pyrazolyl, dioxolanyl, thiazolyl, oxazolyl, imidazolyl, isoxazolyl, oxadiazolyl, pyridinyl or pyrrolidinyl wherein said $Het^9$ or $Het^{10}$ is optionally substituted $C_{1-4}$alkyl, $C_{3-6}$cycloalkyl-$C_{1-4}$alkyl- or amino-$C_{1-4}$alkyl-;

$Het^{11}$ represents a heterocycle selected from indolyl or

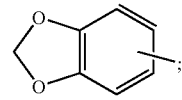

$Het^{12}$ represents a heterocycle selected from morpholinyl, piperazinyl, piperidinyl, pyrrolidinyl, thiomorpholinyl or dithianyl wherein said $Het^{12}$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino- or mono- or di($C_{1-4}$alkyl)amino-$C_{1-4}$alkyl-;

$Het^{13}$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{14}$ represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Het^{17}$ represent a heterocycle selected form pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Ar^1$, $Ar^2$, $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

An interesting group of compounds consists of those compounds of formula (I) wherein one or more of the following restrictions apply:

Z represents NH;

Y represents —$C_{3-9}$alkyl-, —$C_{2-9}$alkenyl-, —$C_{1-5}$alkyl-oxy-$C_{1-5}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-6}$alkyl-NH—CO—, —NH—CO—$C_{1-6}$alkyl-, —CO—$C_{1-7}$alkyl-, —$C_{1-7}$alkyl-CO—, $C_{1-6}$alkyl-CO—$C_{1-6}$alkyl, —$C_{1-2}$alkyl-NH—CO—$CR^{16}R^{17}$—NH—, —$C_{1-2}$alkyl-CO—NH—$CR^{15}R^{19}$—CO—, —$C_{1-2}$alkyl-CO—$NR^{20}$—$C_{1-3}$alkyl-CO—, —$C_{1-2}$alkyl-$NR^{21}$—$CH_2$—CO—NH—$C_{1-3}$alkyl-, —$NR^{22}$—CO—$C_{1-3}$alkyl-NH—, —$C_{1-3}$alkyl-NH—CO- Het$^{20}$-, C$_{1-2}$alkyl-, —O—CO-Het$^{21}$-CO—, or Het$^{22}$-CH$_2$—CO—NH—C$_{1-3}$alkyl-;

X$^1$ represents O, —O—C$_{1-2}$alkyl-, —O—N=CH—, NR$^{11}$ or —NR$^{11}$—C$_{1-2}$alkyl-; in a particular embodiment X$^1$ represents —NR$^{11}$—, —O— or —O—CH$_2$—;

X$^2$ represents a direct bond, O, —O—C$_{1-2}$alkyl-, —O—N=CH—, NR$^{12}$ or NR$^{12}$—C$_{1-2}$alkyl-; in a particular embodiment X$^2$ represents a direct bond, —C$_{1-2}$alkyl-, —O—C$_{1-2}$alkyl, —O— or —O—CH$_2$—;

R$^1$ represents hydrogen, cyano, halo or hydroxy, preferably halo;

R$^2$ represents hydrogen, cyano, halo, hydroxy, hydroxycarbonyl-, C$_{1-4}$alkyloxycarbonyl-, Het$^{16}$-carbonyl-, C$_{1-4}$alkyl-, C$_{2-6}$alkynyl-, Ar$^5$ or Het$^1$;
In a further embodiment R$^2$ represents hydrogen, cyano, halo, hydroxy, C$_{2-6}$alkynyl- or Het$^1$; in particular R$^2$ represents hydrogen, cyano, halo, hydroxy, or Ar$^5$;

R$^3$ represents hydrogen;

R$^4$, represents hydrogen, hydroxy, —C$_{1-4}$alkyloxy- or R$^4$ represents C$_{1-4}$alkyloxy substituted with one or where possible two or more substituents selected from C$_{1-4}$alkyloxy- or Het$^2$-;

R$^{12}$ represents hydrogen, C$_{1-4}$alkyl- or —C$_{1-4}$alkyl-oxy-carbonyl-;

R$^{13}$ represents hydrogen or Het$^4$-C$_{1-4}$alkyl, in particular morpholinyl-C$_{1-4}$alkyl;

R$^{14}$ and R$^{15}$ represents hydrogen;

R$^{16}$ represents hydrogen or C$_{1-4}$alkyl substituted with hydroxy,

R$^{17}$ represents hydrogen or C$_{1-4}$alkyl, in particular hydrogen or methyl;

R$^{19}$ represents hydrogen or C$_{1-4}$alkyl optionally substituted with hydroxy or phenyl;

R$^{19}$ represents hydrogen or C$_{1-4}$alkyl, in particular hydrogen or methyl, even more particular hydrogen;

R$^{20}$ represents hydrogen or C$_{1-4}$alkyl, in particular hydrogen or methyl;

R$^{21}$ represents hydrogen, C$_{1-4}$alkyl, Het$^{23}$-C$_{1-4}$alkylcarbonyl- or R$^{21}$ represents mono- or di(C$_{1-4}$alkyl)amino-C$_{1-4}$alkyl-carbonyl- optionally substituted with hydroxy, pyrimidinyl, dimethylamine or C$_{1-4}$alkyloxy;

R$^{22}$ represents hydrogen or C$_{1-4}$alkyl optionally substituted with hydroxy or C$_{1-4}$alkyloxy;

Het$^1$ represents thiazolyl optionally substituted with amino, C$_{1-4}$alkyl, hydroxy-C$_{1-4}$alkyl-, phenyl, phenyl-C$_{1-4}$alkyl-, C$_{1-4}$alkyl-oxy-C$_{1-4}$alkyl-mono- or di(C$_{1-4}$alkyl)amino- or amino-carbonyl-;

Het$^2$ represents a heterocycle selected from morpholinyl, piperazinyl, piperidinyl or pyrrolidinyl wherein said Het$^2$ is optionally substituted with one or where possible two or more substituents selected from hydroxy, amino or C$_{1-4}$alkyl-; In a further embodiment Het$^2$ represents a heterocycle selected from morpholinyl or piperidinyl optionally substituted with C$_{1-4}$alkyl-, preferably methyl;

Het$^3$ represents a heterocycle selected from morpholinyl, piperazinyl, piperidinyl or pyrrolidinyl wherein said Het$^3$ is optionally substituted with one or where possible two or more substituents selected from hydroxy, amino or C$_{1-4}$alkyl-;

Het$^{12}$ represents a heterocycle selected from morpholinyl, piperazinyl, piperidinyl or pyrrolidinyl wherein said Het$^{12}$ is optionally substituted with one or where possible two or more substituents selected from hydroxy, amino or C$_{1-4}$alkyl-;

Het$^{16}$ represents a heterocycle selected from piperidinyl or pyrrolidinyl;

Het$^{20}$ represents pyrrolidinyl, 2-pyrrolidinonyl, piperidinyl or hydroxy-pyrrolidin yl; preferably pyrrolidinyl or hydroxy-pyrrolidinyl;

Het$^{21}$ represents pyrrolidinyl or hydroxy-pyrrolidinyl;

Het$^{22}$ represents pyrrolidinyl piperazinyl or piperidinyl.

A particular group of compounds consists of those compounds of formula (I) wherein one or more of the following restrictions apply.

Z represents NH;

Y represents —C$_{3-9}$alkyl-, —C$_{2-9}$alkenyl-, —C$_{3-7}$alkyl-CO—NH optionally substituted with amino, mono- or di(C$_{1-4}$alkyl)amino or C$_{1-4}$alkyloxycarbonylamino-, —C$_{3-7}$alkenyl-CO—NH— optionally substituted with amino, mono- or di(C$_{1-4}$alkyl)amino- or C$_{1-4}$alkyloxycarbonylamino-, C$_{1-5}$alkyl-NR$^{13}$C$_{1-5}$alkyl-, —C$_{1-5}$alkyl-NR$^{14}$—CO—C$_{1-5}$alkyl-, —C$_{1-6}$alkyl-CO—NH—, —C$_{1-5}$alkyl-CO NR$^{15}$—C$_{1-5}$alkyl-, —C$_{1-3}$alkyl-NH—CO-Het$^{20}$-, —C$_{1-2}$alkyl-CO-Het$^{21}$-CO—, C$_{1-2}$alkyl-NH—CO—CR$^{16}$R$^{17}$—NH—, —C$_{1-2}$alkyl-CO—NH—CR$^{15}$R$^{19}$—CO—, —C$_{1-2}$alkyl-CO—NR$^{20}$—C$_{1-3}$alkyl-CO—, or —NR$^{22}$—CO—C$_{1-3}$alkyl-NH—;
even more particular Y represents —C$_{3-9}$alkyl-, —C$_{1-5}$alkyl-NR$^{13}$—C$_{1-5}$alkyl-, —C$_{1-5}$alkyl-NR$^{14}$—CO—C$_{1-5}$alkyl-, —C$_{1-3}$alkyl-NH—CO-Het$^{20}$-, —C$_{1-2}$alkyl-CO-Het$^{21}$-CO—, or —C$_{1-2}$alkyl-NH—CO—CR$^{16}$R$^{17}$—NH—;

X$^1$ represents a direct bond, O, or —O—C$_{1-2}$alkyl-;

X$^2$ represents a direct bond, —CO—C$_{1-2}$alkyl-, NR$^{12}$, —NR$^{12}$—C$_{1-2}$alkyl-, —O—N=CH— or —C$_{1-2}$alkyl-; even more particular X$^2$ represents —CO—C$_{1-2}$alkyl- or NR$^{12}$—C$_{1-2}$alkyl-;

R$^1$ represents hydrogen or halo, preferably hydrogen, chloro, fluoro or bromo;

R$^2$ represents hydrogen or halo, preferably hydrogen, chloro, fluoro or bromo;

R$^3$ represents hydrogen;

R$^4$ represents hydrogen or C$_{1-4}$alkyloxy, preferably C$_{1-4}$alkyloxy, even more preferably methoxy;

R$^{12}$ represents hydrogen or C$_{1-4}$alkyl, preferably hydrogen or methyl;

R$^{13}$ represents hydrogen or C$_{1-4}$alkyl;

R$^{14}$ represents hydrogen;

R$^{15}$ represents hydrogen;

R$^{16}$ and R$^{17}$ each independently represent hydrogen or C$_{1-4}$alkyl;

R$^{18}$ and R$^{19}$ each independently represent hydrogen or C$_{1-4}$alkyl optionally substituted with phenyl or hydroxy;

R$^{20}$ and R$^{21}$ each independently represent hydrogen or C$_{1-4}$alkyl optionally substituted with C$_{1-4}$alkyloxy;

Het$^{20}$, Het$^{21}$ and Het$^{22}$ each independently represent a heterocycle selected from the group consisting pyrrolidinyl, 2-pyrrolidinonyl or piperidinyl optionally substituted with hydroxy.

A preferred group of compounds consists of those compounds of formula (I) wherein one or more of the following restrictions apply:

Z represents NH;

Y represents —C$_{3-9}$alkyl-, —C$_{2-9}$alkenyl-, —C$_{1-5}$alkyl-oxy-C$_{1-5}$alkyl-, —C$_{1-5}$alkyl-NR$^{13}$—C$_{1-5}$alkyl-, —C$_{1-6}$alkyl-NH—CO—, —CO—C$_{1-7}$alkyl-, —C$_{1-7}$alkyl-CO— or C$_{1-6}$alkyl-CO—C$_{1-6}$alkyl; alkyl-NH—CO-Het$^{20}$-, C$_{1-2}$alkyl-CO-Het$^{21}$-CO—, —C$_{1-2}$alkyl-NH—CO—CR$^{16}$R$^{17}$—NH—, —C$_{1-2}$alkyl-CO—NH—CR$^{18}$R$^{19}$—CO—, —C$_{1-2}$alkyl-CO—NR$^{20}$—C X$^1$ represents O, —O—C$_{1-2}$alkyl-, —O—N=CH—, NR$^{11}$ or —NR$^{11}$—C$_{1-2}$alkyl-; in a particular embodiment X$^1$ represents NR$^{11}$—, —O— or —O—CH$_2$—;

X² represents a direct bond, O, —O—C$_{1-2}$alkyl-, —O—N=CH—, NR¹² or NR¹²—C$_{1-2}$alkyl-; in a particular embodiment X² represents a direct bond, —C$_{1-2}$alkyl-, —O—C$_{1-2}$alkyl, —O— or —O—CH$_2$—;

R¹ represents hydrogen, cyano, halo or hydroxy, preferably halo;

R² represents hydrogen, cyano, halo, hydroxy, hydroxycarbonyl-, C$_{1-4}$alkyloxycarbonyl-, Het¹⁶-carbonyl-, C$_{1-4}$alkyl-, C$_{2-6}$alkynyl-, Ar⁵ or Het¹; In a further embodiment R² represents hydrogen, -cyano, halo, hydroxy, C$_{2-6}$alkynyl- or Het¹; in particular R² represents hydrogen, cyano, halo, hydroxy, or Ar⁵;

R³ represents hydrogen;

R⁴ represents hydrogen, hydroxy, C$_{1-4}$alkyloxy- or R⁴ represents C$_{1-4}$alkyloxy substituted with one or where possible two or more substituents selected from C$_{1-4}$alkyloxy- or Het²-;

R¹² represents hydrogen, C$_{1-4}$alkyl- or C$_{1-4}$alkyl-oxy-carbonyl-;

R¹³ represents Het¹⁴—C$_{1-4}$alkyl, in particular morpholinyl-C$_{1-4}$alkyl;

Het¹ represents thiazolyl optionally substituted with amino, C$_{1-4}$alkyl, hydroxy-C$_{1-4}$alkyl-, phenyl, phenyl-C$_{1-4}$alkyl-, C$_{1-4}$alkyl-oxy-C$_{1-4}$alkyl-mono- or di(C$_{1-4}$alkyl)amino- or amino-carbonyl-;

Het² represents a heterocycle selected from morpholinyl, piperazinyl, piperidinyl or pyrrolidinyl wherein said Het² is optionally substituted with one or where possible two or more substituents selected from hydroxy, amino or C$_{1-4}$alkyl-; In a further embodiment Het² represents a heterocycle selected from morpholinyl or piperidinyl optionally substituted with C$_{1-4}$alkyl-, preferably methyl;

Het³ represents a heterocycle selected from morpholinyl, piperazinyl, piperidinyl or pyrrolidinyl wherein said Het² is optionally substituted with one or where possible two or more substituents selected from hydroxy, amino or C$_{1-4}$alkyl-;

Het¹² represents a heterocycle selected from morpholinyl, piperazinyl, piperidinyl or pyrrolidinyl wherein said Het³ is optionally substituted with one or where possible two or mote substituents selected from hydroxy, amino or C$_{1-4}$alkyl;

Het¹⁶ represents a heterocycle selected from piperidinyl or pyrrolidinyl.

A further group of compounds consists of those compounds of formula (I) wherein one or more of the following restrictions apply:

Z represents NH;

Y represents —C$_{3-9}$alkyl-, —C$_{1-5}$alkyl-NR¹³—C$_{1-5}$alkyl-, —C$_{1-6}$alkyl-NH—CO—, —CO—C$_{1-7}$alkyl- or —C$_{1-7}$alkyl-CO—;

X¹ represents —NR¹¹, —O— or —O—CH$_2$—;

X² represents a direct bond, —NR¹², —NR¹²—C$_{1-2}$alkyl-, —CO—, —O— or —O—CH$_2$—;

R¹ represents halo; in particular R¹ represents chloro, fluoro or bromo and is at position 5';

R² represents hydrogen, cyano, halo, hydroxy, or Ar⁵;

R³ represents hydrogen;

R⁴ represents C$_{1-4}$alkyloxy substituted with one or where possible two or more substituents selected from C$_{1-4}$alkyloxy- or Het²-;

R¹² represents C$_{1-4}$alkyl or R¹² represents C$_{1-4}$alkyl-oxy-carbonyl; —R¹³ represents Het¹⁴-C$_{1-4}$alkyl;

Het² represents a heterocycle selected from morpholinyl or piperidinyl optionally substituted with C$_{1-4}$alkyl-;

Het³ represents a heterocycle selected from morpholinyl, piperazinyl, piperidinyl or pyrrolidinyl wherein said Het³ is optionally substituted with one or where possible two or more substituents selected from hydroxy, amino or C$_{1-4}$alkyl-;

Het¹² represents a heterocycle selected from morpholinyl, piperazinyl, piperidinyl or pyrrolidinyl wherein said Het¹² is optionally substituted with one or where possible two or more substituents selected from hydroxy, amino or C$_{1-4}$-alkyl-;

Het¹⁴ represents morpholinyl.

In a further embodiment of the present invention the compounds of formula (I) are selected from the group consisting of;

4,6-ethanediylidenepyrimido[4,5-b][6,1,12]benzoxadiazacyclopentadecine, 17-bromo-8,9,10,11,12,13,14,19-octahydro-20-methoxy- 4,6-ethanediylidenepyrimido[4,5-b][6,1,12]benzoxadiazacyclopentadecine, 17-bromo-8,9,10,11,12,13,14,19-octahydro-20-methoxy-13-methyl-benzamide, 4-fluoro-N-(8,9,10,11,12,13-hexahydro-20-methoxy-4,6-ethanediylidene-19H-pyrimido[4,5-b][6,13,1]benzodioxaazacyclopentadecin-16-yl)-

4,6-ethanediylidene-8H,14H-pyrimido[4,5-b][6,12,1]benzodioxaazacylohexadecine, 18-chloro-9,10,11,12,15,20-hexahydro-21-methoxy- 4,6-ethanediylidene-8H-pyrimido[4,5-b][6,1,11]benzoxadiazacyclohexadecin-11(12H)-one, 18-chloro-9,10,13,14,15,20-hexahydro-21-methoxy- 4,6-ethanediylidene-14H-pyrimido[4,5-b][6,9,12,1]benzotrioxaazacyclohexadecine, 18-chloro-8,9,11,12,15,20-hexahydro-21-methoxy- 4,6-ethanediylidenepyrimido[4,5-b]pyrrolo[2,1-k][6,1,9,12]benzoxatriazacyclopentadecin-11(8H)-one, 19-chloro-9,10,11a,12,13,14,16,21-octahydro-22-methoxy- 4,6-ethanediylidenepyrimido[4,5-b][6,1,9,12]benzoxatriazacyclopentadecin-11(8H)-one, 17-chloro-9,10,12,13,14,19-hexahydro-20-methoxy-13-methyl- 4,6-ethanediylidenepyrimido[4,5-b][6,1,9,12]benzoxatriazacyclopentadecin-11(8H)-one, 17-chloro-9,10,12,13,14,19-hexahydro-20-methoxy- 4,6-ethanediylidenepyrimido-12H-pyrimido[4,5-b][6,1,10,13]benzoxatriazacyclohexadecin-12-one, 18-chloro-8,9,10,11,13,14,15,20-octahydro-21-methoxy-14-methyl- 4,6-ethanediylidene-8H-pyrimido[4,5-b][6,1,9,13]benzoxatriazacyclohexadecin-11(12H)-one, 18-chloro-9,10,13,14,15,20-hexahydro-21-methoxy- 4,6-ethanediylidenepyrimido[4,5-b][6,1,10,14]benzoxatriazacycloheptadecin-12(13H)-one, 19-chloro-8,9,10,11,14,15,16,21-octahydro-22-methoxy- 4,6-ethenopyrimido[4,5-b][6,1,9,12]benzoxatriazacyclopentadecine-9,12(8H,13H)-dione, 17-chloro-10,11,14,19-tetrahydro-20-methoxy- 4,6-etheno-8H-pyrimido[4,5-b]pyrrolo[2,1-1][6,1,10,13]benzoxatriazacyclohexadecine-12,15(14H)-dione, 20-chloro-9,10,11,12a,13,17,22-heptahydro-23-methoxy- 4,6-ethanediylidene-12H-pyrimido[4,5-b]pyrrolo[2,1-1][6,1,10,13]benzoxatriazacyclohexadecin-12-one, 20-chloro-8,9,10,11,12a,13,14,15,17,22-decahydro-23-methoxy- 4,6-ethenopyrmido[4,5-b][6,1,9,14]benzoxatriazacycloheptadecine-9,14(8H,15H)-dione, 19-chloro-10,11,12,13,16,21-hexahydro-22-methoxy- 4,6-etheno-8H-pyrimido[4,5-b][6,1,9,13]benzoxatriazacyclohexadecine-9,13(10,11,14H)-dione, 18-chloro-11,12,15,20-tetrahydro-21-methoxy- 4,6-ethenopyrimido[4,5-b][6,1,11,14]benzoxatriazacycloheptadecine-11,14(8H,15H)-dione, 9-chloro-9,10,12,13,16,21-hexahydro-22-methoxy- 4,6-ethenopyrimido[4,5-b][6,1,11,16]benzoxatriazacyclononadecine-11,16(8H,17H)-dione, 21-chloro-9,10,12,13,14,15,18,23-octahydro-24-methoxy- 4,6-etheno-8H-pyrimido[4,5-b][6,1,11,15]benzoxatriazacyclooctadecine-11,15(12H,16H)-dione, 20-chloro-9,10,13,14,17,22-hexahydro-23-methoxy- 4,6-ethenopyimido[4,5-b][6,1,12]benzoxadiazacyclopentadecine, 17-bromo-16-fluoro-8,9,10,11,12,13,14,19-octahydro-20-methoxy- 4,6-ethanediylidenepyrimido[4,5-b][6,1,9,12]benzoxatriazacyclopentadecine-9,12(8H,13H)-dione, 17-chloro-10,11,14,19-tetrahydro-20-methoxy-11-methyl- 4,6-ethanediylidenepyrimido[4,5-b][6,1,9,12]benzoxatriazacyclopentadecine-9,12(8H,13H)-dione, 17-chloro-10,11,14,19-tetrahydro-20-methoxy-11-(1-methylethyl)-

4,6-ethanediylidenepyrimido[4,5-b][6,1,9,12]benzoxatriazacyclopentadecine-9,12(8H,13H)-dione, 11-chloro-10,11,14,19-tetrahydro-20-methoxy-11-(phenylmethyl))-

4,6-ethanediylidene-8H-pyrimido[4,5-b][6,1,9,12]benzoxatriazacyclohexadecine-11,14-dione, 18-chloro-9,10,12,13,15,20-hexahydro-21-methoxy-12-(1-methylethyl)-

4,6-ethanediylidene-8H-pyrimido[4,5-b][6,1,9,12]benzoxatriazacyclohexadecine 11,14-dione, 18-chloro-9,10,12,13,15,20-hexahydro-21-methoxy-12,12-dimethyl- 4,6-ethanediylidene-8H-pyrimido[4,5-b][6,1,9,12]benzoxatriazacyclohexadecine-11,14-dione, 18-chloro-9,10,12,13,15,20-hexahydro-21-methoxy-12-(2-methylpropyl)-

4,6-ethanediylidenepyrimido[4,5-b][6,1,10,13]benzoxatriazacycloheptadecine-12,15-dione, 19-chloro-8,9,10,11,13,14,16,21-octahydro-22-methoxy-13-(2-methylpropyl)-

4,6-ethanediylidene-8H-pyrimido[4,5-b][6,1,9,12]benzoxatriazacyclohexadecine-11,14-dione, 18-chloro-9,10,12,13,15,20-hexahydro-21-methoxy- 4,6-ethanediylidenepyrimido[4,5-b][6,1,10,13]benzoxatriazacycloheptadecine-12,15-dione, 19-chloro-8,9,10,11,13,14,16,21-octahydro-22-methoxy- 4,6-ethanediylidenepyrimido[4,5-b][6,1,9,12]benzoxatriazacyclopentadecine-9,12(8H,13H)-dione, 10,11,14,19-tetrahydro-20-methoxy-11-methyl- 4,6-ethanediylidenepyrimido[4,5-b][6,1,9,12]benzoxatriazacyclopentadecine-9,12(8H,13H)-dione, 10,11,14,19 tetrahydro-20-methoxy-(1-methylpropyl)-

9,11-ethanediylidenepyrimido[4,5-b]pyrrolo[1,2-i][6,1,9,12]benzoxatriazacyclopentadecine-14,19(5H,13H)-dione, 16,17,18,18a,20,21-hexahydro-22-methoxy- 4,6-ethanediylidenepyrimido[4,5-b][6,1,9,12]benzoxatriazacyclopentadecine-9,12(8H,13H)-dione, 10,11,14,19-tetrahydro-20-methoxy- 4,6-ethanediylidene-8H-pyrimido[4,5-b][6,1,9,13]benzoxatriazacyclohexadecine-9,13(10H,14H)-dione, 11,12,15,20-tetrahydro-21-methoxy-, 4,6-ethanediylidenepyrimido[4,5-b][6,1,9,14]benzoxatriazacycloheptadecine-9,14(8H,15H)-dione, 10,11,12,13,16,21-hexahydro-22-methoxy- 4,6-ethanediylidenepyrimido[4,5-b]pyrrolo[2,1-k][6,1,9,12]benzoxatriazacyclopentadecin-11(8H)-one, 19-chloro-18-fluoro-9,10,11a,12,13,14,16,21-octahydro-22-methoxy- 4,6-ethanediylidene-8H-pyrimido[4,5-b][6,1,10,13]benzoxatriazacyclohexadecine, 18-chloro-9,10,11,12,13,14,15,20-octahydro-21-methoxy-14-methyl- 4,6-ethanediylidenepyrimido[4,5-b][6,1,9,12]benzoxatriazacyclopentadecine-11(8H)-one, 17-chloro-16-fluoro-9,10,12,13,14,19-hexahydro-20-methoxy-13-methyl- 4,6-ethanediylidene-12H-pyrimido[4,5-b][6,1,10,13]benzoxatriazacyclohexadecin-12-one, 18-chloro-17-fluoro-8,9,10,11,13,14,15,20-octahydro-21-methoxy-14-methyl- 4,6-ethanediylidenepyrimido[4,5-b][6,1,9,12]benzoxatriazacyclopentadecin-11(8H)-one, 17-chloro-16-fluoro-9,10,12,13,14,19-hexahydro-20-methoxy- 4,6-ethanediylidene-12H-pyrimido[4,5-b][6,1,10,13]benzoxatriazacyclohexadecin-12-one, 18-chloro-17-fluoro-8,9,10,11,13,14,15,20-octahydro-21-methoxy- 4,6-ethanediylidene-12H-pyrimido[4,5-b][6,1,10,13]benzoxatriazacyclohexadecin-12-one, 18-chloro-8,9,10,11,13,14,15,20-octahydro-21-methoxy- 9,11-ethanediylidenepyrimido[4,5-b]pyrrolo[1,2-i][6,1,9,12]benzoxatriazacyclopentadecine-14,19(5H,13H)-dione, 3-chloro-16,17,18,18a,20,21-hexahydro-22-methoxy- 4,6-ethanediylidenepyrimido[4,5-b][6,1,9,12]benzoxatriazacyclopentadecine-9,12(8H,13H)-dione, 17-chloro-10,11,14,19-tetrahydro-20-methoxy-10-methyl- 4,6-ethanediylidenepyrimido[4,5-b][6,1,9,12]benzoxatriazacyclopentadecine-9,12(8H,13H)-dione, 17-chloro-10,11,14,19-tetrahydro-11-(1-hydroxyethyl)-20-methoxy- 4,6-ethanediylidenepyrimido[4,5-b][6,1,11,14]benzoxatriazacycloheptadecine-11,14(8H, 15E)-dione, 19-chloro-9,10,12,13,16,21-hexahydro-22-methoxy-13-(1-methylpropyl)-

4,6-ethanediylidenepyramido[4,5-b][6,1,9,12]benzoxatriazacyclopentadecine-9,12(8H,13H)-dione, 17-chloro-10,11,14,19-tetrahydro-11-(hydroxymethyl)-20-methoxy- 4,6-ethanediylidenepyrimido[4,5][6,1,11,14]benzoxatriazacycloheptadecine-11,14(8H,15H)-dione, 19-chloro-9,10,12,13,16,21-hexahydro-13-methyl- 4,6-ethanediylidenepyrimido[4,5-b][6,1,11,14]benzoxatriazacycloheptadecine-11,14(8H, 15H)-dione, 19-chloro-9,10,12,13,16,21-hexahydro-22-methoxy-13-methyl- 4,6-ethanediylidene-8H-pyrimido[4,5-b][6,1,9,12]benzoxatriazacyclohexadecine-9,12-dione, 18-chloro-10,11,13,14,15,20-hexahydro-21-methoxy- 4,6-ethanediylidene-8H-pyrimido[4,5-b][6,1,9,14]benzoxatriazacyclooctadecine-9,14-dione, 20-chloro-10,11,12,13,15,16,17,22-octahydro-23-methoxy- 4,6-ethanediylidenepyrimido[4,5-b]pyrrolo[2,1-k][6,1,9,12]benzoxatriazacyclopentadecin-11(8H)-one, 19-chloro-9,10,11a,12,13,14,16,21-octahydro-22-methoxy- 4,6-ethanediylidene-12H-pyrimido[4,5-b]pyrrolo[2,1-1][6,1,10,13]benzoxatriazacyclohexadecin-12-one, 20-chloro-8,9,10,11,12a,13,14,15,17,22-decahydro-23-methoxy- 4,6-ethanediylidene-12H-pyrimido[4,5-b]pyrrolo[2,1-1][6,1,10,13]benzoxatriazacyclohexadecin-12-one, 20-chloro-19-fluoro-8,9,10,11,12a,13,14,15,17,22-decahydro-23-methoxy- 4,6-ethanediylidenepyrimido[4,5-b][6,1,11,14]benzoxatriazacycloheptadecin-13(8H)-one, 19-chloro-9,10,11,12,14,15,16,21-octahydro-22-methoxy- 4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-methyl- 4,6-ethanediylidenepyrimido[4,5-b][6,1,9,12]benzoxatriazacycloheptadecin-12(13H)-one, 19-chloro-10-ethyl-8,9,10,11,14,15,16,21-octahydro-22-methoxy- 1,22-ethanediylidene-5H,17H-pyrimido[4,5-b]pyrrolo[2,1-h][6,1,9,12]benzoxatriazacycloheptadecin-14(15H)-one, 7-chloro-10,11,12,13,18,19,19a,20-octahydro-24-methoxy- 4,6-ethanediylidene-8H-pyrimido[4,5-b][6,1,10,13]benzoxatriazacyclooctadecin-13(14H)-one, 20-chloro-9,10,11,12,15,16,17,22-octahydro-23-methoxy- 14H-4,6-ethanediylidene-9,13-methano-8H-pyrimido[4,5-b][6,1,12,15]benzoxatriazacycloeicosin-15(16H)-one, 22-chloro-9,10,11,12,17,18,19,24-octahydro-26-methoxy- 13H-4,6-ethanediylidene-9,12-ethanopyrimido[4,5-b][6,1,11,14]benzoxatriazacyclononadecin-14(15H)-one, 21-chloro-8,9,10,11,16,17,18,23-octahydro-26-methoxy- 14H-4,6-ethanediylidene-10,13-ethano-8H-pyrimido[4,5-b][6,1,12,15]benzoxatriazacycloeicosin-15(16H)-one, 22-chloro-9,10,11,12,17,18,19,24-octahydro-27-methoxy- 4,6-ethanediylidenepyrimido[4,5-b][6,1,9,12]benzoxatriazacycloheptadecin-12(13H)-one, 19-chloro-8,9,10,11,14,15,16,21-octahydro-10-[[[2-hydroxy-1-(hydroxymethyl)ethyl]amino]acetyl]-22-methoxy- 4,6-ethanediylidenepyrimido[4,5-b][6,1,9,12]benzoxatriazacycloheptadecin-12(13H)-one, 19-chloro-8,9,10,11,14,15,16,21-octahydro-10-[[2-(hydroxymethyl)-4-morpholinyl]acetyl]-22-methoxy- 4,6-ethanediylidenepyrimido[4,5-b][6,1,9,12]benzoxatriazacycloheptadecin-12(13H)-one, 19-chloro-8,9,10,11,14,15,16,21-octahydro-22-methoxy- 4,6-ethanediylidenepyrimido[4,5-b][6,1,9,12]benzoxatriazacycloheptadecin-12(13H)-one, 19-chloro-8,9,10,11,14,15,16,21-octahydro-10-[[(2-hydroxyethyl)methylamino]acetyl]-22-methoxy- 4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-[[[2-(4-pyridinyl)ethyl]amino]acetyl]-

4,6-ethanediylidenepyrimido[4,5-b][6,1,9,12]benzoxatriazacycloheptadecin-12(13H)-one, 19-chloro-10-[[[2-(dimethylamino)ethyl]methylamino]acetyl]-8,9,10,11,14,15,16,21-octahydro-22-methoxy- 4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-[[(2-methoxyethyl)amino]acetyl]-

4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-[[(3-methoxypropyl)amino]acetyl]-

4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-(4-morpholinylacetyl)-

4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-[(4-methyl-1-piperazinyl)acetyl]-

4,6-ethenopyrimido[4,5-b][6,1,2]benzoxadiazacyclopentadecine-13(8H)-carboxylic acid, 17-bromo-9,10,11,12,14,19-hexahydro-20-methoxy-, phenylmethyl ester 4,6-ethanediylidenepyrimido[4,5-b]pyrrolo[2,1-m][6,1,11,14]benzoxatriazacycloheptadecin-13(8H)-one, 21-chloro-9,10,11,12,13a,14,15,16,18,23-decahydro-24-methoxy- 4,6-ethanediylidenepyrimido[4,5-b]pyrrolo[2,1-m][6,1,11,14]benzoxatriazacycloheptadecin-13(8H)-one, 21-chloro-20-fluoro-9,10,11,12,13a,14,15,16,18,23-decahydro-24-methoxy- 4,6-ethanediylidenepyrimido[4,5-b][6,1,16]benzoxadiazacyclononadecin-16(17H)-one, 21-chloro-8,9,10,13,14,15,18,23-octahydro-24-methoxy- 4,6-ethanediylidenepyrimido[4,5-b][6,1,16]benzoxadiazacyclononadecin-16(17H)-one, 21-chloro-8,9,10,13,14,15,18,23-octahydro-24-methoxy- 4,6-ethanediylidenepyrimido[4,5-b]pyrrolo[2,1-k][6,1,9,12]benzoxatriazacyclopentadecine-11(8H)-thione, 19-chloro-18-fluoro-9,10,11a,12,13,14,16,21-octahydro-22-methoxy- 4,6-ethanediylidenepyrimido[4,5-b][6,1,11,14]benzoxatriazacycloheptadecine, 19-chloro-8,9,10,11,12,13,14,15,16,21-decahydro-22-methoxy-15-methyl- 4,6-ethanediylidenepyrimido[4,5-b][6,1,9,12]benzoxatriazacyclopentadecine, 17-chloro-8,9,10,11,12,13,14,19-octahydro-20-methoxy-13-methyl- 4,6-ethanediylidenepyrimido[4,5-b][6,1,9,12]benzoxatriazacyclopentadecine-9,12(8H,13H)-dione, 17-chloro-10,11,14,19-tetrahydro-20-methoxy-11,11-dimethyl- 9,11-ethanediylidenepyrimido[4,5-b]pyrrolo[1,2-i][6,1,9,12]benzoxatriazacyclopentadecine-14,19(5H,13H)-dione, 3-chloro-16,17,18,18a,20,21-hexahydro-17-hydroxy-22-methoxy- 4,6-ethanediylidene-8H-pyrimido[4,5-b][6,1,15]benzoxadiazacyclooctadecin-15(16H)-one, 20-chloro-9,12,13,14,17,22-hexahydro-23-methoxy- 4,6-ethanediylidene-8H-pyrimido[4,5-b][6,1,12,15]benzoxatriazacyclooctadecine, 20-chloro-9,10,11,12,13,14,15,16,17,22-decahydro-23-methoxy-16-methyl- 4,6-ethanediylidene-8H-pyrimido[4,5-b][6,1,9,12]benzoxatriazacyclohexadecine-11,14-dione, 18-chloro-9,10,12,13,15,20-hexahydro-21-methoxy-10-(2-methoxyethyl)-

4,6-ethanediylidenepyrimido[4,5-b][6,1,12,16]benzoxatriazacyclononadecine-12,16(13H,17H)-dione, 21-chloro-8,9,10,11,14,15,18,23-octahydro-24-methoxy- 4,6-ethanediylidene-8H-pyrimido[4,5-b][6,1,12,17]benzoxatriazacycloeicosine-12,17(18H)-dione, 22-chloro-9,10,11,13,14,15,16,19,24-nonahydro-25-methoxy- 4,6-ethanediylidene-8H-pyrimido[4,5-b]pyrrolo[1,2-1][6,1,12,15]benzoxatriazacyclooctadecine-12,17(18)-dione, 22-chloro-9,10,11,14,15,16a,19,24-nonahydro-25-methoxy- 4,6-ethanediylidene-8H-pyrimido[4,5-b][6,1,9,12]benzoxatriazacyclohexadecine-9,12-dione, 18-chloro-10,11,13,14,15,20-hexahydro-21-methoxy-11,11-dimethyl- 4,6-ethanediylidene-8H-pyrimido[4,5-b]pyrrolo[1,2-1][6,1,12,15]benzoxatriazacyclooctadecine-12,17(18H)-dione, 22-chloro-9,10,11,14,15,16,16a,19,24-nonahydro-15-hydroxy-25-methoxy- 4,6-ethanediylidene-8H-pyrimido[4,5-b][6,1,12,15]benzoxatriazacyclooctadecine-12,15(16H)-dione, 20-chloro-9,10,11,13,14,17,22-heptahydro-23-methoxy-13-methyl- 4,6-ethanediylidene-8H-pyrimido[4,5-b][6,1,12,15]benzoxatriazacyclooctadecine-12,15(16H)-dione, 20-chloro-9,10,11,13,14,17,22-heptahydro-23-methoxy-14-(2-methylpropyl)-

4,6-ethanediylidene-8H-pyrimido[4,5-b][6,1,12,15]benzoxatriazacyclooctadecine-12,15(16H)-dione, 20-chloro-9,10,11,13,14,17,22-heptahydro-23-methoxy-14,14-dimethyl- 4,6-ethanediylidene-8H-pyrimido[4,5-b][6,1,12,15]benzoxatriacycyclooctadecine-12,15(16H)-dione, 20-chloro-9,10,11,13,14,17,22-heptahydro-23-methoxy-14-(phenylmethyl)-

4,6-ethanediylidene-8H-pyrimido[4,5-b][6,1,12,15]benzoxatriazacyclooctadecine-12,15(16H)-dione, 20-chloro-9,10,11,13,14,17,22-heptahydro-23-methoxy-14-methyl- 4,6-ethanediylidene-8H-pyrimido[4,5-b][6,1,9,12]benzoxatriazacyclohexadecine-9,12-dione, 18-chloro-10,11,13,14,15,20-hexahydro-21-methoxy-11-methyl- 1,21-ethanediylidene-5H-pyrimido[4,5-b]pyrrolo[1,2i][6,1,9,12]benzoxatriazacyclohexadecine-13,18(19H)-dione, 7-chloro-10,11,12,13a,14,15,16-heptahydro-23-methoxy- 4,6-ethanediylidene-8H-pyrimido[4,5-b][6,1,9,12]benzoxatriazacyclohexadecine-9,12-dione, 18-chloro-10,11,13,14,15,20-hexahydro-21-methoxy-10-methyl- 4,6-ethanediylidene-8H-pyrimido[4,5-b][6,1,9,12]benzoxatriazacyclohexadecine-9,12-dione, 18-chloro-10,11,13,14,15,20-hexahydro-21-methoxy-11-(2-methylpropyl)-

4,6-ethanediylidene-8H-pyrimido[4,5-b][6,1,9,12]benzoxatriazacyclohexadecine-9,12-dione, 18-chloro-10,11,13,14,15,20-hexahydro-11-(1-hydroxyethyl)-21-methoxy- 4,6-ethanediylidenepyrimido[4,5-b][6,1,11,14]benzoxatriazacycloheptadecine-11,14(8H,15H)-dione, 19-chloro-9,10,12,13,16,21-hexahydro-22-methoxy-13-(2-methylpropyl)-4,6-ethanediylidenepyrimido[4,5-b][6,1,11,14]benzoxatriazacycloheptadecine-11,14(8H,15H)-dione, 19-chloro-9,10,12,13,16,21-hexahydro-22-methoxy-13,13-dimethyl- 4,6-ethanediylidenepyrimido[4,5-b][6,1,11,14]benzoxatriazacycloheptadecine-11,14(8H, 5H)-dione, 19-chloro-9,10,12,13,16,21-hexahydro-22-methoxy-13-(phenylmethyl)-

4,6-ethanediylidenepyrimido[4,5-b][6,1,11,14]benzoxatriazacycloheptadecine-11,14(8H,15H)-dione, 19-chloro-9,10,12,13,16,21-hexahydro-13-(1-hydroxyethyl)-22-methoxy- 4,6-ethanediylidene-8H-pyrimido[4,5-b][6,1,12,15]benzoxatriazacyclooctadecine-12,15(16H)-dione, 20-chloro-9,10,11,13,14,17,22-heptahydro-14-(1-hydroxyethyl)-23-methoxy- 4,6-ethanediylidene-8H-pyrimido[4,5-b][6,1,9,12]benzoxatriazacyclohexadecine-11,14-dione, 18-chloro-9,10,12,13,15,20-hexahydro-21-methoxy-10-[2-(4-morpholinyl)ethyl]- carbamic acid, (20-chloro-9,10,13,14,15,16,17,22-octahydro-23-methoxy-15-oxo-4,6-ethanediylidene-8H-pyrimido[4,5-b][6,1,15]benzoxadiazacyclooctadecin-14-yl)-, 1,1-dimethylethyl ester carbamic acid, (20-chloro-9,10,13,14,15,16,17,22-octahydro-23-methoxy-15-oxo-4,6-ethanediylidene-8H-pyrimido[4,5-b][6,1,15]benzoxadiazacyclooctadecin-14-yl)-, 1,1-dimethylethyl ester 4,6-ethanediylidene-8H-pyrimido[4,5-b][6,1,9,12]benzoxatriazacyclohexadecine-9,12-dione, 18-chloro-10,11,13,14,15,20-hexahydro-11-(hydroxymethyl)-21-methoxy- 1,21-ethanediylidene-5H-pyrimido[4,5-b]pyrrolo[1,2-i][6,1,9,12]benzoxatriazacyclohexadecine-13,18(19H)-dione, 7-chloro-10,11,12,13a,14,15,16-heptahydro-15-hydroxy-23-methoxycarbamic acid, (20-chloro-9,10,11,12,13,14,15,16,17,22-decahydro-23-methoxy-15-oxo-4,6-ethanediylidene-8H-pyrimido[4,5-b][6,1,15]benzoxadiazacyclooctadecin-14-yl)-, 1,1-dimethylethyl ester 4,6-ethanediylidene-8H-pyrimido[4,5-b][6,1,15]benzoxadiazacyclooctadecin-15(16H)-one, 14-amino-20-chloro-9,10,11,12,13,14,17,22-octahydro-23-methoxycarbamic acid, (18-chloro-11,12,13,14,15,20-hexahydro-21-methoxy-13-oxo-4,6-ethanediylidene-8H-pyrimido[4,5-b][6,1,13]benzoxadiazacyclohexadecin-12-yl)-, 1,1-dimethylethyl ester 4,6-ethanediylidenepyrimido[4,5-b]pyrrolo[2,1-k][6,1,9,12]benzoxatriazacyclopentadecin-11(8H)-one, 19-chloro-9,10,11a,12,13,14,16,21-octahydro-13-hydroxy-22-methoxy- 4,6-ethanediylidene-13,16-ethano-8H-pyrimido[4,5-b][6,1,9,12,15]benzoxatetraazacyclooctadecin-11(12H)-one, 20-chloro-9,10,14,15,17,22-hexahydro-25-methoxy- 8H-4,6-ethanediylidene-12,15-ethanopyrimido[4,5-b][6,1,9,14]benzoxatriazacycloheptadecin-11(12H)-one, 19-chloro-9,10,13,14,16,21-hexahydro-24-methoxy- 4,6-ethanediylidene-12,16-methano-6H-pyrimido[4,5-b][6,1,9,15]benzoxatriazacyclooctadecin-11(8H)-one, 20-chloro-9,10,12,13,14,15,17,22-octahydro-24-methoxy- 4,6-ethanediylidenepyrimido[4,5-b][6,1,12]benzoxatriazacyclopentadecin-11(8H)-one, 17-chloro-9,10,12,13,14,19-hexahydro-20-methoxy-12,13-dimethyl- 4,6-ethanediylidenepyrimido[4,5-b][6,1,9,12]benzoxatriazacyclopentadecin-11(8H)-one, 17-chloro-13-ethyl-9,10,12,13,14,19-hexahydro-20-methoxy- 4,6-ethanediylidenepyrimido[4,5-b][6,1,9,12]benzoxatriazacyclopentadecin-11(8H)-one, 17-chloro-9,10,12,13,14,19-hexahydro-12-(hydroxymethyl)-20-methoxy- 4,6-ethanediylidene-12H-pyrimido[4,5-b]pyrrolo[2,1-1][6,1,10,13]benzoxatriazacyclohexadecin-12-one, 20-chloro-8,9,10,11,12a,13,14,15,17,22-decahydro-14-hydroxy-23-methoxy- 4,6-ethanediylidene-14,17-ethanopyrimido[4,5-b][6,1,10,13,16]benzoxatetraazacyclononadecin-12(13H)-one, 21-chloro-8,9,10,11,15,16,18,23-octahydro-26-methoxy- 4,6-ethanediylidene-13,16-ethano-6H-pyrimido[4,5-b][6,1,10,15]benzoxatriazacyclooctadecin-12(13H)-one, 20-chloro-8,9,10,11,14,15,17,22-octahydro-25-methoxy- 12H-4,6-ethanediylidene-13,17-methanopyrimido[4,5-b][6,1,10,16]benzoxatriazacyclononadecin-12-one, 21-chloro-8,9,10,11,13,14,15,16,18,23-decahydro-25-methoxy- 4,6-ethanediylidene-12H-pyrimido[4,5-b][6,1,10,13]benzoxatriazacyclohexadecin-12-one, 18-chloro-8,9,10,11,13,14,15,20-octahydro-21-methoxy-13,14-dimethyl- 4,6-ethanediylidene-12H-pyrimido[4,5-b][6,1,10,13]benzoxatriazacyclohexadecin-12-one, 18-chloro-14-ethyl-8,9,10,11,13,14,15,20-octahydro-21-methoxy- 4,6-ethanediylidene-12H-pyrimido[4,5-b][6,1,10,13]benzoxatriazacyclohexadecin-12-one, 18-chloro-8,9,10,11,13,14,15,20-octahydro-13-(hydroxymethyl)-21-methoxy- 4,6-ethanediylidenepyrimido[4,5-b][6,1,11,14]benzoxatriazacycloheptadecin-13(8H)-one, 19-chloro-15-ethyl-9,10,11,12,14,15,16,21-octahydro-22-methoxy- 4,6-ethanediylidenepyrimido[4,5-b][6,1,11,14]benzoxatriazacycloheptadecin-13(8H)-one, 19-chloro-9,10,11,12,14,15,16,21-octahydro-22-methoxy-14,15-dimethyl- 4,6-ethanediylidenepyrimido[4,5-b][6,1,16]benzoxadiazacyclononadecin-16(17H)-one, 21-chloro-8,9,10,11,12,13,14,15,18,23-decahydro-24-methoxy- 4,6-ethanediylidene-8H-pyrimido[4,5-b][6,1,15]benzoxadiazacyclooctadecin-15(16H)-one, 20-chloro-14-(dimethylamino)-9,10,11,12,13,14,17,22-octahydro-23-methoxy- In a particular embodiment of the present invention the compounds of formula (I) are selected from the group consisting of;

4,6-ethanediylidenepyrimido[4,5-b][6,1,12]benzoxadiazacyclopentadecine, 17-bromo-8,9,10,11,12,13,14,19-octahydro-20-methoxy-13-methyl, 4,6-ethanediylidenepyrimido[4,5-b][6,1,12]benzoxadiazacyclopentadecine, 17-bromo-8,9,10,11,12,13,14,19-octahydro-20-methoxy-, 4,6-ethanediylidenepyrimido[4,5-b][6,1,10,13]benzoxatriazacycloheptadecine-12,15-dione, 19-chloro-8,9,10,11,13,14,16,21-octahydro-22-methoxy-13-(2-methylpropyl)-, 4,6-ethanediylidenepyrimido[4,5-b][6,1,10,13]benzoxatriazacycloheptadecine-12,15-dione, 19-chloro-8,9,10,11,13,14,16,21-octahydro-22-methoxy-, 4,6-ethanediylidenepyrimido[4,5-b]pyrrolo[2,1-k][6,1,9,12]
benzoxatriazacyclopentadecin-11(8H)-one, 19-chloro-18-
fluoro-9,10,11a,12,13,14,16,21-octahydro-22-methoxy-,
4,6-ethanediylidene-8H-pyrimido[4,5-b][6,1,10,13]benzox-
atriazacyclohexadecine,
18-chloro-9,10,11,12,13,14,15,20-octahydro-21-methoxy-
14-methyl-,
4,6-ethanediylidenepyrimido[4,5-b][6,1,11,14]benzoxatri-
azacycloheptadecine, 19-chloro-8,9,10,11,12,13,14,15,
16,21-decahydro-22-methoxy-15-methyl-,
4,6-ethanediylidenepyrimido[4,5-b][6,1,9,12]benzoxatri-
azacyclopentadecine, 17-chloro-8,9,10,11,12,13,14,19-
octahydro-20-methoxy-13-methyl-,
12H-4,6-ethanediylidene-13,17-methanopyrimido[4,5-b][6,
1,10,16]benzoxatriazacyclononadecin-12-one, 21-chloro-
8,9,10,11,13,14,15,16,18,23-decahydro-25-methoxy-,
4,6-ethanediylidene-12H-pyrimido[4,5-b][6,1,10,13]ben-
zoxatriazacyclohexadecin-12-one, 18-chloro-8,9,10,11,
13,14,15,20-octahydro-21-methoxy-13,14-dimethyl-,
4,6-ethanediylidenepyrimido[4,5-b][6,1,11,14]benzoxatri-
azacycloheptadecin-13(8H)-one, 19-chloro-15-ethyl-9,
10,11,12,14,15,16,21-octahydro-22-methoxy-, or
4,6-ethanediylidenepyrimido[4,5-b][6,1,11,14]-13(8H)-
>one, 19-chloro-9,10,11,12,14,15,16,21-octahydro-22-
methoxy-14,15-dimethyl-
Other special group of compounds are:
those compounds of formula (I) wherein —$X^1$— represents —O—;
those compounds of formula (I) wherein —$X^1$— represents —$NR^{11}$—, in particular —NH—;
those compounds of formula (I) wherein $R^1$ is fluoro, chloro or bromo;
those compounds of formula (I) wherein $R^2$ is fluoro, chloro or bromo;
those compounds of formula (I) wherein $R^2$ is $Het^1$, in particular thiazolyl optionally substituted with methyl;
those compounds of formula (I) wherein $R^2$ is $C_{2-6}$alkynyl-, in particular ethynyl;
those compounds of formula (I) wherein $R^2$ is $Ar^5$, in particular phenyl optionally substituted with cyano;
those compounds of formula (I) wherein $R^4$ represents methoxy and wherein said methoxy is at position 7 of the structure of formula (I).
those compounds of formula (I) wherein $R^4$ represents $C_{1-4}$alkyloxy substituted with one substituent selected from $C_{1-4}$alkyloxy- or $Het^2$-, in particular propyloxy substituted with morpholinyl;
those compounds of formula (I) wherein $R^{12}$ is hydrogen or $C_{1-4}$alkyl-, in particular methyl or wherein $R^{12}$ is $C_{1-4}$alkyl-oxy-carbonyl-, in particular t-butyl-oxy-carbonyl-
those compounds of formula a) wherein $Het^2$ represent morpholinyl optionally substituted with $C_{1-4}$alkyl, preferably morpholinyl attached through the nitrogen atom to the remainder of the compounds of formula (I);
those compounds of formula (I) with $Het^3$ represent morpholinyl optionally substituted with $C_{1-4}$alkyl, preferably morpholinyl attached through the nitrogen atom to the remainder of the compounds of formula (I);
those compounds of formula (I) wherein $Het^{12}$ represent morpholinyl optionally substituted with $C_{1-4}$alkyl, preferably morpholinyl attached through the nitrogen atom to the remainder of the compounds of formula (I).

In a further embodiment of the present invention the $X^2$ substituent is at position 2, the $R^1$ substituent represents hydrogen or halo and is at position 4', the $R^2$ substituent represents halo and is at position 5', the $R^3$ substituent is at position 2 and the $R^4$ substituent at position 7 of the structure of formula (I). Alternatively, the $X^2$ substituent is at position 3', the R substituent represents hydrogen or halo and is at position 4', the $R^2$ substituent represents halo and is at position 5', the $R^3$ substituent is at position 2 and the $R^4$ substituent at position 7 of the structure of formula (I).

The compounds of this invention can be prepared by any of several standard synthetic processes commonly used by those skilled in the art of organic chemistry and described for instance in the following references; "Heterocyclic Compounds"—Vol. 24 (part 4) p 261-304 Fused pyrimidines, Wiley—Interscience; Chem. Pharm. Bull., Vol. 41(2) 362-368 (1993); J. Chem. Soc., Perkin Trans. 1, 2001, 130-137.

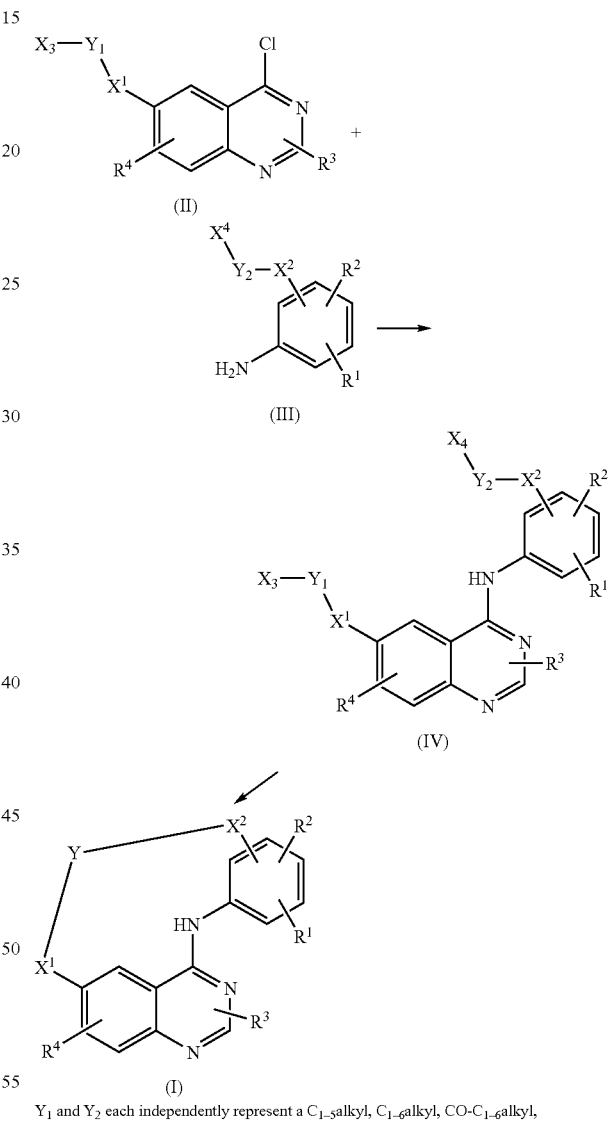

$Y_1$ and $Y_2$ each independently represent a $C_{1-5}$alkyl, $C_{1-6}$alkyl, CO-$C_{1-6}$alkyl, CO-$C_{1-5}$alkyl, $Het^{22}$-$CH_2$—CO,CO—$CR^{16}R^{17}$—NH—, $CR^{18}R^{19}$—CO—, $CH_2$—CO—NH—$C_{1-3}$alkyl-, —$C_{1-2}$alkyl-$NR^{21}$—$CH_2$—CO— or CO—$C_{1-3}$alkyl-NH—

$X_3$ and $X_4$ represent optionally protected functional groups, such as for example a primary or secundary amine, hydroxy, hydrogen, or halo(Cl, Br, or I), which upon reaction produce together with the $Y_1$ respectively $Y_2$ substituent to which they are attached, the divalent Y radical as defined for formula (I)

As further exemplified in the experimental part of the description, a particular group of compounds are those compounds of formula (I) were —$X^1$— represents —O—, hereinafter referred to as compounds of formula (I') which are generally prepared using the following synthesis scheme. The compounds of this invention may be prepared starting from the known 6-acetoxy-4-chloro-7-methoxy quinazoline (II') or from 6-acetoxy-7-benzyloxy-4-chloroquinazoline (II$^a$), which can be prepared from commercially available veratric acid and 4-hydroxy-3-methoxy benzoic acid, respectively.

Coupling of the latter compounds with suitable substituted anilines (III') under standard conditions, for example stirred in propanol at an elevated temperature ranging form 40-100° C. during 3-12 h, anilines which in their turn can be prepared according to reaction schemes 4-8, furnish the intermediate compounds (IV', IV$^a$) (Scheme 1).

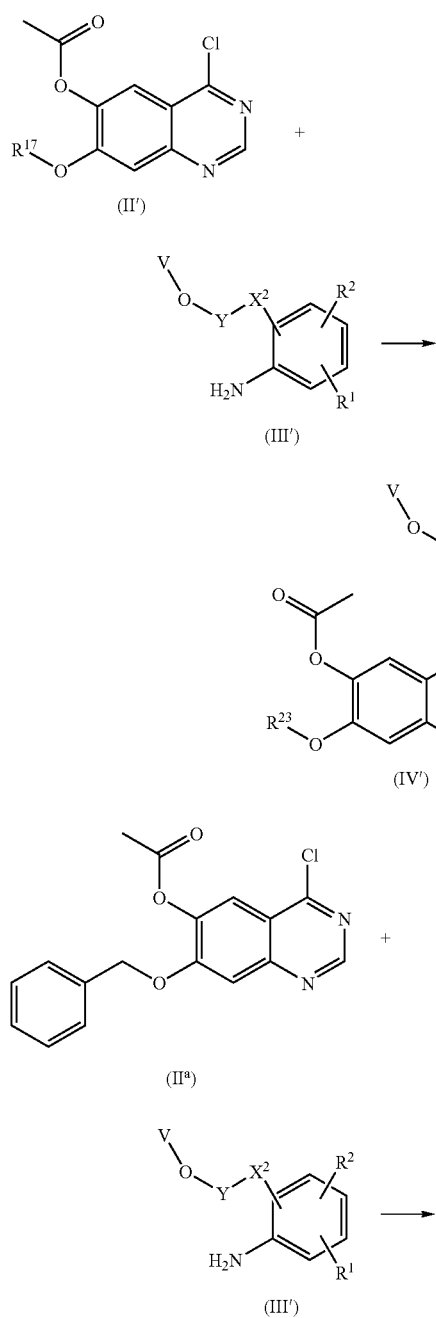

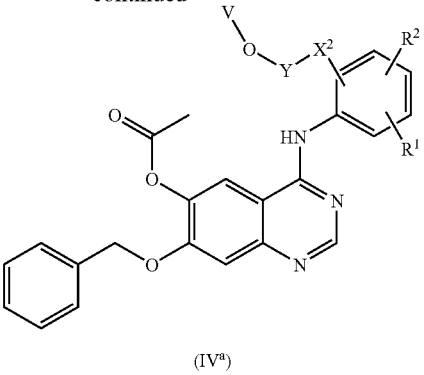

V = hydrogen or a protective group such as for example, methylcarbonyl, t-butyl, methyl, ethyl, benzyl or trialkylsilyl groups
$R^{23}$ represents $Ar^3$, $Ar^4$-$C_{1-4}$alkyl, $C_{1-4}$alkyl, $C_{2-6}$alkenyl optionally substituted with $Het^{12}$ or $R^{23}$ represents $C_{1-4}$alkyl substituted with one or where possible two or more substituents selected from $C_{1-4}$alkyloxy, hydroxy, halo, $Het^2$, $NR^7R^8$, $NR^9R^{10}$-carbonyl or $Het^3$-carbonyl, wherein $X^2$, $Ar^3$, $Ar^4$, $Het^{12}$, $Het^2$, $R^1$, $R^2$, $R^7$, $R^8$, $R^9$, $R^{10}$ and $Het^3$ are defined as for the compounds of formula (I)

Deprotection of the intermediates of formula (IV'-IV$^a$) as described in *Protective Groups in Organic Synthesis by T. W. Greene and P. G. M. Wuts*, 3$^{rd}$ edition, 1998 followed by ring closure under Mitsunobu conditions give the target compounds (I'-I'$^a$). (Scheme 2—wherein V and $R^{16}$ are defined as hereinbefore)

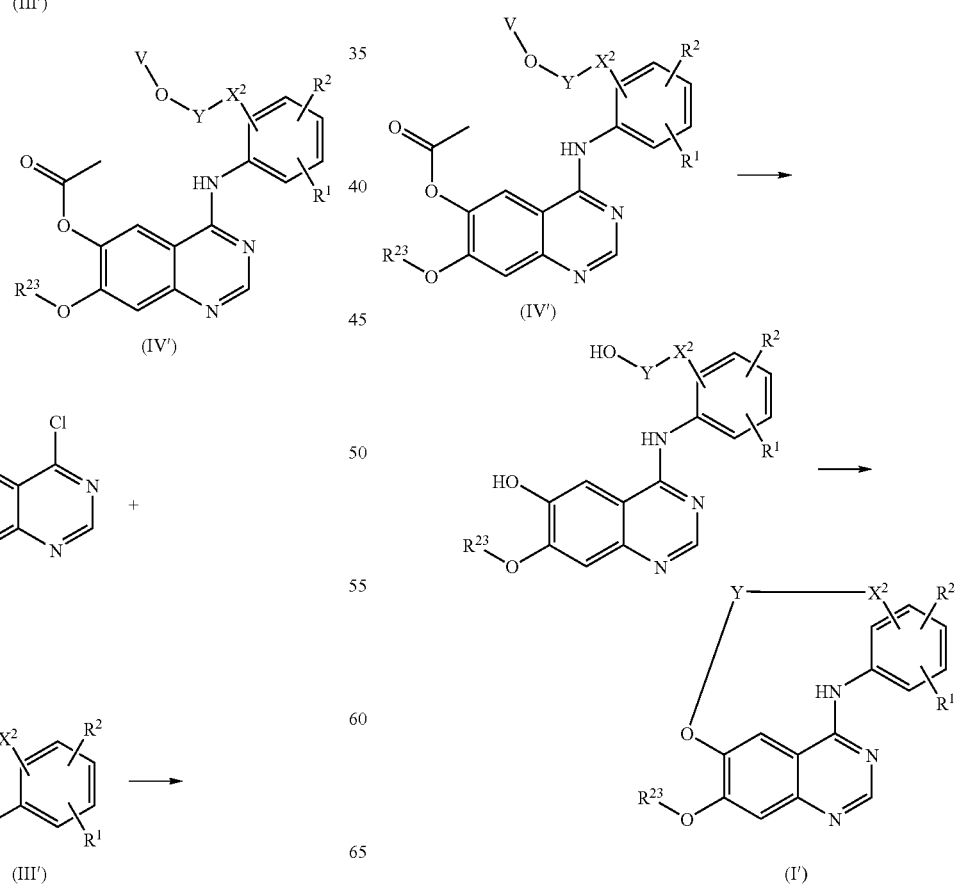

Scheme 3

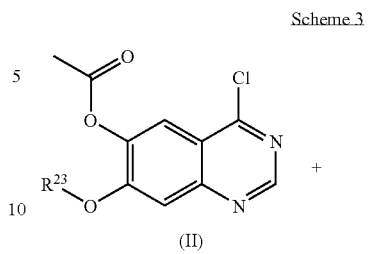

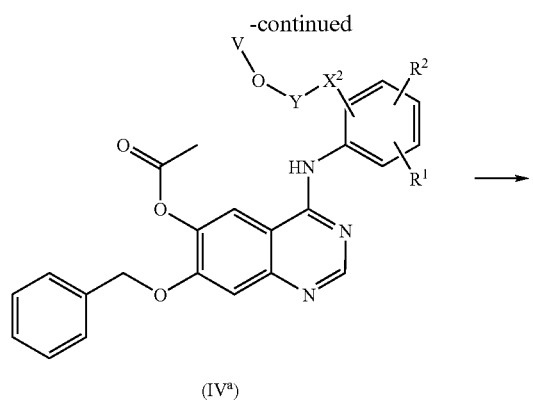

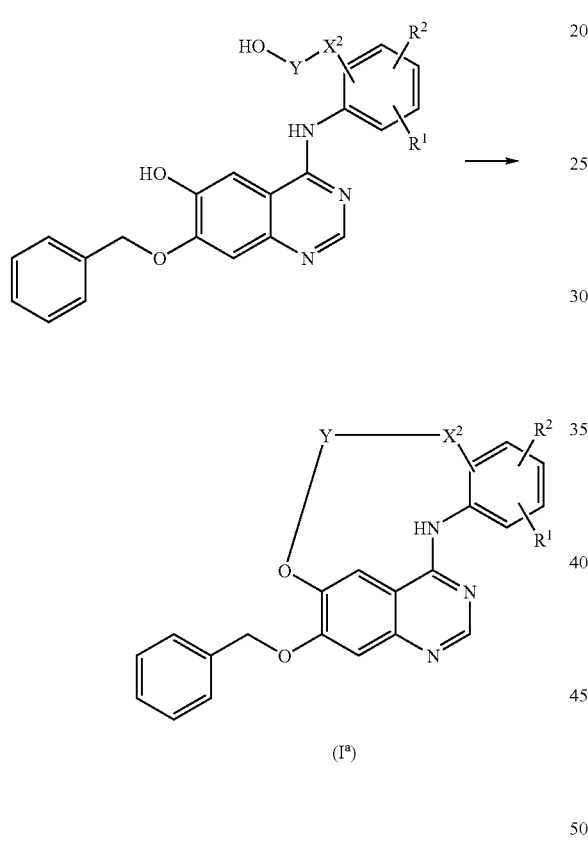

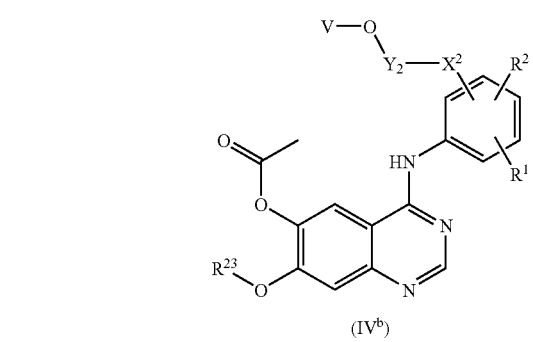

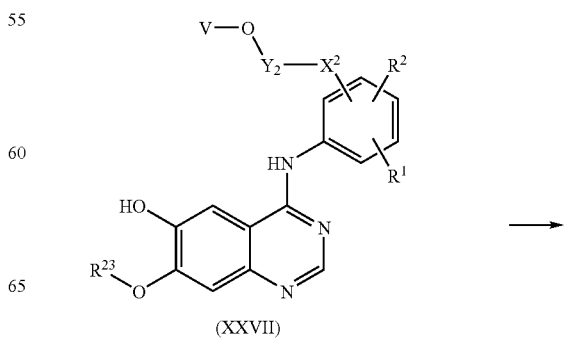

Alternatively, those compounds of formula (I'$^b$) wherein Y represents —$C_{1-5}$alkyl-$NR^{13}$—$C_{1-5}$alkyl-, —$C_{1-5}$alkyl-$NR^{14}$—CO—$C_{1-5}$alkyl-, —$C_{1-5}$alkyl-CO—$NR^{15}$—$C_{1-5}$alkyl-, —$C_{1-6}$alkyl-NH—$C_{1-6}$alkyl-CO—, —$C_{1-3}$alkyl-NH—CO-Het$^{20}$-, -Het$^{22}$-$CH_2$—CO—NH—$C_{1-3}$alkyl-, —$C_{1-2}$alkyl-NH—CO—$CR^{16}R^{17}$—NH—, —$C_{1-2}$alkyl-CO—NH—$CR^{18}R^{19}$—CO—, —$C_{1-2}$alkyl-CO—$NR^{20}$—$C_{1-3}$alkyl-CO—, —$C_{1-2}$alkyl-$NR^{21}$—$CH_2$—CO—NH—$C_{1-3}$alkyl- or —$NR^{22}$—CO—$C_{1-3}$alkyl-NH— are prepared using the following synthesis scheme. The intermediates of formula (IV$^b$) are obtained as described hereinbefore. Deprotection and subsequent formation of the corresponding ether using the appropriate aminated alcohol under standard conditions provides the intermediates of formula (XXVIII). Deprotection followed by ring closure provides the target compounds of formula (I'$^b$)

-continued

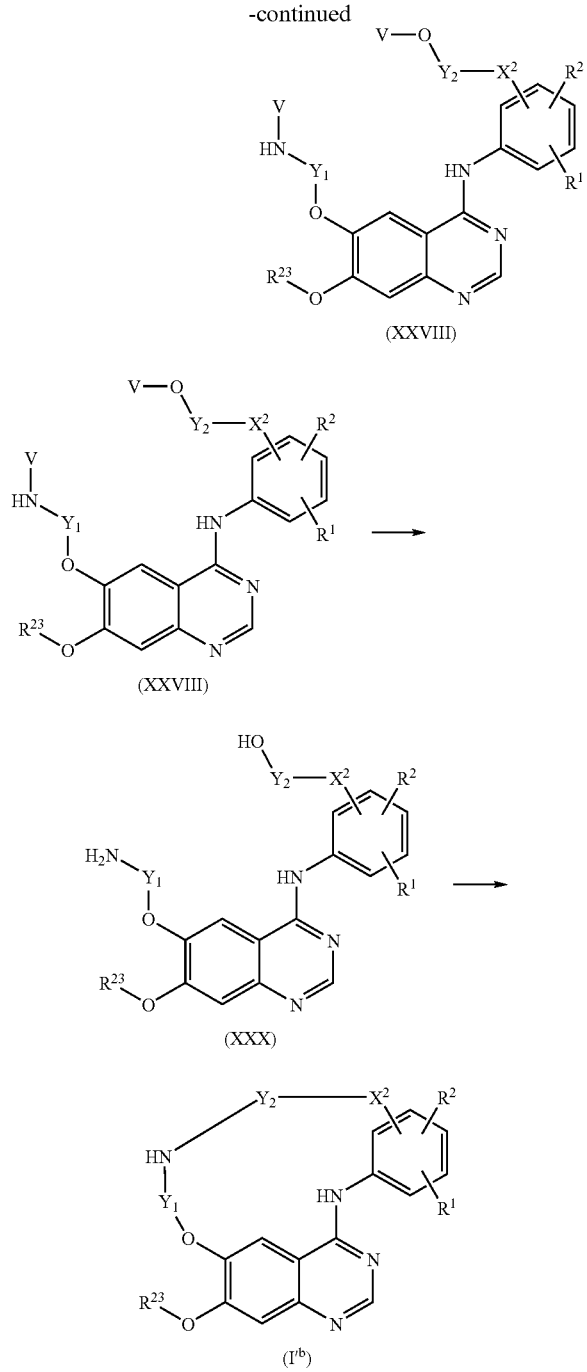

V = hydrogen or a protective group such as for example, methylcarbonyl, t-butyl, methyl, ethyl, benzyl or trialkylsilyl groups or in case of solid phase chemistry the resin to which the remainder of the molecule is attached
$R^{23}$ represents $Ar^3$, $Ar^4$—$C_{1-4}$alkyl, $C_{1-4}$alkyl, $C_{2-6}$ alkenyl optionally substituted with $Het^{12}$ or $R^{23}$ represents $C_{1-4}$alkyl substituted with one or where possible two or more substituents selected from $C_{1-4}$alkyloxy, hydroxy, halo, $Het^2$, $NR^7R^8$, $NR^9R^{10}$-carbonyl or $Het^3$-carbonyl, wherein $Ar^3$, $Ar^4$, $Het^{12}$, $Het^2$, $R^7$, $R^8$, $R^9$, and $Het^3$ are defined as for the compounds of formula (I)
$Y^1$ and $Y^2$ each independently represent a $C_{1-5}$alkyl, $C_{1-6}$alkyl, CO—$C_{1-6}$alkyl, CO—$C_{1-5}$alkyl, $Het^{22}$—$CH_2$—CO, CO—$CR^{16}R^{17}$—NH—, $CR^{18}R^{19}$—CO—, $CH_2$—CO—NH—$C_{1-3}$alkyl-, —$C_{1-2}$alkyl-$NR^{21}$-$CH_2$—CO— or CO—$C_{4-8}$alkyl-NH—

More specific examples for the synthesis of compounds of formula ($I'^b$) are provided in reaction schemes 9-12.

For those compounds where $X^2$ represents —O—, the suitable substituted anilines of formula ($III^a$) are generally prepared from the commercially available nitro-phenols (X) and the α, ω-protected halogenated alcohols (XI) under alkaline conditions in a reaction inert solvent, for example, using dimethylacetamide (DMA) in the presence of $K_2CO_3$. The resulting nitro-phenyl derivative (XII) is subsequently reduced according to standard conditions, for example, using iron/acetic acid, to yield the substituted anilines of formula ($III^a$) (Scheme 4).

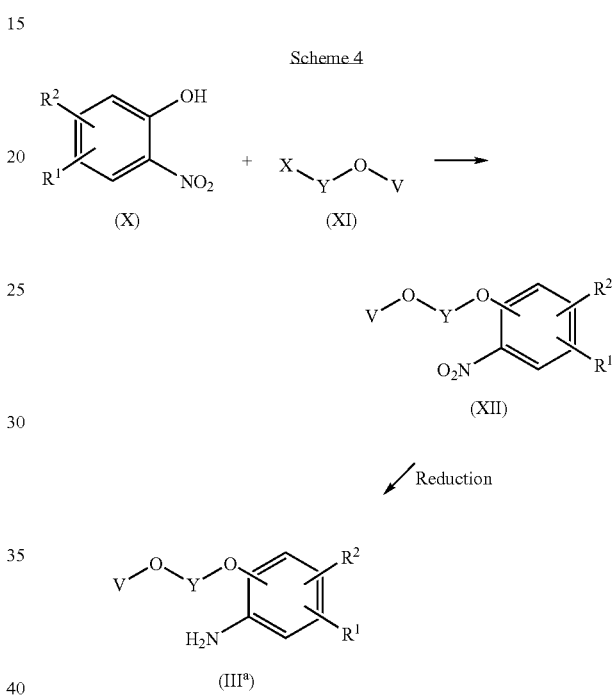

Scheme 4

X represents a halogen such as for example, Cl, Br, and I
V represents hydrogen or a protective group such as for example methylcarbonyl For those compounds where $X^2$ represents —$NR^{12}$—$C_{1-2}$ alkyl-, the suitable substituted anilines of formula ($III^b$) are generally prepared from the commercially available 2-nitrobenzaldehydes (XIII) and the amine substituted alcohols (XIV) by reductive amination under standard conditions, for example using $NaBH_4$ and titanium(iv)isopropoxide as reducing agents in ethanol as solvent, yielding in a first step the nitro-benzylamines of formula (XV).

Next the primary free alcohol is protected using art known procedures, for example, using an esterification reaction with acetic anhydride in the presence of pyridine.

The thus obtained intermediate of formula (XVI) is subsequently reduced according to standard conditions, for example, using hydrogenolysis ($H_2$, Pt/C, thiophene, MeOH) or tin(II)chloride ($SnCl_2.H_2O$, EtOH) to yield the substituted anilines of formula ($III^b$) (Scheme 5).

Scheme 5

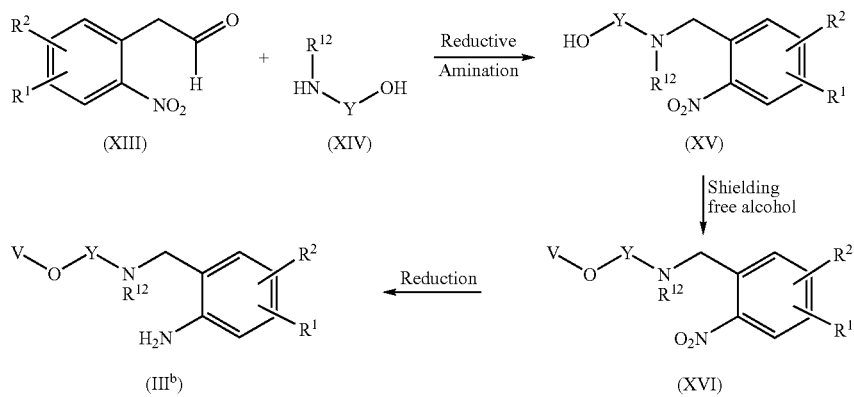

V represents a protective group such as for example methylcarbonyl

Using the aforementioned method in two alternative forms, 4-chloro-2-nitrobenzaldehyde has been converted in suitable substituted anilines of formula (III$^b$). In a first method (Scheme 5a) the suitable substituted anilines of formula (III$^b$) were obtained by reductive amination of 4-chloro-2-nitrobenzaldehyde with primary amino acids.

excess Boc anhydride. Finally, the solution 1 is evaporated to dryness (sublimation of tert-butyl carbamate is observed) and the resulting Boc-protected N-benzyl amino acid 4 is purified by HPLC. When R' is not equal to hydrogen, Boc-protected aniline 5 is observed as the major product. In this case method B can be employed to obtain the aniline of type 4 (vide infra).

Scheme 5a

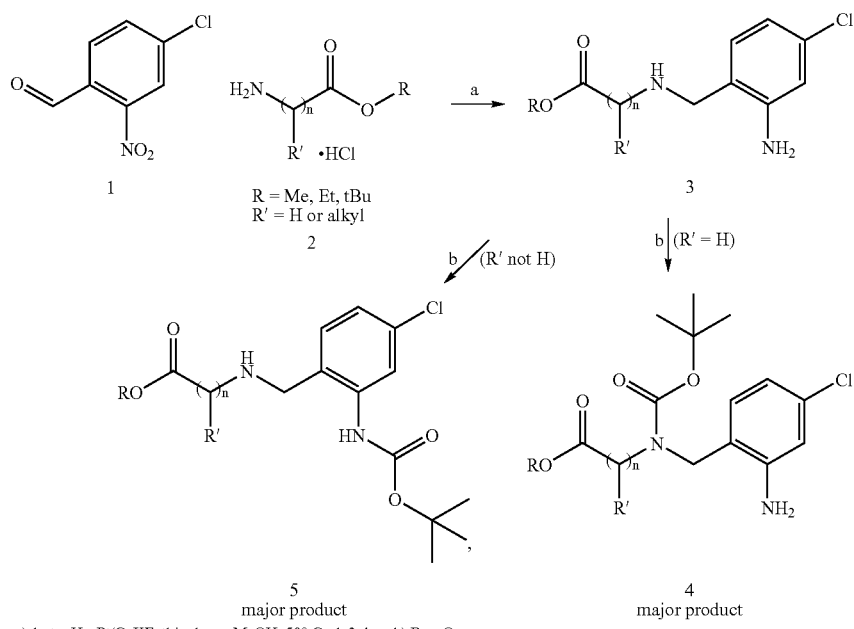

a) 1 atm H$_2$, Pt/C, KF, thiophene, MeOH, 50° C., 1-2 days b) Boc$_2$O, MeOH, RT, 1-3 h.

A methanolic solution of 10 mmol aldehyde 1, 20 mmol amino acid 2, 19 mmol KF, 1 mL 4% thiophene (in DIPE) and 1 g Pt/C (slurry in THF or MeOH) under 1 atm of hydrogen is stirred at 50° C. (scheme 5a). The reaction mixture is filtered after consumption of 4 equivalents of hydrogen (typically after 48 h) and 3 equivalents of Boc anhydride are added. Next, the solution is stirred for 1-3 h at room temperature (LCMS monitoring), then an excess of 6 N ammonia in MeOH is added, and stirring is continued for 1 h to work-up A second method to obtain the suitable substituted anilines of formula (III$^b$) has been the reductive amination of primary and secondary amino acids, amino acid hydrochlorides, N-methylallylamine and methylaminoacetaldehyde dimethyl acetal with 4-chloro-2-nitrobenzaldehyde 1 and 4-chloro-3-fluoro-2-nitrobenzaldehyde 6 (Scheme 5b). Overall yields vary between 13 and 100%.

To a solution (suspension) of 5 mmol amine 7, 5 mmol aldehyde 1 or 6 in 30 mL dichloromethane is added 5 mmol titanium(IV)tert-butoxide and 5 mmol DIPEA (when 7 is hydrochloride).[1] After stirring for 15 min, 12 mmol sodium triacetoxyborohydride is added and stirring is continued for 1-5 h (LCMS monitoring). Next, the reaction is worked up with 10-20 mL of a saturated $NaHCO_3$-solution and stirring is continued until bubbling stops. The resulting emulsion is filtered over a P3 sintered glass filter and washed with dichloromethane. The organic layer is separated and the aqueous phase extracted with dichloromethane. Drying of the combined organic layers with magnesium sulfate (or potassium carbonate), followed by filtration and evaporation of the solvent yields the crude N-benzylamine 8, which is usually pure enough to use for the next reaction step.

[1] With Ti(IV)isopropoxide, transesterification was observed once when 7 was an amino acid tBu ester. The reduction was unexpectedly exothermic in this case, and the heat may have caused this side reaction.

When R is hydrogen, the secondary amine can be protected with a Boc or Cbz, group by respectively adding three equivalents of Boc anhydride or benzyl chloroformate and three eq of DIPEA to a methylene chloride solution of the amine and stirring for 16-24 h at room temperature. When R' is bulky, Boc protection is generally slow and requires prolonged refluxing in methylene chloride. Next, excess protecting agent is worked up by adding 6 N ammonia in methanol and stirring for 1 h at room temperature. After evaporation of the solvent, the product is purified by RP HPLC.

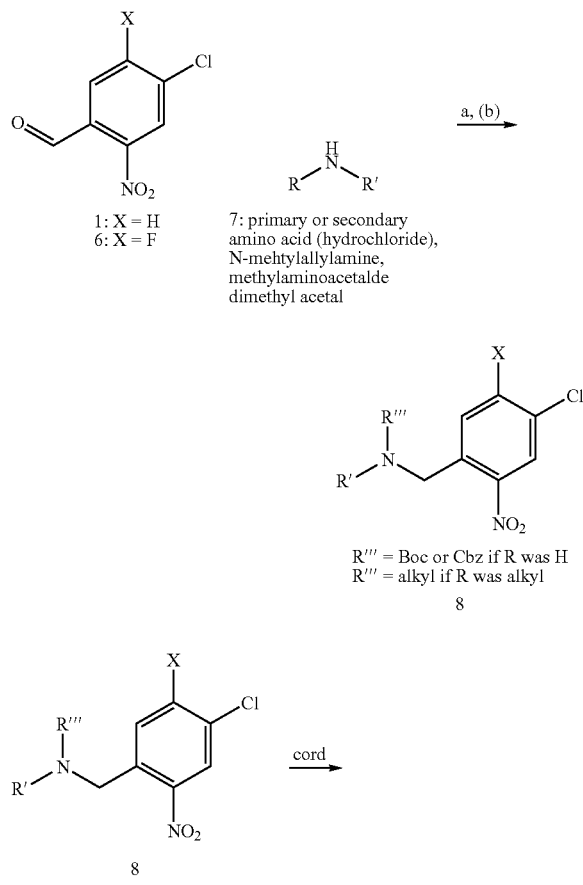

Scheme 5b.

1: X = H
6: X = F

7: primary or secondary amino acid (hydrochloride), N-mehtylallylamine, methylaminoacetaldedimethyl acetal R''' = Boc or Cbz if R was H
R''' = alkyl if R was alkyl

8

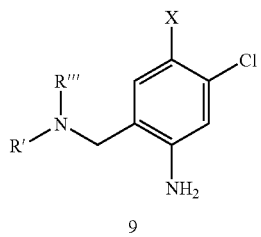

9 a) $NaBH(OAc)_3$, $Ti(OtBu)_4$, (DIPEA when 7 is hydrochloride), RT, 1–2 h b) $Boc_2O$ or CbzCl, DIPEA, $CH_2Cl_2$, RT to reflux, 16–24 h. c) $H_2$, Pt/C, thiophene, MeOH (or EtOAc or THF), 24–48 h d) $SnCl_2 \cdot H_2O$, EtOH, 50° C., 1.5 h.

The thus obtained benzylamine 8 is subsequently reduced either by hydrogenolysis or in case R' contains a double bond by reduction with tin(II)chloride Nitro Reduction by Hydrogenolysis The benzylamine 8 is dissolved in methanol (or ethyl acetate or THF) and, upon addition of 1 g Pt/C (slurry in EtOAc) and thiophene (1 mL 4% in DIPE), stirred under 1 atm hydrogen at 50° C. (scheme. 3, step a). After consumption of three equivalents of hydrogen, the mixture is filtered over dicalite. Removal of the solvent yields the crude aniline 9 which, depending on the nature and purity, can be crystallized from heptane, purified by HPLC or used as a crude in the next reaction step.

Nitro Reduction with tin(II)chloride

This method was used when R' contains a double bond and hence cannot be reduced hydrogenolytically.

To an ethanolic solution of crude nitro compound 8 is added 5 eq of tin(II)chloride dihydrate (scheme 3, step b). This mixture is stirred for 1.5 h at 50° C. Next, the solution is cooled to RT, and saturated sodium bicarbonate and methylene chloride are added (bubbling). The resulting emulsion is filtered over a P3 sintered glass filter. Separation of the organic layer, followed by drying on anhydrous potassium carbonate, filtering and removal of the solvent yields the crude aniline 9, which is usually pure enough to be used in the next reaction step.

For those compounds where $X^2$ represents —O—N=CH—, the suitable substituted anilines of formula ($III^c$) are generally prepared according to reaction scheme 6.

In a first step the known 2-nitro-benzaldehydes (X) are converted into the corresponding oxime (XVII) using, for example, the art known condensation reaction with hydroxylamine.

Next said oxime of formula XVII is allowed to react with an halogenated alkylacetate under alkaline conditions, for example using $K_2CO_3$ in DMSO, followed by reducing the nitro group, for example, with hydrogenolysis ($H_2$, Pt/C, thiophene, MeOH) or tin(II)chloride ($SnCl_2 \cdot H_2O$, EtOH), to provide the suitable substituted aniline of formula ($III^c$).

Scheme 6

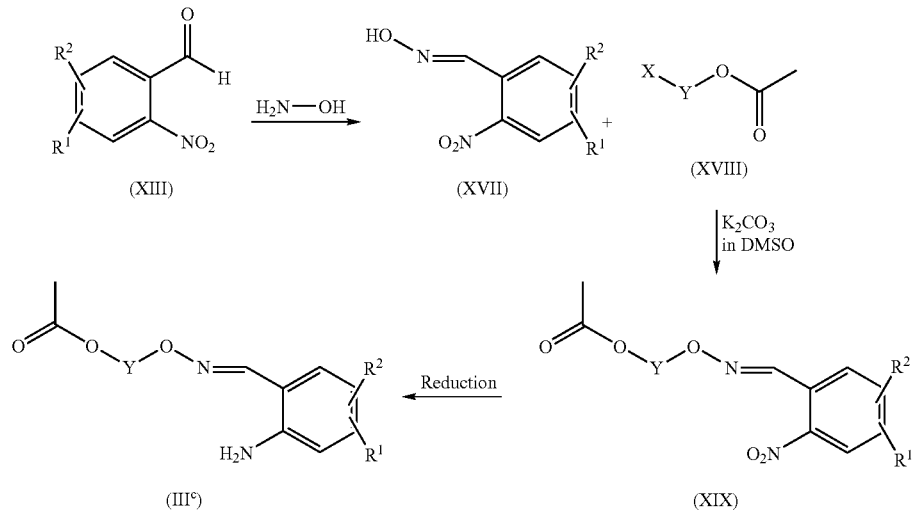

(III$^c$)
X represents a halogen such as for example Cl, Br, or I

For those compounds where $X^2$ represents a direct bond and Y represents $C_{1-6}$alkyl-NH—CO—, the suitable substituted anilines of formula (III$^d$) are generally prepared according to reaction scheme 7.

reduced according to standard conditions, for example, using hydrogenolysis ($H_2$, Pt/C, thiophene, MeOH) or tin(II)chloride ($SnCl_2.H_2O$, EtOH) to yield the substituted anilines of formula (III$^d$).

Scheme 7

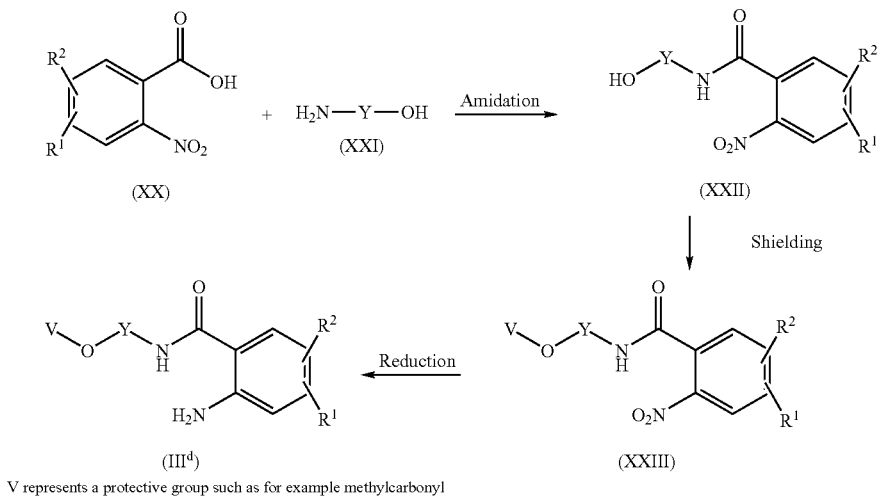

(III$^d$)
V represents a protective group such as for example methylcarbonyl

In a first step the known 2-nitro-benzoic acids (XX) are amidated to the intermediates of formula (XXII) under art known conditions, for example, using a hydroxylated amine of formula (XXI) that is added dropwise to a mixture of (XX) in $CH_2Cl_2$ in the presence of 1,1'carbonylbis-1H-imidazole.

Next the primary free alcohol is protected using art known procedures, for example, using an esterification reaction with acetic anhydride in the presence of pyridine. The thus obtained intermediate of formula (XXIII) is subsequently For those compounds where $X^2$ represents a direct bond the suitable substituted anilines of formula (III$^e$) are generally prepared according to reaction scheme 8. In a first step the known 2-nitro-benzaldehydes (XIII) are alkenated to the intermediates of formula (XXV) under art known conditions, for example, using the Wittig Reaction with the appropriate phosphonium salt of formula (XXIV). Following esterification of the free carboxylic acid under standard conditions for example, using ethanol under acidic conditions, the intermediate of formula (XXVI) are reduced to yield the desired substituted anilines of formula (III$^e$).

Scheme 8

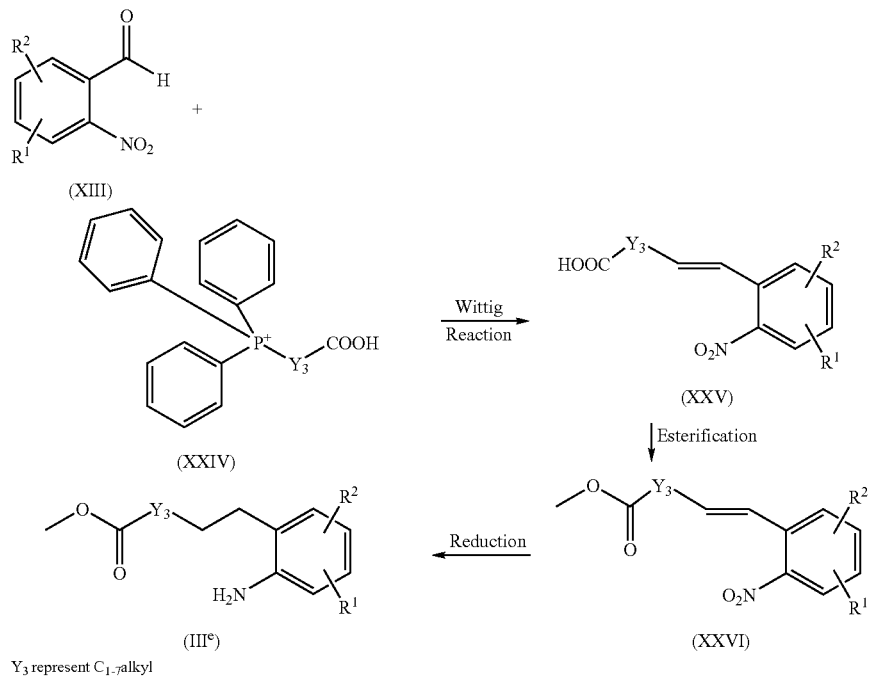

$Y_3$ represent $C_{1-7}$alkyl

Those compounds of formula ($I^b$) wherein —$X_1$—Y—$X_2$— comprises an amine-amide linker, i.e. —$X_1$—Y—$X_2$— represents —O—$C_{1-5}$alkyl-$NR^{14}$—CO—$C_{1-5}$alkyl-$NR^{12}$—$C_{1-2}$alkyl-, —O—$C_{1-3}$alkyl-NH—CO-$Het^{20}$-$C_{1-2}$alkyl- or —$C_{1-6}$alkyl-NH—CO—$CH_2$-$Het^{22}$-O—$C_{1-2}$alkyl-NH—CO—$CR^{16}R^{17}$—NH—$C_{1-2}$alkyl- were either prepared according to reaction scheme 9 in case m is 1, 2 or 4, or by reaction scheme 10 in case m is 3.

Scheme 9a.

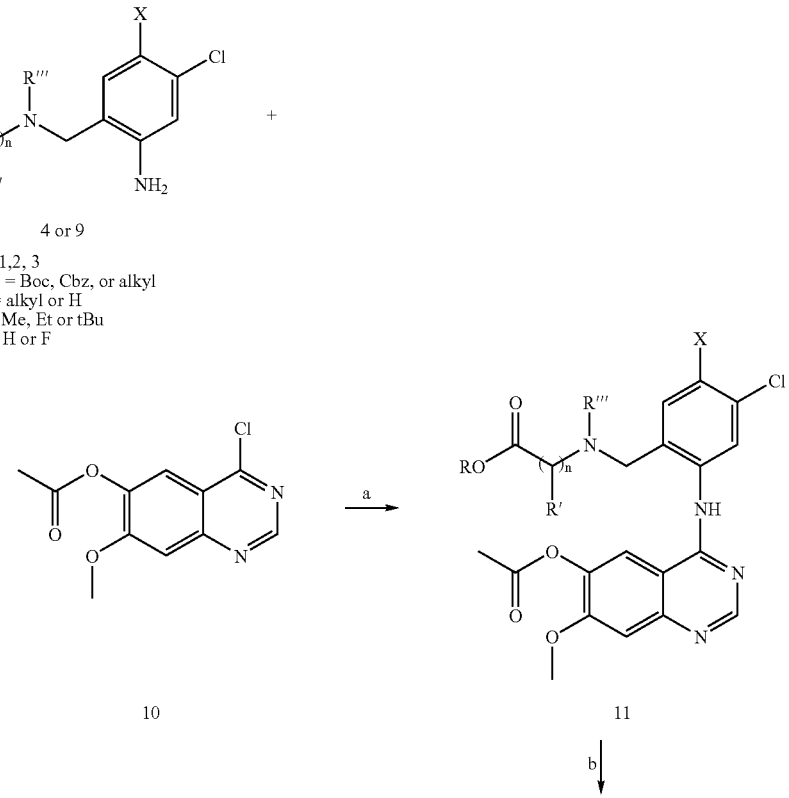

n = 1, 2, 3
R''' = Boc, Cbz, or alkyl
R' = alkyl or H
R = Me, Et or tBu
X = H or F

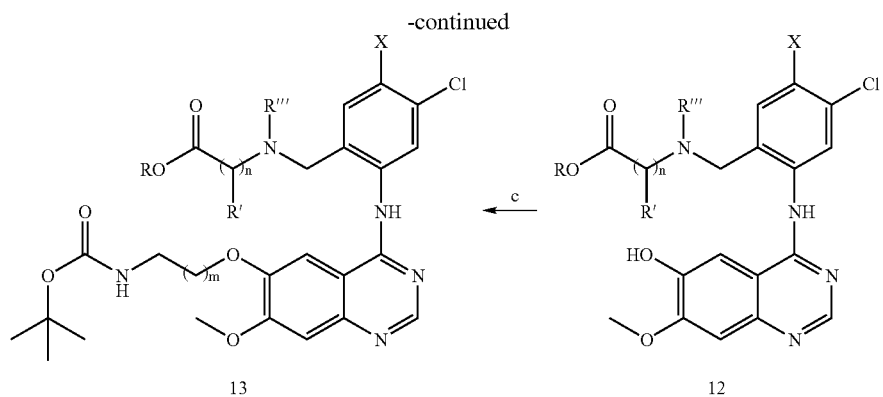

m = 1, 2, 4 a) iPrOH, 80° C., 2-24 h b) 6 N NH$_3$/MeOH, RT, 1 h c) Br(CH$_2$)$_m$CH$_2$NHBoc (m = 1, 2, 4), Cs$_2$CO$_3$, DMF, RT, overnight.

To a solution of N-benzyl amino acid 4 or 9 (See Scheme 5a and 5b) in isopropanol is added one equivalent of chloroquinazoline 10 (Scheme 9a). The resulting solution is stirred for 2-24 h at 80° C. to give 11 (LCMS monitoring). Next, the mixture is cooled to RT and a 6 N methanolic solution of ammonia is added. After stirring for one hour, the solution is evaporated to dryness. The crude phenol 12 is then redissolved in dry DMF and, upon addition of 5 equivalents of cesium carbonate, stirred for one h at RT. To the resulting phenolate is then added 1-1.2 eq (to prevent overalkylation) of Boc-aminoalkyl bromide, and the mixture is stirred overnight at RT, evaporated to dryness, redissolved in dichloromethane and filtered over dicalite to remove cesium salts. This yields the crude Boc-aminoalkylated phenols 13.

Scheme 9b.

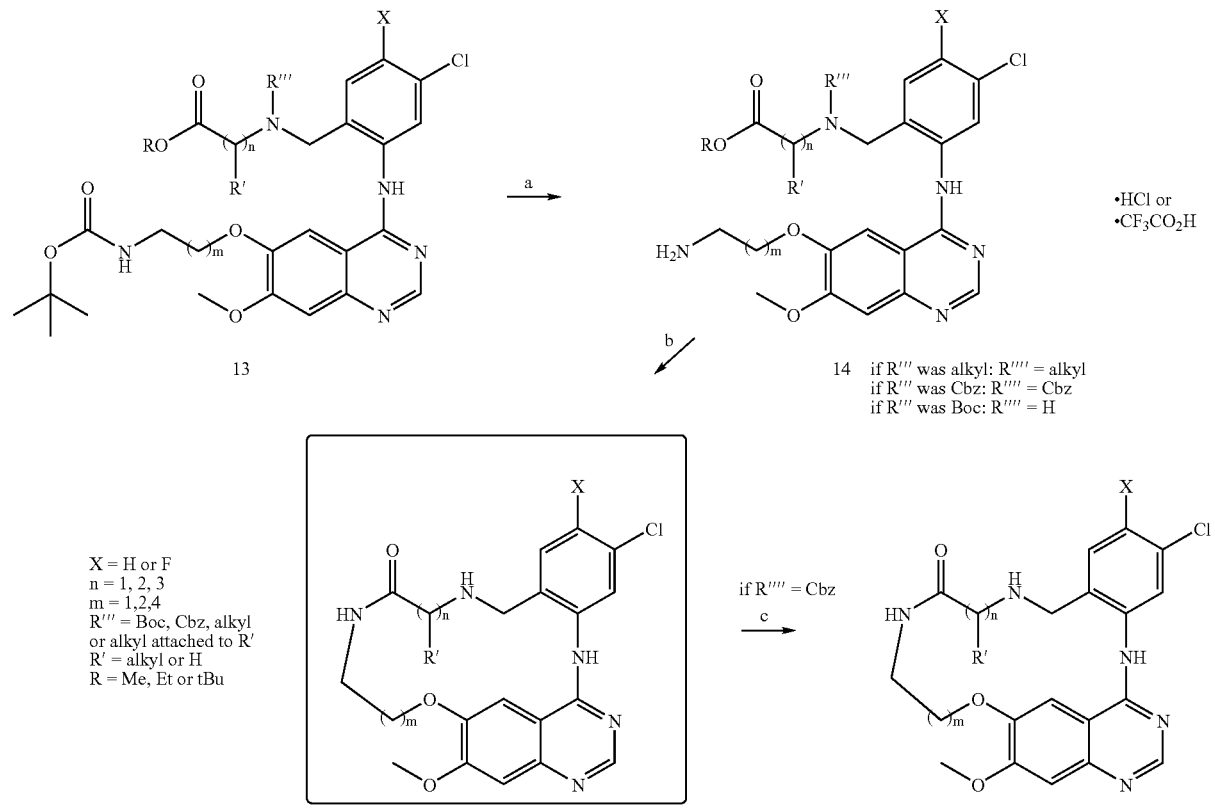

a) 6 N HCl, dioxane, 60° C., overnight (R = Me, Et), or TFA/CH$_2$Cl$_2$/TIS (90:8:2) (R = tBu) b) HBTU (or PyBop), DIPEA, DMF, RT, 1 h c) 8% HBr, RT, 1-2 h.

As shown in scheme 9b, the ester function is then hydrolyzed, and Boc group(s) removed, by stirring a dioxane solution of 13 overnight at 60° C. in the presence of 6 N HCl (R=Me, Et) or at RT in the presence of TFA/CH$_2$Cl$_2$MS (90:8:2) (R=tBu). After evaporation to dryness, the resulting amino acid 14 is redissolved in dry DMF and, upon addition of 6 eq of DIPEA, added dropwise to a solution of 3 eq HBTU (or PyBOP)[2] in dry DMF. Stirring this solution for 1 h at RT, followed by evaporation of the solvent yields the crude macrocycle 15a, which is purified by RP HPLC. A pre-purification can be done by dissolving the residue in CH$_2$Cl$_2$ and washing it with saturated sodium bicarbonate in water, followed by drying on potassium carbonate and removal of the solvent. The yield for this sequence is 10-65% starting from the aniline 4 or 9.

[2] PyBop generates tris(pyrrolidino)phosphinoxide, which is often difficult to separate from the macrocycle. HBTU generates tetramethylurea, which is more easy to remove.

A Cbz group, if present, can be removed prior purification by dissolving the crude macrocycle 15a (R''''=Cbz) in 48% aqueous HBr and stirring for 1-2 h at room temperature (RT). After concentration of the reaction mixture and quenching with solid potassium carbonate, the deprotected macrocycle 15b is obtained by extraction with CH$_2$Cl$_2$ (with added methanol in case of solubility problems), and is similarly purified by RP HPLC. The yield for Cbz deprotection is quantitative by LCMS.

To a solution of N-benzyl amino acid 4 or 9 in isopropanol is added one equivalent of chloroquinazoline 10 (scheme 10a). The resulting solution is stirred for 2-24 h at 80° C. to give 11. Next, the mixture is cooled to RT and a 6 N methanolic solution of ammonia is added. After stirring for one hour, the solution is evaporated to dryness. The crude phenol 12 is then redissolved in dry DMF and, upon addition of 5 equivalents of cesium carbonate, stirred for one hour at RT. To the resulting phenolate is then added 0.8 eq (to prevent overalkylation) of 4-bromobutyronitrile, and the mixture is stirred overnight at RT, evaporated to dryness, redissolved in dichloromethane and filtered over dicalite to remove cesium salts.

Scheme 10a.

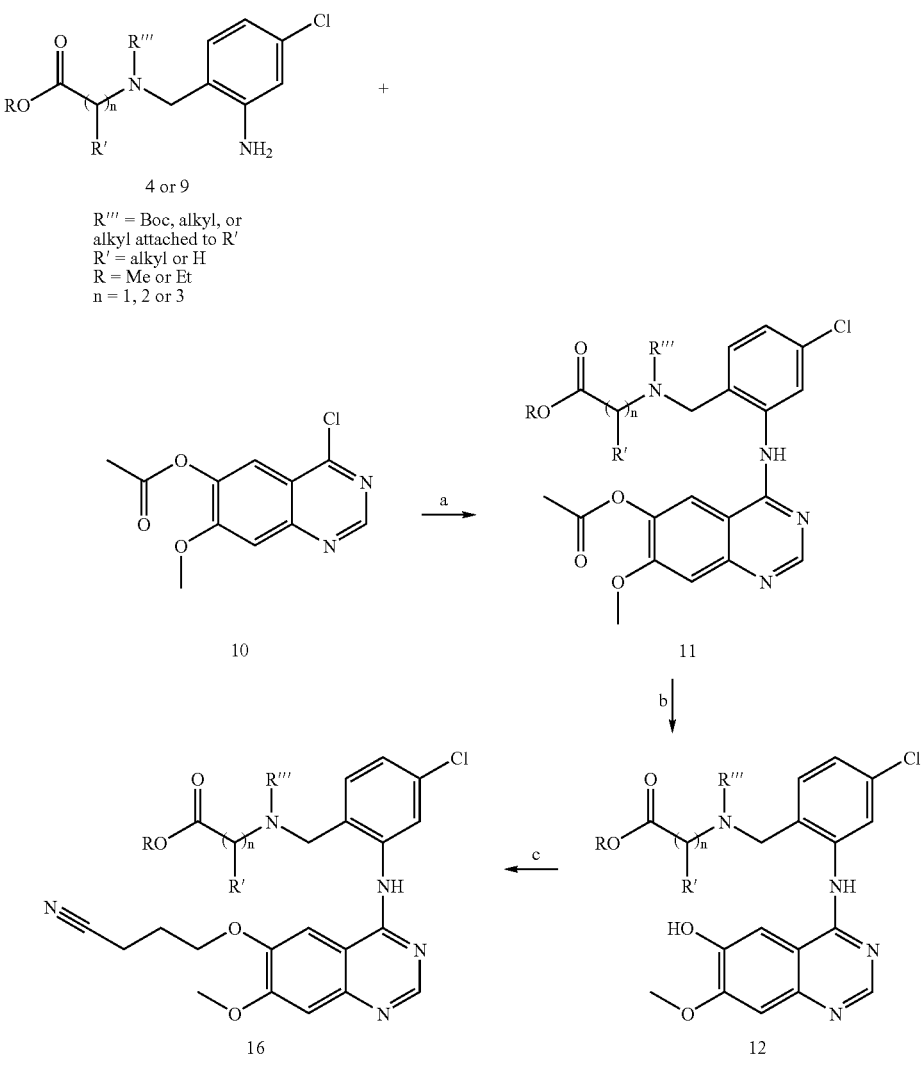

a) iPrOH, 80° C., 2-24 h b) 6 N NH$_3$/MeOH, RT, 1 h c) Br(CH$_2$)$_3$CN, Cs$_2$CO$_3$, DMF, RT, overnight Crude 16 is then thoroughly dried, redissolved in 6 N ammonia/MeOH (to prevent dimerisation) and, after addition of some thiophene solution in DIPE (to prevent dechlorination), treated with wet Raney nickel under 1 atm hydrogen pressure at 14° C. (scheme 10b). After consumption of 2 equivalents of hydrogen gas (typically after 16-24 h), the mixture is filtered over dicalite and concentrated to provide the crude amine 17. The ester function is then hydrolyzed to 18 (and, if R'''=Boc, the Boc group removed) by stirring a dioxane solution of 17 overnight in the presence of 6 N HCl (R=Me, Et). After evaporation to dryness, the resulting amino acid 18 is redissolved in dry DMF and, upon addition of 6 eq of DIPEA, added dropwise to a solution of 3 eq HBTU (or PyBOP) in dry DMF. Stirring this solution for 1 h at RT, followed by evaporation of the solvent yields the crude macrocycle 19, which is purified by RP HPLC. A pre-purification can be done by dissolving the residue in $CH_2Cl_2$ and washing it with saturated sodium bicarbonate in water. The yield for this sequence is 4-30% starting from the aniline 4 or 9.

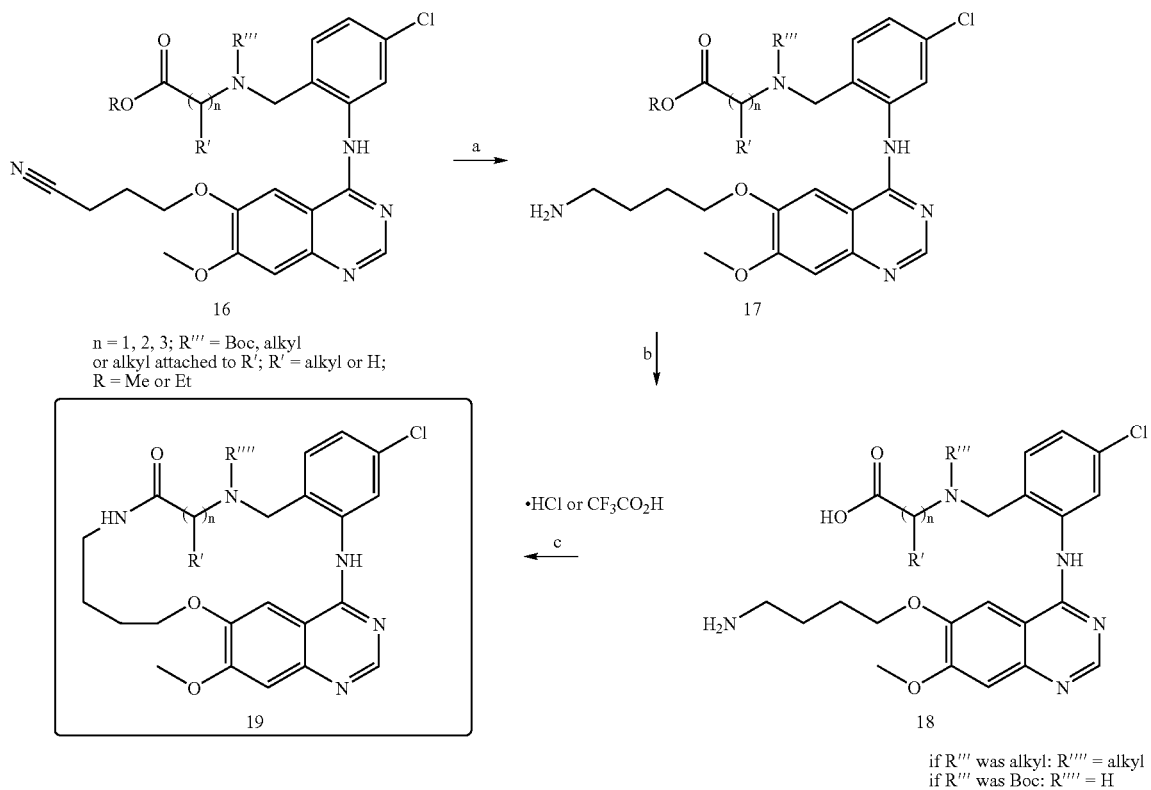

Those compounds of formula ($I'^b$) wherein —$X_1$—Y—$X_2$— comprises an amine-amine linker, i.e. —$X_1$—Y—$X_2$— represents —O—$C_{1-5}$alkyl-$NR^{13}$—$C_{1-5}$alkyl-$NR^{12}$—$C_{1-2}$alkyl- were generally prepared according to reaction scheme 11.

Scheme 11.

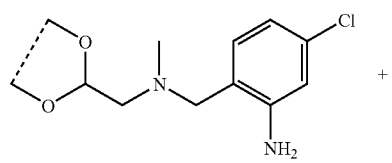

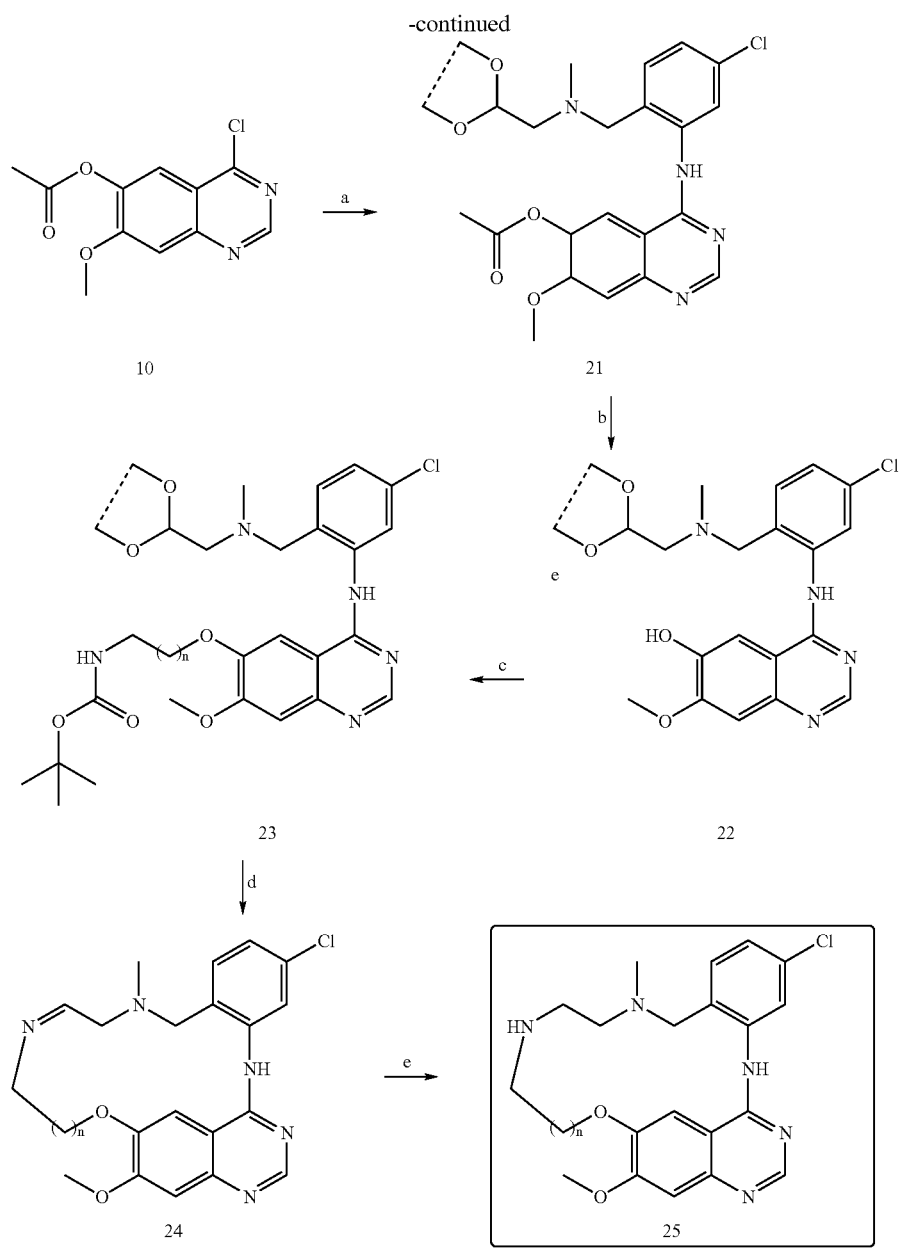

n = 1, 2, 4
(for n = 3, the butyronitrile
can give the desired amine)
a) iPrOH, 80° C., 7-8 h b) NH$_3$/MeOH, 1 h c) BrCH$_2$(CH$_2$)$_n$NHBoc (n = 1, 2, 4),* Cs$_2$CO$_3$, DMF, overnight. *Br(CH$_2$)$_3$CN used instead of n = 3
d) 6 N HCl, dioxane, 60° C., 24 h e) NaBH(OAc)$_3$, CH$_2$Cl$_2$, RT, 1 h.

To a solution of 5-chloro-2-{[2,2-dimethoxyethyl)(methyl)amino]methyl}aniline 20 or the corresponding dioxolane (prepared via reductive amination Scheme 5b) in isopropanol is added one equivalent of chloroquinazoline 10. The resulting solution is stirred for 7-8 h at 80° C. to give 21. Next, the mixture is cooled to RT and a 6 N methanolic solution of ammonia is added to remove the acetyl group. After stirring for one hour, the solution is evaporated to dryness. To the crude phenol 22 is then added 5 eq of cesium carbonate and, after stirring for 1 h, Boc-aminoalkyl bromide (1.0-1.2 eq) or 5-bromobutyronitrile (0.8 eq), and the mixture is subsequently stirred overnight at RT evaporated to dryness, redissolved in dichloromethane and filtered over dicalite to remove cesium salts. This yields the protected aminoalkyl-substituted phenols 23. The butyronitrile-substituted phenol is first hydrogenated to the corresponding amine under the abovementioned conditions.

Next the compounds are dissolved in 6 N HCl and dioxane, and the resulting mixture is stirred for about 24 h at 60° C. (LCMS monitoring, formation of imine 24 is observed) (scheme 11). After completion of the reaction, the mixture is poured carefully into an ice-cooled sodium bicarbonate solution or evaporated to dryness (slow, leads to decomposition). In the first case, the imine is extracted with methylene chloride and, after drying on potassium carbonate, immediately reduced to the corresponding amine by addition of sodium-triacetoxyborohydride. In the latter case, the oily residue is redissolved in methylene chloride and excess sodium triacetoxyborohydride is added to yield the corresponding amine. The crude macrocycle 25 is obtained after addition of saturated sodium carbonate, extraction with dichloromethane followed by drying on potassium carbonate and removal of the solvent, and can be purified RP HPLC.

Those compounds of formula (I$^{tb}$) wherein —X$_1$—Y—X$_2$— comprises an amide-amide linker, i.e. —X$_1$—Y—X$_2$— represents —O—C$_{1-4}$alkyl-CO—NH—CR$^{15}$R$^{19}$—CO—R$^{12}$—C$_{1-2}$alkyl-, —O—C$_{1-4}$alkyl-CO—NR$^{20}$—C$_{1-3}$alkyl-CO—NR$^{12}$—C$_{1-2}$alkyl-, or O—C$_{1-4}$alkyl-CO-Het$^{20}$-CO—NR$^{12}$—C$_{1-2}$alkyl- were generally prepared according to reaction scheme 12.

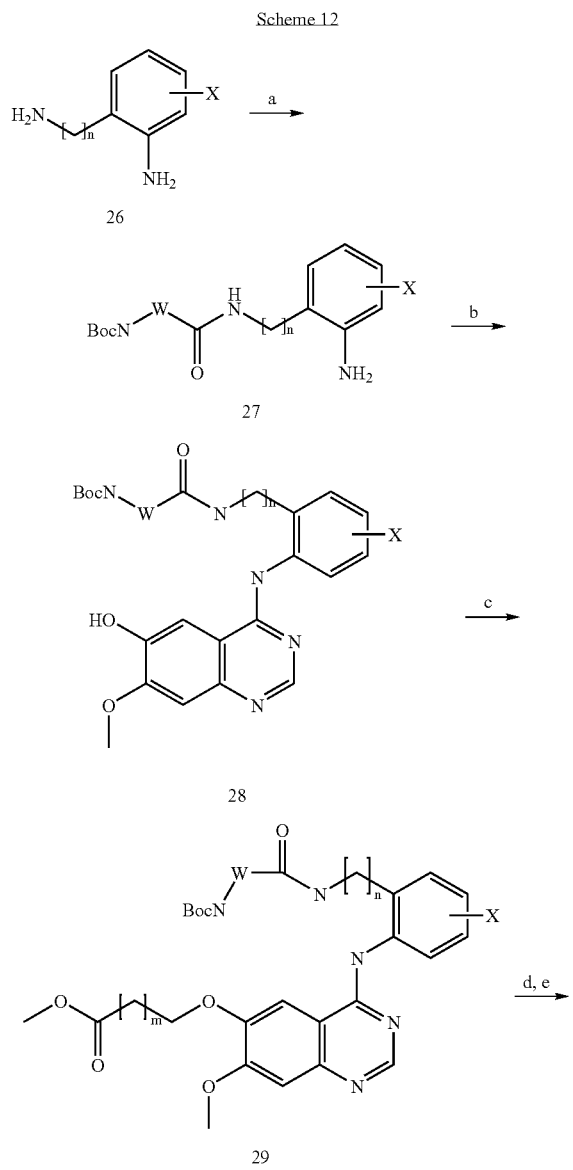

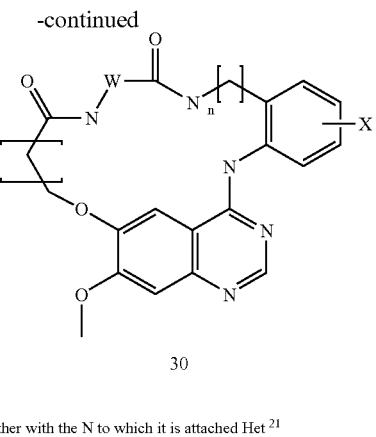

n = 1, 2
m = 0,2,3
w = C$_{1-3}$alkyl, CR$^{18}$R$^{19}$ or together with the N to which it is attached Het$^{21}$ Reagents and conditions: a) i) PL-DCC Resin, HOBt, DCM/DMF, RT, 5 h; ii) Polystyrene-methylisocyanate, (polystyrylmethyl)trimethylammonium bicarbonate, RT, 12 h; b) i) chloro quinazoline, iPrOH, 55° C., 3 h; ii) 7N NH$_3$ in MeOH, rt, 2 h; c) ClCH$_2$(CH$_2$)$_m$CO$_2$CH$_3$, K$_2$CO$_3$; d) conc. HCl, H$_2$O, dioxane, 60° C., 12 h; e) PyBOP, DIPEA, DMF, RT, 3 h.

In this procedure the aniline 26 is coupled with the appropriate amino protected amino acid, to form the amide of formula 27 using art known conditions, see for example A42 d) hereinbelow. Subsequent coupling with the chloroquinazoline under standard conditions, for example stirred in propanol at an elevated temperature ranging form 40-100° C. during 3-12 h, provides the intermediates of formula 28. Alkylation with the appropriate haloacetate followed by deprotection and ring closure, i.e. amide formation using art known conditions, provides the compounds of formula 30. Deprotection of the intermediates of formula 28 can be done as described in *Protective Groups in Organic Synthesis by T. W. Greene and P. G. M. Wuts*, 3$^{rd}$ edition, 1998.

Alternatively, the compounds of formula (I) are prepared by ring closing metathesis of the corresponding olefins (Scheme 13). This reaction is particular useful for those compounds of formula (I) wherein Y represents —C$_{3-9}$alkenyl-, —C$_{3-9}$alkyl-, —C$_{3-7}$alkyl-CO—NH— optionally substituted with amino, mono- or di(C$_{1-4}$alkyl)amino or C$_{1-4}$alkyloxycarbonylamino-, or Y represents —C$_{3-7}$alkenyl-CO—NH— optionally substituted with amino, mono- or di(C$_{1-4}$alkyl) amino or C$_{1-4}$alkyloxycarbonylamino-hereinafter referred to as the compounds of formula (I$^{tc}$).

In a first step the aniline of formula (III$^c$) is coupled to the 4-chloroquinazoline (II$^b$) under standard conditions, for example stirred in propanol art an elevated temperature ranging from 40-100° C. during 3-12 h. Deprotection of the intermediate of formula (IV$^c$) as described in *Protective Groups in Organic Synthesis by T. W. Greene and P. G. M. Wuts*, 3$^{rd}$ edition, 1998, followed by alkylation with the appropriate alkyl bromides (XXXII) under art known conditions, such as for example stirring overnight at room temperature in the presence of —Cs$_2$CO$_3$ in a reaction inert solvent such as for example N,N-dimethylformamide (DMF), provides the olefins of formula (XXXIII). Ring closing metathesis as described in *Advanced Organic Chemistry by J. March*, 3$^{rd}$ edition, 1985, p 1036-1039 provides the compounds of formula (I$^{tc}$) that can optionally be reduced using art known procedures, for example, stirring for 3-10 h at room temperature under H$_2$-atmosphere in the presence of Pt/C in tetrahydrofuran (THF)/methanol as solvent. The aniline of formula (III$^e$) is synthesized similar to the synthesis of the amide of formula 27 (Scheme 12 above) by acylation of the corresponding amine.

Scheme 13

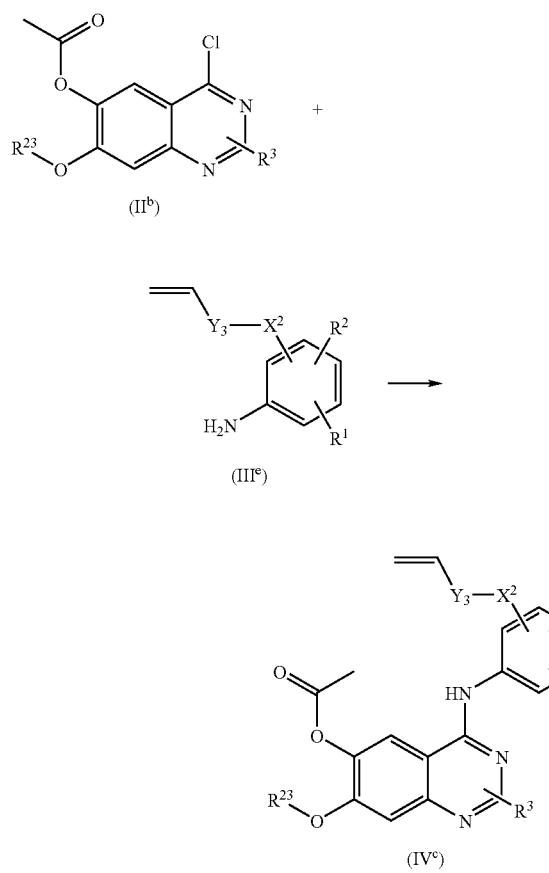

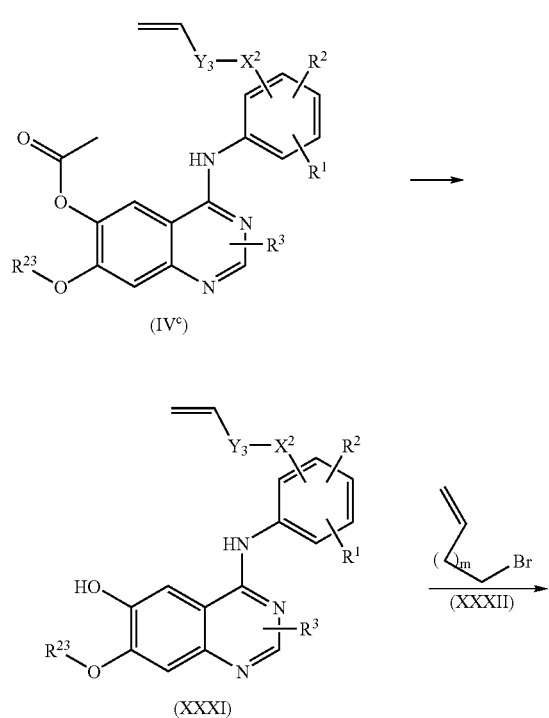

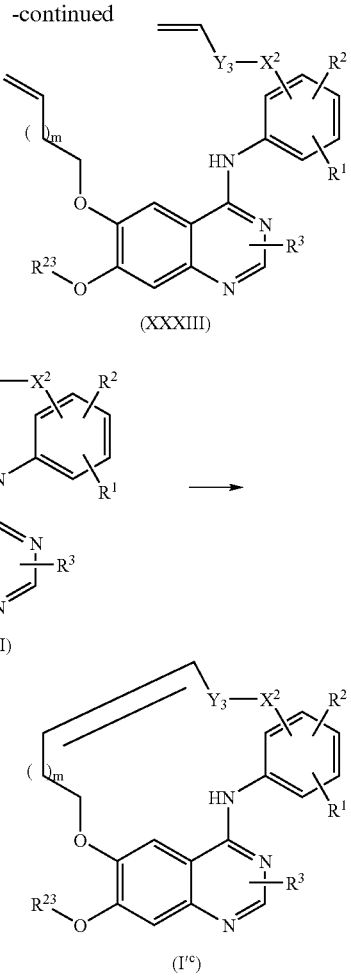

$R^{23}$ represents $Ar^3$, $Ar^4$-$C_{1-4}$alkyl, $C_{1-4}$alkyl, $C_{2-6}$alkenyl optionally substituted with $Het^{12}$ or $R^{23}$ represents $C_{1-4}$alkyl substituted with one or where possible two or more substituents selected from $C_{1-4}$alkyloxy, hydroxy,halo, $Het^2$, $NR^7R^8$, $NR^9R^{10}$-carbonyl or $Het^3$-carbonyl,
wherein $Ar^3$, $Ar^4$, $Het^{12}$, $Het^2$, $R^7$, $R^8$, $R^8$, $R^9$, $X^2$, $R^1$, $R^2$, $R^3$ and $Het^3$ are defined as for the compounds of formula (I)
$Y_3$ represent a $C_{1-5}$alkyl, CO—$C_{1-5}$alkyl or CO—$CR^{16}R^{17}$—NH— or $C_{1-5}$alkyl-CO— optionally substituted with amino, mono- or di($C_{1-4}$alkyl) amino or $C_{1-4}$alkyloxycarbonylamino m represents 1, 2, 3 or 4

Where necessary or desired, any one or more of the following further steps in any order may be performed:

(i) removing any remaining protecting group(s);

(ii) converting a compound of formula (I) or a protected form thereof into a further compound of formula (I) or a protected form thereof;

(iii) converting a compound of formula (I) or a protected form thereof into a N-oxide, a salt, a quaternary amine or a solvate of a compound of formula (I) or a protected form thereof;

(iv) converting a N-oxide, a salt, a quaternary amine or a solvate of a compound of formula (I) or a protected form thereof into a compound of formula (I) or as protected form thereof;

(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;

(vi) where the compound of formula (I) is obtained as a mixture of (R) and (S) enantiomers resolving the mixture to obtain the desired enantiomer.

Compounds of formula (I), N-oxides, addition salts, quaternary amines and stereochemical isomeric forms thereof can be converted into further compounds according to the invention using procedures known in the art.

It will be appreciated by those skilled in the art that in the processes described above the functional groups of intermediate compounds may need to be blocked by protecting groups.

Functional groups, which it is desirable to protect, include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$ alkyl or benzyl esters.

The protection and deprotection of functional groups may take place before or after a reaction step.

Additionally, the N-atoms in compounds of formula (I) can be methylated by art-known methods using $CH_3$—I in a suitable solvent such as, for example 2-propanone, tetrahydrofuran or dimethylformamide.

The compounds of formula (I) can also be converted into each other following art-known procedures of functional group transformation of which some examples are mentioned hereinafter.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earl alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures. However, in the synthesis of the compounds of formula (I), the present invention further provides;

a) the intermediates of formula (III)

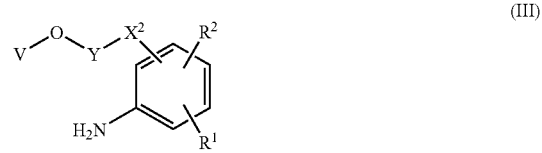

(III)

the pharmaceutically acceptable addition salts and the stereochemically isomeric forms thereof, wherein V represents hydrogen or a protective group preferably selected from the group consisting of methylcarbonyl, t-butyl, methyl, ethyl, benzyl or trialkylsilyl;

Y represents —$C_{3-9}$alkyl-, —$C_{3-9}$alkenyl-, —$C_{3-7}$alkyl-CO—NH— optionally substituted with amino, mono- or di($C_{1-4}$alkyl)amino or $C_{1-4}$alkyloxycarbonylamino-, —$C_{3-7}$alkenyl-CO—NH— optionally substituted with amino, mono- or di($C_{1-4}$alkyl)amino or $C_{1-4}$alkyloxycarbonylamino-, —$C_{1-5}$alkyl-oxy-$C_{1-5}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-5}$alkyl-CO—$NR^{15}$—$C_{1-5}$alkyl-, —$C_{1-6}$alkyl-CO—NH—, —$C_{1-6}$alkyl-NH—CO—, —$C_{1-3}$alkyl-NH—CS-$Het^{20}$-$C_{1-3}$alkyl-NH—CO-$Het^{20}$-, $C_{1-2}$alkyl-CO-$Het^{21}$-CO—, -$Het^{22}$—$CH_2$—CO—NH—$C_{1-3}$alkyl-, —CO—NH—$C_{1-6}$alkyl-, —NH—CO—$C_{1-6}$alkyl-, —CO—$C_{1-7}$alkyl-, —$C_{1-7}$alkyl-CO—, —$C_{1-6}$alkyl-CO—$C_{1-6}$alkyl-, —CO-$Het^{20}$, —$C_{1-2}$alkyl-NH—CO—$CR^{16}R^{17}$—NH—, —$C_{1-2}$alkyl-CO—NH—$CR^{18}R^{19}$—CO—, —$C_{1-2}$alkyl-CO—$NR^{20}$—$C_{1-3}$alkyl-CO—, —$C_{1-2}$alkyl-$NR^{21}$—$CH_2$—CO—NH—$C_{1-3}$alkyl-, or —$NR^{22}$—CO—$C_{1-3}$alkyl-NH—;

$X^2$ represents a direct bond, O, —O—$C_{1-2}$alkyl-, CO, —CO—$C_{1-2}$alkyl-, $NR^{12}$, —$NR^{12}$—$C_{1-2}$alkyl-, $CH_2$—, —O—N=CH— or —$C_{1-2}$alkyl-;

$R^1$ represents hydrogen, cyano, halo, hydroxy, formyl, $C_{1-6}$alkoxy-, $C_{1-6}$alkyl-, halo-phenyl-carbonylamino-, $C_{1-6}$alkoxy- substituted with halo, $C_{1-4}$alkyl substituted with one or where possible two or more substituents selected from hydroxy or halo;

$R^2$ represents hydrogen, cyano, halo, hydroxy, hydroxycarbonyl-, $Het^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, $Het^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, $Ar^5$, $Ar^4$-oxy-, dihydroxyborane, $C_{1-6}$alkoxy- substituted with halo, $C_{1-4}$alkyl substituted with one or where possible two or more substituents selected from halo, hydroxy or $NR^5R^6$, $C_{1-4}$alkylcarbonyl- wherein said $C_{1-4}$alkyl is optionally substituted with one or where possible two or more substituents selected from hydroxy or $C_{1-4}$alkyl-oxy-;

$R^5$ and $R^6$ are each independently selected from hydrogen or $C_{1-4}$alkyl;

$R^{12}$ represents hydrogen, $C_{1-4}$alkyl, $C_{1-4}$alkyl-oxy-carbonyl-, $Het^{18}$-$C_{1-4}$alkyl-, phenyl-$C_{1-4}$alkyl-oxy-carbonyl-, $Het^{17}$, $C_{2-4}$alkenylcarbonyl- optionally substituted with $Het^{19}$-$C_{1-4}$alkylaminocarbonyl-, $C_{2-4}$alkenylsulfonyl-, $C_{1-4}$alkyloxy$C_{1-4}$alkyl- or $R^{12}$ represents phenyl optionally substituted with one or where possible two or more substituents selected from hydrogen, hydroxy, amino or $C_{1-4}$alkyloxy-;

$R^{13}$ represents hydrogen, $C_{1-4}$alkyl, $Het^{13}$, $Het^{14}$-$C_{1-4}$alkyl- or phenyl optionally substituted with one or where possible two or more substituents selected from hydrogen, hydroxy, amino or $C_{1-4}$alkyloxy-;

$R^{14}$ and $R^{15}$ are each independently selected from hydrogen, $C_{1-4}$alkyl, $Het^{15}$-$C_{1-4}$alkyl- or $C_{1-4}$alkyloxy$C_{1-4}$alkyl-;

$R^{16}$ and $R^{17}$ each independently represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino;

$R^{18}$ and $R^{19}$ each independently represents hydrogen or $C_{1-4}$alkyl optionally substituted with phenyl, indolyl, methylsulfide, hydroxy, thiol, hydroxyphenyl, aminocarbonyl, hydroxycarbonyl, mine, imidazoyl or guanidino;

$R^{20}$ and $R^{22}$ each independently represents hydrogen or $C_{1-4}$alkyl optionally substituted with hydroxy or $C_{1-4}$alkyloxy;

$R^{21}$ represents hydrogen, $C_{1-4}$alkyl, $Het^{23}$-$C_{1-4}$alkylcarbonyl- or $R^{21}$ represents mono- or -di($C_{1-4}$alkyl)amino-$C_{1-4}$ alkylcarbonyl- optionally substituted with hydroxy, pyrimidinyl, dimethylamine or $C_{1-4}$alkyloxy;

$Het^1$ represents a heterocycle selected from piperidinyl, morpholinyl, piperazinyl, furanyl, pyrazolyl, dioxolanyl, oxazolyl, imidazolyl, isoxazolyl, oxadiazolyl, pyridinyl or pyrrolidinyl wherein said $Het^1$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^{13}$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{14}$ represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy alkyloxy$C_{1-4}$alkyl or polyhydroxy-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Het^{17}$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{20}$, $Het^{21}$ and $Het^{22}$ each independently represent a heterocycle selected from pyrrolidinyl, 2-pyrrolidinonyl, piperazinyl or -piperidinyl optionally substituted with one or where possible two or more substituents selected from hydroxy, $C_{1-4}$alkyl, hydroxy-$C_{1-4}$alkyl- or polyhydroxy-$C_{1-4}$alkyl-;

$Ar^1$, $Ar^2$, $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

In one embodiment the intermediates of formula (III) consists of the intermediates of formula (III) wherein one or more of the following restrictions apply;

V represents hydrogen or a protective group preferably selected from the group consisting of methylcarbonyl, t-butyl, methyl, ethyl, benzyl or trialkylsilyl;

Y represents —$C_{3-9}$alkyl-, —$C_{3-9}$alkenyl-, —$C_{1-5}$alkyl-oxy-$C_{1-5}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-5}$alkyl-CO—$NR^{15}$—$C_{1-5}$alkyl-, —$C_{1-6}$alkyl-CO—NH—, —$C_{1-6}$alkyl-NH—CO—, —$C_{1-7}$alkyl-CO—, $C_{1-6}$alkyl-CO—$C_{1-6}$alkyl;

$X^2$ represents a direct bond, O, —O—$C_{1-2}$alkyl-, CO, —CO—$C_{1-2}$alkyl-, $NR^{12}$, —$NR^2$—$C_{1-2}$alkyl-, —$CH_2$—, —O—N═CH— or $C_{1-2}$alkyl;

$R^1$ represents hydrogen, cyano, halo, hydroxy, formyl, $C_{1-6}$alkoxy-, $C_{1-6}$alkyl-, $C_{1-6}$alkoxy- substituted with halo, $C_{1-4}$alkyl substituted with one or where possible two or more substituents selected from hydroxy or halo; and $R^2$ represents hydrogen, cyano, halo, hydroxy, hydroxycarbonyl-, $Het^6$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, $Het^1$ formyl, $C_{1-4}$alkyl-, $C_{2-6}$alkynyl-, $C_{3-6}$cycloalkyl-, $C_{3-6}$cycloalkyloxy-, $C_{1-6}$alkoxy-, $Ar^5$, $Ar^1$-oxy-, dihydroxyborane, $C_{1-6}$alkoxy- substituted with halo, $C_{1-4}$alkyl substituted with one or where possible two or more substituents selected from halo, hydroxy or $NR^5R^6$, $C_{1-4}$alkylcarbonyl- wherein said $C_{1-4}$alkyl is optionally substituted with one or where possible two or more substituents selected from hydroxy or $C_{1-4}$alkyl-oxy-;

$R^5$ and $R^6$ are each independently selected from hydrogen or $C_{1-4}$alkyl;

$R^{12}$ represents hydrogen, $C_{1-4}$alkyl, $C_{1-4}$alkyl-oxy-carbonyl-, phenyl-$C_{1-4}$alkyl-oxy-carbonyl-, $Het^{17}$, $Het^8$-$C_{1-4}$alkyl-, —$C_{2-4}$alkenylcarbonyl- optionally substituted with $Het^9$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{13}$ represents hydrogen, $C_{1-4}$alkyl, $Het^{13}$, $Het^4$-$C_{1-4}$alkyl- or phenyl optionally substituted with one or where possible two or more substituents selected from hydrogen, hydroxy, amino or $C_{1-4}$alkyl-;

$R^{14}$ and $R^{15}$ are each independently selected from hydrogen, $C_{1-4}$-alkyl, $Het^{15}$-$C_{1-4}$alkyl- or $C_{1-4}$alkyloxy$C_{1-4}$alkyl-;

$Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

$Het^{13}$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl, $C_{1-4}$alkyloxy$C_{1-4}$alkyl or polyhydroxy-$C_{1-4}$alkyl-;

$Het^{14}$ represent a heterocycle-selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represent a heterocycle selected from morpholinyl; pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represents a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Het^{17}$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Ar^1$, $Ar^2$, $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

In particular the intermediates of formula (III) wherein one or more of the following restrictions apply:

i) V represents hydrogen, methyl or ethyl;
ii) Y represents —$C_{3-9}$alkyl-, —$C_{1-5}$alkyl-oxy-$C_{1-5}$alkyl-, —$C_{1-5}$alkyl-NR$^{13}$—$C_{1-5}$alkyl-, —$C_{1-6}$alkyl-NH—CO—;
iii) Y represents —$C_{1-5}$alkyl-oxy-$C_{1-5}$alkyl, $C_{1-2}$alkyl-CO-Het$^{21}$-CO—, —CO—$C_{1-7}$alkyl-, or —CO-Het$^{20}$;
iv) $X^2$ represents a direct bond, O, —O—$C_{1-2}$alkyl-, NR$^{12}$, —NR$^{12}$—$C_{1-2}$alkyl-, —CH$_2$—, —O—N=CH— or $C_{1-2}$alkyl;
v) $X^2$ represents —NR$^{12}$—$C_{1-2}$alkyl- or $C_{1-2}$alkyl;
vi) $R^1$ represents hydrogen, cyano, halo or hydroxy, preferably halo;
vii) $R^2$ represents hydrogen, cyano, halo, hydroxy, hydroxycarbonyl-, $C_{1-4}$alkyloxycarbonyl-, Het$^{16}$-carbonyl-, $C_{1-4}$alkyl-, $C_{2-6}$alkynyl-, Ar$^5$ or Het$^1$; preferably halo;
viii) $R^2$ represents hydrogen, cyano, halo, hydroxy, $C_{2-6}$alkynyl- or Het$^1$; in particular $R^2$ represents hydrogen, cyano, halo, hydroxy, or Ar$^5$;
ix) $R^{12}$ represents hydrogen, $C_{1-4}$alkyl, $C_{1-4}$alkyloxycarbonyl or phenyl-$C_{1-4}$alkyl-oxy-carbonyl-;

x) $R^{13}$ represents Het$^{14}$-$C_{1-4}$alkyl, in particular morpholinyl-$C_{1-4}$alkyl;
xi) Het$^1$ represents thiazolyl optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl) amino- or amino-carbonyl-;
xii) Het$^{16}$ represents a heterocycle selected from piperidinyl or pyrrolidinyl;
xiii) Het$^{20}$ represents piperidine, piperazine, pyrrolidinyl or 2-pyrrolidinonyl wherein said Het$^{20}$ is optionally substituted with hydroxy.

b) the intermediates of formula (XXX)

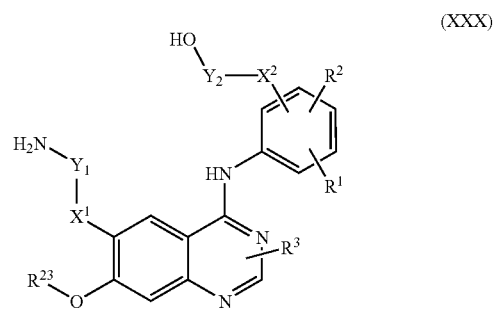

(XXX)

the pharmaceutically acceptable addition salts and the stereochemically isomeric forms thereof, wherein Y1 and Y2 each independently represent a $C_{1-5}$alkyl, $C_{1-6}$alkyl, CO—$C_{1-6}$alkyl, CO—$C_{1-5}$alkyl, Het$^{22}$-CH$_2$—CO, CO—CR$^{16}$R$^{17}$NH—, Het$^{20}$, CR$^{18}$R$^{19}$—CO—, CH$_2$—CO—NH—$C_{1-3}$alkyl-, —$C_{1-2}$alkyl-NR$^{21}$—CH$_2$—CO— or CO—$C_{1-3}$alkyl-NH—;

$X^1$ represents a direct bond, O, —O—$C_{1-2}$alkyl-, CO, —CO—$C_{1-2}$alkyl-, NR$^{11}$, —NR$^{11}$—$C_{1-2}$alkyl-, —CH$_2$—O—N=C— or —$C_{1-2}$alkyl-;

$X^2$ represents a direct bond, O —O—$C_{1-2}$alkyl-, CO, —CO—$C_{1-2}$alkyl-, NR$^{12}$, —NR$^{12}$—$C_{1-2}$alkyl-, —CH$_2$—, —O—N=CH— or —$C_{1-2}$alkyl-;

$R^1$ represents hydrogen, cyano, halo, hydroxy, formyl, $C_{1-6}$alkoxy-, $C_{1-6}$-alkyl-, halo-phenyl-carbonylamino-, $C_{1-6}$alkoxy- substituted with halo, $C_{1-4}$alkyl substituted with one or where possible two or more substituents selected from hydroxy or halo;

$R^2$ represents hydrogen, cyano, halo, hydroxy, hydroxycarbonyl-, Het$^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, Het$^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, Ar$^5$, Ar$^1$-oxy-, dihydroxyborane, $C_{1-6}$alkoxy- substituted with halo, $C_{1-4}$alkyl substituted with one or where possible two or more substituents selected from halo, hydroxy or NR$^5$R$^6$, $C_{1-4}$alkylcarbonyl- wherein said $C_{1-4}$alkyl is optionally substituted with one or where possible two or more substituents selected from hydroxy or $C_{1-4}$alkyl-oxy-;

$R^3$ represents hydrogen, $C_{1-4}$alkyl, or $C_{1-4}$alkyl substituted with one or more substituents selected from halo, $C_{1-4}$alkyloxy-, amino-, mono- or di($C_{1-4}$alkyl)amino-, $C_{1-4}$alkyl-sulfonyl- or phenyl;

$R^5$ and $R^6$ are each independently selected from hydrogen or $C_{1-4}$alkyl;

$R^7$ and $R^8$ are each independently selected from hydrogen, $C_{1-4}$alkyl, Het$^8$, aminosulfonyl-, mono- or di($C_{1-4}$alkyl)- aminosulfonyl, hydroxy-$C_{1-4}$alkyl-, $C_{1-4}$alkyl-oxy-$C_{1-4}$alkyl-, hydroxycarbonyl-$C_{1-4}$alkyl-, $C_{3-6}$cycloalkyl, $Het^9$-carbonyl-$C_{1-4}$alkyl-, $Het^{10}$-carbonyl-, polyhydroxy-$C_{1-4}$alkyl-, $Het^{11}$-$C_{1-4}$alkyl- or $Ar^2$—$C_{1-4}$alkyl-;

$R^9$ and $R^{10}$ are each independently selected from hydrogen, $C_{1-4}$alkyl, $C_{3-6}$cycloalkyl, $Het^4$, hydroxy-$C_{1-4}$alkyl-, $C_{1-4}$alkyloxy$C_{1-4}$alkyl- or polyhydroxy-$C_{1-4}$alkyl-;

$R^{11}$ represents hydrogen, $C_{1-4}$alkyl, $Het^5$, $Het^6$-$C_{1-4}$alkyl-, $C_{2-4}$alkenylcarbonyl-optionally substituted with $Het^7$-$C_{1-4}$alkylaminocarbonyl-, $C_{2-4}$alkenylsulfonyl-, $C_{1-4}$alkyloxy$C_{1-4}$alkyl-, or phenyl optionally substituted with one or where possible two or more substituents selected from hydrogen, hydroxy, amino or $C_{1-4}$alkyloxy-;

$R^{12}$ represents hydrogen, $C_{1-4}$alkyl, $C_{1-4}$alkyl-oxy-carbonyl-, $Het^{17}$, $Het^{18}$-$C_{1-4}$alkyl-, $C_{2-4}$alkenylcarbonyl- optionally substituted with $Het^{19}$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{16}$ and $R^{17}$ each independently represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino;

$R^{18}$ and $R^{19}$ each independently represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino, $R^{21}$ represents hydrogen, $C_{1-4}$alkyl, $Het^{23}$-$C_{1-4}$alkylcarbonyl- or $R^{21}$ represents mono- or di($C_{1-4}$alkyl)amino-$C_{1-4}$alkyl-carbonyl- optionally substituted with hydroxy, pyrimidinyl, dimethylamine or $C_{1-4}$alkyloxy;

$R^{23}$ represents $Ar^3$, $Ar^4$—$C_{1-4}$ alkyl, $C_{1-4}$-alkyl, $C_{2-6}$alkenyl optionally substituted with $Het^{12}$ or $R^{17}$ represents $C_{1-4}$alkyl substituted with one or where possible two or more substituents selected from $C_{1-4}$alkyloxy, hydroxy, halo, $Het^2$, $NR^7R^8$, $NR^9R^{10}$-carbonyl or $Het^3$-carbonyl;

$Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^2$ represents a heterocycle selected from morpholinyl, piperazinyl, piperidinyl, pyrrolidinyl, thiomorpholinyl or dithianyl wherein said $Het^2$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino-, mono- or di($C_{1-4}$alkyl)amino-$C_{1-4}$alkyl-, amino$C_{1-4}$alkyl-, mono- or di($C_{1-4}$alkyl)amino-sulfonyl-, aminosulfonyl-;

$Het^3$, $Het^4$ and $Het^8$ each independently represent a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said $Het^3$, $Het^4$ or $Het^8$ is optionally substituted with one or where possible two or more substituents selected from hydroxy-, amino-, $C_{1-4}$alkyl-, $C_{3-6}$cycloalkyl-$C_{1-4}$alkyl-, aminosulfonyl-, mono- or di($C_{1-4}$alkyl)aminosulfonyl or amino-$C_{1-4}$alkyl-;

$Het^5$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^6$ and $Het^7$ each independently represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^9$ and $Het^{10}$ each independently represent a heterocycle selected from furanyl, piperidinyl, morpholinyl, piperazinyl, pyrazolyl, dioxolanyl, thiazolyl, oxazolyl, imidazolyl, isoxazolyl, oxadiazolyl, pyridinyl or pyrrolidinyl wherein said $Het^9$ or $Het^{10}$ is optionally substituted $C_{1-4}$alkyl, $C_{3-6}$cycloalkyl-$C_{1-4}$alkyl- or amino-$C_{1-4}$alkyl-;

$Het^{11}$ represents a heterocycle selected from indolyl or

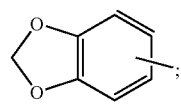

$Het^{12}$ represents a heterocycle selected from morpholinyl, piperazinyl, piperidinyl, pyrrolidinyl, thiomorpholinyl or dithianyl wherein said $Het^{12}$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino- or mono- or di($C_{1-4}$alkyl)amino-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Het^{17}$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{20}$, $Het^{21}$ and $Het^{22}$ each independently represent a heterocycle selected from pyrrolidinyl, 2-pyrrolidinonyl, piperazinyl or piperidinyl optionally substituted, with one or where possible two or more substituents selected from hydroxy, —$C_{1-4}$alkyl, hydroxy-$C_{1-4}$alkyl- or polyhydroxy-$C_{1-4}$alkyl-;

$Het^{23}$ represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Ar^1$, $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

In one embodiment the intermediates of formula (XXX) consists of the intermediates of formula (XXX) wherein one or more of the following restrictions apply;

$Y_1$ and $Y_2$ each independently represent $C_{1-5}$alkyl, CO—$C_{1-5}$alkyl or CO—$CHR^{16}$—NH—;

$X^1$ represents a direct bond, O, —O—$C_{1-2}$alkyl-, CO, —CO—$C_{1-2}$alkyl-, $NR^{11}$, —$NR^{11}$—$C_{1-2}$alkyl-, —$CH_2$—, —O—N=CH— or —$C_{1-2}$alkyl-;

$X^2$ represents a direct bond, O, —O—$C_{1-2}$alkyl-, CO, CO—$C_{1-2}$alkyl-, $NR^{12}$, —$NR^{12}$—$C_{1-2}$alkyl-, —$CH_2$—, —O—N=CH— or $C_{1-2}$alkyl;

$R^1$ represents hydrogen, cyano, halo, hydroxy, formyl, $C_{1-6}$alkoxy-, $C_{1-6}$alkyl-, $C_{1-6}$alkoxy- substituted with halo, $C_{1-4}$alkyl substituted with one or where possible two or more substituents selected from hydroxy or halo; and $R^2$ represents hydrogen, cyano, halo, hydroxy, hydroxycarbonyl-, $Het^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, $Het^1$, formyl, $C_{1-4}$alkyl-, $C_{2-6}$alkynyl-, $C_{3-6}$cycloalkyl-,
$C_{3-6}$cycloalkyloxy-, $C_{1-6}$alkoxy-, $Ar^5$, $Ar^1$-oxy-, dihydroxyborane,
$C_{1-6}$alkoxy- substituted with halo,
$C_{1-4}$alkyl substituted with one or where possible two or more substituents selected from halo, hydroxy or $NR^5R^6$,
$C_{1-4}$alkylcarbonyl- wherein said $C_{1-4}$alkyl is optionally substituted with one or where possible two or more substituents selected from hydroxy or $C_{1-4}$alkyl-oxy-;

$R^3$ represents hydrogen;

$R^5$ and $R^6$ are each independently selected from hydrogen or $C_{1-4}$alkyl;

$R^7$ and $R^5$ are each independently selected from hydrogen, $C_{1-4}$alkyl, $Het^8$, aminosulfonyl-, mono or -di($C_{1-4}$alkyl)-aminosulfonyl, hydroxy-$C_{1-4}$alkyl-, $C_{1-4}$alkyl-oxy-$C_{1-4}$alkyl-, hydroxycarbonyl-$C_{1-4}$alkyl-, $C_{3-6}$cycloalkyl, $Het^9$-carbonyl-$C_{1-4}$alkyl-, $Het^{10}$-carbonyl-, polyhydroxy-$C_{1-4}$alkyl-, $Het^{11}$-$C_{1-4}$alkyl- or $Ar^2$—$C_{1-4}$alkyl-;

$R^9$ and $R^{10}$ are each, independently selected from hydrogen, $C_{1-4}$alkyl, $C_{3-6}$cycloalkyl, $Het^4$, hydroxy-$C_{1-4}$alkyl-, $C_{1-4}$alkyloxy$C_{1-4}$alkyl- or polyhydroxy-$C_{1-4}$alkyl-;

$R^{11}$ represents hydrogen, $C_{1-4}$alkyl, $Het^5$, $Het^6$-$C_{1-4}$alkyl-, $C_{2-4}$alkenylcarbonyl-optionally substituted with $Het^7$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{12}$ represents hydrogen, $C_{1-4}$alkyl, $C_{1-4}$alkyl-oxy-carbonyl-, $Het^7$, $Het^{18}$-$C_{1-4}$alkyl-, $C_{2-4}$alkenylcarbonyl- optionally substituted with $Het^{19}$-$C_{1-4}$alkylaminocarbonyl-, $C_{2-4}$-alkenylsulfonyl-, $C_{1-4}$alkyloxy$C_{1-4}$alkyl- or phenyl optionally substituted with one or where possible two or more substituents selected from hydrogen, hydroxy, amino or —$C_{1-4}$alkyloxy-;

$R^{16}$ represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino;

$R^{23}$ represents $Ar^3$, $Ar^4$—$C_{1-4}$alkyl, $C_{1-4}$alkyl, $C_{2-6}$alkenyl optionally substituted with $Het^{12}$ or $R^{17}$ represents $C_{1-4}$alkyl substituted with one or where possible two or more substituents selected from $C_{1-4}$alkyloxy, hydroxy, halo, $Het^2$, $NR^7R^8$, $NR^9R^{10}$-carbonyl or $Het^3$-carbonyl $Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

$Het^2$ represents a heterocycle selected from morpholinyl, piperazinyl, piperidinyl, pyrrolidinyl, thiomorpholinyl or dithianyl wherein said $Het^2$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino-, mono- or di($C_{1-4}$alkyl)amino-4$C_{1-4}$alkyl-, amino$C_{1-4}$alkyl-, mono- or di($C_{1-4}$alkyl)amino-sulfonyl-, aminosulfonyl-;

$Het^3$, $Het^4$ and $Het^8$ each independently represent a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said $Het^3$, $Het^4$ or $Het^8$ is optionally substituted with one or where possible two or more substituents selected from hydroxy-, amino, $C_{1-4}$alkyl-, $C_{3-6}$cycloalkyl-$C_{1-4}$alkyl-, aminosulfonyl-, mono- or di($C_{1-4}$alkyl)aminosulfonyl or amino-$C_{1-4}$alkyl-;

$Het^5$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^6$ and $Het^7$ each independently represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^9$ and $Het^{10}$ each independently represent a heterocycle selected from furanyl, piperidinyl, morpholinyl, piperazinyl, pyrazolyl, dioxolanyl, thiazolyl, oxazolyl, imidazolyl, isoxazolyl, oxadiazolyl, pyridinyl or pyrrolidinyl wherein said $Het^9$ or $Het^{10}$ is optionally substituted $C_{1-4}$alkyl, $C_{3-6}$cycloalkyl-$C_{1-4}$alkyl- or amino-$C_{1-4}$alkyl-;

$Het^{11}$ represents a heterocycle selected from indolyl or

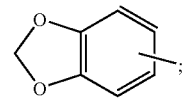

$Het^{12}$ represents a heterocycle selected from morpholinyl, piperazinyl, piperidinyl, pyrrolidinyl, thiomorpholinyl or dithianyl wherein said $Het^{12}$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino- or mono- or di($C_{1-4}$alkyl)amino-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Het^{17}$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^9$ each independently represent a heterocycle selected from morpholinyl, pyrrolidinyl, piperazinyl or piperidinyl optionally, substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Ar^1$, $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, —$C_{1-4}$alkyloxy- or $C_{1-4}$alkyl.

In particular the intermediates of formula (XXX) wherein one or more of the following restrictions apply;

i) $X^1$ represents O, —O—$C_{1-2}$alkyl-, —O—N═CH—, $NR^{11}$ or —$NR^{11}$—$C_{1-2}$alkyl-; in a particular embodiment $X^1$ represents —$NR^{11}$—, —O— or O—$CH_2$—;

ii) $X^2$ represents a direct bond, O, O—$C_{1-2}$alkyl-, —O—N═CH—, $NR^{12}$ or $NR^{12}$—$C_{1-2}$alkyl-; in a particular embodiment $X^2$ represents a direct bond, —$C_{1-2}$alkyl-, —O—$C_{1-2}$alkyl, —O— or O—$CH_2$—;

iii) $R^1$ represents hydrogen, cyano, halo or hydroxy, preferably halo;

iv) $R^2$ represents hydrogen, cyano, halo, hydroxy, hydroxycarbonyl-, $C_{1-4}$alkyloxycarbonyl-, $Het^{16}$-carbonyl-, $C_{1-4}$alkyl-, $C_{2-6}$alkynyl-, $Ar^5$ or $Het^1$; In a further embodiment $R^2$ represents hydrogen, cyano, halo, hydroxy, $C_{2-6}$alkyl- or $Het^1$; in particular $R^2$ represents hydrogen, cyano, halo, hydroxy, or $Ar^5$;

v) $R^{23}$ represents hydrogen, $C_{1-4}$alkyl or $R^{17}$ represents $C_{1-4}$alkyl substituted with one or where possible two or more substituents selected from $C_{1-4}$alkyloxy- or $Het^2$-;

vi) $R^{12}$ represents hydrogen, $C_{1-4}$alkyl- or $C_{1-4}$alkyl-oxy-carbonyl-;

vii) $Het^1$ represents thiazolyl optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

viii) $Het^2$ represents a heterocycle selected from morpholinyl, piperazinyl, piperidinyl or pyrrolidinyl wherein said $Het^2$ is optionally substituted with one or where possible two or more substituents selected from hydroxy, amino or $C_{1-4}$alkyl-; In a further embodiment $Het^2$ represents a heterocycle selected from morpholinyl or piperidinyl optionally substituted with $C_{1-4}$alkyl-, preferably methyl;

ix) $Het^3$ represents a heterocycle selected from morpholinyl, piperazinyl, piperidinyl or pyrrolidinyl wherein said $Het^3$ is optionally substituted with one or where possible two or more substituents selected from hydroxy, amino or $C_{1-4}$alkyl-;

x) $Het^{12}$ represents a heterocycle selected from morpholinyl, piperazinyl, piperidinyl or pyrrolidinyl wherein said $Het^{12}$ is optionally substituted with one or where possible two or more substituents selected from hydroxy, amino or $C_{1-4}$alkyl-;

xi) $Het^{16}$ represents a heterocycle selected from piperidinyl or pyrrolidinyl.

c) the intermediates of formula (XXXIII)

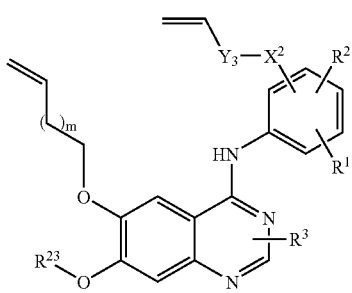

(XXXIII)

the pharmaceutically acceptable addition salts and the stereochemically isomeric forms thereof, wherein m represents 1, 2, 3 or 4;

$X^2$ represents a direct bond O, —O—$C_{1-2}$alkyl, CO, —CO—$C_{1-2}$alkyl-, $NR^{12}$, —$NR^{12}$—$C_{1-2}$alkyl-, —$CH_{12}$, —O—N═CH— or $C_{1-2}$alkyl;

$Y_3$ represents a $C_{1-5}$alkyl, CO—$C_{1-5}$alkyl or CO—$CR^{16}R^{17}$—NH— or $C_{1-5}$alkyl-CO— optionally substituted with amino, mono- or di($C_{1-4}$alkyl)amino or $C_{1-4}$alkyloxycarbonylamino;

$R^1$ represents hydrogen, cyano, halo, hydroxy, formyl, $C_{1-6}$alkoxy-, $C_{1-6}$alkyl-, halo-phenyl-carbonylamino-, $C_{1-6}$alkoxy- substituted with halo, $C_{1-4}$alkyl substituted with one or where possible two or more substituents selected from hydroxy or halo;

$R^2$ represents hydrogen, cyano, halo, hydroxy, hydroxycarbonyl-, $Het^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, $Het^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, $Ar^5$, $Ar^1$-oxy-, dihydroxyborane, $C_{1-6}$alkoxy- substituted with halo, $C_{1-4}$alkyl substituted with one or where possible two or more substituents selected from halo, hydroxy or $NR^5R^6$, $C_{1-4}$alkylcarbonyl- wherein said $C_{1-4}$alkyl is optionally substituted with one or where possible two or more substituents selected from hydroxy or $C_{1-4}$alkyl-oxy-;

$R^3$ represents hydrogen, $C_{1-4}$alkyl, or $C_{1-4}$alkyl substituted with one or more substituents selected from halo, $C_{1-4}$alkyloxy-, amino-, mono- or di($C_{1-4}$alkyl)amino-, $C_{1-4}$alkyl-sulfonyl- or phenyl;

$R^5$ and $R^6$ are each independently selected from hydrogen or $C_{1-4}$alkyl;

$R^{12}$ represents hydrogen, $C_{1-4}$alkyl, $C_{1-4}$alkyl-oxy-carbonyl-, $Het^{18}$-$C_{1-4}$alkyl-, phenyl-$C_{1-4}$alkyl-oxy-carbonyl-$Het^{17}$, $C_{2-4}$alkenylcarbonyl- optionally substituted with $Het^9$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{16}$ and $R^{17}$ each independently represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino;

$Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl mono or di($C_{1-4}$alkyl)amino- or amino-carbonyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl;

$Het^{18}$ and $Het^{19}$ each independently represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-; and $Ar^1$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

In particular the intermediates of formula (XXXIII) wherein one or more of the following restrictions apply;
i) $X^2$ represents a direct bond, $C_{1-2}$alkyl, $NR^{12}$ or —$NR^{12}$—$C_{1-2}$alkyl-; in a particular embodiment $X^2$ represents —$NR^{12}$—$C_{1-2}$alkyl- or $C_{1-2}$alkyl;
ii) $Y_3$ represents a $C_{1-5}$alkyl, CO—$CR^{16}R^{17}$—NH—, or —$C_{1-5}$alkyl-CO—; in a particular embodiment $Y_3$ represents —$C_{1-5}$alkyl-CO—;
iii) $R^1$ represents hydrogen, cyano, halo or hydroxy, preferably halo;
iv) $R^2$ represents hydrogen, cyano, halo, hydroxy, hydroxycarbonyl-, $C_{1-4}$alkyloxycarbonyl-, $Het^{16}$-carbonyl-, $C_{1-4}$alkyl-, —$C_{2-6}$alkynyl-, $Ar^5$ or $Het^1$; In a further embodiment $R^2$ represents hydrogen, cyano, halo or hydroxy; in particular $R^2$ represents hydrogen, cyano, halo, hydroxy, or $Ar^5$;
v) $R^3$ represents hydrogen;
vi) $R^{12}$ represents hydrogen or $C_{1-4}$alkyl;
vii) $R^{16}$ represents hydrogen or $C_{1-4}$alkyl substituted with hydroxy;
viii) $R^{17}$ represents hydrogen or $C_{1-4}$alkyl, in particular hydrogen or methyl;
ix) $Het^1$ represents thiazolyl optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl) amino- or amino-carbonyl-;
x) $Het^{16}$ represents a heterocycle selected from piperidinyl or pyrrolidinyl;
xi) $Ar^5$ represents phenyl.

It is also an object of the present invention to provide the use of the intermediates of formula (III), (XXX) or (XXXIII) in the synthesis of a compound of formula (I).

The compounds of the present invention, including the compounds of formula (I) and the intermediates of formula (III), (XXX) and (XXXIII) are useful because they possess pharmacological properties. They can therefore be used as medicines.

As described in the experimental part hereinafter, the growth inhibitory effect and anti-tumour activity of the present compounds has been demonstrated in vitro, in enzymatic assays on the receptor tyrosine kinases EGFR, ErbB2, ErbB4, FlT3, BLK or the Sar kinase family such as for example Lyn, Yes cSRC. In an alternative assay, the growth inhibitory effect of the compounds was tested on a number of carcinamo cell lines, in particular in the ovarian carcinoma cell line SKOV3 and the squamous carcinoma cell line A431 using art known cytotoxicity assays such as MTT.

Accordingly, the present invention provides the compounds of formula (I) and their pharmaceutically acceptable N-oxides, addition salts, quaternary amines and stereochemically isomeric forms for use in therapy. More particular in the treatment or prevention of cell proliferation mediated diseases. The compounds of formula (I) and their pharmaceutically acceptable N-oxides, addition salts, quaternary amines and the stereochemically isomeric forms may hereinafter be referred to as compounds according to the invention.

Disorders for which the compounds according to the invention are particularly useful are atherosclerosis, restenosis, cancer and diabetic complications e.g. retinopathy.

In view of the utility of the compounds according to the invention, there is provided method of treating a cell proliferative disorder such as atherosclerosis, restenosis and cancer, the method comprising administering to an animal in need of such treatment, for example, a mammal including humans, suffering from a cell proliferative disorder, a therapeutically effective amount of a compound according to the present invention.

Said method comprising the systemic or topical administration of an effective amount of a compound according to the invention, to animals, including humans. One skilled in the art will recognize that a therapeutically effective amount of the EGFR inhibitors of the present invention is the amount sufficient to induce the growth inhibitory effect and that this amount varies inter alia, depending on the size, the type of the neoplasia, the concentration of the compound in the therapeutic formulation, and the condition of the patient. Generally, an amount of EGFR inhibitor to be administered as a therapeutic agent for treating cell proliferative disorder such as atherosclerosis, restenosis and cancer, will be determined on a case by case basis by an attending physician.

Generally, a suitable dose is one that results in a concentration of the EGFR inhibitor at the treatment site in the range of 0.5 nM to 200 µM, and more usually 5 nM to 10 µM. To obtain these treatment concentrations, a patient in need of treatment likely will be administered between 0.01 mg/kg to 300 mg/kg body weight, in particular from 10 mg/kg to 100 mg/kg body weight. As noted above, the above amounts may vary on a case-by-case basis. In these methods of treatment the compounds according to the invention are preferably formulated prior to admission. As described herein below, suitable pharmaceutical formulations are prepared by known procedures using well known and readily available ingredients.

Due to their high degree of selectivity as EGFR inhibitors, the compounds of formula (I) as defined above, are also useful to mark or identify the kinase domain within the receptor tyrosine kinase receptors. To this purpose, the compounds of the present invention can be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}$C-atom or tritium atom.

One particular group consists of those compounds of formula (I) wherein $R^1$ is a radioactive halogen atom. In principle, any compound of formula (I) containing a halogen atom is prone for radiolabelling by replacing the halogen atom by a suitable isotope. Suitable halogen radioisotopes to this purpose are radioactive iodides, e.g. $^{122}$I, $^{123}$I, $^{125}$I, $^{131}$I; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using any one of the procedures as described hereinabove to prepare halogen derivatives of formula (I).

Another interesting form of radiolabelling is by substituting a carbon atom by a $^{11}$C-atom or the substitution of a hydrogen atom by a tritium atom.

Hence, said radiolabelled compounds of formula (I) can be used in a process of specifically marking receptor sites in biological material. Said process comprises the steps of (a) radiolabelling a compound of formula (I), (b) administering this radio-labelled compound to biological material and subsequently (c) detecting the emissions from the radiolabelled compound.

The term biological material is meant to comprise every kind of material which has a biological origin. More in particular this term refers to tissue samples, plasma or body fluids but also to animals, specially warm-blooded animals, or parts of animals such as organs.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or positron Emission Tomography (PET) and the like. In this manner the distribution of the particular receptor sites throughout the body can be detected and organs containing said receptor sites can be visualized by the imaging techniques mentioned hereinabove. This process of imaging an organ by administering a radiolabelled compound of formula (I) and detecting the emissions from the radioactive compound also constitutes a part of the present invention.

In yet a further aspect, the present invention provides the use of the compounds according to the invention in the manufacture of a medicament for treating any of the aforementioned cell proliferative disorders or indications.

The amount of a compound according to the present invention, also referred to here as the active ingredient, which is required to achieve a therapeutic effect will be, of course, vary with the particular compound, the route of administration, the age and condition of the recipient, and the particular disorder or disease being treated. A suitable daily dose would be from 0.01 kg to 300 mg/kg body weight, in particular from 10 mg/kg to 100 mg kg/body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects or the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

EXPERIMENTAL PART

Hereinafter, the term 'RT' means room temperature, 'ADDP' means 1,1'-(azodicarbonyl)dipiperidine, 'DCM' dichloromethane, 'DMA' means dimethylacetamide, 'DME' means dimethyl ether, 'DMF' means N,N-dimethylformamide, 'DMSO' means dimethylsulfoxide, 'DIPE' means diisopropyl ether, 'DIPEA' means N-ethyl-N-(1-methylethyl)-2-propanamine, 'EtOH' means ethanol, 'EtOAc' means ethyl acetate, 'HBTU' means 1-[bis(dimethylamino) methylene]-H-benzotriazoalium, hexafluorophosphate(1-), 3-oxide) 'LAH' means lithiumaluminiumhydride i.e. LiAlH$_4$, 'TFA' means trifluoroacetic acid and 'THF' means tetrahydrofuran, 'PyBOP' means (1-hydroxy-1H-benzotriazolato-O)tri-1-pyrrolidinyl-, (T-4)-phosphorus(1+), hexafluorophosphate(1−), 'NaBH(OAc)$_3$' means sodium triacetoxyborohydride, RP means reversed-phase.

A. Preparation of the Intermediates

Example A1 a) Preparation of hexanoic acid, 6-(2-methyl-6-nitrophenoxy)-, methyl ester (intermediate 1)

A mixture of 2-methyl-6-nitro-phenol (0.0065 mol) and K$_2$CO$_3$(0.026 mol) in N,N-dimethyl-formamide (DMF) (80 ml) was stirred at 50° C. for 15 min., then 6-bromo-methyl ester hexanoic acid (0.0195 mol) was added dropwise and the reaction mixture was stirred for 18 hours at 50° C. After completion, the reaction was quenched with ice-water and the mixture was extracted 3 times with toluene. The organic layer was separated, dried (MgSO$_4$), filtered and concentrated. The residue was used as such in the next step, yielding 100% of intermediate 1.

b) Preparation of hexanoic acid, 6-(2-amino-6-methylphenoxy)-, methyl ester (intermediate 2)

A mixture of intermediate (0.013 mol) and ethylamine (0.5 g) in THF (100 ml) vas hydrogenated with Pt/C 5% (2 g) as a catalyst. After uptake of H$_2$ (3 equiv.), the reaction mixture was filtered over a small plug of Dicalite and the filtrate was concentrated, yielding 1.4 g of intermediate 2 which was used as such in the next step.

c) Preparation of hexanoic acid, 6-[2-[[6-(acetyloxy)-4-methoxy-4-quinazolinyl]amino]-6-methylphenoxy], methyl ester (intermediate 3)

A mixture of 4-chloro-6-methylcarbonyloxy-7-methoxyquinazoline 0.0045 intermediate 2(0.6056 mol) in 2-propanol (40 ml) was stirred and refluxed for 1 day. The reaction mixture was concentrated and the residue, treated with DIPE and this mixture was stirred overnight. The solid was collected by filtration, washed and dried, yielding intermediate 3.

d) Preparation of hexanoic acid, 6-[2-[(6-hydroxy-7-methoxy-4-quinazolinyl)amino]-6-methylphenoxy]-, methyl ester (intermediate 4)

A solution of intermediate 3 (0.0045 mol) and $NH_4OH$ (1.5 ml) in $CH_3OH$ (50 ml) was stirred for 18 hours at RT and the solvent was evaporated, yielding intermediate 4 (impure, used as such in the next reaction step).

e) Preparation of hexanoic acid, 6-[2-[(6-hydroxy-7-methoxy-4-quinazolinyl)amino]-6-methylphenoxy] (intermediate 5)

A mixture of intermediate 4 (0.00024 mol), LiOH (0.00047 mol), THF (3 ml), $CH_3OH$ (1 ml) and $H_2O$ (1 ml) was stirred and heated at 70° C. for 30 min. and then the reaction mixture was allowed to reach RT. The organic solvent (THF/$CH_3OH$) was evaporated and the aqueous concentrate was neutralised with HCl (1N) filtered and the solid retained was washed and dried (vac.) at 65° C.; yielding 0.040 g of intermediate 5.

Example A2 a) Preparation of hexanoic acid, 6-(2-chloro-6-nitrophenoxy)-, methyl ester (intermediate 6)

A solution of 2-chloro-6-nitro phenol 0.046 mol) in N,N-dimethylformamide (150 ml) was heated to 50° C., then $K_2CO_3$ (0.069 mol) was added and the reaction mixture was stirred for 15 min. 6-Bromo-, methyl ester hexanoic acid (0.069 mol) was added and the mixture was stirred overnight. The reaction mixture was filtered and the filtrate was concentrated and the residue was used as such in the next step, yielding 13.88 g of intermediate 6.

b) Preparation of hexanoic acid, 6-(2-amino-6-chlorophenoxy)-, methyl ester (intermediate 7)

A mixture of intermediate 6 (0.046 mol) and ethanime (2 g) in THF (ml) was hydrogenated with Pt/C 5% (3 g) as a catalyst in the presence of DIPE (2 ml). After uptake of $H_2$ (3 equiv.), the reaction mixture was filtered over small plug of Dicalite the filtrate was concentrated, yielding intermediate 7.

c) Preparation of hexanoic acid, 6-[2-[[6-(acetyloxy)-7-methoxy-4-quinazolinyl]amino]-6-chlorophenoxy]-, methyl ester (intermediate 8)

A mixture of 4-chloro-6-methylcarbonyloxy-7-methoxyquinazoline (0.022 mol) and intermediate 7 (0.022 mol) in 2-propanol (170 ml) was stirred and heated at 80° C. for 2 hours, concentrated and the residue was chromatographed over silica gel (eluent: DCM/$CH_3OH$ 97/3). The product fractions were collected and the solvent was evaporated, yielding 5.1 g intermediate 8 (used as such in the next reaction step).

d) Preparation of 6-quinazolinol, 4-[[3-chloro-2-[(6-hydroxyhexyl)oxy]phenyl]amino]-7-methoxy- (intermediate 9)

A mixture of LAH (0.0246 mol) in THF (40 ml) was stirred at RT. A solution of intermediate 8 (0.006 mol) in THF (60 ml) was added dropwise. The reaction mixture was stirred for 1 day then, extra LAH (0.0123 mol) was added portionwise. The mixture was stirred further over the weekend then, $H_2O$ (2 ml) was added dropwise, followed by the dropwise addition of a 15% NaOH soln. (2 ml) and $H_2O$ (6 ml). This mixture was stirred for 15 min filtered and the filtrate was concentrated. The residue was stirred in boiling $CH_3CN$, filtered and the solid retained was dried (vac.) at 60° C. The solids were re-dissolved in $CH_3OH$/DCM (10/90) and this mixture was neutralised with HCl (1N). The organic layer was separated, dried ($MgSO_4$), filtered and concentrated, yielding 1 g of intermediate 9.

Example A3 a) Preparation of hexanoic acid, 6-(4-chloro-2'-nitrophenoxy)-, methyl ester (intermediate 10)

A mixture of 4-chloro-6-nitro-phenol (0.029 mol) and $K_2CO_3$ (0.035 mol) in DMA (80 ml) was stirred at 50° C. for 30 min., then 6-bromo-, methyl ester hexanoic acid (0.035 mol) was added dropwise and the reaction mixture was stirred for another 1-8 hours at 50° C. After completion, the mixture was filtered and the filtrate was neutralised with HCl (1N), then poured onto ice water and stirred for 30 min. The resulting precipitate was collected by filtration; washed, dissolved in DCM, dried ($MgSO_4$), filtered and concentrated, yielding intermediate 10 (used as such in the next reaction step).

b) Preparation of hexanoic acid, 6-(2-amino-4-chlorophenoxy)-, methyl ester (intermediate 11)

A mixture of intermediate 10 (0.026 mol) and ethylamine (1 g) in THF (100 ml) was hydrogenated with Pt/C 5% (5 g) as a catalyst in the presence of DIPE (1 ml). After uptake of $H_2$ (3 equiv.), and the reaction mixture was filtered over a small plug of Dicalite, the filtrate was concentrated, yielding intermediate 11.

c) Preparation of hexanoic acid, 6-[2-[[6-(acetyloxy)-7-methoxy-4-quinazolinyl]amino]-4-chlorophenoxy]-, methyl ester (intermediate 12)

A mixture of 4-chloro-6-methylcarbonyloxy-7-methoxyquinazoline (0.014 mol) and intermediate 11(0.014 mol) in 2-propanol (120 ml) was heated at 80° C. and stirred for 3 hours. The reaction mixture was filtered and the filtrate was concentrated. The residue was purified by column chromatography over silica gel (eluent: DCM/$CH_3OH$ 96.5/3.5). The product fractions were collected and the solvent was evaporated to dryness, yielding 1.8 g of intermediate 12 (used as such in the next reaction step).

d) Preparation of 6-quinazolinol, 4-[[5-chloro-2-[(6-hydroxyhexyl)oxy]phenyl]amino]-7-methoxy- (intermediate 13)

LAH (0.015 mol) was stirred in THF (40 ml) and then a solution of intermediate 12 (0.0037 mol) in THF (80 ml) was added dropwise under $N_2$ at RT. The reaction mixture was stirred over the weekend, then treated with H$_2$O (0.9 ml), aq. NaOH soln. (15%, 0.9 ml) and H$_2$O (2.7 ml). The reaction mixture was filtered, the residue washed and the filtrate was concentrated under reduced pressure. The residue was stirred in DIPE and the solid was collected by filtration, yielding 0.8 g (53%) of intermediate 13.

Example A4 a) Preparation of pentanoic acid, 5-(4-chloro-2-nitrophenoxy)-, methyl ester (intermediate 14)

A mixture of 4-chloro-6-nitrophenol (0.023 mol, K$_2$CO$_3$ (0.027 mol) and N,N-dimethylformamide (80 ml) was stirred at 50° C. for 30 min., then 5-bromo-, methylester pentanoic acid (0.627 mol) was added dropwise end the reaction mixture was stirred for 18 hours at 50° C. The mixture was filtered and the filtrate was neutralised with HCl (1N). This mixture was poured in ice water and stirred for 30 min. The resulting precipitate was collected by filtration, washed, re-dissolved in DCM/CH$_3$OH(95/5) dried (MgSO$_4$), filtered and concentrated, yielding 6.6 g of intermediate 14 (used as such in the next reaction step).

b) Preparation of pentanoic acid, 5-(2-amino-4-chlorophenoxy)-, methyl ester (intermediate 15)

A mixture of intermediate 14 (0.023 mol) and ethylamine (1 g) in THF (100 ml) was hydrogenated with Pt/C 5% (2 g) as catalyst in the presence of DIPE (1 ml). After uptake of H$_2$ (3 equiv.), the reaction mixture was over a small plug of Dicalite and the filtrate was concentrated, yielding intermediate 15.

c) Preparation of pentanoic acid, 5-[2-[[6-(acetyloxy)-7-methoxy-4-quinazolinyl]amino]-4-chlorophenoxy]-, methyl ester (intermediate 16)

A mixture of 4-chloro-6-methylcarbonyloxy-7-methoxyquinazoline (0.0067 mol) and intermediate 15 (0.0048 mol) in 2-propanol (60 ml) was stirred and heated at 80° C. for 4 hours. The reaction mixture was filtered, the solid retained was washed and dried 0.7 g. The filtrate was concentrated and the residue (oil) was chromatographed over silica gel (eluent: DCM/CH$_3$OH 96.5/3.5). The pure fraction were collected and concentrated, yielding 1.5 g of intermediate 16.

d) Preparation of 6-quinazolinol, 4-[[5-chloro-2-[(5-hydroxypentyl)oxy]phenyl]amino]-7-methoxy- (intermediate 17)

A mixture of LAH (0.013 mol) in THF (25 m) was stirred at RT under N$_2$, then a solution of intermediate 16 (0.0032 mol) in THF (45 ml) was added dropwise and the reaction mixture was stirred overnight. The reaction mixture was treated with water (0.8 ml), NaOH (0.8 ml, 15%) and again water (2.4 ml) and the mixture was stirred for 15 min. The mixture was filtered and the filtrate was concentrated, re-dissolved in DCM/CH$_3$OH (95/5), neutralised with HCl (1N), concentrated and then purified over silica gel (eluent: DCM/CH$_3$OH 91.5/8.5). The product fractions were collected and concentrated, yielding 0.400 g of intermediate 17.

Example A5 a) Preparation of hexanoic acid, 6-(2-nitrophenoxy)-, methyl ester- (intermediate 18)

A mixture of 2-nitro-phenol (0.014 mol) and K$_2$CO$_3$ (0.017 mol) in N,N-dimethylformamide (50 ml) was stirred for 15 min. at 50° C., then 6-bromo-hexanoic acid methyl ester (0.017 mol) was added dropwise and the reaction mixture was stirred for 18 hours at 50° C. The reaction mixture was filtered and poured onto ice water. The resulting precipitate was filtered, washed and dried, yielding 3.0 g of intermediate 18 (used as such in the next reaction step).

b) Preparation of hexanoic acid, 6-(2-aminophenoxy)-, methyl ester (intermediate 19)

A mixture of intermediate 18 (0.011 mol) in THF (100 ml) was hydrogenated with Pt/C 5% (0.5 g) as a catalyst in the presence of DIPE (0.5 ml). After uptake of H$_2$ (3 equiv.), the reaction mixture was filtered over a small plug of Dicalite and concentrated, yielding intermediate 19.

c) Preparation of hexanoic acid, 6-[2-[[6-(acetyloxy)-7-methoxy-4-quinazolinyl]amino]phenoxy]-, methyl ester (intermediate 20)

A mixture of 4-chloro-6-methylcarbonyloxy-7-methoxyquinazoline (0.011 mol) and intermediate 19 (0.011 mol) in 2-propanol (100 ml) was heated and stirred at 80° C. for 5 hours. The reaction mixture was concentrated and the residue (oil) was purified over silica gel (eluent: DCM/CH$_3$OH 96.5/3.5). The product fractions were collected and and concentrated, yielding 2.3 g of intermediate 20 (used as such in the next reaction step).

d) Preparation of 6-quinazolinol, 4-[[2-[(6-hydroxyhexyl)oxy]phenyl]amino]-7-methoxy- (intermediate 21)

A mixture of LAH (0.020 mol) in THF (30 ml) was stirred at RT and then a solution of intermediate 20 (0.005 mol) in THF (50 ml) was added dropwise. The reaction mixture was stirred overnight, treated with H$_2$O (1 ml), aqueous NaOH soln. (1 ml, 15%) and again with H$_2$O (3 ml). This mixture was filtered, the residue was washed and the filtrate was neutralised with HCl (1N). The filtrate was then concentrated and the residue was dried (vac.) at 55° C., yielding 0.5 g of intermediate 21.

Example A6 a) Preparation of hexanoic acid, 6-(4-bromo-2-nitrophenoxy)-, methyl ester (intermediate 22)

A mixture of 4-bromo-2-nitrophenol (0.046 mol) in DMA (100 ml) was heated to 40° C. and then K$_2$CO$_3$ (0.046 mol) was added. The reaction mixture was stirred for 15 min. 6-Bromo-hexanoic acid methyl ester (0.046 mol) was added and the mixture was stirred overnight at 40° C. Extra 6-bromo-hexanoic acid methyl ester (2 g) was added and the reaction mixture was stirred for another 2 hours; The mixture was cooled to RT and poured into ice water (400 ml). The resulting precipitate was filtered, dissolved in DCM, dried (MgSO$_4$) and filtered again. Finally, the filtrate was evaporated, yielding 14.24 g (90%) of intermediate 22.

b) Preparation of hexanoic acid, 6-(2-amino-4-bromophenoxy)-, methyl ester (intermediate 23)

A mixture of intermediate 22 (0.04 mol) and ethylamine (0.044 mol) in THF (250 ml) was hydrogenated with Pt/C 5% (2 g) as a catalyst in the presence of DIPE (2 ml). After uptake of $H_2$ (3 equiv.), the reaction mixture was filtered over a small plug of Dicalite and concentrated, yielding 12.8 g of intermediate 23 (98%).

c) Preparation of hexanoic acid, 6-[2-[[6-(acetyloxy)-7-methoxy-4-quinazolinyl]amino]-4-bromophenoxy]-, methyl ester (intermediate 24)

A mixture of 4-chloro-6-acetoxy-7-methoxyquinazoline hydrochloride (0.00554 mol) and intermediate 23 (0.00554 mol) in 2-propanol (10 ml) was heated to 80° C. After 1 hour, the reaction mixture was homogeneous and was coloured black. The mixture was stirred overnight at RT, concentrated and then purified by column chromatography over silica gel. Two product fractions were collected and concentrated. Fraction 2 was stirred in 2-propanol/DIPE (1/24), filtered and the solid retained was dried, yielding intermediate 24.

d) Preparation of 6-quinazolinol, 4-[[5-bromo-2-[(6-hydroxyhexyl)oxy]phenyl]amino]-7-methoxy- (intermediate 25)

A mixture of intermediate 24 (0.00188 mol) in THF (40 ml) was added dropwise to a stirred suspension of LAH (0.0075 mol) in THF (20 ml) at RT under $N_2$-atm., for 16 h. The reaction mixture was subsequently treated with $H_2O$ (0.4 ml), and after 15 min with aqueous NaOH soln. (0.4 ml, 15%), and finally with $H_2O$ (1.2 ml) (colour change from grey/green to yellow). The reaction mixture was filtered and the filtrate was neutralised with HCl (1N) and concentrated. The residue was stirred in $CH_3CN$/DIPE (24/1) and the solid was collected by filtration and dried, yielding intermediate 25.

Example A7 a) Preparation of heptanoic acid, 7-(4-chloro-2-nitrophenoxy)-, ethyl ester (intermediate 26)

A mixture of 4-chloro-6-nitro-phenol (0.017 mol) and $K_2CO_3$ (0.019 mol) in DMA (70 ml) was stirred at 50° C. for 15 min., then 6-bromo-, ethyl ester hexanoic acid (0.019 mol) was added and the reaction mixture was stirred overnight at 50° C. The resulting precipitate was filtered and the filtrate was concentrated under reduced pressure, yielding intermediate 26 (used as such in the next reaction step).

b) Preparation of heptanoic acid, 7-(2-amino-4-chlorophenoxy)-, ethyl ester (intermediate 27)

A mixture of intermediate 26 (0.017 mol) and dimethylamine (1 g) in THF (100 ml) was hydrogenated with Pt/C 50/(2 g) as a catalyst in the presence of DIPE (1 ml). After uptake of $H_2$ (3 equiv.), The reaction mixture was filtered over a small plug of Dicalite and concentrated, yielding intermediate 27.

c) Preparation of heptanoic acid, 7-[2-[[6-(acetyloxy)-7-methoxy-4-quinazolinyl]amino]-4-chlorophenoxy]-, ethyl ester (intermediate 28)

A mixture of 4-chloro-6-methylcarbonyloxy-7-methoxyquinazoline (0.0051 mol) and intermediate 27 (0.006 mol) in 2-propanol (50 ml) was stirred and heated at 80° C. for 6 hours, then the solvent was evaporated under reduced pressure. The crude residue was purified by column chromatography over silica gel (eluent: DCM/$CH_3OH$ 97.5/2.5). The product fractions were collected and concentrated, yielding 2.4 g (92%) of intermediate 28.

d) Preparation of 6-quinazolinol, 4-[[5-chloro-2-[(7-hydroxyheptyl)oxy]phenyl]amino]-7-methoxy- (intermediate 29)

A mixture of LAH (0.0186 mol) in THF (40 ml) was stirred at RT and then a solution of intermediate 28 (0.0047 mol) in THF (40 ml) was added dropwise. The reaction mixture was stirred for 18 hours and extra LAH (0.0092 mol) was added, then the resulting mixture was stirred for another 1 day. The reaction mixture was subsequently treated with $H_2O$ (1.5 ml), aq. NaOH soln. (15%, 1.5 ml) and then $H_2O$ (4.5 ml) and the mixture was stirred for 10 min. This mixture was filtered and the filtrate was neutralised with HCl (1N), concentrated and the residue was purified by column chromatography (silica gel, eluent: DCM/$CH_3OH$ 95/5). The product fractions were collected and concentrated, yielding 0.5 g (25%) of intermediate 29.

Example A8 a) Preparation of 1-octanol, 8-(4-chloro-2-nitrophenoxy)-, acetate (ester) (intermediate 30)

A mixture of 4-chloro-6-nitro-phenol (0.0205 mol), fine molecular sieves (3.5 g), DMA, p.a. (50 ml) and $K_2CO_3$ (0.0238 mol) was stirred for 1 hour, then 8-bromo-1-octanol-acetate (0.0235 mol) was added and the reaction mixture was heated at 50° C. for 16 hours. The mixture was cooled and poured out into ice water, then extracted with toluene (2 times 150 ml). The organic layers were combined, dried ($MgSO_4$), filtered off and the solvent was evaporated (vac.). The residue was purified by Column chromatography over silica gel (eluent: DCM/Hexane 80/20). The product fractions were collected and the solvent was evaporated, yielding 6.2 g (87.9%) of intermediate 30.

b) Preparation of 1-octanol, 8-(2-amino-4-chlorophenoxy)-, acetate (ester) (intermediate 31)

A mixture of intermediate 30 (0.018 mol) in THF (100 ml) was hydrogenated with Pt/C 5% (1 g) as a catalyst in the presence of thiophene (1 ml) [1178-005]. After uptake of $H_2$ (3 equiv.), the reaction mixture was filtered over a small plug of Dicalite and concentrated, yielding 5.6 g of intermediate 31 (used as such in the next reaction step).

c) Preparation of 6-quinazolinol, 4-[[2-[[8-(acetyloxy)octyl]oxy]-5-chlorophenyl]amino]-7-methoxy-, acetate (ester) (intermediate 32)

A mixture of 4-chloro-6-methylcarbonyloxy-7-methoxyquinazoline (0.01 mol) and intermediate 31 (0.01 mol) in 2'-propanol (60 ml) was heated at 80° for 2 hours and the reaction mixture was cooled, then concentrated. DIPE was added and the mixture was stirred for 2 hours. The solids were collected and then dried, yielding 5.0 g of intermediate 32.

d) Preparation of 6-quinazolinol, 4-[[5-chloro-2-[(8-hydroxyoctyl)oxy]phenyl]amino]-7-methoxy- (intermediate 33)

A mixture of intermediate 32 (0.0094 mol) in methanol (100 ml) was heated at 60° C. Then a solution of $K_2CO_3$ (0.019 mol) in $H_2O$ (10 ml) was added dropwise. The organic solvent was evaporated and the aqueous concentrate was treated with acetic acid. The resulting precipitate was filtered off, washed with $H_2O$ and dried (vac.) at 60° C., yielding 3.7 g (88%) of intermediate 33.

Example A9 a) Preparation of 1-nonanol, 9-(4-chloro-2-nitrophenoxy)-, acetate (ester) (intermediate 34)

A mixture of 4-chloro-6-nitro-phenol (0.02 mol), DMA, p.a. (70 ml) and $K_2CO_3$ (0.0246 mol) was heated at 50° C. for 1 hour and then 9-bromo, 1-nonanol acetate (0.024 mol) was added. The reaction mixture was heated over the weekend and poured into ice (250 ml). The solids were collected by filtration, dissolved in DCM., dried ($MgSO_4$), filtered and concentrated, yielding 8.6 g of intermediate 34.

b) Preparation of 1-nonanol, 9-(2-amino-4-chlorophenoxy)-, acetate (ester) (intermediate 35)

A mixture of intermediate 34 (0.023 mol) in THF (200 ml) was hydrogenated at 50° C. with Pt/C 5% (2 g) as a catalyst in the presence of thiophene (2 ml). After uptake of $H_2$ (3 equiv.), the catalyst was filtered off and the filtrate was evaporated (vac.) yielding intermediate 35.

c) Preparation of 6-quinazolinyl, 4-[[2-[[9-(acetyloxy)nonyl]oxy]-5-chlorophenyl]amino]-7-methoxy-, acetate (ester) (intermediate 36)

A mixture of 4-chloro-6-methylcarbonyloxy-7-methoxyquinazoline (0.00099 mol) and intermediate 35 (0.0010 mol) in 2-propanol (15 ml) was heated at 80° C. for 1.5 hours and then the reaction mixture was concentrated under a dry $N_2$-flow. DIPE was added; the solids were collected and then dried. Yielding intermediate 36 (off-white solid) Alternatively a mixture of 4-chloro-6-methylcarbonyloxy-7-methoxyquinazoline (0.051 mol) and intermediate 35 (0.0051 mol) in 2-propanol (40 ml) was heated at 80° C. for 4 hours and then the reaction mixture was concentrated under a dry $N_2$-flow. DIPE was added; the solids were collected and then dried, yielding 2.38 g (84.3%) of intermediate 36.

d) Preparation of 6-quinazolinol, 4-[[5-chloro-2-[(9-hydroxynonyl)oxy]phenyl]amino]-7-methoxy- (intermediate 37)

$K_2CO_3$ (0.34 g) was added to a solution of intermediate 36 (0.00437 mol) in methanol (40 ml) and $H_2O$ (8 ml) and after 2 hours the resulting precipitate was filtered, giving solids (I) and filtrate (I). Filtrate (I) was evaporated and then $H_2O$ was added to the residue (pH: 10). Acetic acid was added until pH: 5-6 and the mixture was stirred for 10 min., then the solids were filtered off. These solids and solids (I) were combined in $H_2O/CH_3OH$ (20 ml/100 ml) and then $K_2CO_3$ (0.380 g) was added. The reaction mixture was heated at 60° C. for 30 min. and extra $K_2CO_3$ (0.400 g) was added, then the resulting mixture was stirred overnight. The solvent was evaporated and the residue was treated with $H_2O$ and acetic acid. The resulting solids were filtered off, washed with $CH_3OH$ and dried in a vacuum oven at 60° C., yielding 1.7 g of intermediate 37.

Example A10 a) Preparation of benzoic acid, 5-hydroxy-2-nitro-4-(phenylmethoxy)- (intermediate 38)

KOH (75 g) was added to $H_2O$ (175 ml), stirred at RT. 4-benzyloxy-5-methoxy-2-nitro-benzoic acid (0.031 mol;) was added portionwise and the suspension was heated for 12 hours at 75° C. The reaction mixture was filtered and the filtrate was acidified with HCl (conc.). The resulting precipitate was filtered off, stirred in DIPE, filtered off and dried, yielding 5.75 g (65%) of intermediate 38.

b) Preparation of benzoic acid, 5-hydroxy-2-nitro-4-(phenylmethoxy), methyl ester (intermediate 39)

A mixture of intermediate 38 (0.020 mol) in thionylchloride (50 ml) was stirred and refluxed for 2 hours and the solvent was evaporated under reduced pressure. The residue was quenched with methanol (50 ml) and the mixture was stirred over the weekend. The solvent was evaporated and then co-evaporated with toluene, yielding intermediate 39.

c) Preparation of benzoic acid, 5-(acetyloxy)-2-nitro-4-(phenylmethoxy)-, methyl ester (intermediate 40)

A mixture of intermediate 39 (0.020 mol) in acetic anhydride (40 ml) and pyridine (6 ml) was heated to 90° C. and the reaction mixture was stirred for 2 hours. The solvent was evaporated under reduced pressure and the residue was filtered over silica gel (eluent: DCM). The product fractions were collected and the solvent was evaporated, yielding 5.4 g (78%) of intermediate 40.

d) Preparation of benzoic acid; 5-(acetyloxy)-2-amino-4-(phenylmethoxy)-, methyl ester (intermediate 41)

A mixture of intermediate 40 (0.015 mol) in THF (100 ml) was hydrogenated with Pt/C 5% (2 g) as a catalyst in the presence of thiophene solution (1 ml) [H178-032]. After uptake of $H_2$ (3 equiv.), the catalyst was filtered off and the filtrate was evaporated, yielding 4.7 g of intermediate 41.

e) Preparation of 4(3H)-quinazolinone, 6-hydroxy-7-(phenylmethoxy)- (intermediate 42)

A mixture of intermediate 41 (0.015 mol) and ammonium and formic acid (0.0225 mol) in formamide (50 ml) was heated to 150° C. and the reaction mixture was stirred for 4 hours, then the mixture was allowed to reach RT and poured out into ice-water. The resulting precipitate was filtered off, washed with $H_2O$ and dried (vac.) at 60° C., yielding 2.9 g (72.5%) of intermediate 42.

f) Preparation of 4(3H)-quinazolinone, 6-(acetyloxy)-7-(phenylmethoxy)- (intermediate 43)

A mixture of intermediate 42 (0.011 mol) in monoacetate 1,1-1,1-ethenediol (12 ml) and pyridine (2 ml) was heated to 90° C. and the reaction mixture was stirred for 3 hours, then the mixture was poured out into ice-water. The resulting precipitate was filtered off, washed and dried, yielding 3.3 g of (97%) of intermediate 43.

g) Preparation of 6-quinazolinol, 4-chloro-7-(phenylmethoxy)-, acetate (ester) (intermediate 44)

A solution of intermediate 43 (0.0032 mol) and N,N-dimethylformamide (cat. quant.) in thionyl chloride (30 ml) was stirred and refluxed for 6 hours and then the solvent was evaporated under reduced pressure and co-evaporated with toluene. The residue was dissolved in DCM and washed with NaHCO$_3$. The organic layer was separated, dried (MgSO$_4$), filtered off and the solvent was evaporated. The residue was used as such in the next reaction step, yielding 0.6 g (60 to) of intermediate 44.

h) Preparation of 1-hexanol, 6-(4-bromo-2-nitrophenoxy)-, acetate (ester) (intermediate 44a)

A stirring solution of 4-bromo-2-nitrophenol (0.115 mol) in DMA (250 ml) was heated at 40° C., then K$_2$CO$_3$ (0.1-15 mol) was added and the reaction mixture was stirred for 15 min. 6-bromo-1-hexanol, acetate (0.115 mol) was added and the mixture was stirred overnight at 40° C. Extra 6-bromo-1-hexanol, acetate (4 g) was added, then the resulting mixture was stirred for 2 hours, cooled to RT and stirred overnight. The mixture was filtered off and the filtrate was poured out into ice-water (2000 ml) and then extracted with EtOAc. The organic layer was separated, dried (MgSO$_4$), filtered off and the solvent was evaporated under reduced pressure, yielding 39.6 g of intermediate 44a.

i) Preparation of 1-hexanol, 6-(2-amino-4-bromophenoxy)-, acetate (ester) (intermediate 45)

A mixture of intermediate 44a (0.105 mol) in THF (250 ml) was hydrogenated with Pt/C 5% (3 g) as a catalyst in the presence of thiophene solution (3 ml). After uptake of H$_2$ (3 equiv.), the catalyst was filtered off and the filtrate was evaporated under reduced pressure. The residue was dissolved in DIPE and converted into the hydrochloric acid salt (1:1) with HCl (20 ml, 6N in 2-propanol). The resulting precipitate was filtered off, washed and dried, yielding 36.91 g (96%) of intermediate 45.

j) Preparation of 6-quinazolinol, 4-[[2-[[6-(acetyloxy)hexyl]oxy]-5-bromophenyl]amino]-7-(phenylmethoxy)-, acetate (ester) (intermediate 46)

A mixture of intermediate 44 (0.0031 mol) and intermediate 45 (0.0031 mol) in 2-propanol (50 ml) was heated to 80° C. and the reaction mixture was stirred for 6 hours, then the mixture was allowed to reach RT and stirred overnight. Finally, the solvent was evaporated under reduced pressure, yielding 1.9 g of intermediate 46.

k) Preparation of 6-quinazolinol, 4-[[5-bromo-2-[(6-hydroxyhexyl)oxy]phenyl]amino]-7-(phenylmethoxy)- (intermediate 47)

A solution of intermediate 46 (0.0031 mol) in methanol (25 ml) was heated to 60° C. and a solution of K$_2$CO$_3$ (0.0062 mol) in H$_2$O (2.5 ml) was added, then the reaction mixture was stirred for 18 hours. Extra K$_2$CO$_3$ (0.0031 mol) was added and the mixture was stirred for 3 hours at 60° C. The organic solvent (CH$_3$OH) was evaporated under reduced pressure and the aqueous concentrate was treated with acetic acid. The resulting precipitate was filtered off, washed and dried (vac.) at 60° C., yielding 1.4 g (84%) of intermediate 47.

Example A11 a) Preparation of 6-quinazolinol, 4-[[2-[[6-(acetyloxy)hexyl]oxy]-5-bromophenyl]amino]-, acetate (ester) (intermediate 48)

A mixture of intermediate 45 (0.0045 mol) and 4-chloro-6-quinazolinol acetate (ester) (0.0045 mol) in 2-propanol (50 ml) was heated to 80° C. and the reaction mixture was stirred for 2.5 hours. The solvent was evaporated under reduced pressure and the residue was used as such in the next reaction step, yielding intermediate 48.

b) Preparation of 6-quinazolinol, 4-[[5-bromo-2-[(6-hydroxyhexyl)oxy]phenyl]amino]- (intermediate 49)

A mixture of intermediate 48 (0.0045 mol) and K$_2$CO$_3$ (0.0135 mol) in H$_2$O (2.5 ml) and methanol (25 ml) was stirred at 60° C. for 16 hours and the organic solvent was evaporated, then the aqueous concentrate was extracted with CH$_3$OH/DCM. The organic layer was separated, dried (MgSO$_4$), filtered off and the solvent was evaporated. The residue was dried (vac.) at 60° C. and used as such in the next reaction step, yielding intermediate 49.

Example A12 a) Preparation of 1-pentanol, 5-[[(4-bromo-2-nitrophenyl)methyl]amino]- (intermediate 50)

A solution of 4-bromo-2-nitro-benzaldehyde, (0.013 mol), 5-amino-1-pentanol (0.013 mol) and titanium, tetrakis (2-propanolato) (0.014 mol) in EtOH (15 ml) was stirred at RT for 1 hour, then the reaction mixture was heated to 50° C. and stirred for 30 min. The mixture was cooled to RT and NaBH$_4$ (0.013 mol) was added, portionwise. The reaction mixture was stirred overnight and then poured out into ice-water (50 ml). The resulting mixture was stirred for 20 min., the formed precipitate was filtered off (giving Filtrate (I)), washed with H$_2$O and stirred in DCM (to dissolve the product and to remove it from the Ti-salt). The mixture was filtered and then the filtrate was dried (MgSO$_4$) and filtered, finally the solvent was evaporated. Filtrate (I) was evaporated until EtOH was removed and the aqueous concentrate was extracted 2 times with DCM. The organic layer was separated, dried MgSO$_4$), filtered off and the solvent was evaporated, yielding 3.8 g (93%) of intermediate 50.

b) Preparation of carbamic acid, [(4-bromo-2-nitrophenyl)methyl](5-hydroxypentyl)-, 1,1-dimethylethyl ester (intermediate 51)

A solution of intermediate 50 (0.0032 mol) in DMC (20 ml) was stirred at RT and a solution of dicarbonic acid, bis(1,1-dimethylethyl)ester (0.0032 mol) in DMC (5 ml) was added dropwise. The reaction mixture was stirred for 1 hour at RT and washed 2 times with H$_2$O. The organic layer was separated, dried (MgSO$_4$), filtered off and the solvent was evaporated, yielding intermediate 51.

c) Preparation of carbamic acid, [5-(acetyloxy)pentyl][(4-bromo-2-nitrophenyl)methyl]-, 1,1-dimethylethyl ester (intermediate 52)

A solution of intermediate 51 (0.0032 mol) and pyridine (0.032 mol) in acetic anhydride (15 ml) was stirred at RT for 16 hours, then the solvent was evaporated under reduced pressure and co-evaporated with toluene. The residue was used as such in the next reaction step, yielding 1.47 g (100%) of intermediate 52.

d) Preparation of carbamic acid, [5-(acetyloxy)pentyl][(2-amino-4-bromophenyl)methyl]-1,1-dimethylethyl ester (intermediate 53)

A mixture of intermediate 52 (0.0033 mol) in THF (50 ml) was hydrogenated with Pt/C 5% (0.5 g) as a catalyst in the presence of thiophene solution (0.5 ml) [H179-007]. After uptake of $H_2$ (3 equiv.), the catalyst was filtered off and the filtrate was evaporated, yielding intermediate 53.

e) Preparation of carbamic acid, [[2-[[6-(acetyloxy)-7-methoxy-4-quinazolinyl]amino]-4-bromophenyl]methyl][5-(acetyloxy)pentyl]-, 1,1-dimethylethyl ester (intermediate 54)

A mixture of intermediate 53 (0.0028 mol) and 4-chloro-7-methoxy-, acetate 6-quinazolinol (ester) (0.0028 mol) in 2-propanol (50 ml) was heated to 60° C. and the reaction mixture was stirred for 1 hour. The solvent was evaporated under reduced pressure and the residue was used as such in the next reaction step, yielding intermediate 54.

f) Preparation of carbamic acid, [[4-bromo-2-[(6-hydroxy-7-methoxy-4-quinazolinyl)amino]phenyl]methyl](5-hydroxypentyl)-, 1,1-dimethylethyl ester (intermediate 55)

A solution of intermediate 54 (0.0028 mol) in methanol (50 ml) was stirred at RT and a solution of $K_2CO_3$ (0.0056 mol) in $H_2O$ (5 ml) was added, then the reaction mixture was heated to 60° C. and stirred for 18 hours. The organic solvent was removed and the aqueous concentrate was acidified with acetic acid. The resulting precipitate was filtered off, dissolved in DCM, dried ($MgSO_4$), filtered and the solvent was evaporated, yielding 1.2 g of intermediate-55.

Example A13 a) Preparation of 6-heptenoic acid, 7-(4-bromo-2-nitrophenyl)-, (6E)- (intermediate 56)

A mixture of NaH, 60% (0.026 mol, free from mineral oil) in DMSO, dry (15 ml) was heated to 65° C. and the mixture was stirred for 1.5 hour (until the generation of $H_2$ stopped), then the suspension (dark green) was cooled to 15° C. and a solution of 5-carboxypentyltriphenylphosponium bromide (0.013 mol) in DMSO (10 ml) was added dropwise. The resulting solution (red) was stirred at RT for 10 min. and a solution of 4-bromo-2-nitro-benzaldehyde (0.013 mol; 4-Bromo-2-nitrobenzaldehyde) in DMSO, dry (8 ml) was added rapidly. The solution (dark brown) was stirred for 105 min. and quenched with $H_2O/Et_2O$ (2575, 100 ml). The $Et_2O$-layer was removed and the aqueous layer was extracted 2 times with ethylacetate, then acidified (pH: 1-2) with HCl (37%) and extracted again with ethylacetate. The organic layer was separated, dried ($MgSO_4$), filtered off and the solvent was evaporated, yielding intermediate 56.

b) Preparation of 6-heptenoic acid, 7-(4-bromo-2-nitrophenyl)-, methyl ester, (6E)- (intermediate 57)

A solution of intermediate 56 (0.013 mol) in concentrated HCl (0.20 ml) and methanol (10 ml) was stirred overnight at RT and then the solvent was evaporated under reduced pressure. The residue was dissolved in DCM and washed with a $NaHCO_3$ soln. The organic layer was separated, dried ($MgSO_4$), filtered off and the solvent was evaporated. The residue was filtered over silica gel (eluent: DCM); the product fractions were collected and the solvent was evaporated, yielding 0.800 g of intermediate 57.

c) Preparation of benzeneheptanoic acid, 2-amino-4-bromo-, methyl ester (intermediate 58)

A mixture of intermediate 57 (0.0023 mol) in THF (50 ml) was hydrogenated with 5% concentrated Pt/C 5% (0.5 g) as a catalyst in the presence of thiophene solution (0.5 ml) [H179-035]. After uptake of $H_2$ (4 equiv.), the catalyst was filtered off and the filtrate was evaporated, yielding 0.72 g of intermediate 58.

d) Preparation of benzeneheptanoic acid, 2-[[6-(acetyloxy)-7-methoxy-4-quinazolinyl]amino]-4-bromo-, methyl ester (intermediate 59)

A mixture of intermediate 58 (0.0023 mol) and 4-chloro-7-methoxy-6-quinazolinol acetate (ester) (0.0023 mol) in 2-propanol (40 ml) was heated to 80° C. and stirred for 4 hours, then the solvent was evaporated under reduced pressure. The residue was stirred in $CH_3OH/DIPE$ (1/9); the resulting precipitate was filtered off, washed with DIPE and dried (vac.) it 60° C., yielding 0.55 g of intermediate 59.

e) Preparation of 6-quinazolinol, 4-[[5-bromo-2-(7-hydroxyheptyl)phenyl]amino]-7-methoxy- (intermediate 60)

A mixture of LAH (0.005 mol) in 2-propanol (20 ml) was stirred at RT. A solution of intermediate 59 (0.001 mol) in 2-propanol (30 ml) was added dropwise, then the reaction mixture was stirred overnight. Ethylacetate. (20 ml) was added and the excess of 4-chloro-7-methoxy-6-quinazolinol acetate (ester) was decomposed with a 10% HCl soln. (5 ml). The organic layer was separated, dried ($MgSO_4$), filtered off and the solvent was evaporated. The residue was used as such in the next reaction step, yielding intermediate 60.

Example A14 a) Preparation of 1-pentanol, 5-[[(4-bromo-2-nitrophenyl)methyl]methylamino]- (intermediate 61)

A solution of intermediate 50 (0.0047 mol), formaldehyde (0.025 mol) and titanium, tetrakis (2-propanolato) (0.0051 mol) in EtOH (150 ml) was heated to 50° C. and stirred for 1 hour, then $NaBH_4$ (0.026 mol) was added portionwise at RT. The reaction mixture was stirred overnight and then quenched with water (100 ml). The resulting mixture was stirred for 1 hour; the formed precipitate was filtered off and washed. The organic filtrate was concentrated, then the aqueous concentrate was extracted with DCM and dried. The solvent was evaporated and the residue was filtered over silica gel (eluent: $DCM/CH_3OH$ from 98/2 to 95/5). The product fractions were collected and the solvent was evaporated, yielding 0.5 g of intermediate 61.

b) Preparation of 1-pentanol, 5-[[(4-bromo-2-nitrophenyl)methyl]methylamino]-, acetate (ester) (intermediate 62)

A solution of intermediate 61 (0.0015 mol) and pyridine (0.015 mol) in acetic anhydride (8 ml) was stirred overnight at RT, then the solvent was evaporated and co-evaporated with toluene, yielding intermediate 62.

c) Preparation of 1-pentanol, 5-[[(2-amino-4-bromophenyl)methyl]methylamino]-, acetate (ester) (intermediate 63)

A mixture of intermediate 62 (0.0015 mol) in THF (50 ml) was hydrogenated with Pt/C 5% (0.5 g) as a catalyst in the presence of thiophene solution (0.5 ml) [H179-034]. After uptake of $H_2$ (3 equiv.), the catalyst was filtered off and the filtrate was evaporated, yielding 0.5 g of intermediate. 63.

d) Preparation of 6-quinazolinol, 4-[[2-[[[5-(acetyloxy)pentyl]methylamino]methyl]-5-bromophenyl]amino]-7-methoxy-, acetate (ester) (intermediate 64)

A mixture of intermediate 63 (0.0015 mol) and 4-chloro-7-methoxy-6-quinazolinol acetate (ester) (0.0015 mol) in 2-propanol (30 ml) was heated to 80° C. and the reaction mixture was stirred for 1 day. The solvent was evaporated under reduced pressure and the residue was used as such in the next reaction step, yielding 0.83 g of intermediate 64.

e) Preparation of 6-quinazolinol, 4-[[5-bromo-2-[[(5-hydroxypentyl)methylamino]methyl]phenyl]amino]-7-methoxy- (intermediate 65)

A solution of intermediate 64 (0.0015 mol) in methanol (25 ml) was stirred at RT and a solution of $K_2CO_3$ (0.003 mol) in $H_2O$ (2.5 ml) was added, then the reaction mixture was heated to 60° C. and stirred for 18 hours. The solvent was evaporated and $H_2O$ (20 ml) was added, then the mixture was neutralised with acetic acid and the formed precipitate was filtered off. The filtrate was concentrated under reduced pressure and the concentrate was extracted with DCM, filtered, then dried ($MgSO_4$) and the mixture was concentrated under reduced pressure, yielding 0.5 g (70%) of intermediate 65.

Example A15 a) Preparation of methanesulfonic acid, trifluoro-, 2-(4-chloro-2-nitrophenyl)ethyl ester (intermediate 66)

A mixture of 2-(4-chloro-2-nitrophenyl)-ethanol (0.01 mol) and 2,6-di-tert-butylpyridine (0.012 mol) in nitromethane (30 ml) was stirred under $N_2$ at 0° C. and a mixture of trifluoromethylsulfonic anhydride (0.011 mol) in nitromethane (10 ml) was added dropwise at 0° C., then the reaction mixture was allowed to reach RT and stirred for 1 hour, yielding intermediate 66.

b) Preparation of 1-butanol, 4-[2-(4-chloro-2-nitrophenyl)ethoxy]-, acetate (ester) (intermediate 67)

A mixture of 1-acetoxy-4-hydroxybutane (0.01 mol) in nitromethane (10 ml) was added dropwise to intermediate 66 and then the reaction mixture was stirred for 1 hour at 65° C. The mixture was cooled and water was added. The layers were separated and the aqueous layer was extracted 2 times with DCM. The organic layers was separated, dried ($MgSO_4$), filtered-off and the solvent was evaporated. The residue was purified 2 times by column chromatography over silica gel (eluent 1: DCM; eluent 2: hexane/EtOAc 90/10). The product fractions were collected and the solvent evaporated, yielding 0.800 g (25%) of intermediate 67.

c) Preparation of 1-butanol, 4-[2-<2-amino-4-chlorophenyl)ethoxy]-, acetate (ester) (intermediate 68)

A mixture intermediate 67 in dioxane (40 ml) was hydrogenated at 40° C. with Pt/C (0.300 g) as a catalyst in the presence of thiophene solution (0.3 ml). After uptake of $H_2$ (3 equiv.), the catalyst was filtered off and the filtrate was evaporated, yielding intermediate 68.

d) Preparation of 6-quinazolinol, 4-[[2-[2-[4-(acetyloxy)butoxy]ethyl]-5-chlorophenyl]amino]-7-methoxy-, acetate (ester) (intermediate 69)

A mixture 4-chloro-6-acetoxy-7-methoxyquinazoline (0.00040 mol) and intermediate 68 (0.00035 mol) in dioxane (q.s.) was stirred for 3 hours at 80° C. and then the solvent was evaporated, yielding intermediate 69.

e) Preparation of 6-quinazolinol, 4-[[5-chloro-2-[2-(4-hydroxybutoxy)ethyl]phenyl]amino]-7-methoxy- (intermediate 70)

A mixture of intermediate 69 (residue) and $K_2CO_3$ (0.0144 mol) in $H_2O$ (25 ml) and EtOH (25 ml) was stirred over the weekend at RT, then $H_2O$ (150 ml) was added and the reaction mixture was extracted 3 times with DCM. The organic layer was separated, dried ($MgSO_4$), filtered off and the solvent was evaporated. The residue (0.900 g) was purified by HPLC. The product fractions were collected and the solvent was evaporated, yielding 0.300 g of intermediate-70.

Example A16 a) Preparation of benzaldehyde, 4-chloro-2-nitro-, oxime (intermediate 71)

A mixture of 4-chloro-2-nitrobenzaldehyde (0.01077 mol) and hydroxylamine hydrochloride (1:1) (0.01184 mol) in pyridine (20 ml) was heated on an oil bath for 2 hours at 80° C. and then the solvent was evaporated under reduced pressure. The residue was taken up in $CH_3OH$/DCM (10/90) and the resulting mixture was extracted with 1N HCl and then washed with a $NaHCO_3$ solution and water. The organic layer was separated, dried ($MgSO_4$), filtered off and the solvent was evaporated under reduced pressure. The residue was dried (vacuum) at 50° C., yielding 1.75 g (81%) of intermediate 71.

b) Preparation of benzaldehyde, 4-chloro-2-nitro-, 0-[8-(acetyloxy)octyl]oxime (intermediate 72)

$K_2CO_3$ (0.00887 mol) was added under heavy stirring to a solution of intermediate 71 (0.00887 mol) in DMSO (25 ml), then 8-bromooctyl acetate (0.00887 mol) was added and the reaction mixture was stirred for 4 hours at RT. The mixture was heated for 1 hour on an oil bath at 50-60° C. and then extra 8-bromooctyl acetate. (0.669 g) and $K_2CO_3$ (0.369 g) were added. The reaction mixture was stirred for 4 hours at 50-60° C. and cooled. The mixture was poured out into $H_2O$/$NH_4Cl$ and extracted with EtOAc. The EtOAc-layer was dried ($MgSO_4$), filtered off and the solvent was evaporated (vac.). The residual oil (4 g) was purified by column chromatography over silica gel (eluent: DCM/Hexane 70/30, 80/20, 100/0). The pure product fractions were collected and the solvent was evaporated under reduced pressure, yielding 1.34 g of intermediate 72.

c) Preparation of benzaldehyde, 2-amino-4-chloro-, O-[8-(acetyloxy)octyl]oxime (intermediate 73)

A mixture of intermediate 72 (0.0036 mol) in THF (100 ml) was hydrogenated overnight under $H_2$ at RT with Pt/C 5% (0.5 g) as a catalyst in the presence of thiophene-solution. (1 ml) and then the reaction mixture was heated overnight at 50° C. After uptake of $H_2$, the mixture was filtered and the filtrate was evaporated. The residue was taken up in THF (100 ml) and the reaction mixture was hydrogenated overnight at 50° C. with Pt/C 5% (0.3 g) as a catalyst in the presence of thiophene solution. (0.1 ml). This mixture in THF (100 ml) was hydrogenated further overnight at RT with Pt/C 5% (0.5 g) as a catalyst. After uptake of $H_2$ (3 equiv.), the catalyst was filtered off and the filtrate was evaporated, yielding intermediate 73.

d) Preparation of benzaldehyde, 2-[[6-(acetyloxy)-7-methoxy-4-quinazolinyl]amino]-4-chloro-, O-[8-(acetyloxy)octyl]oxime (intermediate 74)

A mixture of 4-chloro-6-acetoxy-7-methoxyquinazoline (0.0021 mol) and intermediate 73 (0.0022 mol) in 2-propanol, p.a. (30 ml) was heated for 1 hour on an oil bath at 80° C. and then the solvent was evaporated. The residue was purified by column chromatography over silica gel (eluent: DCM/ $CH_3OH$ 99.5/0.5 to gradient with $CH_3OH$). The pure fractions were collected and the solvent was evaporated, yielding 0.300 g of intermediate 74.

e) Preparation of benzaldehyde, 4-chloro-2-[(6-hydroxy-7-methoxy-4-quinazolinyl)amino]-, O-(8-hydroxyoctyl)oxime (intermediate 75)

A mixture of intermediate 74 (0.00026 mol) in $CH_3OH$ (10 ml) was treated with a mixture of $K_2CO_3$ (0.0011 mol) in $H_2O$ (1 ml) and then the reaction mixture was stirred overnight at RT. The organic solvent ($CH_3OH$) was evaporated and the aqueous concentrate was diluted with $H_2O$ (30 ml). The resulting mixture was acidified with acetic acid until pH: 4-5, then the mixture was stirred for 1 hour and filtered. The obtained solid was washed with $CH_3OH$ (5 ml) and dried in a vacuum oven at 60° C., yielding 0.199 g (78%) of intermediate 75.

Example A17 a) Preparation of 1-octanol, 8-(3-nitrophenoxy)-, acetate (ester) (intermediate 76)

A mixture of 3-nitrophenol (0.0144 mol) and $K_2CO_3$ (0.0144 mol) in 2-propanone (20 ml) was stirred for 2.5 hours at RT and then 8-bromooctyl acetate (0.0144 mol) was added. The reaction mixture was stirred for 3 hours at RT and was then stirred and refluxed for 18 hours. Extra 8-bromooctyl acetate (0.004 mol) was added and then the resulting mixture was stirred and refluxed for 18 hours. The mixture was cooled to RT, filtered and the filter residue was washed with 2-propanone. The filtrates were combined and concentrated under reduced pressure. The concentrate was then purified by column chromatography (eluent: Hexane/EtOAc 85/15). The product fractions were collected and the solvent was evaporated, yielding intermediate 76.

b) Preparation of 1-octanol, 8-(3-aminophenoxy)-, acetate (ester) (intermediate 77)

A mixture of intermediate 76 (9.0123 mol) in THF (50 ml), was hydrogenated at 50° C. with Pt/C 5% (2 g) as a catalyst in the presence of thiophene solution. (1 ml). After uptake of $H_2$ (3 equiv.), the catalyst was filtered off and the filtrate was evaporated, yielding 3.6 g of intermediate 77.

c) Preparation of 6-quinazolinol, 4-[[3-[[8-(acetyloxy)octyl]oxy]phenyl]amino]-7-methoxy-, acetate (ester) (intermediate 78)

A mixture of intermediate 77 (0.0123 mol) and 4-chloro-6-acetoxy-7-methoxyquinazoline (0.0123 mol) in 2-propanol (50 ml) was heated at 85° C. until complete dissolution and then the reaction mixture was cooled to RT. The resulting precipitate was filtered off, washed with DIPE and dried (vacuum), yielding 5.33 g (88%) of intermediate 78.

d) Preparation of 6-quinazolinol, 4-[[3-[(8-hydroxyoctyl)oxy]phenyl]amino]-7-methoxy- (intermediate 79)

A mixture of intermediate 78 (0.00404 mol) and $K_2CO_3$ (0.00807 mol) in $H_2O$ (8 ml) and $CH_3OH$ (80 ml) was heated at 65° C. for 18 hours and then the organic solvent was evaporated under reduced pressure. The residue was diluted with $H_2O$ and the resulting mixture was acidified with 1N HCl to pH: 4. The precipitate was filtered off and dried (vacuum), yielding 1.5 g (90%) of intermediate 79.

Example A18 a) Preparation of 2-propenamide, 3-(4-chloro-2-nitrophenyl)-N-(3-hydroxypropyl)-, (intermediate 80)

1,1'-carbonylbis-1H-imidazole (0.009 mol) was added to a mixture of 4-chloro-2-nitro-cinnamic acid (0.006 mol) in THF (100 ml) at RT and the resulting mixture was stirred for 2 hours at RT, giving Mixture (I). Mixture (I) was added portionwise to a mixture of 3-amino-1-propanol (0.06 mol) in THF (100 ml) and the reaction mixture was stirred for 2 hours at RT. The solvent was evaporated and the residue was taken up in water (100 ml). The aqueous layer was extracted with DCM (3 times-100 ml), then the organic layers were combined, dried and filtered. The solvent was evaporated under reduced pressure (several co-evaporations with toluene were required). The residue was stirred overnight in toluene at RT and the resulting precipitate was filtered off, then purified by column chromatography over silica gel (eluent: DCM/ $CH_3OH$ 100/0 to 97/3). The product fractions were collected and the solvent was evaporated, yielding 1 g (59%) of intermediate 80.

b) Preparation of 2-propenamide, N-[3-(acetyloxy)propyl]-3-(4-chloro-2-nitrophenyl)- (intermediate 81)

Pyridine (0.035 mol) was added dropwise to a mixture of intermediate 80 (0.0035 mol) in acetic anhydride (20 ml) at RT and then the reaction mixture was stirred for 1 hour at RT. Finally, the solvent was evaporated under reduced pressure, yielding 1.1 g (100%) of intermediate 81.

c) Preparation of benzenepropanamide, N-[3-(acetyloxy)propyl]-2-amino-4-chloro- (intermediate 82)

A mixture of intermediate 81 (0.0033 mol) in THF (50 ml) was hydrogenated at RT for 10 days with Pt/C 5% (0.5 g) as a catalyst in the presence of thiophene solution (0.5 ml). After uptake of $H_2$ (4 equiv.), the catalyst was filtered off and the filtrate was evaporated under reduced pressure. The residue was purified by column chromatography over silica gel (eluent: DCM/$CH_3OH$ 99.5/0.5 to 95/5). The product, fractions were collected and the solvent was evaporated under reduced pressure, yielding 0.8 g (81%) of intermediate 82.

d) Preparation of benzenepropanamide, 2-[[6-(acetyloxy)-7-methoxy-4-quinazolinyl]amino]-N-[3-(acetyloxy)propyl]-4-chloro- (intermediate 83)

A mixture of intermediate 82 (0.0027 mol) and 4-chloro-6-acetoxy-7-methoxyquinazoline (0.0027 mol) in 2-propanol (50 ml) was stirred and refluxed for 2 hours and then the solvent was evaporated under reduced pressure. The residue was purified by column chromatography over silica gel (eluent: DCM/CH$_3$OH 99/1 to 90/10). The product fractions were collected and the solvent was evaporated under reduced pressure, yielding 0.91 g (65%) of intermediate 83.

e) Preparation of benzenepropanamide, 4-chloro-2-[(6-hydroxy-7-methoxy-4-quinazolinyl)amino]-N-(3-hydroxypropyl)- (intermediate 84)

A mixture of intermediate 83 (0.0017 mol) and potassium carbonate (0.0072 mol) in methanol (20 ml) and water (2 ml) was stirred for 1 hour at RT and then the solvent was evaporated under reduced pressure. The residue was taken up in water and the aqueous layer was acidified with acetic acid. The resulting precipitate was filtered off and dried, yielding 0.46 g (63%) of intermediate 84.

Example A19 a) Preparation of 6-quinazolinol, 4-chloro-7-methoxy-, acetate (ester) (intermediate 85)

A mixture of 6-(acetyloxy)-7-methoxy-4(1H)-quinazolinone (0.23 mol) and DMF (1 ml) in thionyl chloride (500 ml) was stirred and refluxed for 5 hours and then the reaction mixture was cooled to RT. The solvent was evaporated under reduced pressure and then co-evaporated with toluene. The residue was dissolved in DCM and washed with a saturated aqueous NaHCO$_3$ solution. The organic layer was separated, dried (MgSO$_4$), filtered off and the solvent was evaporated under reduced pressure. The residue was stirred in DIPE and then the resulting precipitate was filtered off, yielding 55.4 g (95%) of intermediate 85.

b) Preparation of 6-quinazolinol, 4-[(4-chloro-2-hydroxyphenyl)amino]-7-methoxy-6-acetate monohydrochloric acid (intermediate 86)

A mixture of intermediate 85 (0.00696 mol) and 2-amino-5-chloro-phenol (0.00696 mol) in 2-propanol (100 ml) was heated under stirring for 4 hours at 85° C. and the reaction mixture was cooled to RT, then the resulting precipitate was filtered off, yielding intermediate 86, isolated as a monohydrochloric acid.

c) Preparation of 6-quinazolinol, 4-[[4-chloro-2-[(6-hydroxyhexyl)oxy]phenyl]amino]-7-methoxy-, 6-acetate (intermediate 87)

A solution of intermediate 86 (0.00076 mol) in DMA (20 ml) was stirred at RT and sodium hydride (0.00091 mol) was added portionwise, then the mixture was stirred for 30 min. and a solution of 6-bromo-1-hexanol (0.00091 mol) in DMA (2 ml) was added dropwise. The reaction mixture was stirred overnight at RT and an aqueous NH$_4$Cl solution (1 ml) was added. The reaction mixture was poured out into ice water and the solvent was evaporated. The residue was purified by HPLC and then the product fractions were collected and the solvent was evaporated, yielding 0.030 g of intermediate 87.

Example A20

Preparation of boronic acid, (8,9,10,11,12,13-hexahydro-26-methoxy-4,6-ethanediylidene-19H-pyrimido[4,5-b][6,13,1]benzodioxaazacyclopentadecin-17-yl)- (intermediate 88)

A mixture of compound 6(0.0006 mol), 4,4,4',4',5,5,5',5'-octamethyl-2,2'-bi-1,3,2-dioxaborolane (0.00066 mol), dichloro[1,1'-bis(diphenylphosphino)ferrocene]palladium (0.024 g), potassium acetate (0.00092 mol) and [1,1'-biphenyl]-2-yldicyclohexyl-phosphine (0.024 g) in DMSO (5 ml) was stirred at 80° C. for 2 hours, then the reaction mixture was poured out into ice-water and was stirred for 1 hour. The resulting precipitate was filtered off and then purified by column chromatography (eluent: DCM/CH$_3$OH from 98/2 to 90/10). The pure fractions were collected and the solvent was evaporated, yielding 0.080 g (33%) of intermediate 88.

Example A21 a) Preparation of 1-pentanol, 5-[[(4-chloro-5-fluoro-2-nitrophenyl)methyl]amino](intermediate 89)

A solution of 4-chloro-5-fluoro-2-nitro-benzaldehyde (0.0098 mol), pentanolamine (0.0098 mol) and tetrakis (2-propanolato) titanium, (0.011 mol) EtOH (10 ml) was stirred for 1 hour at RT and sodium hydroborate (0.615-mol) was added portionwise, then the reaction mixture was stirred overnight at RT and H$_2$O was added. The mixture was stirred for 15 min. and the precipitate was filtered off. The filtrate was evaporated and then the residue was dissolved in DCM and washed with H$_2$O. The organic layer was separated, dried (MgSO$_4$), filtered off and the solvent was evaporated. The residue was purified by column chromatography over silica gel. The product fractions were collected and the solvent was evaporated, yielding 2.3 g (48%) of intermediate 89.

b) Preparation of carbamic acid, [5-(acetyloxy)pentyl][(4-chloro-5-fluoro-2-nitrophenyl)methyl]-, 1,1-dimethylethyl ester (intermediate 90)

A solution of intermediate 89 (0.0079 mol) in DCM (20 ml) was treated for 30 min. with a solution of tert-butoxycarbonyl anhydride (0.082 mol) in DCM (20 ml) and then the reaction mixture was washed with H$_2$O (2×20 ml). The organic layer was separated, dried (MgSO$_4$), filtered off and the solvent was evaporated. The residue was dissolved in acetic anhydride (30 ml) and then the solution was treated with pyridine (5 ml) and stirred over the weekend. The solvent was evaporated and co-evaporated with toluene. The residue was purified by column chromatography over silica gel (eluent: DCM). The product fractions were collected and the solvent was evaporated, yielding 1.4 g (40.9%) of intermediate 90.

c) Preparation of carbamic acid, [5-(acetyloxy)pentyl][(2-amino-4-chloro-5-fluorophenyl)methyl]-, 1,1-dimethylethyl ester (intermediate 91)

A mixture of intermediate 90 (0.0016 mol); Fe (0.009 mol) and NH$_4$Cl (0.016 mol) in toluene (40 ml), CH$_3$OH (40 ml)

d) Preparation of carbamic acid, [[2-[[6-(acetyloxy)-7-methoxy-4-quinazolinyl]amino]-4-chloro-5-fluorophenyl]methyl][5-(acetyloxy)pentyl]-, 1,1-dimethylethyl ester (intermediate 92)

A mixture of intermediate 91 (0.000379 mol) and 4-chloro-6-acetoxy-7-methoxyquinazoline (0.000379 mol) in 2-propanol (10 ml) was heated on an oil bath for 3-hours at 80° C. and then the solvent was evaporated. The residue was purified by column chromatography over silica gel (gradient eluent: DCM/CH$_3$OH 100/0 to 99/1). The product fractions were collected and the solvent was evaporated, yielding 0.148 g 63%) of intermediate 92.

e) Preparation of carbamic acid, [[4-chloro-5-fluoro-2-[(6-hydroxy-7-methoxy-4-quinazolinyl)amino]phenyl]methyl](5-hydroxypentyl)-, 1,1-dimethylethyl ester (intermediate 93)

A solution of intermediate 92 (0.000239 mol) in CH$_3$OH (10 ml) was treated with a solution of K$_2$CO$_3$ (0.00051 mol) in H$_2$O (1 ml). The reaction mixture was stirred overnight, then the mixture was neutralized with acetic acid and the solvent was evaporated. The residue was diluted with DCM and washed with H$_2$O. The organic layer was separated, dried (MgSO$_4$), filtered off and the solvent was evaporated, yielding 0.120 g (93,7%) of intermediate 93.

Example A22 a) Preparation of 1-butanol, 4-[[2-(4-chloro-2-nitrophenyl)ethyl]amino](intermediate 94)

1-amino-4-butanol (0.0300 mol) was added to a stirred suspension of 2-propanol (30 ml) and molecular sieves (8 g) under N$_2$ at RT and then a mixture of 4-chloro-2-nitro-benzeneacetaldehyde (0.0100 mol) in 2-propanol (10 ml) was added dropwise. The mixture was stirred for 90 min. and sodium cyanotrihydroborate (0.120 mol) was added portionwise (generation of gas). The reaction mixture was stirred overnight and acidified with 6N HCl to pH<2. A saturated aqueous K$_2$CO$_3$ solution was added to pH: 10 and the resulting mixture was filtered over dicalite. The residual fraction was washed with 2-propanol and stirred in hot EtOAc, then this mixture was filtered over dicante and the filtrate was evaporated under reduced pressure. The residue was taken up in EtOAc and the mixture was extracted with 1N HCl (250 ml), then the layers were separated to give an aqueous layer (*) and an organic layer (1).

(*) Aqueous layer was separated, neutralized with K$_2$CO$_3$ and extracted with EtOAc. The organic layer was separated, dried, (MgSO$_4$), filtered off and the solvent was evaporated, under reduced pressure, yielding intermediate 94. (fraction 1).

Organic layer (1) was dried (MgSO$_4$), filtered off and the solvent was evaporated under reduced pressure. The residue was purified by column chromatography over silica gel. The product fractions were collected and the solvent was evaporated yielding intermediate 94. (fraction 2) The product fractions were collected (Yield 100%).

b) Preparation of carbamic acid, [2-(4-chloro-2-nitrophenyl)ethyl](4-hydroxybutyl)-, 1,1-dimethylethyl ester (intermediate 95)

A mixture of intermediate 94 (0.0015 mol) in DCM (10 ml) was stirred at RT and a solution of bis(1,1-dimethylethyl) dicarbonate (0.0015 mol) in DCM (5 ml) was added dropwise, then the reaction mixture was stirred for 1 hour and an extra solution of bis(1,1-dimethylethyl) dicarbonate (0.0015 mol) in DCM (5 ml) was added. The resulting mixture was stirred for 1 hour and washed 2 times with water. The organic layer was separated, dried (MgSO$_4$), filtered off and the solvent was evaporated, yielding 0.56 g of intermediate 95.

c) Preparation of carbamic acid, [4-(acetyloxy)butyl] [2-(4-chloro-2-nitrophenyl)ethyl]-, 1,1-dimethylethyl ester (intermediate 96)

A solution of intermediate 95 (0.0015 mol) and pyridine (0.015 mol) in acetic anhydride (10 ml) was stirred for 18 hours at RT, then the solvent was evaporated under reduced pressure and co-evaporated with toluene. The residue was purified over silica gel (eluent: DCM/CH$_3$OH 100/0 to 98/2). The product fractions were collected and the solvent was evaporated, yielding 0.2 g (33%) of intermediate 96.

d) Preparation of carbamic acid, [4-(acetyloxy)butyl] [2-(2-amino-4-chlorophenyl)ethyl]-, 1,1-dimethylethyl ester (intermediate 97)

A mixture of intermediate 96 (0.0005 mol) in THF (40 ml) was hydrogenated with Pt/C 5% (0.1 g) as a catalyst in the presence of thiophene solution. (0.1 ml). After uptake of H$_2$ (3 equiv.), the catalyst was filtered off and the filtrate was evaporated, yielding (quantitive yield) intermediate 97.

e) Preparation of carbamic acid, [4-(acetyloxy)butyl] [2-[2-[[6-(acetyloxy)-7-methoxy-4-quinazolinyl] amino]-4-chlorophenyl]ethyl]-1-dimethylethyl ester (intermediate 98)

A solution of intermediate 97 (0.0005 mol) and 4-chloro-6-acetoxy-7-methoxyquinazoline (0.0005 mol) in 2-propanol (15 ml) was stirred for 2 hours at 80° C. and then the solvent was evaporated under reduced pressure. The crude residue was purified by Flash column chromatography ever silica gel (eluent: DCM/CH$_{13}$—OH 99.8/0.2 to 96/4). The product fractions were collected and the solvent was evaporated yielding 0.150 g of intermediate 98.

f) Preparation of carbamic acid, [2-[4-chloro-2-[(6-hydroxy-7-methoxy-4-quinazolinyl)amino]phenyl] ethyl](4-hydroxybutyl)-, 1,1-dimethylethyl ester (intermediate 99)

A mixture of intermediate 98 (0.00025 mol) and K$_2$CO$_3$ (0.0005 mol) in methanol (20 ml) and water (2 ml) was heated and stirred for 18 hours at 50° C. and then the solvent was evaporated under reduced pressure. The aqueous layer was neutralised with acetic acid and the product was extracted with DCM. The extract was washed with water, dried (MgSO$_4$) and filtered off and then the filtrate was evaporated, yielding 0.130 g of intermediate 99.

Example A23 a) Preparation of benzene, 4-chloro-1-(3-chloropropoxy)-2-nitro- (intermediate 100)

Potassium carbonate (0.15 mol) was added portionwise to a mixture of 4-chloro-2-nitrophenol (0.1 mol) in 2-propanone (500 ml) at RT. The mixture was stirred and refluxed for 30 min. 1-bromo-3-chloro-propane (0.11 mol) was added dropwise and then the reaction mixture was stirred and refluxed for 45 min. Extra 1-bromo-3-chloro-propane (0.44 mol) was added, followed by potassium iodide (1 g) and then the reaction mixture was stirred and refluxed overnight. The obtained mixture was filtered and the filter residue was washed with 2-propanone. The filtrate was evaporated under reduced pressure and the residue was purified by column chromatography over silica gel (eluent: hexane/EtOAc 80/20). The product fractions were collected and the solvent was evaporated, yielding 17.30 g (69%) of intermediate 100.

b) Preparation of ethanol, 2-[[3-(4-chloro-2-nitrophenoxy)propyl][2-(4-morpholinyl)ethyl]amino]- (intermediate 101)

A mixture of 2-(2-morpholinoethylamino)-ethanol (0.0083 mol), intermediate 100 (0.0085 mol) and sodium carbonate (0.016 mol) in acetonitrile (150 ml) was stirred at reflux temperature for 92 hours and the reaction mixture was filtered off. The filtrate was evaporated under reduced pressure and the residue was purified over silica gel (eluent: DCM/(CH$_3$OH/NH$_3$) 99/1 to 95/5). The product fractions were collected and the solvent was evaporated under reduced pressure, yielding 1.4 g (44%) of intermediate 101.

c) Preparation of ethanol, 2-[[3-(4-chloro-2-nitrophenoxy)propyl][2-(4-morpholinyl)ethyl]amino]-, acetate (ester) (intermediate 102)

Pyridine (0.036 mol) was added to a mixture of intermediate 101 (0.0036 mol) in acetic anhydride (25 ml) at RT and then the reaction mixture Gas stirred for 1 hour at RT. Finally, the solvent was evaporated under reduced pressure, yielding 1.6 g (100%) of intermediate 102.

d) Preparation of ethanol, 2-[[3-(2-amino-4-chlorophenoxy)propyl][2-(4-morpholinyl)ethyl]amino]-, acetate (ester) (intermediate 103)

A mixture of intermediate 102 (0.0037 mol) in THF (50 ml) was hydrogenated at 50° C. with Pt/C 5% (0.5 g) as a catalyst in the presence of thiophene solution (0.5 ml). After uptake of H$_2$ (3 equiv.), the catalyst was filtered off and the filtrate was evaporated under reduced pressure. The residue was purified by column chromatography over silica gel (eluent: DCM/CH$_3$OH 96/4) The product fractions were collected and the solvent was evaporated under reduced pressure, yielding 0.88 g (60%) of intermediate 103.

e) Preparation of 6-quinazolinol, 4-[[2-[3-[[2-(acetyloxy)ethyl][2-(4-morpholinyl)ethyl]amino]propoxy]-5-chlorophenyl]amino]-7-methoxy-, acetate (ester) (intermediate 104)

A mixture of intermediate 103 (0.0021 mol and 4-chloro-6-acetoxy-7-methoxyquinazoline (0.0021 mol) in 2-propanol (100 ml) was stirred at reflux temperature for 4 hours and DIPEA (0.3 ml) was added, then the reaction mixture was stirred and refluxed for 2 hours. Finally, the solvent was evaporated under reduced pressure, to give residue (I). A mixture of residue (I) (max. 0.0021 mol), tris[α-[(1,2-α:4,5-α)-(1E,4E)-1,5-diphenyl-1,4-pentadien-3-one]]di-palladium (=Pd$_2$(DBA)$_3$) (0.00013 mol), [1,1'-binaphthalene]-2,2'-diylbis[diphenyl-phosphine] (=BINAP) (0.00026 mol) and calcium oxide (0.021 mol) in dioxane (40 ml) was stirred in a sealed tube at 130° C. for 16 hours and then the reaction mixture was filtered over dicalite. The filtrate was evaporated under reduced pressure and the residue was purified by column chromatography over silica gel (eluent: DCM/CH$_3$OH 98/2 to 90/10). The product fractions were collected and the solvent was evaporated under reduced pressure, yielding 0.480 g (37%) of intermediate 104.

f) Preparation of 6-quinazolinol, 4-[[5-chloro-2-[3-[(2-hydroxyethyl)[2-(4-morpholinyl)ethyl]amino]propoxy]phenyl]amino]-7-methoxy- (intermediate 105)

A mixture of intermediate 104 (0.00073 mol) and potassium carbonate (0.0057 mol) in methanol (20 ml) and water (2 ml) was stirred for 16 hours at RT, then the solvent was evaporated under reduced pressure and the residue was taken up in water. The aqueous layer was washed with DCM, acidified with acetic acid until pH: 7 and extracted with DCM. The organic layer was dried (MgSO$_4$), filtered off and the solvent was evaporated, yielding 0.250 g (64%) of intermediate 105.

Example A24 a) Preparation of benzamide, 4-chloro-N-(6-hydroxyhexyl)-2-nitro- (intermediate 106)

1,1'-carbonylbis-1H-imidazole (0.01 mol) was added portionwise to a mixture of 4-chloro-2-nitrobenzoic acid (0.01 mol) in DCM (40 ml) at RT and the mixture was stirred for 1 hour at RT, then 6-hydroxyhexylamine (0.01 mol) was added dropwise at RT and the reaction mixture was stirred for 1 hour at RT. The mixture was washed with water (40 ml) and with. HCl (1N, 40 ml). The organic layer was separated, dried, filtered off and the solvent was evaporated under reduced pressure, yielding 1.7 g (57%) of intermediate 106.

b) Preparation of benzamide, N-[6-(acetyloxy)hexyl]-4-chloro-2-nitro- (intermediate 107)

Pyridine (0.057 mol) was added dropwise to a mixture of intermediate 106 (0.0057 mol) in acetic anhydride (26.7 ml) at RT and then the reaction mixture was stirred for 1 hour at RT. The solvent was evaporated under reduced pressure and the residue was taken up in water, then the mixture was extracted with toluene. The organic layer was separated, dried, filtered off and the solvent was evaporated under reduced pressure, yielding 1.8 g (92%) of intermediate 107.

c) Preparation of benzamide, N-[6-(acetyloxy)hexyl]-2-amino-4-chloro- (intermediate 108)

A mixture of intermediate 107 (0.0053 mol) in THF (40 ml) was hydrogenated at 50° C. with Pt/C (0.5 g) as a catalyst in the presence of thiophene solution (0.5 ml). Then the reaction mixture was filtered off and the filtrate was evaporated under reduced pressure. The residue was hydrogenated again and after uptake of H$_2$ (3 equiv.), the catalyst was filtered off and the filtrate was evaporated under reduced pressure, yielding 1.56 g (94%) of intermediate 108.

d) Preparation of benzamide, N-[6-(acetyloxy)hexyl]-2-[[6-(acetyloxy)-7-methoxy-4-quinazolinyl]amino]-4-chloro- (intermediate 109)

A mixture of intermediate 108 (0.0042 mol) and 4-chloro-6-acetoxy-7-methoxyquinazoline (0.0042 mol) in 2-propanol (100 ml) was stirred at 50° C. for 16 hours and then the solvent was evaporated under reduced pressure. The residue e) Preparation of benzamide, 4-chloro-N-(6-hydroxyhexyl)-2-[(6-hydroxy-7-methoxy-4-quinazolinyl)amino]- (intermediate 110)

Intermediate 109 (0.0023 mol) and potassium carbonate (0.0046 mol) were stirred in water (2 ml) and methanol (20 ml) at 50° C. for 16 hours, then the reaction mixture was concentrated. The residue was acidified with acetic acid and the aqueous layer was extracted with DCM. The organic layer was separated, dried, filtered off and the solvent was evaporated under reduced pressure yielding 0.99 g (97%) of intermediate 110.

Example A25 a) Preparation of carbamic acid, [(4-bromo-2-nitrophenyl)methyl](5-hydroxypentyl)-, phenylmethyl ester (intermediate 111)

Phenylmethyl chloroformate (0.033 mol) was added dropwise to admixture of intermediate 50 (max. 0.022 mol) and triethylamine (0.04 mol) in DCM (100 ml) at RT and then the reaction mixture was stirred for 1 hour at RT. Water (100 ml) was adde and the mixture was stirred for 30 min. at RT. The organic layer was separated, dried, filtered off and the solvent was evaporated under reduced pressure. The residue was purified by column chromatography (eluent: DCM/CH$_3$OH 99.5/0.5). The product fractions were collected and the solvent was evaporated, yielding 6.8 g (68%) of intermediate 111.

b) Preparation of carbamic acid, [(2-amino-4-bromophenyl)methyl](5-hydroxypentyl)-, phenylmethyl ester (intermediate 112)

A mixture of intermediate 111 (0.015 mol) in EtOAc (200 ml) was hydrogenated for 40 hours with Pt/C 5% (2 g) as a catalyst in the presence of thiophene solution (3 ml). After uptake of H$_2$ (3 equiv.), the catalyst was filtered off and the filtrate was evaporated under reduced pressure, yielding 6.3 g of intermediate 112.

c) Preparation of carbamic acid, [[2-[[6-(acetyloxy)-7-methoxy-4-quinazolinyl]amino]-4-bromophenyl]methyl](5-hydroxypentyl)-, phenylmethyl ester HCl (1:1) (intermediate 113)

A solution of 6-acetoxy-4-chloro-7-methoxyquinazoline (0.015 mol) in 2-propanol (q.s.) was added to a solution of intermediate 112 (0.015 mol) in 2-propanol (q.s.) at 60° C. and then the reaction mixture was stirred for 1 hour at 70° C. The solvent was evaporated under reduced pressure and the obtained residue was stirred in hexane. The resulting precipitate was filtered off and dried, yielding 9.35 g (98%) of intermediate 113, isolated as a hydrochloric salt (1:1).

d) Preparation of carbamic acid, [[2-[[6-acetyloxy)-7-methoxy-4-quinazolinyl]amino]-4-bromophenyl]methyl](5-chloropentyl)-, phenylmethyl ester (intermediate 114)

Methanesulfonyl chloride (0.12 mol) was added to a solution of intermediate 113 (0.0125 mol) in 1-methyl-2-pyrrolidinone (50 ml) at RT and the reaction mixture was stirred for 1 hour at 90° C. The mixture was poured out into water (300 ml) and the aqueous layer was extracted with EtOAc (3×100 ml). The organic layer was separated, washed with water (2×200 ml), dried, filtered off and the solvent was evaporated under reduced pressure. The obtained residue was purified by column chromatography (eluent: DCM/CH$_3$OH 99.5/0.5 to 94/6). The pure fractions were collected and the solvent was evaporated under reduced pressure, yielding 3.9 g of intermediate 114.

Example A26 a) Preparation of glycine, N-[(4-chloro-2-nitrophenyl)acetyl]-, ethyl ester (intermediate 115)

A slurry of 4-chloro-2-nitro-benzeneacetic acid (0.0051 mol) and 1-hydroxy-1H-benzotriazole (0.0051 mol) in DCM (50 ml) was treated with 1,1'-carbonylbis-1H-imidazole (0.0051 mol), then after 10 min. DIPEA (0.0051 mol) was added, followed by glycine hydrochloride, ethyl ester (0.0051 mol). The reaction mixture was stirred for 2 hours and was washed with water (50 ml), with a Na$_2$CO$_3$ solution (30 ml) and with 1N HCl. The organic layer was separated, dried (MgSO$_4$), filtered off and the solvent was evaporated. DIPE (100 ml) was added to the obtained residue and after stirring the resulting solids were collected, yielding 1.1 g of intermediate 115.

b) Preparation of glycine, N-[(2-amino-4-chlorophenyl)acetyl]-, ethyl ester (intermediate 116)

A mixture of intermediate 115 (0.023 mol) in THF (250 ml) was hydrogenated with Pt/C (2.0 g) as a catalyst in the presence of thiophene solution (1 ml). After uptake of H$_2$ (3 equiv.), the catalyst was filtered off and the filtrate was evaporated. The obtained residue was suspended in DIPE, then the suspension was stirred at boiling temperature, cooled and the desired product was collected, yield 6.2 g of intermediate 116.

c) Preparation of glycine, N-[[2-[[6-(acetyloxy)-7-methoxy-4-quinazolinyl]amino]-4-chlorophenyl]acetyl]-, ethyl ester (intermediate 117)

A mixture of intermediate 85 (0.00050 mol) and intermediate 116 (0.00050 mol) in 2-propanone (5 ml) was stirred for 16 hours in a pressure tube at 80° C. oil bath temperature), then the reaction mixture was filtered and the filter residue was air-dried, yielding 0.165 g of intermediate 117.

d) Preparation of glycine, N-[[4-chloro-2-[(6-hydroxy-7-methoxy-4-quinazolinyl)amino]phenyl]acetyl]-, ethyl ester (intermediate 118)

A mixture of intermediate 117 (0.0244 mol) in NH$_3$/CH$_3$OH (7N) (50 ml) and CH$_3$OH (100 ml) was stirred overnight at RT and then the solvent was evaporated under reduced pressure and at RT. Finally, the obtained residue was dried (vac.) overnight at 60° C., yielding 8.2 g (75%) of intermediate 118.

e) Preparation of glycine, N-[[4-chloro-2-[[6-[3-[[(1,1-dimethylethoxy)carbonyl]amino]propoxy]-7-methoxy-4-quinazolinyl]amino]phenyl]acetyl]-, ethyl ester (intermediate 119)

A mixture of intermediate 118 (0.00308 mol) and cesium carbonate (0.0154 mol) in DMA (20 ml) was stirred for 1-hour at RT, then N-(3-bromopropyl)carbamate (0.00308 mol) was added and the reaction mixture was stirred for 1 hour at RT. Extra N-(3-bromopropyl)carbamate (0.00308 mol) was added and the resulting mixture was stirred overnight. The mixture was filtered and the filter residue was washed with DMA. The filtrates were combined and concentrated under reduced pressure. The crude concentrate was purified by column chromatography (eluent: DCM/CH₃OH 100/0 to 95/5). The pure product fractions were collected and the solvent was evaporated under reduced pressure, yielding intermediate 119.

f) Preparation of glycine, N-[[2-[[6-(3-aminopropoxy)-7-methoxy-4-quinazolinyl]amino]-4-chlorophenyl]acetyl]-, ethyl ester (intermediate 120)

A mixture of intermediate 119 (0.003 mol) in TFA (50 ml) and DCM (50 ml) was stirred for 1 hour at RT, then the reaction mixture was concentrated under reduced pressure and the concentrate was used as such in the next reaction step without further purification, yielding intermediate 120.

g) Preparation of glycine, N-[[2-[[6-(3-aminopropoxy)-7-methoxy-4-quinazolinyl]amino]-4-chlorophenyl]acetyl]- (intermediate 121)

A mixture of intermediate 1206(0.003 mol) and LiOH.H₂O (0.018 mol) in ethanol (15 ml) and water (1 ml) was stirred for 2 hours and then this reaction mixture was used as such in the next reaction step without further purification, yielding intermediate 121.

Example A27 a) Preparation of 1-pentanol, 5-[[(4-bromo-5-fluoro-2-nitrophenyl)methyl]amino]- (intermediate 122)

Reaction under N₂: a mixture of 4-bromo-5-fluoro-2-nitrobenzaldehyde (0.9379 mol) and 5-amino-1-pentanol (0.0379 mol; 97%) in 1,2-dichloro-ethane (150 ml) was stirred for 20 min. and NaBH(OAc)₃ (0.0417 mol) was added at RT, then the reaction mixture was stirred overnight at RT (after 2 hours, extra NaBH(OAc)₃ (q.s.) was added). The mixture was washed with a saturated NaHCO₃ solution. The organic layer was separated, dried (MgSO₄), filtered off and the solvent was evaporated. The residue was purified by column chromatography (eluent: DCM/(CH₃OH/NH₃) 90/10). The pure product fractions were collected and the solvent was evaporated, yielding 10.5 of intermediate 122.

b) Preparation of carbamic acid, [(4-bromo-5-fluoro-2-nitrophenyl)methyl](5-hydroxypentyl)-, 1,1-dimethylethyl ester (intermediate 123)

A solution of dicarbonic acid, bis(1,11-dimethylethyl)ester (0.034 mol) in DCM (20 ml) was added dropwise to a mixture of intermediate 122 (0.031 mol) in DCM (200 ml) and then the resulting mixture was reacted for 4 hours. The reaction mixture was washed with water and the organic layer was separated. The organic layer was then dried (MgSO₄), filtered off and the solvent was evaporated. The residue was purified by column chromatography (eluent: DCM/CH₃OH 95/5). The product fractions were collected and then the solvent was evaporated and co-evaporated with toluene, yielding 9.8 g of intermediate 123.

c) Preparation of carbamic acid, [(2-amino-4-bromo-5-fluorophenyl)methyl](5-hydroxypentyl)-, 1,1-dimethylethyl ester (intermediate 124)

A mixture of intermediate 123 (0.0022 mol) in EtOAc (100 ml) was hydrogenated with Pt/C 5% (0.5 g) as a catalyst in the presence of thiophene solution (q.s.). After uptake of H2 (3 equiv.), the reaction mixture was filtered over dicalite and the filtrate was evaporated. The residue was purified by column chromatography (gradient eluent: DCM to DCM/CH₃OH). The pure product fractions were collected and the solvent was evaporated, yielding 0.623 g of intermediate 124.

d) Preparation of carbamic acid, [[2-[[6-(acetyloxy)-7-methoxy-4-quinazolinyl]amino]-4-bromo-5-fluorophenyl]methyl](5-hydroxypentyl)-, 1,1-dimethylethyl ester (intermediate 125)

A mixture of intermediate 85 (0.00154 mol) in acetonitrile (3 ml) was warmed to 60° C. and then a solution intermediate 124 (0.00154 mol) in acetonitrile (3 ml) was added dropwise at 6° C. The reaction mixture was stirred for 30 min. at 60° C. and then cooled to RT. The solvent was evaporated and the residue was purified by column chromatography over Biotage (gradient eluent: DCM/CH₃OH). The pure product fractions were collected and the solvent was evaporated, yielding 0.800 g of intermediate 125.

e) Preparation of carbamic acid, [[4-bromo-5-fluoro-2-[(6-hydroxy-7-methoxy-4-quinazolinyl)amino]phenyl]methyl](5-hydroxypentyl)-, 1,1-dimethylethyl ester (intermediate 126)

A solution of potassium carbonate (0.00105 mol) in water (5 ml) was added dropwise to a mixture of intermediate 125 (0.00105 mol) in methanol (50 ml) and then the reaction mixture was stirred for 1 hour at RT. The solvent was evaporated and the residue was extracted with DCM. The organic layer was separated, dried (MgSO₄), filtered off and the solvent was evaporated. The residue was purified by column chromatography over Biotage (gradient eluent: DCM/CH₃OH). The pure product fractions were collected and the solvent was evaporated, yielding 0.590 g of intermediate 126.

f) Preparation of 4,6-ethenopyrimido[4,5-b][6,1,12]benzoxadiazacyclopentadecine-13(8H)-carboxylic acid, 17-bromo-16-fluoro-9,10,11,12,14,19-hexahydro-20-methoxy-, 1,1-dimethylethyl ester (intermediate 127)

A mixture of ADDP (0.00166 mol) in TH dry (70 ml) under N₂ was cooled on an ice bath to 5° C., then tributyl-phosphine (0.00166 mol) was added and the mixture was stirred for 5 min. at 5° C. A solution of intermediate 126. (0.00055 mol) in THF dry (10 ml) was slowly added dropwise and the reaction mixture was stirred for 20 min. at 5° C. and was then allowed to reach RT. The mixture was stirred for 3 hours at RT and the solvent was evaporated. The residue was purified by column chromatography (gradient eluent: DCM/CH₃OH). The pure product fractions were collected and the solvent was evaporated, yielding intermediate 127.

Example A28 a) Preparation of glycine, N-[[2-[[6-(2-bromoethoxy)-7-methoxy-4-quinazolinyl]amino]-4-chlorophenyl]acetyl]-, ethyl ester (intermediate 128)

A mixture of intermediate 118 (0.0138 mol) and cesium carbonate (0.0690 mol) in DMF (120 ml) was stirred for 30 min. at RT, then 1,2-dibromo-ethane (0.117 mol) was added and the reaction mixture was stirred overnight at RT. The solvent was evaporated under reduced pressure and the residue was co-evaporated with toluene. The obtained residue was stirred in DIPE and the desired product was filtered off, yielding 6.93 g (91%) of intermediate 128.

b) Preparation of glycine, N-[[4-chloro-2-[[7-methoxy-6-[2-[[2-(4-morpholinyl)ethyl]amino]ethoxy]4-quinazolinyl]amino]phenyl]acetyl]-, ethyl ester (intermediate 129)

A mixture of intermediate 128 (0.00181 mol) and 4-morpholineethanamine (0.00907 mol) in ethanol (20 ml) was heated in a microwave oven for 90 min. at 100° C. and then the reaction mixture was purified by RP high-performance liquid chromatography. The product fractions were collected and the solvent was evaporate yielding 0.39 g (36%) of intermediate 129.

c) Preparation of glycine, N-[[4-chloro-2-[[7-methoxy-6-[2-[[2-(4-morpholinyl)ethyl]amino]ethoxy]-4-quinazolinyl]amino]phenyl]acetyl]- (intermediate 130)

A mixture of intermediate 129 (0.00065 mol) and LiOH.H$_2$O (0.0032 mol) in ethanol (20 ml) and water (2 ml) was stirred for 2 hours at RT and then the solvent was evaporated under reduced pressure, yielding intermediate 130 (used as such in the next reaction step without further purification).

Example A29 a) Preparation of benzoic acid, 4-fluoro-, 5-[(4-fluorobenzoyl)amino]-2-nitrophenyl ester (intermediate 131)

A solution of 5-amino-2-nitro-phenol (0.032 mol) and triethylamine (0.065° mol) in DCM (100 ml) was stirred at RT, then a solution of 4-fluoro-benzoyl chloride (0.065 mol) in DCM (10 ml) was added dropwise and the reaction mixture was stirred for 1 day at RT. The mixture was washed 2 times with 1N HCl and once with water. The organic layer was separated, dried (MgSO$_4$), filtered off and the solvent was evaporated. The obtained residue was stirred in ethanol/hexane (50/50), filtered off and dried, yielding 5.25 g of intermediate 131.

b) Preparation of benzamide, 4-fluoro-N-(3-hydroxy-4-nitrophenyl)- (intermediate 132)

A mixture of intermediate 131 (0.0132 mol) in methanol (80 ml) was stirred at RT and then a solution of NaOCH$_3$ 30% in methanol (0.0132 mol) in methanol (10 ml) was added. The reaction mixture was stirred for 30 minutes and the organic solvent was evaporated under reduced pressure. The obtained concentrate was stirred in 1N HCl, then the resulting precipitate was filtered off, washed with water and dried (vacuum) at 60° C., yielding 3.3 g of intermediate 132.

c) Preparation of benzamide, N-[3-[[6-(acetyloxy) hexyl]oxy]-4-nitrophenyl]-4-fluoro- (intermediate 133

A mixture of intermediate 132 (0.011 mol) and potassium carbonate (0.012 mol) in DMA (100 ml) was stirred for 1 hour at 60° C., then 6-bromohexyl acetate (0.012 mol) was added and the reaction mixture was stirred for 18 hours at 60° C. Extra 6-bromohexyl acetate (0.300 g) was added and the mixture was stirred for 5 hours more. The resulting-mixture was poured out into ice, water and was extracted with EtOAc. The organic layer was separated, dried (MgSO$_4$), filtered off and the solvent was evaporated, yielding 4.6 g of intermediate 133.

Preparation of benzamide, N-[3-[[6-(acetyloxy) hexyl]oxy]-4-aminophenyl]-4-fluoro- (intermediate 134)

A mixture of intermediate 133 (0.0024 mol) in methanol (75 ml) in a closed vessel was hydrogenated overnight at 50° C. with Pd/C 10% (1 g) as a catalyst in the presence of thiophene solution (1 ml). After uptake of H$_2$ (3 equiv.), the catalyst was filtered off, to give Filtrate (I). A mixture of intermediate 133 (0.0024 mol) in THF (75 ml) in a closed vessel was hydrogenated overnight at 50° C. with Pd/C 10% (1 g) as a catalyst in the presence of thiophene solution (1 ml). After uptake of H$_2$ (3 equiv.), the catalyst was filtered off, to give Filtrate (II). Filtrate (I) and Filtrate (II) were combined and evaporated under reduced pressure, yielding 1.85 g of intermediate e) Preparation of benzamide, N-[3-[[6-(acetyloxy) hexyl]oxy]-4-[[6-(acetyloxy)-7-methoxy-4-quinazolinyl]amino]phenyl]-4-fluoro- (intermediate 135)

A mixture of intermediate 85 (0.0048 mol) and intermediate 134 (0.0048 mol) in 2-propanol (80 ml) was stirred for 1 hour at 80-C, then the resulting precipitate was filtered off, washed and dried, yielding 1.15 g of intermediate 135.

f) Preparation of benzamide, 4-fluoro-N-[3-[(6-hydroxyhexyl)oxy]-4-[(6-hydroxy-7-methoxy-4-quinazolinyl)amino]phenyl]- (intermediate 136)

A solution of intermediate 135 (0.0019 mol) and potassium carbonate (0.0038 mol) in water (4 ml) and methanol (40 ml) was stirred for 1 hour at 50° C., then a mixture of potassium carbonate (0.26 g) in water (2 ml) was added and the reaction mixture was stirred for 4 hours. The solvent was evaporated under reduced pressure and the obtained residue was dissolved in acetic acid (100%). After stirring for 30 min., the solvent was evaporated and the crude residue was stirred in DCM. The formed precipitate was filtered off, washed and then stirred in water. The obtained precipitate was filtered off, washed and dried (vacuum) at 60° C., yielding 0.650 g (66%) of intermediate 136.

Example A30 a) Preparation of alanine, N-[(4-chloro-2-nitrophenyl)acetyl]-2-methyl-, ethyl ester (intermediate 137)

A mixture of 4-chloro-2-nitro-benzeneacetic acid (0.00456 mol), 1-hydroxy-1H-benzotriazole (0.00456 mol), 1,1'-carbonylbis-1H-imidazole (0.00456 mol) and DIPEA (0.00456 mol) in DCM (20 ml) was stirred at RT for 15 min., then 2-methyl-alanine, ethyl ester (0.00456 mol) was added and the reaction mixture was stirred over the weekend at RT. The mixture was washed 2 times with a saturated potassium carbonate solution, 2 times with 1N HCl and once with water. The organic layer was separated, dried (MgSO$_4$), filtered off and the solvent was evaporated, yielding intermediate 137.

b) Preparation of alanine, N-[(2-amino-4-chlorophenyl)acetyl]-2-methyl-, ethyl ester (intermediate 138)

A mixture of intermediate 137 (0.00456 mol) in ethanol (25 mol) and THF (25 ml) was hydrogenated at 50° C. with Pt/C 5% (0.5 g) as a catalyst in the presence of thiophene solution (0.3 ml). After uptake of HE (3 equiv.), the catalyst was filtered off and the filtrate was evaporated, yielding 0.65 g of intermediate 338.

c) Preparation of alanine, N-[[2-[[6-(acetyloxy)-7-methoxy-4-quinazolinyl]amino]+chlorophenyl]acetyl]-2-methyl-, ethyl ester (intermediate 139)

A mixture of intermediate 138 (0.0022 mol) and intermediate 85 (0.0022 mol) in acetonitrile (25 ml) was heated to 80° C. and stirred for 2 hours. The solvent was evaporated and the residue was purified by flash column chromatography (eluent: DCM/CH$_3$OH 100/0, 95/5); then the product fractions were collected and the solvent was evaporated, yielding 0.68 g of intermediate 139.

d) Preparation of alanine, N-[[4-chloro-2-[(6-hydroxy-7-methoxy-4-quinazolinyl)amino]phenyl]acetyl]-2-methyl-, ethyl ester (intermediate 140)

A mixture of intermediate 139 (0.0013 mol) in CH$_3$OH/NH$_3$ (7N) (10 ml) and methanol (10 ml) was stirred for 18 hours at RT and then the solvent was evaporated under reduced pressure, yielding 0.600 g of intermediate 140.

e) Preparation of alanine, N-[[4-chloro-2-[[6-[2-[[(1,1-dimethylethoxy)carbonyl]amino]ethoxy]-7-methoxy-4-quinazolinyl]amino]phenyl]acetyl]-2-methyl-, ethyl ester (intermediate 141)

A mixture of intermediate 140 (0.0013 mol) and cesium carbonate (0.0063 mol) in DMA (20 ml) was stirred for 45 min. at RT, then (2-bromoethyl)-carbamic acid 1,1-dimethylethyl ester (0.0014 mol) was added and the mixture was stirred for 4 hours. Extra (2-bromoethyl)-carbamic acid 1,1-dimethylethyl ester (0.0014 mol) was added and the reaction mixture was stirred overnight at RT. The resulting precipitate was filtered off and the filtrate was evaporated, yielding intermediate 141 (quantitative yield, used as such in the next reaction step).

f) Preparation of alanine, N-[[2-[[6-(2-aminoethoxy)-7-methoxy-4-quinazolinyl]amino]-4-chlorophenyl]acetyl]-2-methyl-, ethyl ester (intermediate 142)

A solution of intermediate 141 (0.0013 mol) in TFA (15 ml) and DCM (15 ml) was stirred for 1 hour at RT and then the solvent was evaporated, yielding 0.670 g of intermediate 142.

g) Preparation of alanine, N-[[2-[[6-(2-aminoethoxy)-7-methoxy-4-quinazolinyl]amino]-4-chlorophenyl]acetyl]-2-methyl- (intermediate 143)

A mixture of intermediate 142 (0.0013 mol) and LiOH.H$_2$O (0.0039 mol) in ethanol (20 ml) and water (1 ml) was heated and stirred for 1 hour at 40° C., then extra LiOH H$_2$O (0.01192 mol) was added and the reaction mixture was stirred for 3 hours. Again LiOH.H$_2$O (0.00477 mol) was added and the resulting mixture was stirred for 1 hour at 40° C. Finally, the solvent was evaporated under reduced pressure, yielding intermediate 143 (Quantitative Yield).

Example A31 a) Preparation of beta-alanine, N-[(2-amino-4-chlorophenyl)methyl]-, methyl ester (intermediate 144)

A mixture of β-Alanine, methyl ester, hydrochloride (0.020 mol), 4-chloro-2-nitro-benzaldehyde (0.010 mol) and potassium fluoride (0.019 mol) in methanol (100 ml) was hydrogenated at 50° C. for 24 hours with Pt/C (1 g, slurry in THF) as a catalyst in the presence of thiophene solution (1 ml, 4% in 2-propanol). After uptake of H$_2$ (4 equiv.), the reaction mixture was filtered over dicalite, then the filter residue was washed with DCM and the solvent was evaporated. The obtained residue was Redissolved in methanol and was used as such in the next reaction step, yielding intermediate 144.

b) Preparation of beta-alanine, N-[(2-amino-4-chlorophenyl)methyl]-N-[(1,1-dimethylethoxy)carbonyl]-, methyl ester (intermediate 145)

Tert-butyl dicarbonate (0.060 mol) was added to intermediate 144 (0.020 mol) and the reaction mixture was stirred for 1 hour, then NH$_3$/CH$_3$OH was added and the mixture was stirred for 1 hour. The solvent was evaporated and the dry residue was filtered over silica gel with DCM as eluent. The filter residue was purified by RP high-performance liquid chromatography, then the product fractions were collected and the solvent was evaporated, yielding 1.206 g (36%) of intermediate 145.

c) Preparation of beta-alanine, N-[[2-[[6-(acetyloxy)-7-methoxy-4-quinazolinyl]amino]-4-chloro-phenyl]methyl]-N-[(1,1-dimethylethoxy)carbonyl]-, methyl ester (intermediate 146)

A solution of intermediate 145 (0.0035 mol) in acetonitrile (40 ml) was heated to 80° C., then intermediate 85 (0.0035° mol) was added and the reaction mixture was stirred for 4 hours at 80° C. Finally, the solvent was evaporated to dryness, yielding intermediate 146 (used as such in the next reaction step).

d) Preparation of beta-alanine, N-[[4-chloro-2-[(6-hydroxy-7 ethoxy-4-quinazolinyl)amino]phenyl]methyl]-N-[(1,1-dimethylethoxy)carbonyl]-, methyl ester (intermediate 147)

NH$_3$/CH$_3$OH (7N) (0.035 mol) was added to a solution of intermediate 146 (0.0035 mol) in methanol (5 ml) and the reaction mixture was stirred for 30 min. at RT. The solvent was evaporated and the obtained residue was dissolved in methanol. DIPE was added and the resulting precipitate was filtered off and dried, yielding 0.9125 g. A second crop could be obtained by adding heptane to the filtrate, yielding 0.8794 g (total: 93%) of intermediate 147.

e) Preparation of beta-alanine, N-[[4-chloro-2-[[6-[3-[[(1,1-dimethylethoxy)carbonyl]amino]propoxy]-7-methoxy-4-quinazolinyl]amino]phenyl]methyl]-N-[(1,1-dimethylethoxy)carbonyl]-, methyl ester (intermediate 148)

cesium carbonate (0.00775 mol) was added to a solution of intermediate 147(0.001155 mol) in DMF dry (15 ml) and the mixture was stirred for 15 min. at RT, then (3-bromopropyl)-carbamic acid 1,1-dimethylethyl ester (0.00155 mol) was added and the reaction mixture was stirred overnight at RT. The solvent was evaporated and the residue was dissolved in DCM. This solution was slowly filtered and the filter residue was washed with DCM, yielding intermediate 148 (used as such in the next reaction step).

f) Preparation of beta-alanine, N-[[2-[[6-(3-aminopropoxy)-7-methoxy-4-quinazolinyl]amino]-4-chlorophenyl]methyl]-hydrochloric acid salt (1:1) (intermediate 149)

Water (4 ml) was added to a solution of intermediate 148 (0.00155 mol) in dioxane (10 ml), then hydrochloric acid (4 ml, 36-38%) was added and the mixture was stirred until the generation of gas stopped. Extra hydrochloric acid (2 ml, 36-38%) was added and the reaction mixture was stirred in a closed vessel for 8 hours. Finally, the solvent was evaporated, yielding intermediate 149 (used as such in the next reaction step).

Example A32 a) Preparation of (R)proline, 1-[(4-chloro-2-nitrophenyl)methyl]-, 1,1-dimethylethyl ester (intermediate 150)

Tetrakis (2-propanolato) titanium (0.010 mol) was added to a solution of D-Proline, 1,1-dimethylethyl ester, hydrochloride (0.010 mol) and 4-chloro-2-nitro-benzaldehyde (0.010 mol) in DCM (30 ml), then the mixture was stirred for 1 hour at RT and NaBH(OAc)$_3$ (0.011 mol) was added. The reaction mixture was stirred for 2 hours at RT and then water was added. The mixture was filtered over a P2 glass filter and washed with DCM, then the organic layer was separated and the aqueous layer was extracted 2 times with DCM. The organic layers were combined, dried, filtered off and the solvent was evaporated, yielding intermediate 150 (used as such in the next reaction step).

b) Preparation of (R) proline, 1-[(2-amino-4-chlorophenyl)methyl]-, 1,1-dimethylethyl ester (intermediate 151)

A mixture of intermediate 150 (0.01 mol) in ethanol (100 ml) and THF (50 ml) was hydrogenated with Pt/C 5% (1 g) as a catalyst in the presence of thiophene solution (1 ml: 4% in DIPE). After uptake of H$_2$ (3-equiv.), the catalyst was filtered off and the filtrate was evaporated. The residue was purified by RP high-performance liquid chromatography, then the product fractions were collected and the organic solvent was evaporated. The obtained concentrate was filtered and then the filter residue was washed with water and dried in an oven, to give 1.0453 g (34%) of intermediate 151. The filter was washed with DCM and the aqueous layer was extracted with DCM. The organic layer was then dried and filtered over potassium carbonate, to give 0.0480 g intermediate 151.

c) Preparation of (R)proline, 1-[[2-[[6-(acetyloxy)-7-methoxy-4-quinazolinyl]amino]-4-chlorophenyl]methyl]-, 1,1-dimethylethyl ester (intermediate; 152)

Intermediate 85 (0.001 mol) was added to a solution of intermediate 151 (0.001 mol) in 2-propanol (q.s.) and then the reaction mixture was stirred for 2 hours and the solvent was evaporated. Extra Intermediate 85 (0.0185 g) was added to the previous prepared reaction mixture, then the mixture was stirred for one more hour and the solvent was evaporated, yielding intermediate 152.

d) Preparation of (R)proline, 1-[[4-chloro-2-[(6-hydroxy-7-methoxy-4-quinazolinyl)amino]phenyl] methyl]-, 1,1-dimethylethyl ester (intermediate 153)

NH$_3$/CH$_3$OH (10 ml) was added to intermediate 152 (0.001 mol) and the reaction mixture was shaken for 1 hour and then the solvent was evaporated, yielding intermediate 153 (used as such in the next reaction step).

e) Preparation of (R)proline, 1-[[4-chloro-2-[[6-(3-cyanopropoxy)-1-methoxy-4-quinazolinyl]amino] phenyl]methyl]-, 1,1-dimethylethyl ester (intermediate 154)

A mixture of intermediate 153 (0.0005 mol), 4-bromo-butanenitrile (0.04 ml) and cesium carbonate (0.815 g) was stirred overnight at RT and then the reaction mixture was stirred for 30 min at 50° C. Extra 4-bromo-butanenitrile (0.009 ml) was added and the mixture was stirred for 4 hours at RT and for another 15 min. at 50° C. The solvent was evaporated and the residue was dissolved in DCM. This solution was filtered over dicalite and the filtrate was evaporated, yielding intermediate 154.

f) Preparation of (R)proline, 1-[[2-[[6-(4-aminobutoxy)-7-methoxy-4-quinazolinyl]amino]-4-chlorophenyl]methyl]-, 1,1-dimethylethyl ester (intermediate 155)

A mixture of intermediate 154 (0.0005 mol) in CH$_3$OH/ NH$_3$ (40 ml) was hydrogenated at 14° C. with raney nickel (cat. quant.) as a catalyst in the presence of thiophene solution (0.1 ml). After uptake of H$_2$ (2 equiv.), the catalyst was filtered off and the filtrate was evaporated, yielding intermediate 155.

g) Preparation of (R)proline, 1-[[2-[[6-(4-aminobutoxy)-7-methoxy-4-quinazolinyl]amino]-4-chlorophenyl]methyl]-.TFA (1:1) (intermediate 156)

A solution of intermediate 155 (residue) in TFA/DCM/TIS (909/12) (5 ml) was stirred for 7-8 hours, then the solvent was evaporated and the obtained residue was dried overnight in an oven, yielding intermediate 156, isolated as a trifluoro acetic acid salt.

Example A33 a) Preparation of (S)proline, 1-[(4-chloro-5-fluoro-2-nitrophenyl)methyl]-, 1,1-dimethylethyl ester (intermediate 157)

A solution of L-Proline, 1,1-dimethylethyl ester (0.010 mol) and 4-chloro-5-fluoro-2-nitro-benzaldehyde (0.010 mol) in DCM (30 ml) was cooled to 0° C. and tetrakis (2-propanolato) titanium (0.010 mol) was added, then the mixture was stirred for 1 hour at RT and NaBH(OAc)$_3$ (0.011 mol) was added. The reaction mixture was stirred for 3-hours at RT and extra tetrakis (2-propanolato) titanium (0.001 mol) and NaBH(OAc)$_3$ (0.001 mol) were added. The resulting mixture was stirred for 6 hours at RT. Water was added and the mixture was filtered. The organic layer was separated, dried, filtered off and the solvent was evaporated, yielding intermediate 157 (used as such in the next reaction step).

b) Preparation of (S) proline, 1-[(2-amino-4-chloro-5-fluorophenyl)methyl]-, 1,1-dimethylethyl ester (intermediate 158)

A mixture of intermediate 157 (0.009 mol) in EtOAc (150 ml) was hydrogenated with Pt/C 5% (1 g) as a catalyst in the presence of thiophene solution (1 ml: 4% in DIPE). After uptake of H$_2$ (3 equiv.), the catalyst was filtered off and the filtrate was evaporated. The residue was purified by RP high-performance liquid chromatography, then the product fractions were collected and the organic solvent was evaporated. The obtained precipitate was filtered off washed with water and dried to give 1.1286 g (34%) of intermediate 158.

c) Preparation of (S)proline, 1-[[2-[[6-(acetyloxy)-7-methoxy-4-quinazolinyl]amino]-4-chloro-5-fluorophenyl]methyl]-, 1,1-dimethylethyl ester Intermediate 85 (0.001 mol) was added to a solution of intermediate 158 (0.001 mol) in 2-propanol (q.s.) and then the reaction mixture was stirred for 2 hours and the solvent was evaporated, yielding intermediate 159 (used as such in the next reaction step).

d) Preparation of (S)proline, 1-[[4-chloro-5-fluoro-2-[(6-hydroxy-7-methoxy-4-quinazolinyl)amino]phenyl]methyl]-, 1,1-dimethylethyl ester (intermediate 160)

$NH_3/CH_3OH$ (10 ml) was added to intermediate 159 (0.001 mol) and the reaction mixture was shaken for 1 hour and then the solvent was evaporated, yielding intermediate 160 (used as such in the next reaction step).

e) Preparation of (S) proline, 1-[[4-chloro-2-[[6-[3-[[(1,1-dimethylethoxy)carbonyl]amino]propoxy]-7-methoxy-4-quinazolinyl]amino]-5-fluorophenyl]methyl]-, 1,1-dimethylethyl ester (intermediate 161)

A mixture of intermediate 160 (0.0005 mol), (3-bromopropyl)-carbamic acid, 1,1-dimethylethyl ester (0.12326 ml) and cesium carbonate (0.815 g) was stirred overnight at RT and then the reaction mixture was stirred for 30 min. at 50° C. Extra (3-bromopropyl)-carbamic acid, 1,1-dimethylethyl ester (0.013 g) was added and the mixture was stirred for 4 hours at RT and for another 15 min. at 50° C. The solvent was evaporated and the residue was dissolved in DCM. This solution was filtered over dicalite and the filtrate was evaporated, yielding intermediate 161.

f) Preparation of (S)proline, 1-[[2-[[6-(3-aminopropoxy)-7-methoxy-4-quinazolinyl]amino]-4-chloro-5-fluorophenyl]methyl]-TFA salt (intermediate 162)

A solution of intermediate 161 (residue) in TFA/DCM/TIS (90/8/2) (25 ml) was stirred overnight, then the solvent was evaporated and the obtained residue was dried overnight in an oven at 80° C., yielding intermediate 162, isolated as trifluoroacetic acid salt.

Example A34 a) Preparation of 5-hexenamide, N-[(2-amino-4-chlorophenyl)methyl]- (intermediate A mixture of 5-hexenoic acid (0.0075 mol) and PL-DCC resin (0.015 mol; Polymer Laboratories: 3417) in DCM (100 ml) was stirred for 15 min. at RT, then 2-amino-4-chlorobenzenemethanamine (0.01125 mol) was added and the resulting mixture was stirred for 3 hours. After addition of methylisocyanate polystyrene (0.01125 mol; Novabiochem: 01-64-0169), the reaction mixture was stirred for 4 hours, filtered and then the solvent was evaporated, yielding 1.43 g (76%) of intermediate 163.

b) Preparation of 5-hexenamide, N-[[4-chloro-2-[(6-hydroxy-7-methoxy-4-quinazolinyl)amino]phenyl]methyl]- (intermediate 164)

A solution of intermediate 163 (0.0057 mol) and intermediate 85 (0.0052 mol) in 2-propanol (20 ml) was stirred for 5 hours at 60° C. and then the mixture was cooled. 7N $NH_3$ in methanol (20 ml) was added and the reaction mixture was stirred for 2 hours at RT. Finally, the solvent was evaporated, yielding 1.5 g of intermediate 164.

c) Preparation of 5-hexenamide, N-[[4-chloro-2-[[7-methoxy-6-(4-pentenyloxy)-4-quinazolinyl]amino]phenyl]methyl]- (intermediate 165)

A mixture of intermediate 164 (0.0018 mol) and cesium carbonate (0.0090 mol) in DMF (20 ml) was stirred for 15 min., then 5-bromo-1-pentene (0.0021 mol) was added and the reaction mixture was stirred overnight at RT. Water and DCM were added and the layers were separated. The organic layer was washed with a 10% citric acid solution and with brine, then it was dried ($MgSO_4$), filtered and the solvent was evaporated. The residue (0.694 g) was then purified by RP high-performance liquid chromatography. The product fractions were collected and the solvent was evaporated, yielding 0.270 g of intermediate 165.

Example A35 a) Preparation of (S)carbamic acid, [1-[[[(4-chloro-2-nitrophenyl)methyl]amino]carbonyl]-3-butenyl]-, 1,1-dimethylethyl ester (intermediate 166)

1-[bis(dimethylamino)methylene]-1H-benzotriazolium, hexafluorophosphate (1-), 3-oxide (0.0056 mol) was slowly added to a solution of 2-[[(1,1-dimethylethoxy)carbonyl]amino]-4-pentenoic acid (0.0046 mol), 4-chloro-2-nitro-benzenemethanamine (0.0056 mol), 1-hydroxy-1H-benzotriazole (0.0056 mol) and DIPEA (0.93 ml) in DMF (25 ml) and then the reaction mixture was stirred for 3 hours at RT. The mixture was diluted with EtOAc (200 ml) and then washed with a 10% aq. citric acid solution (50 ml), with water (50 ml), with an aqueous $NaHCO_3$ solution (50 ml) and with brine (50 ml). The organic layer was separated, dried ($MgSO_4$), filtered off and the solvent was evaporated, yielding 2.00 g (100%) of intermediate 166.

b) Preparation of (S)carbamic acid, [1-[[[(2-amino-4-chlorophenyl)methyl]amino]carbonyl]-3-butenyl]-1,1-dimethylethyl ester (intermediate 167)

A mixture of intermediate 166 (0.003 mol) and tin(II) chloride dihydrate (0.015 mol) in ethanol (50 ml) was stirred for 90 min. at 60° C., then the reaction mixture was poured out into water and extracted 3 times with toluene. The organic layer was separated, dried ($MgSO_4$), filtered off and the solvent was evaporated (vacuum), yielding intermediate 167.

c) Preparation of (S) carbamic acid, [1-[[[[4-chloro-2-[(6-hydroxy-7-methoxy-4-quinazolinyl)amino]phenyl]methyl]amino]carbonyl]-3-butenyl]-1,1-dimethylethyl ester (intermediate 168)

A solution of intermediate 167 (0.003 mol) and intermediate 85 (0.0025 mol) in 2-propanol (150 ml) was stirred overnight at 55° C. and then the mixture was cooled. 7N $NH_3$ in methanol (50 ml) was added and the reaction mixture was stirred for 2 hours at RT. Finally, the solvent was evaporated, yielding 2.17 g of intermediate 168.

d) Preparation of (S)carbamic acid, [1-[[[[4-chloro-2-[[7-methoxy-6-(4-pentenyloxy)-4-quinazolinyl]amino]phenyl]methyl]amino]carbonyl]-3-butenyl]-, 1,1-dimethylethyl ester (intermediate 169)

A solution of intermediate 168 (0.0015 mol) and cesium carbonate (0.0075 mol) in DMF (30 ml) was stirred for 15 min. at RT, then 5-bromo-1-pentene (0.0018 mol) was added and the reaction mixture was stirred for 24 hours at RT. Water and DCM were added and the layers were separated. The organic layer was washed with a 10% citric acid solution and with brine, then it was dried ($MgSO_4$), filtered and the solvent was evaporated, yielding intermediate 169.

Example A36 a) Preparation of 1-pentanol, 5-[2-(2-amino-4-chlorophenyl)ethoxy]-, acetate (ester) (intermediate 170)

Reaction (I): A mixture of 2,6-bis(1,1-dimethylethyl)-pyridine (0.012 mol) and 4-chloro-2-nitro-benzeneethanol (0.01 mol) in 1,2-dichloro-ethane (30 ml) was stirred under $N_2$ and at 0° C., then a mixture of triflic anhydride (0.011 mol) in 1,2-dichloro-ethane (10 ml) was added dropwise at 0° C. and the reaction mixture was stirred for 1 hour at RT, to give Mixture. (I). Reaction (II): A solution of 1,5-pentanediol, monoacetate (0.011 mol) in 1,2-dichloro-ethane (10 ml) was added dropwise to Mixture (I) and the resulting mixture was stirred for 1 hour at 65° C. After cooling, water was added and the mixture was partitioned between ethanol/DCM. The organic layer was separated, dried filtered off and the solvent was evaporated. The obtained residue was purified by flash column chromatography (eluent: $DCM/CH_3OH$ 100/0, 98/2). The product fractions were collected and the solvent was evaporated, to give Mixture (II). A mixture of Mixture (II) (0.0133 mol) in THF (50 ml) was hydrogenated 2 times at 50° C. with Pt/C (1 g) as a catalyst in the presence of thiophene solutions (1 ml). After uptake of $H_2$ (3 equiv.), the catalyst was filtered off and the filtrate was evaporated. The obtained residue was purified over silica gel on a glass filter (eluent: Hexane/EtOAc 80/20, 70/30). The product fractions were collected and the solvent was evaporated, yielding 1.5 g of intermediate 170.

b) Preparation of 6-quinazolinol, 4-[[2-[2-[[5-(acetyloxy)pentyl]oxy]ethyl]-5-chlorophenyl]amino]-7-methoxy-, acetate (ester) (intermediate 171)

A mixture of intermediate 170 (0.005 mol) and intermediate 85 (0.005 mol) in dioxane (20 ml) was reacted for 16 hours at 80° C. and then the solvent was evaporated, yielding intermediate 171.

c) Preparation of 6-quinazolinol, 4-[[5-chloro-2-[2-[(5-hydroxypentyl)oxy]ethyl]phenyl]amino]-7-methoxy- (intermediate 172)

A mixture of intermediate 171 (residue) and potassium carbonate (5 g) in water (50 ml) and methanol (50 ml) was stirred overnight at RT, then water was added and the mixture was extracted with DCM. The organic layer was washed 2 times with water, then dried, filtered and the solvent was evaporated. Toluene was added and the solvent was evaporated again, yielding 2 g of intermediate 172.

Example A37 a) Preparation of carbamic acid, [3-(4-chloro-2-nitrophenyl)-2-propynyl]-, 1,1-dimethylethyl ester (intermediate 173)

A mixture of 1-bromo-4-chloro-2-nitro-benzene (0.15 mol), dichlorobis(triphenylphosphine)-palladium (0.0075 mol) and copper (I) iodide (0.0075 mol) in triethylamine (300 ml) was stirred at 50° C. and 2-propynyl-carbamic acid, 1,1-dimethylethyl ester (0.375 mol) was added portionwise, then the reaction mixture was stirred for 2 hours at 50° C. and the solvent was evaporated. The residue was taken up in water and the mixture was extracted with EtOAc. The organic layer was separated, dried, filtered off and the solvent was evaporated. The residue was purified twice by column chromatography (eluent: Hexane/EtOAc 80/20). The product fractions were collected and the solvent was evaporated. The obtained residue (31.8 g) was stirred in hexane, and then the resulting precipitate was filtered off and dried, yielding 31.5 g, (67.6%) of intermediate 173.

b) Preparation of carbamic acid, [3-(2-amino-4-chlorophenyl)propyl]-, 1,1-dimethylethyl ester (intermediate 174)

A mixture of intermediate 173 (0.04 mol) in THF (200 ml) was hydrogenated at 50° C. for with Pt/C (3 g) as a catalyst in the presence of thiophene solution (1 ml) (in the meantime; the catalyst was changed 2 times). After uptake of $H_2$ (6 equiv.), the catalyst was filtered off and the filtrate was evaporated, yielding (66%) of intermediate 174.

c) Preparation of carbamic acid, [3-[2-[[6-(acetyloxy)-7-methoxy-4-quinazolinyl]amino]-4-chlorophenyl]propyl]-, 1,1-dimethylethyl ester (intermediate 175)

A mixture of intermediate 174 (0.04 mol) and intermediate 85 (0.035 mol) in acetonitrile (100 ml) was; reacted for 3 hours at 75° C. and then the reaction mixture was cooled. The resulting precipitate was filtered off and dried, yielding 12.2 g (69.6%) of intermediate 175.

d) Preparation of butanoic acid, 4-[[4-[[5 chloro-2-[3-[[(1,1-dimethylethoxy)carbonyl]amino]propyl] phenyl]amino]-7-methoxy-6-quinazolinyl]oxy]-, ethyl ester (intermediate 176)

A mixture of intermediate 175 (0.0020 mol) and potassium carbonate (0.00072 mol) in water (1 ml) and methanol (1 ml) was stirred for 16 hours at RT and then the solvent was evaporated. The residue was taken up in water, then the mixture was neutralised with NaOAc and extracted with DCM. The organic layer was separated, dried, filtered off and the solvent was evaporated, yielding 0.850 g of intermediate 176.

(e) Preparation of butanoic acid, 4-[[4-[[2-(3-aminopropyl)-5-chlorophenyl]amino]-7-methoxy-6-quinazolinyl]oxy]- (intermediate 177)

A mixture of intermediate 176 (0.00035 mol) in THF (10 ml)/HCl 36% (2 ml)/water (3 ml) was reacted for 16 hours at RT and then the solvent was evaporated. The obtained residue was stirred in acetonitrile, then the resulting precipitate was filtered off and dried, yielding 0.200 g of intermediate 177.

Example A38 a) Preparation of carbamic acid, [3-[4-chloro-2-[(6-hydroxy-7-methoxy-4-quinazolinyl)amino]phenyl] propyl]-, 1,1-dimethylethyl ester (intermediate 178)

A mixture of hydrochloric acid salt of intermediate 175 (0.056 mol) and potassium carbonate (25 g) in water (250 ml) and methanol (200 ml) was stirred for 6 hours at RT and then the solvent was evaporated. The residue was taken up in a small amount of water, then NaOAc (25 g) was added and the mixture was extracted with $DCM/CH_3OH$. The organic layer was separated, dried, filtered off and the solvent was evaporated. The obtained residue was stirred in DIPE and after filtration the filter residue was dried, yielding 23.5 g (91.5%) of intermediate 178.

b) Preparation of 6-quinazolinol, 4-[[2-(3-aminopropyl)-5-chlorophenyl]amino]-7-methoxy-HCl (1:1) (intermediate 179)

A mixture of intermediate 178 (0.015 mol) in methanol (50 ml) and HCl/2-propanol (10 ml) was stirred for 16 hours at RT and then the solvent was evaporated. The obtained residue was stirred in DIPE and after filtration the filter residue was dried, yielding 6.1 g (94.6%) of intermediate 179, isolated as a hydrochloric acid salt.

c) Preparation of acetamide, N-[3-[4-chloro-2-[(6-hydroxy-7-methoxy-4-quinazolinyl)amino]phenyl]propyl]-2-[(2-hydroxyethyl)amino]- (intermediate 180)

Intermediate 179 (0.02 mol), DMF (100 ml) and DIPEA (0.1 mol) were stirred at 0-10° C., then a mixture of bromoacetyl chloride (0.05 mol) in DCM (10 ml) was added dropwise and the reaction mixture was stirred for 2 hours at RT, to give mixture (I). A mixture of 2-amino-ethanol (0.2 mol) in DMF (20 ml) was added dropwise to mixture (I) and the resulting mixture was stirred for 5 hours at 60° C. The solvent was evaporated and the obtained residue was purified by RP high-performance liquid-chromatography. The product fractions were collected and the solvent was evaporated, yielding 10.7 g of intermediate 180.

d) Preparation of carbamic acid; [2-[[3-[4-chloro-2-[(6-hydroxy-7-methoxy-4-quinazolinyl)amino]phenyl]propyl]amino]-2-oxoethyl](2-hydroxyethyl)-, 1,1-dimethylethyl ester (intermediate 181)

A mixture of intermediate 180 (0.0043 mod) in DCM (50 ml) and THF (50 ml) was stirred and dicarbonic acid, bis(1, 1-dimethylethyl)ester (0.0046 mol) was added, then the reaction mixture was stirred for 2 hours and the solvent was evaporated. The residue was taken up in a small amount of water and the mixture was extracted with DCM. The organic layer was separated and the solvent was evaporated. The obtained residue was taken up in methanol and then $CH_3OH/NH_3$ was added. The mixture was stirred for 2 hours and the solvent was evaporated. The residue was purified on a glass filter (eluent: $DCM/CH_3OH$ 90/10). The product fractions were collected and the solvent was evaporated, yielding 0.500 g of intermediate 181.

Example A39

Preparation of

A mixture of intermediate 179 (0.016 mol) in DMF (80 ml) was stirred and DIPEA (0.040 mol) was added to give Solution (*). 2-(3,5-Dimethoxy-4-formylphenoxy)ethoxymethyl polystyrene (0.00528 mol, Novabiochem: 01-64-0269 previously washed with DCM, was stirred in DCM 120 ml), then tetrakis (2-propanolato) titanium 0.016 mol) was added and the mixture was stirred. Solution (*) was added and the resulting mixture was stirred for 2 hours. After addition of NaBH(OAc)$_3$ (0.016 mol), the reaction mixture was stirred for 16 hours and was filtered off. The filter residue was washed 2 times with DCM (100 ml)/THF (100 ml), 3 times with successively DCM (200 ml) and methanol (200 ml) and finally 3 times with DCM (200 ml). The washed residue was dried for 16 hours at 50° C. and the desired product was collected, yielding 9.46 g (77%) of intermediate 182.

Example A40 a) Preparation of 1,3-dioxolane-2-methanamine, N-[(2-amino-4-chlorophenyl)methyl]-N-methyl- (intermediate 183)

A solution of N-methyl-1,3-dioxolane-2-methanamine (0.020 mol) and 4-chloro-2-nitro-benzaldehyde (0.010 mol) in methanol (200 ml) was hydrogenated at 50° C. over the weekend with Pt/C (cat. quant., slurry in EtOAc) as a catalyst in the presence of thiophene solution (q.s., 4% in THF). After uptake of H$_2$ (4 equiv.), the reaction mixture was filtered over dicalite and the solvent was evaporated. The residue was purified by RP high-performance liquid chromatography. The product fractions were collected and the organic component of the eluent was evaporated. The precipetate was filtered off, to give 0.7879 g (31%) of intermediate 183.

b) Preparation of 6-quinazolinol, 4-[[5-chloro-2-[[(1,3-dioxolan-2-ylmethyl)methylamino]methyl]phenyl]amino]-7-methoxy-, acetate (ester) (intermediate 184)

A solution of intermediate 85 (0.00156 mol) and intermediate 183 (0.00156 mol) in acetonitrile (15 ml) was stirred for 3 hours at 80° C. and then the reaction mixture was allowed to cool overnight. The mixture was stirred for another hour at 80° C. and then 3 drops of glacial acetic acid was added. The (intermediate 182)

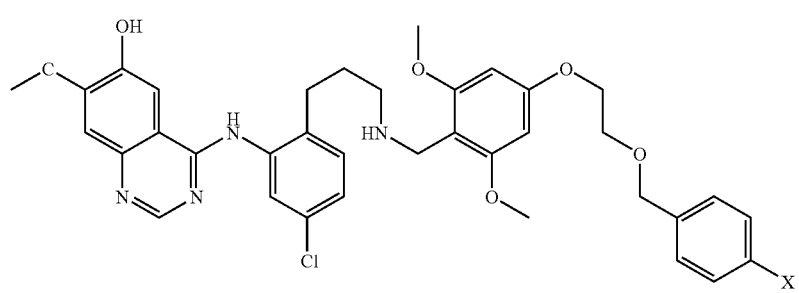

resulting mixture was stirred at 80° C. and again glacial, acetic acid (1 ml) were added. After stirring overnight at 80° C., the mixture was cooled to RT and the obtained precipitate was filtered off. The filtrate was evaporated and the residue was dried in an oven, yielding intermediate 184 (used as such in the next reaction step).

c) Preparation of 6-quinazolinol, 4-[[5-chloro-2-[[(1, 3-dioxolan-2-ylmethyl)methylamino]methyl]phenyl] amino]-7-methoxy- (intermediate 185)

A solution of intermediate 184 (0.00156-mol) in $NH_3$/$H_3OH$ (q.s.) was stirred for 1 hour at RT and then the reaction mixture was filtered, to give filter residue and filtrate. The filtrate was triturated with acetonitrile and then the desired product was collected, yielding 0.1350 g of intermediate 185.

d) Preparation of carbamic acid, [3-[[4-[[5-chloro-2-[[(1,3-dioxolan-2-ylmethyl)methylamino]methyl] phenyl]amino]-7-methoxy-6-quinazolinyl]oxy]propyl]-, 1,1-dimethylethyl ester (intermediate 186)

cesium carbonate (0.00464 mol) was added to a solution of intermediate 185 (0.00093 mol) in DMF (9 ml) and the mixture was stirred for 1 hour at RT. (3-bromopropyl)-carbamic acid, 1,1-dimethylethyl ester (0.00093 mol) was added and the reaction mixture was stirred overnight at RT, then the solvent was evaporated and the residue was dissolved in DCM. This solution was filtered over dicalite and the filtrate was evaporated to dryness, yielding intermediate 186 (used as such in the next reaction

Example A41 a) Preparation of benzenemethanamine, 4-chloro-N-methyl-2-nitro-N-2-propenyl- (intermediate 187)

A solution of 4-chloro-2-nitro-benzaldehyde (0.010 mol) and N-methyl-2-propen-1-amine (0.010 mol) in DCM (q.s.) was stirred for 15 hours at RT, then $NaBH(OAc)_3$ (0.011 mol) was added and the reaction mixture was stirred for 3.5 hours at RT. Extra $NaBH(OAc)_3$ (0.002 mol) was added and the mixture was filtered over silica gel (eluent: DCM). The second fraction was repurified by column chromatography over silica gel and combined with previously obtained 1st fraction and then the solvent was evaporated, yielding 2.0689 g (86%) of intermediate 187.

b) Preparation of benzenemethanamine, 2-amino-4-chloro-N-methyl-N-2-propenyl- (intermediate 188)

Tin (II) chloride dihydrate (0.043 mol) was added to a solution of intermediate 187 (0.0086 mol) in ethanol (40 ml) and after stirring the reaction mixture was heated for 90 min. at 50° C. A saturated aqueous $NaHCO_3$ solution was added, followed by addition of DCM, then the layers were separated and the separated organic layer was filtered. The aqueous layer was extracted 3 times with DCM and the separated organic layer was filtered again. The filter residue was washed 3 times with DCM and the organic layer of the filtrate was separated, then dried, filtered and the solvent was evaporated, yielding 1.3772 g (76%) of intermediate 188.

c) Preparation of 6-quinazolinol, 4-[[5-chloro-2-[(methyl-2-propenylamino)methyl]phenyl]amino]-7-methoxy-, acetate (ester) (intermediate 189)

Intermediate 85 (0.016 mol) was added to a solution of intermediate 188 (0.0016 mol) in 2-propanol (20 ml), then reaction mixture was stirred for 3 hours at 80° C. and the desired product was collected, yielding intermediate 189.

d) Preparation of 6-quinazolinol, 4-[[5-chloro-2-[(methyl-2-propenylamino)methyl]phenyl]amino]-7-methoxy (intermediate 190)

A solution of intermediate 189 (0.0016 mol) in $NH_3$/$CH_3OH$ (10 ml) was shaken for 1 hour and then the solvent was evaporated to dryness, yielding intermediate 190.

e) Preparation of 4-quinazolinamine, 6-(3-butenyloxy)-N-[5-chloro-2-[(methyl-2-propenylamino) methyl]phenyl]-7-methoxy- (intermediate 191)

A mixture of intermediate 190 (0.00042 mol), 4-bromo-1-butene (0.0005 mol) and cesium carbonate (q.s.) in DMF (q.s.) was stirred overnight at RT and then the solvent was evaporated. The dry residue war dissolved in DCM and the obtained solution was filtered over dicalite, then the desired product was collected, yielding intermediate 191.

Example A42 a) Preparation of 1H-isoindole-1,3(2H)-dione, 2-[2-(4-chloro-2-nitrophenyl)ethyl](intermediate 192)

A mixture of 4-chloro-1-(2-chloroethyl)-2-nitro-benzene (0.37 mol) and 1H-isoindole-1,3(2H)-dione, potassium salt (0.55 mol) in DMF (1000 ml) was reacted for 2 hours at 90° C., then the reaction mixture was cooled and poured out into ice-water. The resulting mixture was stirred for 30 min. at RT and the precipitate was filtered off. The filter residue was dissolved in DCM with $MgSO_4$ and after filtration the filtrate was evaporated. Yield: 118 g (96%) of intermediate 192.

b) Preparation of benzeneethanamine, 4-chloro-2-nitro- (intermediate 193)

Hydrazine, monohydrate (2.0 mol) was slowly added dropwise to a mixture of intermediate 192 (0.37 mol) in methanol (1000 ml) and then the reaction mixture was reacted for 6 hours at 55° C. After filtration, the filtrate was evaporated and water was added to the obtained residue. The mixture was extracted 3 times with toluene, then the organic layer was separated, dried ($MgSO_4$), filtered and the solvent was evaporated, yielding 61.5 g of intermediate 193.

c) Preparation of benzeneethanamine, 2-amino-4-chloro- (intermediate 194)

A mixture of intermediate 193 (0.225 mol) in THF (500 ml) was hydrogenated with, Pt/C 5% (5 g) as a catalyst in the presence of thiophene solution (5 ml). After uptake of $H_2$ (3 equiv.), the catalyst was filtered off and the filtrate was evaporated. The obtained residue was dissolved in toluene and a 1N HCl solution (600 ml), then this solution was stirred for 1 hour at 60° C. and after cooling sodium hydroxide was added until pH: 9. The organic layer was separated and the aqueous layer was extracted 2 times with toluene. The organic layers were combined, dried: (MgSO$_4$), filtered off and the solvent was evaporated, yielding 30 g of intermediate 194.

d) Preparation of (S) carbamic acid, [2-[[2-(2-amino-4-chlorophenyl)ethyl]amino]-1-methyl-2-oxoethyl]-1,1-dimethylethyl ester (intermediate 195)

A mixture of N-[(1,1-dimethylethoxy)carbonyl]-L-Alanine (0.0015 mol) and PL-DCC resin (0.0030 mol; Polymer Laboratories, Part No 3417) in DCM (20 ml) was stirred for 30 min at RT. A mixture of 1-[bis(dimethylamino)methylene]-1H-benzotriazolium, hexafluorophosphate (1-), 3-oxide (0.0015 mol) in a small amount of DMF (5 ml) was added. A mixture of intermediate 194 (0.00225 mol) in DCM (2 ml) was added and the reaction mixture was stirred for 5 hours, then methylisocyanate polystyrene (0.00225 mol; NovaBiochem, No 01-640169) was added [and additionally, (polystyrylmethyl)trimethylammonium bicarbonate (0.00450 mol; NovaBiochem, No 01-64-0419) was added. After 15 hours, the reaction mixture was filtered and the solvent was evaporated, yielding intermediate 195.

e) Preparation of (S) carbamic acid, [2-[[2-[4-chloro-2-[(6-hydroxy-7-methoxy-4-quinazolinyl)amino]phenyl]ethyl]amino]-1-methyl-2-oxoethyl]-1,1-dimethylethyl ester (intermediate 196)

A solution of intermediate 195 (0.00110 mol) and intermediate 85 (0.00100 mol) in 2-propanol (20 ml) was stirred for 5 hours at 50° C., then the mixture was cooled and NH$_3$, 7N in methanol (10 ml) was added. The reaction mixture was stirred for 2 hours at RT and the solvent was evaporated, yielding intermediate 196.

f) Preparation of (S) acetic acid, [[4-[[2-[2-[(2-amino-1-oxopropyl)amino]ethyl]-5-chlorophenyl]amino]-7-methoxy-6-quinazolinyl]oxy]-.HCl (1:1) (intermediate 197)

Step I 'alkylation with chloroacetate': A solution of intermediate 196 (0.001 mol), chloro-acetic acid, methyl ester (0.002 mol) and potassium carbonate (0.003 ml) in acetonitrile dry (20 ml) was stirred for 3 hours at 75° C., then water (2 ml) and DCM (10 ml) were added and the reaction mixture was stirred for 5 min. at RT. The mixture was filtered through Isolute HM-N cartridges, followed by elution with DCM and then the solvent was evaporated, to give Residue (1). Step II 'deprotection': A solution of Residue (I) in concentrated HCl (2.5 ml), water (2.5 ml) and dioxane (5.0 ml) was stirred for 24 hours at 60° C. and then the solvent was evaporated, yielding intermediate 197 isolated as a hydrochloric acid salt (1:1).

Example A43 a) Preparation of carbamic acid, [4-[[(4-chloro-2-nitrophenyl)methyl]amino]oxobutyl]-, 1,1-dimethylethyl ester (intermediate 198)

N'-(ethylcarbonimidoyl)-N,N-dimethyl-1,3-propanediamine (0.0049 mol) was added portionwise to a mixture of 4-[[(1,1-dimethylethoxy)carbonyl]amino]-butanoic acid (0.0049 mol), 4-chloro-2-nitro-benzenemethanamine (0.0041 mol) and DIPEA (0.0049 mol) in DMF (30 ml) at and then the reaction mixture was stirred 3 hours at RT. The mixture was diluted with EtOAc (150 ml), washed with a 10% aqueous citric acid solution, with water, with an aqueous NaHCO$_3$ solution and then with brine. The organic layer was separated, dried, filtered off and the solvent was evaporated, yielding 1.225 g of intermediate 198.

b) Preparation of carbamic acid, [4-[[(2-amino-4-chlorophenyl)methyl]amino]-4-oxobutyl]-, 1,1-dimethylethyl ester (intermediate 199)

A mixture of intermediate 198 (0.003 mol) in THF (25 ml) and methanol (25 ml) was hydrogenated at 50° C. with Pt/C 5% (0.5 g) as a catalyst in the presence of thiophene solution (0.5 ml). After uptake of H$_2$ (3 equiv.), the catalyst was filtered off and the filtrate was evaporated, yielding intermediate 199.

c) Preparation of carbamic acid, [4-[[[4-chloro-2-[(6-hydroxy-7-methoxy-4-quinazolinyl-amino]phenyl]methyl]amino-4-oxobutyl]-, 1,1-dimethylethyl ester (intermediate 120)

A solution of intermediate 199 (0.0033 mol) and intermediate 85 (0.00275 mol) in 2-propanol (100 ml) was stirred for 3 hours at 50° C. and after cooling NH$_3$, 7N in to methanol (50 ml) was added. The reaction mixture was stirred for 2 hours and then the solvent was evaporated, yielding intermediate 120.

d) Preparation of acetic acid, [[4-[[5-chloro-2-[[[4-[[(1,1-dimethylethoxy)carbonyl]amino]-1-oxobutyl]amino]methyl]phenyl]amino]-7-methoxy-6-quinazolinyl]oxy]-, methyl ester (intermediate 121)

A mixture of intermediate 120 (0.001 mol), potassium carbonate (0.003 mol) and chloro-acetic acid, methyl ester (0.003 mol) in acetonitrile (10 ml) was stirred for 3 hours at 75° C., then the reaction mixture was filtered over silica gel and the filter residue was washed with 2-propanone. Finally, the filtrate was evaporated overnight under vacuum, yielding intermediate 121.

e) Preparation of acetic acid, [[4-[[2-[[(4-amino-1-oxobutyl)amino]methyl]-5-chlorophenyl]amino]-7-methoxy-6-quinazolinyl]oxy]- (intermediate 122)

A solution of intermediate 121 (0.001 mol) in HCl concentrated (3 ml), THF (6 ml) and water (3 ml) was stirred for 24 hours at 60° C. and then the solvent was evaporated, yielding intermediate 122.

B. Preparation of the Compounds

Example B1

Preparation of 4,6-ethanediylidene-19H-pyrimido[4,5-b][6,13,1]benzodioxaacyclo-pentadecin-8(9H)-one, 10,11,12,13-tetrahydro-20-methoxy-15-methyl- (compound 1)

A solution of intermediate 5 (0.00008 mol), N'-(ethylcarbonimidoyl)-N,N-dimethyl-1,3-propanediamine (0.00024 mol) and DMC (5 ml) was stirred at RT and then N'-(ethylcarbonimidoyl)-N,N-dimethyl-1,3-propanediamine, monohydrochloride (0.00008 mol) was added. The reaction mixture was stirred over the weekend at RT. The reaction was completed and the mixture was washed 2 times with H$_2$O. The organic layer was separated, dried (MgSO$_4$), filtered off and the solvent was evaporated. The residue was purified by high-performance liquid chromatography over RP-18 (Normal Phase). The product fractions were collected, the solvent was evaporated and the residue was dried (vac.) at 65° C., yielding 0.009 g of compound 1.

Example B2

Preparation of 4,6-ethanediylidene-19H-pyrimido[4,5-b][6,13,1]benzodioxaazacyclo-pentadecine, 15-chloro-8,9,10,11,12,13-hexahydro-20-methoxy- (compound 2)

A solution of intermediate 9 (0.0024 mol) and triphenylphosphine (0.0036 mol) in THF, dry (100 ml) was stirred at RT and then a solution of bis(1-methylethyl)diazenedicarboxylate (0.0036 mol) in THF (10 ml) was added dropwise. The reaction mixture was stirred for 6 hours and extra bis(1-methylethyl)diazenedicarboxylate (0.35 ml) in THF (10 ml) was added. The mixture was stirred overnight and concentrated. The residue was purified by column chromatography over silica gel (eluent: DCM/CH$_3$OH/THF 90/5/5). The product fractions were collected and further purified by RP high-performance liquid chromatography. The product fractions were collected and concentrated. The aqueous concentrate was filtered, and the solid retained washed and dried (vac.) at 65° C., yielding 0.065 g of compound 2, melting point 255.5-260.2° C.

Example B3

Preparation of 4,6-ethanediylidene-19H-pyrimido[4,5-b][6,13,1]benizodioxaazacyclo-pentadecine, 17-chloro-8,9,10,11,12,13-hexahydro-20-methoxy- (compound 3)

A solution of intermediate, 13 (0.0012 mol) and tributylphosphine (0.0018 mol) in THF (dry)(50 ml) was stirred under N$_2$ conditions at RT and then a mixture of 1,1'-(azodicarbonyl)bis-piperidine (0.0018 mol) in THF (dry) (10 ml) was added dropwise. The reaction mixture was stirred overnight and extra tributylphosphine (0.30 ml) was added. The mixture was stirred for another 4 hours and the solvent was evaporated. The residue was purified by RP high-performance liquid chromatography and the product fractions were collected and concentrated, the aqueous concentrate was filtered, and the solid retained washed and dried (vac.) at 65° C., yielding 0.040 g of compound 3, melting point 241.5-242.7° C.

Example B4

Preparation of 4,6-ethanediylidene-8H,18H-pyrimido[4,5-b][6,12,1]benzo-dioxaazacyclotetradecine, 16-chloro-9,10,11,12-tetrahydro-19-methoxy- (compound 4)

A solution of intermediate 17 (0.001 mol) and tributylphosphine (0.012 mol) in (40 ml) was stirred at RT under N$_2$ and then a solution off 1,1-(azodicarbonyl)bis-piperidine (0.0012 mol) in THF (10 ml) was added dropwise. The reaction mixture was stirred for 4 h and then an extra amount of tributylphosphine (1 ml) and 1,1'-(azodicarbonyl)bis-piperidine-(1 g) were added. The resulting mixture was stirred overnight and the solvent was concentrated under reduced pressure. The residue was purified by RP high-performance liquid chromatography. The product fractions were collected and the organic solvent was evaporated. The resulting precipitate was filtered, washed and dried (vacuum) at 65° C., yielding 0.065 g of compound 4, melting point 213.5-221.2° C.

Example B5

Preparation of 4,6-ethanediylidene-19H-pyrimido[4,5-b][6,13,1]benzodioxaazacyclo-pentadecine, 8,9,10,11,12,13-hexahydro-20-methoxy- (compound 5)

A solution of intermediate 21 (0.0013 mol) and tributylphosphine (0.002 mol) in THF (50 ml) was stirred at RT and then a solution of 1,1'-(azodicarbonyl)bis-piperidine (0.002 mol) in THE (5 ml) was added. After addition, the reaction mixture was stirred for 6 hours and the reaction was completed. The solvent was evaporated and the residue was purified by RP high-performance liquid chromatography. The product fractions were collected and the organic solvent was evaporated. The aqueous concentrate was filtered and the solid retained washed and dried (vac.) at 65° C., yielding 0.100 g of compound 5, melting point 243.3-251.2° C.

Example B6

Preparation of 4,6-ethanediylidene-19H-pyrimido[4,5-b][6,13,1]benzodioxaazacyclo-pentadecine, 17-bromo-8,9,10,11,12,13-hexahydro-20-methoxy- (compound 6)

A solution of intermediate 25 (0.00079 mol) and tributylphoshine (0.00316 mol) in THF, dry (50 ml) was stirred at RT under N$_2$-atm., then a solution of 1,1'-(azodicarbonyl)bis-piperidine (0.00316 mol) in THF, dry (10 ml) was added and the reaction mixture was stirred for 12 hours at RT under N$_2$-atm. The solvent was evaporated, the residue was stirred in DIPE and the mixture was filtered. The filtrate and the residue were combined and purified by RP high-performance liquid chromatography. The product fractions were collected and concentrated, yielding 0.180 g (51%) of compound 6, melting point 228.6-234.8° C.

Example B7

Preparation of 4,6-ethanediylidene-8H,20H-pyrimido[4,5-b][6,14,1]benzo-dioxaazacyclohexadecine, 18-chloro-9,10,11,12,13,14-hexahydro-21-methoxy-(compound 7)

Tributylphoshine (0.0017 mol) and 1,1'-(azodicarbonyl)bis-piperidine (0.0017 mol) were added at RT to a solution of intermediate 29 (0.0012 mol) in THF (80 ml) and reaction mixture was stirred for 2 hours. The solvent was evaporated under reduced pressure and the residue was stirred in boiling DIPE/CH$_3$CN (20 ml/5 ml). This mixture was filtered, the solid retained was washed with CH$_3$CN and purified by RP high-performance liquid-chromatography. The product fractions were collected and the organic solvent was evaporated. The aqueous concentrate was filtered, and the solid retained washed and dried (vac.) at 65° C., yielding 0.145 g (30%) of compound 7, melting point 240.6-243.7° C.

Example B8

Preparation of 4,6-ethanediylidene-21H-pyrimido[4,5-b][6,15,1]benzodioxaazacyclo-heptadecine, 19-chloro-8,9,10,11,12,13,14,15-octahydro-22-methoxy- (compound 8)

A solution of intermediate 33 (0.0045 mol) in THF (200 ml) was stirred at RT and tributylphosphine (0.0047 mol), then 1,1'-(azodicarbonyl)bis-piperidine (0.0047 mol) were added. The reaction mixture was stirred for 4 hours and the solvent was evaporated until 2/3 of the initial volume. The mixture was filtered and the residue washed with a small amount of THF. The filtrate was concentrated and this residue was suspended in $H_2O$ and stirred. The resulting precipitate was collected by filtration, washed with water and treated with boiling 2-propanol. The mixture was cooled and filtered, the solid retained was washed with 2-propanol and DIPE and dried (vac.) at 60° C., yielding 1.4 g (74%) of compound 8, melting point 147.7-151.1° C.

Example B9

Preparation of 4,6-ethanediylidene-8H,22H-pyrimido[4,5-b][6,16,1]benzo-dioxaazacyclooctadecine, 20-chloro-9,10,11,12,13,14,15,16-octahydro-23-methoxy-(compound 9)

A solution of intermediate 37 (0.0022 mol) in THF (100 ml) was stirred at RT and tributylphosphine (0.0023 mol), then 1,1'-(azodicarbonyl)bis-piperidine (0.0023 mol) was added. The reaction mixture was stirred for 4 hours and the solvent was evaporated until ⅔ of the initial volume. The precipitate was filtered and washed with a small amount of THF. The filtrate was concentrated and the residue was stirred in $H_2O$. The resulting precipitate was collected by filtration, washed with water and treated with boiling 2-propanol. The mixture was cooled and filtered, then the solid retained was washed with 2-propanol and with DIPE and dried (vacuum) at 60° C.), yielding 0.6 g (63%) of compound 9, melting point 177.4-183.8° C.

Example B10 a) Preparation of 4,6-ethanediylidene-19H-pyrimido[4,5-b][6,13,1]benzodioxaazacyclo-pentadecine-17-carboxylic acid, 8,9,10,11,12,13-hexahydro-20-methoxy-, methyl ester (compound 10)

A mixture of compound 6 (0.0005 mol), Pd(OAC)$_2$ (0.022 g), 1,3-propanediylbis[diphenyl-phosphine] (0.088 g) and potassiumacetate (0.100 g) in methanol (q.s.; dry) was reacted under CO-gas (30 atm) for 16 hours at 125° C. The solvent was evaporated. The residue was taken up into water and this mixture was extracted with DCM. The separated organic layer was dried, filtered and the solvent evaporated. The residue was purified by HPLC over X-Terra (gradient elution with eluent: $CH_3CN/CH_3OH/NH_4OAc$). The product fractions were collected and the solvent was evaporated. The residue was taken up into water, alkalised with $K_2CO_3$, then extracted with DCM. The separated organic layer was dried, filtered and the solvent evaporated, yielding 0.057 g of compound 10.

b) Preparation of 4,6-ethanediylidene-19H-pyrimido[4,5-b][6,13,1]benzodioxaazacyclo-pentadecine-17-carboxylic acid, 8,9,10,11,12,13-hexahydro-20-methoxy- (compound A mixture of compound 10 (0.0002 mol) in THF (3 ml), methanol (3 ml), NaOH 1N (1 ml) and $H_2O$ (2 ml) was stirred at 50° C. for 3 hours. The solvent was evaporated. Water (2 ml) was added. HCl (1 N, 1 ml) was added and the mixture was stirred for a while. The precipitate was filtered off, washed with water, then filtered off again and stirred in THF, then filtered off and dried, yielding 0.036 g of compound 11.

Example B11

Preparation of pyrrolidine, 1-[(8,9,10,11,12,13-hexahydro-20-methoxy-4,6-ethane-diylidene-19H-pyrimido[4,5-b][6,13,1]benzodioxaazacyclopentadecin-17-yl)carbonyl](compound 12)

A mixture of compound 6(0.0004 mol), Pd(OAc)$_2$ (6-0.011 g), 1,3-propanediylbis[diphenyl-phosphine] (0.044 g) and pyrrolidine (0.100 g) in THF (q.s., dry) was reacted under CO-gas (30 atm) for 16 hours at 125° C. The solvent was evaporated. The residue was taken up into water and this mixture was extracted with DCM. The separated organic layer was dried, filtered and the solvent evaporated. The residue was purified by HPLC over X-Terra (gradient elution with eluent: $CH_3CN/CH_3OH$ $NH_4OAc$). The product fractions were collected and the solvent was evaporated. The residue was taken up into water, alkalised with $K_2CO_3$, then extracted with DCM. The separated organic layer was dried, filtered and the solvent evaporated, yielding 0.051 g of compound 12.

Example B12

Preparation of 4,6-ethanediylidene-19H-pyrimido[4,5-b][6,13,1]benzodioxaazacyclo-pentadecine-17-carbonitrile, 8,9,10,11,12,13-hexahydro-20-methoxy- (compound 13)

A mixture of compound 6 (0.0002 mol), tris[μ-[(1,2-η:4,5-η)-(1E,4E)-1,5-diphenyl-,1,4-pentadien-3-one]]di-palladium, (0.011 g), 1,1'-bis(diphenylphosphino)-ferrocene (0.013 g), Zn (0.005 g) and Zn(CN)$_2$ (0.045 g) in (2-oxo-1-pyrrolidinyl)-methyl (2 ml) was reacted in the microwave for 30 min at 150° C. Water (4 ml) was added and this mixture was extracted three times with ethyl acetate. The combined organic layers were washed with water (2×), dried, filtered and the solvent was evaporated. The residue was purified by reversed-phase HPLC over X-Terra (gradient elution with eluent: $CH_3CN/CH_3OH/NH_4OAc$). The product fractions were collected and the solvent was evaporated. The residue was taken up into water, then alkalised with $K_2CO_3$. This mixture was extracted with DCM. The separated organic layer was dried, filtered and the solvent evaporated, yielding 0.063 g (81%) of compound 13.

Example B13

Preparation of morpholine, 4-[(8,9,10,11,12,13-hexahydro-20-methoxy-4,6-ethane-diylidene-19H-pyrimido[4,5-b][6,13,1]benzodioxaazacyclopentadecin-17-yl)carbonyl]- (compound 14)

A mixture of compound 6 (0.0002 mol), Pd(OAc)$_2$ (0.022 g), 1,3-propanediylbis[diphenyl-phosphine] (0.088 g) and morpholine (0.200 g) in THF (q.s., dry) was reacted under CO-gas (30 atm) for 24 hours at 125° C. The solvent was evaporated. The residue was taken up into water and this mixture was extracted with DCM. The separated organic layer was dried, filtered and the solvent evaporated. The residue was purified by HPLC over X-Terra (gradient elution with eluent: $CH_3CN/CH_3OH/NH_4OAc$). The product fractions were collected and the solvent was evaporated. The residue was taken up into water, alkalised with $K_2CO_3$, then % extracted with DCM. The separated organic layer was dried, filtered and the solvent evaporated, yielding 0.005 g of compound 14.

Example B14 a) Preparation of 4,6-ethanediylidene-19H-pyrimido[4,5-b][6,13,1]benzodioxaazacyclo-pentadecine, 17-bromo-8,9,10,11,12,13-hexahydro-20-(phenyl-methoxy)- (compound 15)

A solution of intermediate 47 (0.0026 mol) in THF (140 ml) was stirred at RT, tributylphosphine (0.0035 mol) was added and then ADDP (0.0035 mol). The reaction mixture was stirred for 6 hours and extra ADDP (0.0035 mol) and tributylphosphine (0.0035 mol) were added. The resulting mixture was stirred for 12 hours. The formed precipitate was removed and the solvent was evaporated under reduced pressure. The residue was dissolved in THF (100 ml) with molecular sieves. Extra ADDP (0.0035 mol) and tributylphosphine (0.0035 mol) were added and the mixture was stirred for 2 hours. The resulting precipitate was filtered off and the solvent was evaporated under reduced pressure. The residue was filtered over silica gel (eluent: $DCM/CH_3OH$ 98/2) the product fractions were collected and the solvent was evaporated, yielding 0.600 g of compound 15.

b) Preparation of 4,6-ethanediylidene-9H-pyrimido[4,5-b][6,13,1,i]benzodioxaazacyclo-pentadecin-20-ol, 17-bromo-8,9,10,11,12,13-hexahydro- (compound 16)

A solution of compound 15 (0.0006 mol) and (methylthio)-benzene (0.006 mol) in trifluoroacetic acid (6 ml) was stirred for 3 days at RT and then the solvent was evaporated. The residue was quenched with $H_2O$ and the aqueous layer was extracted with DCM. The precipitate between the two layers was filtered off, washed and dried (vacuum) at 60° C., yielding compound 16.

Example B15

Preparation of 4,6-ethanediylidene-19H-pyrimido[4,5-b][6,13,1]benzodioxaazacyclo-pentadecine, 17-bromo-8,9,10,11,12,13-hexahydro-20-[3-(4-morpholinyl)propoxy]-acetic acid (compound 17)

A mixture of compound 16 (0.000065 mol) and $K_2CO_3$ (0.00013 mol) in DMA 2 ml) was stirred at 60° C. for 30 min., then 4-(3-chloro-propyl)-morpholine (0.000065 mol) was added and the reaction mixture was stirred for 1 day at 60° C. Extra 4-(3-chloro-propyl)-morpholine (0.000065 mol) was added and the mixture was stirred for 1 day. After the starting material was consumed, the mixture was purified by RP high-performance liquid chromatography. The product fractions were collected and the organic solvent was evaporated. The aqueous concentrate was extracted with $DCM/CH_3OH$ (98/2) and the organic layer was dried ($MgSO_4$), filtered, then the solvent was evaporated, yielding 0.004 g of compound 17.

Example B16 a) Preparation of 4,6-ethanediylidene-19H-pyrimido[4,5-b][6,13,1]benzodioxaazacyclo-pentadecine, 17-bromo-8,9,10,11,12,13-hexahydro- (compound 18)

A solution of intermediate 49 (0.0012 mol) in THF (50 ml) was stirred at RT under $N_2$ and tributylphosphine (0.0017 mol) was added, then 1,1'-(azodicarbonyl)bis-piperidine (0.0017 mol) was added and the reaction mixture was stirred for 1 hour. The solvent was evaporated until ⅓ of the initial volume and the formed precipitate was filtered off, then washed. The filtrate was evaporated and the residue was quenched with $H_2O$. The mixture was acidified with HCl (1N) and extracted with $DCM/CH_3OH$ (99/1). The organic layer was dried ($MgSO_4$), filtered and the solvent was evaporated. The residue was purified by Flash column chromatography (eluent: $DCM/CH_3OH$ 99/1). The product fractions were collected and the solvent was evaporated. The residue was stirred in boiling 2-propanol, then the resulting precipitate was filtered off, washed with 2-propanol and with DIPE and dried (vacuum) at 60° C., yielding 0.111 g of compound 18.

Example B17 a) Preparation of 4,6-ethanediylidenepyrimido[4,5-b][6,1,12]benzoxadiazacyclo-pentadecine-13(8H)-carboxylic acid, 17-bromo-9,10,11,12,14,19-hexahydro-20-methoxy-, 1,1-dimethylethyl ester (compound 19)

A solution of intermediate 55 (0.0021 mol) in THF (dry) (120 ml) was stirred at RT and tributylphosphine (0.0032 mol) was added, then 1,1'-(azodicarbonyl)bis-piperidine, (0.0032 mol) was added and the reaction mixture was stirred for 3 hours. The solvent was evaporated until ⅓ of the initial volume. The resulting precipitate was filtered off and washed. The filtrate was evaporated and used as such in the next reaction step. A part of the residue (0.200 g) was purified by RP high-performance liquid chromatography. The product fractions were collected and the organic solvent was evaporated. The aqueous concentrate was extracted with. DCM and the organic layer was dried ($MgSO_4$), filtered off, then the solvent was evaporated, yielding 0.005 g of compound 19.

b) Preparation of 4,6-ethanediylidenepyrimido[4,5-b][6,1,12]benzoxadiazacyclo-pentadecine, 17-bromo-8,9,10,11,12,13,14,19-octahydro-20-methoxy- (compound 20)

A solution of compound 19 (0.00092 mol) in mono(trifluoroacetate) (20 ml) was stirred for 1 hour at RT, then the solvent was evaporated under reduced pressure and co-evaporated with toluene. The residue was stirred in boiling 2-propanol, then the resulting precipitate was filtered off, washed and dried. The filtrate was evaporated and the residue was purified by RP high-performance liquid chromatography. The product fractions were collected and the organic solvent was evaporated. The aqueous concentrate was filtered off, washed and dried (vac.) at 70° C., yielding 0.040 g (5%) of compound 20.

Example B18 a) Preparation of 4,6-ethanediylidenepyrimido[4,5-b][6,1]benzoxaazacyclopentadecine, 17-bromo-8,9,10,11,12,13,14,19-octahydro-20-methoxy- (compound 21)

A solution of intermediate 60 (0.0011 mol) in THF dry (50 ml) was stirred at RT and tributylphosphine (0.0016 mol) was added, then 1,1'-(azodicarbonyl)bis-piperidine (0.0016 mol) was added and the reaction mixture was stirred for 4 hours. The solvent was evaporated until ⅓ of the initial volume. The resulting precipitate was filtered off and washed. The filtrate was evaporated and the residue was purified by RP high-performance liquid chromatography. The product fractions were collected and the organic solvent was evaporated. The aqueous concentrate was filtered off, washed with $H_2O$ and dried (vac.) at 65° C., yielding 0.037 g (7.5%) of compound 21.

Example B19 a) Preparation of 4,6-ethanediylidenepyrimido[4,5-b][6,1,12]benzoxadiazacyclo-pentadecine, 17-bromo-8,9,10,11,12,3,14,19-octahydro-20-methoxy-13-methyl (compound 22)

A solution of intermediate 65 (0.0011 mol) in THF (50 ml) was stirred at RT and tributylphosphine (0.0016 mol) was added, then 1,1'-(azodicarbonyl)bis-piperidine (0.0016 mol) was added and the reaction mixture was stirred for 2 hours. The solvent was evaporated until ⅓ of the initial volume. The resulting precipitate was filtered off and washed. The filtrate was evaporated and the residue was purified by RP high-performance liquid chromatography. The product fractions were collected and the organic solvent was evaporated. The aqueous concentrate was extracted 2 times with DCM and the organic layer was dried ($MgSO_4$), then filtered off. The solvent was evaporated and the residue was dried (vac.) at 50° C., yielding 0.004 g (0.8%) of compound 22.

Example B20

Preparation of 4,6-ethanediylidene-13H-pyrimido[4,5-b][6,11,1]benzodioxaazacyclo-pentadecine, 17-chloro-8,9,10,11,14,19-hexahydro-20-methoxy- (compound 23)

A mixture of intermediate 70 (0.0007 mol) in THF (50 ml) was stirred until complete dissolution and tributylphosphine (0.0014 mol) was added, then the mixture was stirred and ADDP (0.0014 mol) was added. The reaction mixture was stirred at RT and then extra ADDP (q.s.) and tributylphosphine (q.s.) were added. The resulting mixture was stirred at 60° C. for 10 hours and again extra ADDP (q.s.) and tributylphosphine (q.s.) were added. The mixture was stirred at 100° C. for 16 hours. The solvent was evaporated and the residue was purified by HPLC. The product fractions were collected and the solvent was evaporated, yielding 0.017 g of compound 23.

Example B21

Preparation of 4,6-ethanediylidene-23H-pyrimido[4,5-b][6,15,1,16]benzo-dioxadiazacyclononadecine, 21-chloro-8,9,10,11,12,13,14,15-octahydro-24-methoxy-(compound 24)

A solution of intermediate 75(0.000355 mol) and tributylphosphine (0.000356 mol) in THF (20 ml) and DMF p.a. dried on molecular sieves (5 ml) was treated with ADDP (0.000353 mol) and the reaction mixture was stirred at RT, then extra ADDP (q.s.) and tributylphosphine (q.s.) were added and the reaction mixture was stirred at RT. The solvent was evaporated and the residue was purified by HPLC the product fractions were collected and the solvent was evaporated, yielding 0.0274 g (17%) of compound 24, melting point 127.2-132.2° C.

Example B22

Preparation of 22H-4,6-ethanediylidene-21,17-methenopyrimido[5,4-d][1,12,6]dioxaazacycloeicosine, 8,9,10,11,12,13,14,15-octahydro-24-methoxy-(compound 25)

A solution of intermediate 79 (0.0012 mol) in THF (75 ml) was stirred at RT and then ADDP (0.0018 mol) and tributylphosphine (0.0018 mol) were added. The reaction mixture was stirred for 3 hours and extra ADDP (0.0018 mol) and tributylphosphine (0.0018 mol) were added. The resulting mixture was stirred for 2 hours and the solvent was evaporated under reduced pressure. The residue was stirred in 2-propanol and filtered off, then the filtrate was evaporated and the residue was purified by HPLC. The product fractions were collected and the solvent was evaporated, yielding 0.0027 g (72%) of compound 25.

Example B23 a) Preparation of 4,6-ethenopyrimido[4,5-b][6,1,10]benzoxadiazacyclopentadecin-12(13H)-one, 17-chloro-8,9,10,11,14,19-hexahydro-20-(methoxy-(compound 26)

ADDP (0.00034 mol) was added to a solution of intermediate 84 (0.00023 mol) and tributylphosphine (0.0042 mol) in THF (20 ml) and DMF (20 ml) at RT and the reaction mixture was stirred at RT for 1 hour. Extra ADDP and tributylphosphine were added at RT and then the resulting mixture was stirred for 1 hour at RT. The solvent was evaporated off and again extra ADDP and tributylphosphine were added. The mixture was warmed to 100° C. and stirred for 18 hours at 100° C., then the solvent was evaporated under reduced pressure and the residue was purified by HPLC. The product fractions were collected and the solvent was evaporated, yielding 0.0094 g (10%) of compound 26.

b) Preparation of 4,6-ethanediylidenepyrimido[4,5-b][6,1,12]benzoxadiazacyclopentadecin-14(19H)-one, 17-chloro-8,9,10,11,12,13-hexahydro-20-methoxy- (compound 27)

Compound 27 is made in a similar way as compound 26.

Example B24

Preparation of 4,6-ethanediylidene-19H-pyrimido[4,5-b][6,13,1]benzodioxaazacyclopentadecine, 17-bromo-8,9,10,11,12,13-hexahydro-20-(2-methoxyethoxy)- (compound 28)

A mixture of compound 16 (0.00023 mol), 1-bromo-2-methoxy-ethane (0.0046 mol) and $K_2CO_3$ (0.00046 mol) in DMA (10 ml) was stirred for 18 hours at 60° C. and then the reaction mixture was quenched with ice-water. The precipitate was filtered off, washed and stirred in boiling 2-propanol. The resulting precipitate was filtered off, washed and dried (vacuum) at 53° C., yielding 0.030 g (74%) of compound 28.

Example B25 a) Preparation of 4,6-ethanediylidenepyrimido[4,5-b][6,1,12]benzoxadiazacyclopentadecine-13(8H)-carboxylic acid, 17-chloro-16-fluoro-9,10,11,12,14,19-hexahydro-20-methoxy-, 1,1-dimethylethyl ester (compound 29)

Tributylphosphine (0.00044 mol) was added to a solution of intermediate 93 (0.00022 mol) and ADDP (0.00044 mol) in THF (30 ml) and then extra ADDP (0.00044 mol) and tributylphosphine (0.00044 mol) were added. The reaction mixture was stirred was stirred over the weekend and the solvent was evaporated. $CH_3OH$ (5 ml) was added and the resulting mixture was then filtered and the filtrate evaporated. The residue was purified by reversed phase HPLC. The product fractions were collected and the solvent was evaporated, yielding 0.04 g (35.2%) of compound 29.

b) Preparation of 4,6-ethanediylidenepyrimido[4,5-b][6,1,12]benzoxadiazacyclopentadecine, 17-chloro-16-fluoro-8,9,10,11,12,13,14,19-octahydro-20-methoxy- (compound 30)

A solution of compound 29 (0.000077 mot) in $CH_3OH$ (5 ml) was treated with HCl/2-propanol (6N) (1 ml) and then the reaction mixture was stirred overnight at RT. The solvent was evaporated and the residue was diluted with $DCM/NaHCO_3$. After stirring the mixture for 1 hour, the organic layer was separated, dried ($MgSO_4$), filtered off and the solvent was evaporated, yielding 0.0089 g (27.7%) of compound 30, melting point 265.9-261.3° C.

Example B26 a) Preparation of 4,6-ethanediylidenepyrimido[4,5-b][6,1,11]benzoxadiazacyclopentadecine-12(13H)-carboxylic acid, 17-chloro-8,9,10,11,14,19-hexahydro-20-methoxy-, 1,1-dimethylethyl ester (compound 31)

A solution of intermediate 99 (0.00025 mol), ADDP (0.000375 mol) and tributylphosphine (0.000375 mol) in THF (20 ml) was stirred for 4 hours at RT and then the solvent was evaporated until ⅓ of the initial volume. The resulting precipitate was filtered off and washed, then the filtrate was evaporated and the residue was purified by reversed phase HPLC. The product fractions were collected and the solvent was evaporated, yielding 0.02 g of compound 31.

b) Preparation of 4,6-ethanediylidenepyrimido[4,5-b][6,1,11]benzoxadiazacyclopentadecine, 17-chloro-8,9,10,11,12,13,14,19-octahydro-20-methoxy- (compound 32)

A solution of compound 31 (0.00004 mol) in TFA, (5 ml) was stirred for 4 hours at RT and then the solvent was removed under $N_2$ at 40° C. The residue was purified by HPLC. The product fractions were collected and the solvent evaporated, yielding 0.0037 g (69%) of compound 32.

Example B27

Preparation of 4,6-etheno-19H-pyrimido[5,4-k][11,8,5,13]benzodioxadiazacyclopentadecine, 17-chloro-8,9,10,11,12,13-hexahydro-20-methoxy-10-[2-(4-morpholinyl)ethyl]- (compound 33)

ADDP (0.00068 mol) and tributylphosphine (0.00085 mol) were added to a solution of intermediate 105 (0.00047 mol) in THF (30 ml) at RT and then the reaction mixture was stirred for 2 hours at RT. The solvent was evaporated under reduced pressure and the residue was purified by column chromatography over silica gel (eluent: $DCM/(CH_3OH/NH_3)$ 99/1 to 80/20). The pure fractions were collected and the solvent was evaporated under reduced pressure. The residue (0.032 g) was then purified by HPLC. The product fractions were collected and the solvent was evaporated, yielding 0.0055 g of compound 33.

Example B28 a) Preparation of 4,6-ethanediylidene-19H-pyrimido[4,5-b][6,13,1]benzodioxaazacyclopentadecine, 8,9,10,11,12,13-hexahydro-20-methoxy-17-phenyl- (compound 34)

A mixture of intermediate 88 (0.0001 mol), iodo-benzene (0.0002 mol), dichloro[1,1'-bis(diphenylphosphino)ferrocene]palladium (cat.quant., 5%), sodium, carbonate 2M in water (0.0003 mol) in DMSO (2 ml) was stirred at 80° C. for 3 hours, then the reaction mixture was poured out into ice-water and the aqueous layer was extracted with DCM. The organic layer was separated, dried, filtered off and the solvent was evaporated under reduced pressure. The residue was purified by column chromatography over silica gel (eluent: $DCM/CH_3OH$ 98/2). The product fractions were collected and the solvent was evaporated, yielding 0.016 g (36%) of compound 34.

b) Preparation of benzonitrile, 3-(8,9,10,11,12,13-hexahydro-20-methoxy-4,6-ethanediylidene-19H-pyrimido[4,5-b][6,13,1]benzodioxaazacyclopentadecin-17-yl)-(compound 35)

Compound 35 is made on the same way accordingly compound 34.

Example B29

Preparation of 4,6-ethanediylidene-8H-pyrimido[4,5-b][6,1,13]benzoxadiazacyclohexadecin-15(20H)-one, 18-chloro-9,10,11,12,13,14 hexahydro-21-methoxy- (compound 36)

ADDP (0.0016 mol) was added to a mixture of intermediate 110 (0.0011 mol) and tributylphosphine (0.0020 mol) in THF. (50 ml) and the reaction mixture was stirred for 1 hour at RT. The solvent was evaporated under reduced pressure, then the residue was stirred and refluxed in methanol (80 ml) for 1 hour. The resulting precipitate was filtered off and dissolved in DMF (50 ml). The solution was concentrated again under reduced pressure and the residue was stirred in methanol. Finally, the resulting precipitate was filtered off and dried, yielding 0.242 g (52%) of compound 36.

Example B30

Preparation of 4,6-ethanediylidene-19H-pyrimido[4,5-b][6,13,1]benzodioxaazacyclopentadecine, 16-chloro-8,9,10,11,12,13-hexahydro-20-methoxy- (compound 37)

A solution of intermediate 87 (0.00007 mol) in THF (3 ml) was stirred at RT and then ADDP (0.0001 mol) and tributylphosphine (0.0001 mol) were added. The reaction mixture was stirred for 18 hours and extra ADDP (0.0001 mol) and tributylphosphine (0.0001 mol) were added. The resulting mixture was stirred for 18 hours and the solvent was evaporated. The residue was purified by HPLC and the product fractions were collected, then the solvent was evaporated and the residue was dried (vacuum) at 50° C., yielding 0.002 g of compound 37.

Example B31

Preparation of 4,6-ethanediylidene-8H,14H-pyrimido[4,5-b][6,12,1]benzodioxaazacyclohexadecine, 18-chloro-9,10,11,12,15,20-hexahydro-21-methoxy- (compound 38)

A mixture of intermediate 172 (0.0046 mol) in THF (400 ml) was stirred at RT, then tributyl-phosphine (0.0092 mol) was added, followed by ADDP (0.0092 mol) and the reaction mixture was stirred for 2 hours. The solvent was evaporated and the residue was purified by RP high-performance liquid chromatography (Hypersil) (eluent: (0.5 NH$_4$OAc in water)/ CH$_3$CN 90/10). The product fractions were collected and the solvent was evaporated. The obtained residue was taken up in water and then the mixture was alkalised with K$_2$CO$_3$ and extracted with DCM. The organic layer was separated, dried, filtered off and the solvent was evaporated. The residue (1.1 g) stirred in DIPE and the precipitate was filtered off and then dried, yielding 0.976 g of compound 38.

Compound 39 is made on the same way accordingly compound 38.

4,6-ethanediylidene-14H-pyrimido[4,5-b][6,9,12,1] benzotrioxaazacyclohexadecine, 18-chloro-8,9,11, 12,15,20-hexahydro-21-methoxy- (compound 39)

Example B32

Preparation of 4,6-ethanediylidene-8H-pyrimido[4,5-b][6,1,11]benzoxadiazacyclohexadecin-11(12)-one, 18-chloro-9,10,13,14,15,20-hexahydro-21-methoxy- (compound 40)

A mixture of intermediate 177 (0.00045 mol), PyBOP (0.00135 mol) and triethylamine (0.00135 mol) was reacted for 3 hours at 60° C. and the solvent was evaporated. The residue was purified by RP high-performance liquid chromatography, then the product fractions were collected and the solvent was evaporated, yielding 0.008 g of compound 40.

Example B33 a) Preparation of 4,6-ethanediylidenepyrimido[4,5-b] [6,1,9,12]benzoxatriazacycloheptadecine-10(11H)-carboxylic acid, 19-chloro-8,9,12,13,14,15,16,21-octahydro-22-methoxy-12-oxo-, 1,1-dimethylethyl ester (compound 41)

THF p.a. (150 ml) and tributyl-phosphine (0.003 mol) were stirred under N$_2$ at 50° C. and ADDP (0.003 mol) was added, then a mixture of intermediate 181 (0.0009 mol) in THF p.a. (15 ml) was added and the reaction mixture was stirred for 2 hours at 60° C. Extra tributyl-phosphine (0.003 mol) and ADDP (0.003 mol) were added and the resulting mixture was stirred for 2 hours at 60° C. Finally, the solvent was evaporated, yielding (used as such in the next reaction step) compound 41.

b) Preparation of 4,6-ethanediylidenepyrimido[4,5-b][6,1,9,12]benzoxatriazacycloheptadecin-12(13H)-one, 1-chloro-8,9,10,11,14,15,16,21-octahydro-22-methoxy- (compound 42)

A mixture of compound 41 (residue) in methanol (50 ml) and 2-propanol/HCl (5 ml) was stirred for 72 hours at RT and then the solvent was evaporated. The residue was taken up in water and washed 3 times with DCM. The aqueous layer was alkalised with K$_2$CO$_3$ and extracted with DCM. The crude mixture was then purified on a glass filter (eluent: DCM/ CH$_3$OH/NH$_3$) 90/10). The product fractions were collected and the solvent was evaporated, yielding 0.322 g of compound 42.

c) Preparation of 4,6-ethanediylidenepyrimido[4,5-b] [6,1,9,12]benzoxatriazacycloheptadecin-12(13H)-one, 19-chloro-8,9,10,11,14,15,16,21-octahydro-10-[[(2-hydroxyethyl)methylamino]acetyl]-22-methoxy- (compound 43)

Compound 42 (0.0.000045 mol), DMA (2 ml) and DIPEA (0.00013-mol) were stirred and bromo-acetyl chloride (0.00011 mol) was added dropwise, then 2-(methylamino)-ethanol (0.00044 mol) was added and the reaction mixture was stirred for 16 hours at 60° C., yielding 0.013 g of compound 43.

Following compounds were made accordingly:

| Compound No. | Name |
|---|---|
| 44 | 4,6-ethanediylidenepyrimido[4,5-b][6,1,9,12]benzoxatriazacycloheptadecin-12(13H)-one, 19-chloro-8,9,10,11,14,15,16,21-octahydro-10-[[[2-hydroxy-1-(hydroxymethyl)ethyl]amino]acetyl]-22-methoxy- |
| 45 | 4,6-ethanediylidenepyrimido[4,5-b][6,1,9,12]benzoxatriazacycloheptadecin-12(13H)-one, 19-chloro-8,9,10,11,14,15,16,21-octahydro-10-[[2-(hydroxymethyl)-4-morpholinyl]acetyl]-22-methoxy- |
| 46 | 4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-[[[2-(4-pyridinyl)ethyl]amino]acetyl]- |
| 47 | 4,6-ethanediylidenepyrimido[4,5-b][6,1,9,12]benzoxatriazacycloheptadecin-12(13H)-one, 19-chloro-10-[[[2-(dimethylamino)ethyl]methylamino]acetyl]-8,9,10,11,14,15,16,21-octahydro-22-methoxy- |
| 48 | 4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-[[(2-methoxyethyl)amino]acetyl]- |

-continued

| Compound No. | Name |
|---|---|
| 49 | 4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-[[(3-methoxypropyl)amino]acetyl]- |
| 50 | 4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-(4-morpholinylacetyl)- |
| 51 | 4,6-ethanediylidenepyrimido[4,5-b][6,1,9,12]benzoxatriazacycloheptadecin-12(13H)-one, 19-chloro-8,9,10,11,14,15,16,21-octahydro-22-methoxy-10-[(4-methyl-1-piperazinyl)acetyl]- |

Example B34

Preparation of 4,6-ethanediylidenepyrimido[4,5-b][6,1,9,12]benzoxatriaizacycloheptadecin-12(13H)-one, 19-chloro-8,9,10,11,14,15,16,21-octahydro-22-methoxy-1-methyl- (compound 52)

4-steps reaction procedure Step (I): intermediate 182 (0.0002 mol), DIPEA (0.0008 mol) and DCM (7 ml) was shaken and bromo-acetyl chloride (0.0008 mol) was added, then the reaction mixture was stirred for 3 hours and washed 3 times with DCM, to give Resin-(I). Step (II): Resin (I), 2-(methylamino)ethanol (0.0020 mol) and 1-methyl-2-pyrrolidinone (6 ml) was shaken for 6 hours at 60° C., then the reaction mixture was washed [3 times with DMF and 3 times with DCM]×2, to give Resin 4-(II). Step-(III): Resin (II), triphenyl-phosphine (0.0020 mol), ADDP (0.0020 mol) and 1-methyl-2-pyrrolidinone (8 ml) was shaken for 6 hours at 60° C., then the reaction mixture was washed 3 times with DMF and 3 times with DCM, to give Resin (III). Step (IV): Resin (III) and DCM/TFA/triisopropylsilane (7 ml) was shaken for 16 hours and filtered, then the filter residue was washed and the solvent was evaporated. The obtained residue was purified by RP high-performance liquid chromatography. The desired product fractions were collected and the solvent was evaporated, yielding 0.001 g of compound 52.

Following compounds are made on the same way accordingly compound 52:

| Compound No. | Name |
|---|---|
| 53 | 4,6-ethanediylidenepyrimido[4,5-b][6,1,9,12]benzoxatriazacycloheptadecin-12(13H)-one, 19-chloro-10-ethyl-8,9,10,11,14,15,16,21-octahydro-22-methoxy- |
| 54 | 1,22-ethanediylidene-5H,17H-pyrimido[4,5-b]pyrrolo[2,1-h][6,1,9,12]benzoxatriazacycloheptadecin-14(15H)-one, 7-chloro-10,11,12,13,18,19,19a,20-octahydro-24-methoxy- |
| 55 | 4,6-ethanediylidene-8H-pyrimido[4,5-b][6,1,10,13]benzoxatriazacyclooctadecin-13(14H)-one, 20-chloro-9,10,11,12,15,16,17,22-octahydro-23-methoxy- |
| 56 | 14H-4,6-ethanediylidene-9,13-methano-8H-pyrimido[4,5-b][6,1,12,15]benzoxatriazacycloeicosin-15(16H)-one, 22-chloro-9,10,11,12,17,18,19,24-octahydro-26-methoxy- |
| 57 | 13H-4,6-ethanediylidene-9,12-ethanopyrimido[4,5-b][6,1,11,14]benzoxatriazacyclononadecin-14(15H)-one, 21-chloro-8,9,10,11,16,17,18,23-octahydro-26-methoxy- |
| 58 | 14H-4,6-ethanediylidene-10,13-ethano-8H-pyrimido[4,5-b][6,1,12,15]benzoxatriazacycloeicosin-15(16H)-one, 22-chloro-9,10,11,12,17,18,19,24-octahydro-27-methoxy- |

Example B35

Preparation of 4,6-ethenopyrimido[4,5-b][6,1,12]benzoxadiazacyclopentadecine-13(8H)-carboxylic acid, 17-bromo-9,10,11,12,14,19-hexahydro-20-methoxy-, phenylmethyl ester (compound 59)

A mixture of intermediate 114 (0.005 mol) and $K_2CO_3$ (0.025 mol) in DMA (25 ml) and water (25 ml) was stirred under microwave conditions for 30 min. at 150° C. and then the solvent was evaporated under reduced pressure. The obtained residue was stirred in EtOAc and the precipitate was filtered off. The filtrate was evaporated under reduced pressure and the residue was purified by column chromatography (eluent: DCM/$CH_3OH$ 98/2 to 96/4). The product fractions were collected and the solvent was evaporated. The obtained residue (1.1 g-38%) was crystallised from $CH_3CN$. The resulting precipitate was filtered off and dried. A part of this fraction was extra dried, yielding compound 59.

Example B36

Preparation of 4,6-ethanediylidenepyrimido[4,5-b][6,1,10,13]benzoxatriazacycloheptadecine-12,15-dione; 19-chloro-8,9,10,11,13,14,16,21-octahydro-22-methoxy- (compound 60)

A mixture of intermediate 121 (0.00308 mol) in DMF (300 ml) was dropwise added overnight to admixture of PyBOP (0.00616 mol) and DIPEA (0.0154 mol) in DMF (300 ml), then extra PyBOP (0.00616 mol) and DIPEA (0.0154 mol) were added and the reaction mixture was stirred over the weekend. The solvent was evaporated under reduced pressure and the residue was dissolved in a 10% solution of methanol in DCM and was then washed with water. The organic layer was separated, dried ($MgSO_4$), filtered off and the solvent was evaporated under reduced pressure. The residue was purified by RP high-performance liquid chromatography. The pure product fractions were collected and then concentrated until precipitation occurred, yielding compound 60.

Example B37

Preparation of 4,6-ethenopyrimido[4,5-b][6,1,12]benzoxadiazacyclopentadecine, 17-bromo-16-fluoro-8,9,10,11,12,13,14,19-octahydro-20-methoxy- (compound 61)

TFA (2 ml) was added to a mixture of intermediate 127 (0.00055 mol) in DCM (10 ml), then the reaction mixture was stirred for 3 hours at RT and neutralised with a NaOH solution. The organic layer was separated, dried ($MgSO_4$), filtered off and the solvent was evaporated. The residue was purified by column chromatography (gradient eluent: DCM/CH₃OH). The pure product fractions were collected and the solvent was evaporated, yielding 0.042 g of compound 61.

Example B38

Preparation of 4,6-ethanediylidene-8H-pyrimido[4,5-b][6,1,9,12]benzoxatriazacyclohexadecine-11,14-dione, 18-chloro-9,10,12,13,15,20-hexahydro-21-methoxy-10-[2-(4-morpholinyl)ethyl]- (compound 62)

HBTU (0.00195 mol) was added to a stirred solution of intermediate 130 (0.00069 mol) and DIPEA (0.00324 mol) in DMA (250 ml) at RT, then the reaction mixture was stirred for 3 hours and the solvent was co-evaporated with toluene under reduced pressure. The obtained residue was purified by RP high-performance liquid chromatography (eluent 1: NH₄OAc; eluent 2: NH₄HCO₃). The pure product fractions were collected and the solvent was evaporated under reduced pressure. The obtained residue (0.030 g) was crystallised from 2-propanol, then the resulting precipitate was filtered off and dried (vac.), yielding 0.0165 g of compound 62.

The following compound 63 was made accordingly; 4,6-ethanediylidene-8H-pyrimido[4,5-b][6,1,9,12]benzoxatriazacyclohexadecine-11,14-dione, 18-chloro-9,10,12, 13,15,20-hexahydro-21-methoxy-10-(2-methoxyethyl)- (compound 63).

Example B39

Preparation of benzamide, 4-fluoro-N-(8,9,10,11,12, 13-hexahydro-20-methoxy-4,6-ethanediylidene-19H-pyrimido[4,5-b][6,13,1]benzodioxaazacyclopentadecin-16-yl)- (compound 64)

A solution of intermediate 136 (0.0002 mol) in THF (20 ml) was stirred at Ret and then ADDP (0.0003 mol) and tributyl-phosphine (0.0003 mol) were added. The reaction mixture was stirred for 6 hours at RT and then extra ADDP (0.0003 mol) and tributyl-phosphine (0.0003 mol) were added. The resulting mixture was stirred for 1 hour and the solvent was evaporated under reduced pressure. The residue was stirred in methanol and filtered. The filter residue was stirred in boiling 2-propanol, then the resulting precipitate was filtered off and stirred in a mixture of CH₃OH/HCl(1N)/H₂O. After filtration, the filter residue was stirred in a CH₃OH/NH₃ solution and the resulting precipitate was filtered off and dried (vac.) at 60° C., yielding 0.015 g of compound 64.

Example B40

Preparation of 4,6-ethanediylidene-8H-pyrimido[4,5-b][6,1,9,12]benzoxatriazacyclohexadecine-11,14-dione, 18-chloro-9,10,12,13,15,20-hexahydro-21-methoxy-12,12-dimethyl- (compound 65)

A solution of PyBOP (0.0013 mol) and DIPEA (0.0065 mol) in DMA (70 ml) was stirred at RT and then a solution of intermediate 143 (0.0013 mol) in DMA (70 ml) was added dropwise. The reaction mixture was stirred for 18 hours at RT and the solvent was evaporated under reduced pressure. The residue was dissolved in DCM and was washed 2 times with a saturated NaHCO₃ solution and 2 times with water. The organic layer was separated, dried (MgSO₄), filtered off and the solvent was evaporated. The dry residue was stirred in boiling 2-propanol, then the formed precipitate was filtered off, washed and dried (vacuum) at 60° C., yielding 0.133 g of compound 65, melting point 285° C.

Following compounds were made according to the synthesis of compound 65:

| Compound No. | Name |
|---|---|
| 66 | 4,6-ethanediylidene-8H-pyrimido[4,5-b][6,1,9,12]benzoxatriazacyclohexadecine-11,14-dione, 18-chloro-9,10,12,13,15,20-hexahydro-21-methoxy-12-(1-methylethyl)-melting point: 335° C. |
| 67 | 4,6-ethanediylidene-8H-pyrimido[4,5-b][6,1,9,12]benzoxatriazacyclohexadecine-11,14-dione, 18-chloro-9,10,12,13,15,20-hexahydro-21-methoxy-12-(2-methylpropyl)- |
| 68 | 4,6-ethanediylidenepyrimido[4,5-b][6,1,10,13]benzoxatriazacycloheptadecine-12,15-dione, 19-chloro-8,9,10,11,13,14,16,21-octahydro-22-methoxy-13-(2-methylpropyl)- |
| 69 | 4,6-ethanediylidene-8H-pyrimido[4,5-b][6,1,9,12]benzoxatriazacyclohexadecine-11,14-dione, 18-chloro-9,10,12,13,15,20-hexahydro-21-methoxy-melting point: 292° C. |

Example B41

Preparation of 4,6-ethanediylidenepyrimido[4,5-b][6,1,10,14]benzoxatriazacycloheptadecin-12(13H)-one, 19-chloro-8,9,10,11,14,15,16,21-octahydro-22-methoxy- (compound 70)

DIPEA (0.00930 mol) was added to a solution of intermediate 149 (0.00155 mol) in dry DMF (10 ml) and the mixture was stirred for 15 min. then this solution was cannulated slowly to a solution of HBTU (0.00465 mol) in DMF (40 ml) and the reaction mixture was stirred for 30 min. The solvent was evaporated. The residue was purified by RP high-performance liquid chromatography. The product fractions were collected and the solvent was evaporated, yielding 0.258 g of compound 70, melting point 236.4-237.3° C.

The following compounds were made accordingly

| Compound No. | Name |
|---|---|
| 71 | 4,6-ethanediylidenepyrimido[4,5-b]pyrrolo[2,1-k][6,1,9,12]benzoxatriazacyclopentadecin-11(8H)-one, 19-chloro-9,10,11a,12,13,14,16,21-octahydro-22-methoxy-melting point 261.2-265° C. |
| 72 | 4,6-ethanediylidenepyrimido[4,5-b][6,1,9,12]benzoxatriazacyclopentadecin-11(8H)-one, 17-chloro-9,10,12,13,14,19-hexahydro-20-methoxy-13-methyl-melting point 288.5-290.5° C. |

-continued

| Compound No. | Name |
|---|---|
| 73 | 4,6-ethanediylidenepyrimido[4,5-b][6,1,9,12]benzoxatriazacyclopentadecin-11(8H)-one, 17-chloro-9,10,12,13,14,19-hexahydro-20-methoxy-<br>melting point: 294.2-295.2° C. |
| 74 | 4,6-ethanediylidene-12H-pyrimido[4,5-b][6,1,10,13]benzoxatriazacyclohexadecin-12-one, 18-chloro-8,9,10,11,13,14,15,20-octahydro-21-methoxy-14-methyl-<br>melting point: 240.0-240.3° C. |
| 75 | 4,6-ethanediylidene-8H-pyrimido[4,5-b][6,1,9,13]benzoxatriazacyclohexadecin-11(12H)-one, 18-chloro-9,10,13,14,15,20-hexahydro-21-methoxy-<br>melting point: 254.4-256.5° C. |
| 76 | 4,6-etheno-8H-pyrimido[4,5-b]pyrrolo[2,1-l][6,1,10,13]benzoxatriazacyclohexadecine-12,15(14H)-dione, 20-chloro-9,10,11,12a,13,17,22-heptahydro-23-methoxy-<br>melting point: 350.5-352.5° C. |
| 77 | 4,6-ethanediylidene-12H-pyrimido[4,5-b]pyrrolo[2,1-l][6,1,10,13]benzoxatriazacyclohexadecin-12-one, 20-chloro-8,9,10,11,12a,13,14,15,17,22-decahydro-23-methoxy-<br>melting point: 129.8-132.8° C. |
| 78 | 4,6-ethanediylidenepyrimido[4,5-b]pyrrolo[2,1-k][6,1,9,12]benzoxatriazacyclopentadecin-11(8H)-one, 19-chloro-18-fluoro-9,10,11a,12,13,14,16,21-octahydro-22-methoxy-<br>melting point: 261.4-264.0° C. |
| 79 | 4,6-ethanediylidenepyrimido[4,5-b][6,1,9,12]benzoxatriazacyclopentadecin-11(8H)-one, 17-chloro-16-fluoro-9,10,12,13,14,19-hexahydro-20-methoxy-13-methyl-<br>melting point: 306.3-307.4° C. |
| 80 | 4,6-ethanediylidene-12H-pyrimido[4,5-b][6,1,10,13]benzoxatriazacyclohexadecin-12-one, 18-chloro-17-fluoro-8,9,10,11,13,14,15,20-octahydro-21-methoxy-14-methyl-<br>melting point 260.4-261.1° C. |
| 81 | 4,6-ethanediylidenepyrimido[4,5-b][6,1,9,12]benzoxatriazacyclopentadecin-11(8H)-one, 17-chloro-16-fluoro-9,10,12,13,14,19-hexahydro-20-methoxy-<br>melting point 304.2-304.4° C. |
| 82 | 4,6-ethanediylidene-12H-pyrimido[4,5-b][6,1,10,13]benzoxatriazacyclohexadecin-12-one, 18-chloro-17-fluoro-8,9,10,11,13,14,15,20-octahydro-21-methoxy-<br>melting point: 311.0-311.9° C. |
| 83 | 4,6-ethanediylidenepyrimido[4,5-b]pyrrolo[2,1-k][6,1,9,12]benzoxatriazacyclopentadecin-11(8H)-one, 19-chloro-9,10,11a,12,13,14,16,21-octahydro-22-methoxy-<br>melting point: 262.0-262.8° C. |
| 84 | 4,6-ethanediylidene-12H-pyrimido[4,5-b]pyrrolo[2,1-l][6,1,10,13]benzoxatriazacyclohexadecin-12-one, 20-chloro-8,9,10,11,12a,13,14,15,17,22-decahydro-23-methoxy-<br>melting point: 231.9-232.8° C. |
| 85 | 4,6-ethanediylidenepyrimido[4,5-b]pyrrolo[2,1-k][6,1,9,12]benzoxatriazacyclopentadecin-11(8H)-one, 19-chloro-9,10,11a,12,13,14,16,21-octahydro-13-hydroxy-22-methoxy-<br>melting point: 279.4-280.7° C. |
| 86 | 4,6-ethanediylidene-13,16-ethano-8H-pyrimido[4,5-b][6,1,9,12,15]benzoxatetraazacyclooctadecin-11(12H)-one, 20-chloro-9,10,14,15,17,22-hexahydro-25-methoxy-<br>melting point 296.4-297.0° C. |
| 87 | 8H-4,6-ethanediylidene-12,15-ethanopyrimido[4,5-b][6,1,9,14]benzoxatriazacycloheptadecin-11(12H)-one, 19-chloro-9,10,13,14,16,21-hexahydro-24-methoxy-<br>melting point: 246.6-248.2° C. |
| 88 | 4,6-ethanediylidene-12,16-methano-6H-pyrimido[4,5-b][6,1,9,15]benzoxatriazacyclooctadecin-11(8H)-one, 20-chloro-9,10,12,13,14,15,17,22-octahydro-24-methoxy-<br>melting point: 160-170° C. |
| 89 | 4,6-ethanediylidenepyrimido[4,5-b][6,1,9,12]benzoxatriazacyclopentadecin-11(8H)-one, 17-chloro-9,10,12,13,14,19-hexahydro-20-methoxy-12,13-dimethyl-<br>melting point: 265° C. |
| 90 | 4,6-ethanediylidenepyrimido[4,5-b][6,1,9,12]benzoxatriazacyclopentadecin-11(8H)-one, 17-chloro-13-ethyl-9,10,12,13,14,19-hexahydro-20-methoxy-<br>melting point: 261.1-262° C. |
| 91 | 4,6-ethanediylidenepyrimido[4,5-b][6,1,9,12]benzoxatriazacyclopentadecin-11(8H)-one, 17-chloro-9,10,12,13,14,19-hexahydro-12-(hydroxymethyl)-20-methoxy-<br>melting point: 276.3-277.4° C. |

-continued

| Compound No. | Name |
|---|---|
| 92 | 4,6-ethanediylidene-12H-pyrimido[4,5-b]pyrrolo[2,1-l][6,1,10,13]benzoxatriazacyclohexadecin-12-one, 20-chloro-8,9,10,11,12a,13,14,15,17,22-decahydro-14-hydroxy-23-methoxy- melting point: 267.8-268.5° C. |
| 93 | 4,6-ethanediylidene-14,17-ethanopyrimido[4,5-b][6,1,10,13,16]benzoxatetraazacyclononadecin-12(13H)-one, 21-chloro-8,9,10,11,15,16,18,23-octahydro-26-methoxy- melting point: 286.8-287.6° C. |
| 94 | 4,6-ethanediylidene-13,16-ethano-6H-pyrimido[4,5-b][6,1,10,15]benzoxatriazacyclooctadecin-12(13H)-one, 20-chloro-8,9,10,11,14,15,17,22-octahydro-25-methoxy- melting point: 253.1-255.9° C. |
| 95 | 12H-4,6-ethanediylidene-13,17-methanopyrimido[4,5-b][6,1,10,16]benzoxatriazacyclononadecin-12-one, 21-chloro 8,$$,10,11,13,14,15,16,18,23-decahydro-25-methoxy- melting point: 240.1-242.8° C. |
| 96 | 4,6-ethanediylidene-12H-pyrimido[4,5-b][6,1,10,13]benzoxatriazacyclohexadecin-12-one, 18-chloro-8,9,10,11,13,14,15,20-octahydro-21-methoxy-13,14-dimethyl- melting point: 241.9-243.0° C. |
| 97 | 4,6-ethanediylidene-12H-pyrimido[4,5-b][6,1,10,13]benzoxatriazacyclohexadecin-12-one, 18-chloro-14-ethyl-8,9,10,11,13,14,15,20-octahydro-21-methoxy- melting point: 212.8-214.0° C. |
| 98 | 4,6-ethanediylidene-12H-pyrimido[4,5-b][6,1,10,13]benzoxatriazacyclohexadecin-12-one, 18-chloro-8,9,10,11,13,14,15,20-octahydro-13-(hydroxymethyl)-21-methoxy- melting point: 287.6-288.3° C. |
| 99 | 4,6-ethanediylidene-12H-pyrimido[4,5-b][6,1,10,13]benzoxatriazacyclohexadecin-12-one, 18-chloro-8,9,10,11,13,14,15,20-octahydro-21-methoxy- melting point: 304.6-304.8° C. |
| 166 | 4,6-ethanediylidenepyrimido[4,5-b][6,1,11,14]benzoxatriazacycloheptadecin-13(8H)-one, 19-chloro-15-ethyl-9,10,11,12,14,15,16,21-octahydro-22-methoxy- |
| 167 | 4,6-ethanediylidenepyrimido[4,5-b][6,1,11,14]benzoxatriazacycloheptadecin-13(8H)-one, 19-chloro-9,10,11,12,14,15,16,21-octahydro-22-methoxy-14,15-dimethyl- |

Example B42

Preparation of 4,6-ethanediylidenepyrimido[4,5]pyrrolo[2,1-m][6,1,11,14]benzoxatriazacycloheptadecin-13(8H)-one, 21-chloro-9,10,11,12,13a,14,15,16,18,23-decahydro-24-methoxy- (compound 100)

A solution of intermediate 156 (0.0005 mol) and DIPEA (0.003 mol) was added to a solution of HBTU (0.0015 mol) and 1-hydroxy-1H-benzotriazole (0.001 mol) in DMF dry (125 ml) and then the reaction mixture was reacted for 1 hour. The solvent was evaporated and the dry residue was purified by RP high-performance liquid chromatography. The product fractions were collected, sodium carbonate was added and the organic solvent was evaporated. DCM was added to the aqueous concentrate and the resulting mixture was extracted 3 times with DCM, then the organic extract was dried and collected, yielding 0.0394 g (16%) of compound 100, melting point 226.3-227.7° C.

The following compounds were made accordingly;
4,6-ethanediylidenepyrimido[4,5-b][6,1,11,14]benzoxatriazacycloheptadecin-13(8H)-one, 19-chloro-9,10,11,12,14,15,16,21-octahydro-22-methoxy-(compound 101) melting point: 286.7-287.2° C.
4,6-ethanediylidenepyrimido[4,5-b]pyrrolo[2,1-m][6,1,11,14]benzoxatriazacycloheptadecin-13(8H)-one, 21-chloro-20-fluoro-9,10,11,12,13a,14,15,16,18,23-decahydro-24-methoxy-(compound 102), melting point: 234.7-236.8° C.

Example B43

Preparation of 4,6-ethanediylidene-12H-pyrimido[4,5-b]pyrrolo[2,1-l][6,1,10,13]benzoxatriazacyclohexadecin-12-one, 20-chloro-19-fluoro-8,9,10,11,12a,13,14,15,17,22-decahydro-23-methoxy- (compound 103)

A solution of intermediate 162 (0.001 mol) and DIPEA (1.034 ml) in DMF (20 ml) was added to a solution of PyBOP (0.003 mol) and 1-hydroxy-1H-benzotriazole (0.001 mol) in DMF (200 ml) and then the reaction mixture was purified by RP high-performance liquid chromatography (CH$_3$CN/NH$_4$OAc buffer). The product fractions were collected, sodium carbonate was added and the organic solvent was evaporated (precipitation). The aqueous concentrate was cooled in the fridge, then filtered and washed with water, yielding: 0.2087 g (43%) of compound 103 melting point 241.6-242.6° C.

The following compound was made accordingly;
4,6-ethanediylidenepyrimido[4,5-b]pyrrolo[2,1-k][6,1,9,12]benzoxatriazacyclopentadecine-11(8H)-thione, 19-chloro-18-fluoro-9,10,11a,12,13,14,16,21-octahydro-22-methoxy- (compound 104)
melting point: 211.3-212.7° C.

Example B44 a) preparation of 4,6-ethanediylidenepyrimido[4,5-b][6,1,16]benzoxadiazacyclononadecin-16(17H)-one, 21-chloro-8,9,10,13,14,15,18,23-octahydro-24-methoxy-(B) (compound 105) and 4,6-ethanediylidenepyrimido[4,5-b][6,1,16]benzoxadiazacyclononadecin-16(17H)-one, 21-chloro-8,9,10,13,14,15,18,23-octahydro-24-methoxy-(A) (compound 106)

A mixture of intermediate 165 (0.000424 mol) and Grubbs II catalyst (0.000042) in DCM (200 ml; degassed) was stirred for 6 hours at RT and under $N_2$, then the solvent was evaporated and the residue was purified by RP high-performance liquid chromatography. Two product fractions were collected and the solvent was evaporated, yielding 0.046 g (23.3%) of compound 106 (A) and 0.078 g (39.5%) of compound 105 (B).

b) preparation of 4,6-ethanediylidenepyrimido[4,5-b][6,1,16]benzoxadiazacyclononadecin-16(17H)-one, 21-chloro-8,9,10,11,12,13,14,15,18,23-decahydro-24-methoxy- (compound 107)

A mixture of compound 105 (0.000064 mol) in TAP (15 ml) and methanol (15 ml) was hydrogenated for 3 hours with Pt/C 5% (0.03 g) as a catalyst. After uptake of $H_2$ (1 equiv.), the catalyst was filtered off and the filtrate was evaporated, yielding compound 107.

The following compounds were made accordingly;
4,6-ethanediylidene-8H-pyrimido[4,5-b][6,1,15]benzoxadiazacyclooctadecin-15(16H)-one, 20-chloro-9,12,13,14,17,22-hexahydro-23-methoxy- (compound 108).

Example B45 a) Preparation of carbamic acid, (20-chloro-9,10,13,14,15,16,17,22-octahydro-23-methoxy-15-oxo-4,6-ethanediylidene-8H-pyrimido[4,5-b][6,1,15]benzoxadiazacyclooctadecin-14-yl)-, 1,1-dimethylethyl ester (A) (compound 109) and Preparation of carbamic acid, (20-chloro-9,10,13,14,15,16,17,22-octahydro-23-methoxy-15-oxo-4,6-ethanediylidene-8H-pyrimido[4,5-b][6,1,15]benzoxadiazacyclooctadecin-14-yl)-, 1,1-dimethylethyl ester (B) (compound 110)

A solution of intermediate 169 (0.0015 mol) and Grubbs II catalyst (0.00015) in DCM (150 ml) was stirred overnight at RT, then the solvent was evaporated and the residue was purified by RP high-performance liquid chromatography. Two product fractions were collected and the solvent was evaporated, yielding 0.110 g of compound 109 (A) and 0.064 g of compound 110 (B).

b) Preparation of carbamic acid, (20-chloro-9,10,11,12,13,14,15,16,17,22-decahydro-23-methoxy-15-oxo-4,6-ethanediylidene-8H-pyrimido[4,5-b][6,1,15]benzoxadiazacyclooctadecin-14-yl)-, 1,1-dimethylethyl ester (compound 111)

A mixture of compound 109 (0.00025 mol) in THF (15 ml) and methanol (15 ml) was hydrogenated for 3 hours with Pt/C 5% (0.1 g) as a catalyst. After uptake of $H_2$ (1 equiv.), the catalyst was filtered off and the filtrate was evaporated. The residue was filtered over silica gel with $DCM/CH_3OH$ (10/1) and the filtrate was evaporated, then the obtained residue was crystallised from methanol and the resulting solids were collected, yielding compound 111.

Following compound was made accordingly:
carbamic acid, (18-chloro-11,12,13,14,15,20-hexahydro-21-methoxy-13-oxo-4,6-ethanediylidene-8H-pyrimido[4,5-b][6,1,13]benzoxadiazacyclohexadecin-12-yl)-, 1,1-dimethylethyl ester (compound 165)

c) Preparation of 4,6-ethanediylidene-8H-pyrimido[4,5-b][6,1,15]benzoxadiazacyclooctadecin-15(16H)-one, 14-amino-20-chloro-9,10,11,12,13,14,17,22-octahydro-23-methoxy-HCl (1:2) (compound 112)

6N HCl in 2-propanol (5 ml) was added to a solution of compound 111 (0.000088 mol) in THF (q.s.) and the reaction mixture was stirred for 1 hour at RT and then the solvent was evaporated, yielding 0.050 g of compound 112, isolated as a hydrochloric acid salt.

d) Preparation of 4,6-ethanediylidene-8H-pyrimido[4,5-b][6,1,15]benzoxadiazacyclooctadecin-15(16H)-one, 20-chloro-14-(dimethylamino)-9,10,11,12,13,14,17,22-octahydro-23-methoxy- (compound 113)

A mixture of compound 112 (0.000085 mol) and formaldehyde (0.00052 g) in methanol (2 ml) was hydrogenated with Pt/C 5% (0.04 g) as a catalyst in the presence of thiophene solution (0.04 ml). After uptake of $H_2$ (2 equiv.), the catalyst was filtered off and the filtrate was evaporated. The obtained residue was purified by RP high-performance liquid chromatography, then the product fractions were collected and the solvent was evaporated, yielding compound 113.

Example B46

Preparation of 4,6-ethanediylidene-8H-pyrimido[4,5-b][6,1,10,13]benzoxatriazacyclohexadecine, 18-chloro-9,10,11,12,13,14,15,20-octahydro-21-methoxy-14-methyl- (compound 114)

A solution of intermediate 186 (0.00095 mol) in dioxane (10 ml), water (5 ml) and HCl concentrated (5 ml) was stirred for 27 hours at 50° C. and then the reaction mixture was poured out into a saturated aqueous $NaHCO_3$ solution and extracted with DCM. The organic extract was then dried and filtered over potassium carbonate. $NaBH(OAc)_3$ (0.00095 mol) was immediately added. The reaction mixture was stirred for 1 hour at RT. The mixture was purified by RP high-performance liquid chromatography, then the product fractions were collected and the solvent was evaporated, yielding 0.6576 g of compound 114, melting point 202.8-203.6° C.

The following compounds were made accordingly;

| Compound No. | Name |
| --- | --- |
| 115 | 4,6-ethanediylidenepyrimido[4,5-b][6,1,11,14]benzoxatriazacycloheptadecine, 19-chloro-8,9,10,11,12,13,14,15,16,21-decahydro-22-methoxy-15-methyl-melting point: 196.9-197.8° C. |
| 116 | 4,6-ethanediylidenepyrimido[4,5-b][6,1,9,12]benzoxatriazacyclopentadecine, 17-chloro-8,9,10,11,12,13,14,19-octahydro-20-methoxy-13-methyl-melting point: 195.8-196.6° C. |
| 117 | 4,6-ethanediylidene-8H-pyrimido[4,5-b][6,1,12,15]benzoxatriazacyclooctadecine, 20-chloro-9,10,11,12,13,14,15,16,17,22-decahydro-23-methoxy-16-methyl- |

Example B47

Preparation of 4,6-ethanediylidenepyrimido[4,5-b][6,1,12]benzoxadiazacyclopentadecine, 17-chloro-8,9,12,13,14,19-hexahydro-20-methoxy-13-methyl- ±75% E and ±25% Z (compound 118)

Grubbs II catalyst (a total of 0.0012 mol) was added in several portions to a solution of intermediate 191 (0.0016 mol) in DCM (100 ml) and the reaction mixture was stirred and refluxed for a total of 4 days. The obtained mixture was purified 2 times by RP high-performance liquid chromatography. The product fractions were collected and the solvent was evaporated, yielding 0.0116 g of compound 118.

Example B48

Preparation of 4,6-ethanediylidene-8H-pyrimido[4,5-b][6,1,9,12]benzoxatriazacyclohexadecine-9,12-dione, 18-chloro-10,11,13,14,15,20-hexahydro-21-methoxy-11-methyl-hydrate (1:1) (compound 119)

A mixture of intermediate 197 (0.0010 mol) and DIPEA (0.0040 mol) in DMF dry (50 ml) was slowly added to a solution of 1-[bis(dimethylamino)methylene]-1H-benzotriazolium, hexafluorophosphate (1-), 3-oxide (0.0025 mol) in DMF dry (200 ml) at RT, then the reaction mixture was quenched with water (5 ml) and the solvent was evaporated. The obtained residue was purified by RP high-performance liquid chromatography. The product fractions were collected and the organic solvent was evaporated, yielding 0.024 g of compound 119.

The following compounds were made accordingly;

| Compound No. | Name |
|---|---|
| 120 | 4,6-ethanediylidenepyrimido[4,5-b][6,1,9,12]benzoxatriazacyclopentadecine-9,12(8H,13H)-dione, 17-chloro-10,11,14,19-tetrahydro-20-methoxy-11-methyl- |
| 121 | 4,6-ethanediylidenepyrimido[4,5-b][6,1,9,12]benzoxatriazacyclopentadecine-9,12(8H,13H)-dione, 17-chloro-10,11,14,19-tetrahydro-20-methoxy-11-(1-methylethyl)- |
| 122 | 4,6-ethanediylidenepyrimido[4,5-b][6,1,9,12]benzoxatriazacyclopentadecine-9,12(8H,13H)-dione, 17-chloro-10,11,14,19-tetrahydro-20-methoxy-11-(phenylmethyl)- |
| 123 | 4,6-ethanediylidenepyrimido[4,5-b][6,1,9,12]benzoxatriazacyclopentadecine-9,12(8H,13H)-dione, 10,11,14,19-tetrahydro-20-methoxy-11-methyl- |
| 124 | 4,6-ethanediylidenepyrimido[4,5-b][6,1,9,12]benzoxatriazacyclopentadecine-9,12(8H,13H)-dione, 10,11,14,19-tetrahydro-20-methoxy-11-(1-methylpropyl)- |
| 125 | 9,11-ethanediylidenepyrimido[4,5-b]pyrrolo[1,2-i][6,1,9,12]benzoxatriazacyclopentadecine-14,19(5H,13H)-dione, 16,17,18,18a,20,21-hexahydro-22-methoxy- |
| 126 | 9,11-ethanediylidenepyrimido[4,5-b]pyrrolo[1,2-i][6,1,9,12]benzoxatriazacyclopentadecine-14,19(5H,13H)-dione, 3-chloro-16,17,18,18a,20,21-hexahydro-22-methoxy- |
| 127 | 4,6-ethanediylidenepyrimido[4,5-b][6,1,9,12]benzoxatriazacyclopentadecine-9,12(8H,13H)-dione, 17-chloro-10,11,14,19-tetrahydro-11-(1-hydroxyethyl)-20-methoxy- |
| 128 | 4,6-ethanediylidenepyrimido[4,5-b][6,1,11,14]benzoxatriazacycloheptadecine-11,14(8H,15H)-dione, 19-chloro-9,10,12,13,16,21-hexahydro-22-methoxy-13-(1-methylpropyl)- |
| 129 | 4,6-ethanediylidenepyrimido[4,5-b][6,1,9,12]benzoxatriazacyclopentadecine-9,12(8H,13H)-dione, 17-chloro-10,11,14,19-tetrahydro-11-(hydroxymethyl)-20-methoxy- |
| 130 | 4,6-ethanediylidenepyrimido[4,5-b][6,1,11,14]benzoxatriazacycloheptadecine-11,14(8H,15H)-dione, 19-chloro-9,10,12,13,16,21-hexahydro-13-(hydroxymethyl)-22-methoxy- |
| 131 | 4,6-ethanediylidenepyrimido[4,5-b][6,1,11,14]benzoxatriazacycloheptadecine-11,14(8H,15H)-dione, 19-chloro-9,10,12,13,16,21-hexahydro-22-methoxy-13-methyl- |
| 132 | 4,6-ethanediylidenepyrimido[4,5-b][6,1,9,12]benzoxatriazacyclopentadecine-9,12(8H,13H)-dione, 17-chloro-10,11,14,19-tetrahydro-20-methoxy-11,11-dimethyl- |
| 133 | 9,11-ethanediylidenepyrimido[4,5-b]pyrrolo[1,2-i][6,1,9,12]benzoxatriazacyclopentadecine-14,19(5H,13H)-dione, 3-chloro-16,17,18,18a,20,21-hexahydro-17-hydroxy-22-methoxy- |
| 134 | 4,6-ethanediylidene-8H-pyrimido[4,5-b]pyrrolo[1,2-l][6,1,12,15]benzoxatriazacyclooctadecine-12,17(18H)-dione, 22-chloro-9,10,11,14,15,16,16a,19,24-nonahydro-25-methoxy- |
| 135 | 4,6-ethanediylidene-8H-pyrimido[4,5-b][6,1,9,12]benzoxatriazacyclohexadecine-9,12-dione, 18-chloro-10,11,13,14,15,20-hexahydro-21-methoxy-11,11-dimethyl- |
| 136 | 4,6-ethanediylidene-8H-pyrimido[4,5-b][6,1,12,15]benzoxatriazacyclooctadecine-12,15(16H)-dione, 20-chloro-9,10,11,13,14,17,22-heptahydro-23-methoxy-14-(2-methylpropyl)- |

-continued

| Compound No. | Name |
|---|---|
| 137 | 4,6-ethanediylidene-8H-pyrimido[4,5-b][6,1,12,15]benzoxatriazacyclooctadecine-12,15(16H)-dione, 20-chloro-9,10,11,13,14,17,22-heptahydro-23-methoxy-14,14-dimethyl- |
| 138 | 4,6-ethanediylidene-8H-pyrimido[4,5-b][6,1,12,15]benzoxatriazacyclooctadecine-12,15(16H)-dione, 20-chloro-9,10,11,13,14,17,22-heptahydro-23-methoxy-14-(phenylmethyl)- |
| 139 | 4,6-ethanediylidene-8H-pyrimido[4,5-b][6,1,12,15]benzoxatriazacyclooctadecine-12,15(16H)-dione, 20-chloro-9,10,11,13,14,17,22-heptahydro-23-methoxy-14-methyl- |
| 140 | 1,21-ethanediylidene-5H-pyrimido[4,5-b]pyrrolo[1,2-i][6,1,9,12]benzoxatriazacyclohexadecine-13,18(19H)-dione, 7-chloro-10,11,12,13a,14,15,16-heptahydro-23-methoxy- |
| 141 | 4,6-ethanediylidene-8H-pyrimido[4,5-b][6,1,9,12]benzoxatriazacyclohexadecine-9,12-dione, 18-chloro-10,11,13,14,15,20-hexahydro-21-methoxy-11-(2-methylpropyl)- |
| 142 | 4,6-ethanediylidene-8H-pyrimido[4,5-b][6,1,9,12]benzoxatriazacyclohexadecine-9,12-dione, 18-chloro-10,11,13,14,15,20-hexahydro-11-(1-hydroxyethyl)-21-methoxy- |
| 143 | 4,6-ethanediylidenepyrimido[4,5-b][6,1,11,14]benzoxatriazacycloheptadecine-11,14(8H,15H)-dione, 19-chloro-9,10,12,13,16,21-hexahydro-22-methoxy-13-(2-methylpropyl)- |
| 144 | 4,6-ethanediylidenepyrimido[4,5-b][6,1,11,14]benzoxatriazacycloheptadecine-11,14(8H,15H)-dione, 19-chloro-9,10,12,13,16,21-hexahydro-22-methoxy-13,13-dimethyl- |
| 145 | 4,6-ethanediylidenepyrimido[4,5-b][6,1,11,14]benzoxatriazacycloheptadecine-11,14(8H,15H)-dione, 19-chloro-9,10,12,13,16,21-hexahydro-22-methoxy-13-(phenylmethyl)- |
| 146 | 4,6-ethanediylidenepyrimido[4,5-b][6,1,11,14]benzoxatriazacycloheptadecine-11,14(8H,15H)-dione, 19-chloro-9,10,12,13,16,21-hexahydro-13-(1-hydroxyethyl)-22-methoxy- |
| 147 | 4,6-ethanediylidene-8H-pyrimido[4,5-b][6,1,12,15]benzoxatriazacyclooctadecine-12,15(16H)-dione, 20-chloro-9,10,11,13,14,17,22-heptahydro-14-(1-hydroxyethyl)-23-methoxy- |
| 148 | 4,6-ethanediylidene-8H-pyrimido[4,5-b][6,1,9,12]benzoxatriazacyclohexadecine-9,12-dione, 18-chloro-10,11,13,14,15,20-hexahydro-11-(hydroxymethyl)-21-methoxy- |
| 149 | 1,21-ethanediylidene-5H-pyrimido[4,5-b]pyrrolo[1,2-i][6,1,9,12]benzoxatriazacyclohexadecine-13,18(19H)-dione, 7-chloro-10,11,12,13a,14,15,16-heptahydro-15-hydroxy-23-methoxy- |

Example B49

Preparation of 4,6-ethenopyrimido[4,5-b][6,1,9,14]benzoxatriazacycloheptadecine-9,14(8H,15H)-dione, 19-chloro-10,11,12,13,16,21-hexahydro-22-methoxy- (compound 150)

Intermediate 122 (0.001 mol) and DIPEA (0.004 mol) were added to a mixture of PyBOP (0.003 mol) in DMF (250 ml) and the reaction mixture was stirred for 2 hours, then water was added and the solvent was evaporated. The obtained residue was purified by RP high-performance liquid chromatography. The product fractions were collected and the organic solvent was evaporated. The aqueous concentrate was allowed to precipitate overnight in the fridge and the resulting solids were then filtered off, yielding 0.093 g (20%) of compound 150.

The following compounds were made accordingly;

| Compound No. | Name |
|---|---|
| 151 | 4,6-ethenopyrimido[4,5-b][6,1,9,12]benzoxatriazacyclopentadecine-9,12(8H,13H)-dione, 17-chloro-10,11,14,19-tetrahydro-20-methoxy- |
| 152 | 4,6-etheno-8H-pyrimido[4,5-b][6,1,9,13]benzoxatriazacyclohexadecine-9,13(10H,14H)-dione, 18-chloro-11,12,15,20-tetrahydro-21-methoxy- |
| 153 | 4,6-ethenopyrimido[4,5-b][6,1,11,14]benzoxatriazacycloheptadecine-11,14(8H,15H)-dione, 19-chloro-9,10,12,13,16,21-hexahydro-22-methoxy- |
| 154 | 4,6-ethenopyrimido[4,5-b][6,1,11,16]benzoxatriazacyclononadecine-11,16(8H,17H)-dione, 21-chloro-9,10,12,13,14,15,18,23-octahydro-24-methoxy- |
| 155 | 4,6-etheno-8H-pyrimido[4,5-b][6,1,11,15]benzoxatriazacyclooctadecine-11,15(12H,16H)-dione, 20-chloro-9,10,13,14,17,22-hexahydro-23-methoxy- |
| 156 | 4,6-ethanediylidenepyrimido[4,5-b][6,1,9,12]benzoxatriazacyclopentadecine-9,12(8H,13H)-dione, 10,11,14,19-tetrahydro-20-methoxy- |

-continued

| Compound No. | Name |
|---|---|
| 157 | 4,6-ethanediylidene-8H-pyrimido[4,5-b][6,1,9,13]benzoxatriazacyclohexadecine-9,13(10H,14H)-dione, 11,12,15,20-tetrahydro-21-methoxy- |
| 158 | 4,6-ethanediylidenepyrimido[4,5-b][6,1,9,14]benzoxatriazacycloheptadecine-9,14(8H,15H)-dione, 10,11,12,13,16,21-hexahydro-22-methoxy- |
| 159 | 4,6-ethanediylidenepyrimido[4,5-b][6,1,9,12]benzoxatriazacyclopentadecine-9,12(8H,13H)-dione, 17-chloro-10,11,14,19-tetrahydro-20-methoxy-10-methyl- |
| 160 | 4,6-ethanediylidene-8H-pyrimido[4,5-b][6,1,9,12]benzoxatriazacyclohexadecine-9,12-dione, 18-chloro-10,11,13,14,15,20-hexahydro-21-methoxy- |
| 161 | 4,6-ethanediylidene-8H-pyrimido[4,5-b][6,1,9,14]benzoxatriazacyclooctadecine-9,14-dione, 20-chloro-10,11,12,13,15,16,17,22-octahydro-23-methoxy- |
| 162 | 4,6-ethanediylidenepyrimido[4,5-b][6,1,12,16]benzoxatriazacyclononadecine-12,16(13H,17H)-dione, 21-chloro-8,9,10,11,14,15,18,23-octahydro-24-methoxy- |
| 163 | 4,6-ethanediylidene-8H-pyrimido[4,5-b][6,1,12,17]benzoxatriazacycloeicosine-12,17(18H)-dione, 22-chloro-9,10,11,13,14,15,16,19,24-nonahydro-25-methoxy- |
| 164 | 4,6-ethanediylidene-8H-pyrimido[4,5-b][6,1,9,12]benzoxatriazacyclohexadecine-9,12-dione, 18-chloro-10,11,13,14,15,20-hexahydro-21-methoxy-10-methyl- |
| 168 | 4,6-ethanediylidene-8H-pyrimido[4,5-b][6,1,12,15]benzoxatriazacyclooctadecine-12,15(16H)-dione, 20-chloro-9,10,11,13,14,17,22-heptahydro-23-methoxy-13-methyl- |

Compound Identification

The compounds were identified by LC/MS using a gradient elution system on a reversed phase HPLC. The compounds are identified by their specific retention time and their protonated molecular ion MH+ peak. The TALC gradient was supplied by a Waters Alliance HT 2790 system with a column heater set at 40° C. Flow from the column was split to a Waters 996 photodiode array (PDA) detector and a Waters-Micromass ZQ mass spectrometer with an electrospray ionization source operated in positive and negative ionization mode. Reversed phase HPLC was carried out on a Xterra MS C18 column (3.5 μm, 4.6×100 mm) with a flow rate of 16 ml/min. Three mobile phases (mobile phase A 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 μL was used.

Mass spectra were acquired by scanning from 100 to 1000 in is using a dwell time of 0.1 s. The capillary needle voltage was 3 kV and the source temperature was maintained at 140° C. Nitrogen was used a the nebulizer gas. Cone voltage was 10 V for positive ionization mode and 20 V for negative ionization mode. Data acquisition was performed with a Waters-Micromass MassLynx-Openlynx data system.

TABLE retention time (RT in minutes) and molecular weight as the MH+

| Compound No. | Rt | MH+ | Compound No. | Rt | MH+ |
|---|---|---|---|---|---|
| 64 | 6.38 | 503 | 121 | 4.32 | 470 |
| 38 | 6.64 | 414 | 122 | 4.84 | 518 |
| 40 | 4.93 | 427 | 60 | 4.53 | 456 |
| 71 | 5.66 | 454 | 123 | 3.05 | 408 |
| 150 | 3.84 | 454 | 124 | 4.08 | 450 |
| 153 | 3.89 | 546 | 125 | 3.56 | 434 |
| 120 | 3.77 | 442 | 156 | 2.83 | 394 |
| 157 | 3.01 | 408 | 168 | 4.17 | 484 |
| 158 | 3.3 | 422 | 136 | 4.62 | 526 |
| 126 | 4.33 | 468 | 137 | 4.18 | 498 |
| 159 | 4.02 | 442 | 138 | 4.62 | 560 |
| 127 | 3.62 | 472 | 139 | 3.88 | 456 |
| 128 | 5.34 | 512 | 119 | 4.5 | 456 |
| 129 | 3.47 | 458 | 140 | 5.03 | 482 |
| 130 | 3.93 | 486 | 164 | 4.74 | 456 |
| 131 | 4.34 | 470 | 141 | 5.41 | 498 |
| 160 | 4.04 | 442 | 142 | 4.17 | 486 |
| 161 | 3.86 | 470 | 143 | 5.16 | 512 |
| 106 | 8.73 | 467 | 144 | 4.42 | 484 |
| 105 | 9.6 | 467 | 145 | 5.18 | 546 |
| 132 | 3.74 | 456 | 147 | 4.3 | 514 |
| 133 | 3.63 | 484 | 110 | 6.2 | 568 |
| 108 | 6.09 | 453 | 109 | 6.14 | 568 |
| 117 | 5.95 | 456 | 148 | 3.92 | 472 |
| 63 | 4.75 | 500 | 149 | 4.45 | 498 |
| 162 | 4 | 484 | 111 | 6.26 | 570 |
| 163 | 3.91 | 498 | 165 | 5.82 | 540 |
| 134 | 4.51 | 510 | | | |
| 135 | 4.56 | 470 | | | |

C. Pharmacological Examples

Example C.1

In Vitro Inhibition of EGFR Using a Scintillant Proximity Assay

In the present EGFR SPA kinase reaction assay, a kinase substrate consisting of biotinylated poly(L-glutamic acid-L-tyrosine) (poly(GT)biotin), is incubated with the aforementioned protein in the presence of ($^{33}$P) radiolabeled ATP. ($^{33}$P)

phosporylation of the substrate is subsequently measured as light energy emitted using streptavidin-coated SPA beads (Amersham Pharmacia Biotech) by trapping and quantifying the binding of the biotin tagged and radiolabeled substrate.

Detailed Description

The EGFR SPA kinase reaction is performed at 30° C. for 60 minutes in a 96-well microtiter plate. For each of the tested compounds a full dose response $1.10^{-6}$M to $1.10^{-10}$M has been performed. IRESSA® and Tarceva™ (erlotinib) were used as reference compounds. The 100 µl reaction volume contains 54.5 mM Tris HCl pH 8.0, 10 mM MgCl$_2$, 100 µM Na$_3$VO$_4$, 5.0 µM unlabeled ATP, 1 mM DTT, 0.009% BSA, 0.8 µCi $^{33}$P-ATP, 0.35 µg/well poly(GT)biotin and 0.5 µg EGFR-kinase domain/well. The reaction is stopped by adding to each well 100 µl of the streptavidin beads (10 mg/ml in PBS+100 mM EDTA+100 µM ATP). The plates are than shaked at 300 rpm for 30 min to allow binding of the biotinylated substrate to the streptavidin coated beads. Than the beads are allowed to settle at the bottom of the plate for 30 minutes. The microtiterplates are centrifuges at 800 rpm for 10 minutes and the amount of phosphorylated ($^{33}$) Poly(GT) biotin is determined by counting (30 sec/well) in a microtiterplate scintillation counter.

Example C.2

In Vitro Inhibition of EGFR

The in vitro inhibition of EGFR was assessed using either the Flash Plate technology or the glass-fiber filter technology as described by Davies, S. P. et al., Biochem J. (2000), 351; p. 95-105. The Flash Plate technology is generally described by B. A. Brown et al. in High Throughout Screening (1997), p. 317-328. Editor(s): Devlin, John P. Publisher: Dekker; New York, N.Y.

In the Flash Plate EGFR kinase reaction assay, a kinase substrate consisting of biotinylated poly(L-glutamic acid-L-tyrosine) (poly(GT)biotin), is incubated with the aforementioned protein, in the presence of ($^{33}$P) radiolabeled ATP. ($^{33}$P) phosporylation of the substrate is subsequently measured as light energy emitted using a streptavidin-coated Flash Plate (PerkinElmer Life Sciences) by trapping and quantifying the binding of the biotin tagged and radiolabeled substrate.

Detailed Description

The EGFR kinase reaction is performed at 30° C. for 60 minutes in a 96-well microtiter FlashPlate (PerkinElmer Life Sciences). For each of the tested compounds a full dose response $1.10^{-6}$ to $1.10^{-10}$M has been performed. IRESSA® and Tarceva™ (erlotinib) were used as reference compounds. The 100 µl reaction volume contains 54.5 mM Tris HCl pH 8.0, 10 mM MgCl$_2$, 100 µM Na$_3$VO$_4$, 5.0 µM unlabeled ATP, 1 mM DTT, 0.009% BSA, 0.8 µCi AT$^{33}$P, 0.35 µg/well poly (GT)biotin and 0.5 µg EGFR-kinase domain/well.

The reaction is stopped by aspirating the reaction mixture and washing the plate 3× with 200 µl wash/stop buffer (PBS+100 mM EDTA). After the final wash step 200 µl of wash/stop buffer was added to each well and the amount of phosphorylated ($^{33}$P) Poly(GT)biotin determined by counting (30 sec/well) in a microtiterplate scintillation counter.

In the glass-fiber filter technology EGFR kinase reaction assay, a kinase substrate consisting of poly(L-glutamic acid-1-tyrosine) (poly(GT)), is incubated with the aforementioned protein in the presence of ($^{33}$P) radiolabeled ATP. ($^{33}$P) Phosporylation of the substrate is subsequently measured as radioactivity bound on a glassfiber-filter.

Detailed Description

The EGFR kinase reaction is performed at 25° C. for 10 minutes in a 96-well microtiterplate. For each of the tested compounds a full dose response $1.10^{-6}$M to $1.10^{-10}$M has been performed. IRESSA® and Tarceva™ (erlotinib) were used as reference compounds. The 25 µl reaction volume contains 60 mM Tris HCl pH 7.5, 3 mM MgCl$_2$, 3 mM Mn Cl$_2$, 3 µM Na$_3$VO$_4$, 50 µg/ml PEG20000, 5.0 µM unlabeled ATP, 1 mM DTT, 0.1 µCi AT$^{33}$P, 62.5 ng/well poly(GT) and 0.5 µg EGFR-kinase domain/well.

The reaction is stopped by adding 5 µl of a 3% phosphoric acid solution. 10 µl of the reaction mixture is then spotted onto a Filtermat A filter (Wallac) and washed 3 times for 5 min. in 75 mM phosphoric acid and 1 time for 5 min. in methanol prior to drying and quantification on the Typhoon (Amersham) using a LE phosphorage storage screen.

Example C.3

Serum Starved Proliferation Assay on the Ovarian Carcinoma SKOV3 Cells

The ovarian carcinoma cell line (SKOV3) was used in an epidermal growth factor stimulated cell proliferation assay, to assess the inhibitory effect of the compounds on EGF in whole cells.

In a first step the SKOV3 cells were incubated for 24 hours in the presence of 10% FCS serum. In the second step the cells were incubated with the compounds to be tested in a serum free condition (37° C. and 5% (v/v) CO$_2$) and subsequently stimulated for 72 hours with EGF at a final concentration of 100 ng/ml. The effect of the compounds on the EGF stimulation was finally assessed in a standard MIT cell viability assay.

Alternatively, the SKOV3 cells were incubated for 24 hours in the presence of 10% FCS serum. In the second step the cells were incubated for 72 hours with the compounds to be tested and the effect of the compounds on cell proliferation was finally assessed in a standard MTT cell viability assay.

Example C.4

ELISA Assay of EGFR Tyrosine Kinase Activity

The EGFR ELISA is generally described by Yang, E. B. et al., 2001, Biochimica et Biophysica Acta, 1550; 144.

For the determination of EGFR tyrosine kinase activity, 100 µl of 0.4 µg/ml poly(Glu, Tyr) in PBS was coated per well on a 96-well microplate at 37° C. overnight. The non-specific binding sites were subsequently blocked by incubation for 30 minutes at room temperature with 200 µl BSA dilution (10 mg/ml in PBS) per well. After washing three times with PBS the plates were either used immediately or stored at 4° C. Prior to the determination of the EGFR tyrosine kinase activity, the coated plates were washed two times with PBS. Next, to each well 88 µl of an ATP dilution (50 mM Tris HCl pH 8.0, 10 mM MgCl$_2$, 100 µM Na$_3$VO$_4$, 1 mM DTT, 5 µM ATP) and 2 µl with various concentrations of the compounds to be tested, were added. The EGFR tyrosine kinase-catalysed reaction was started by the addition of –10 µl of diluted EGFR tyrosine (dilution→0.05 µg per well enzyme diluted in 50 mM Tris HCl pH 8.0+0.1% BSA).

After incubation at room temperature for 10 min, the reaction was stopped by washing five times with PBS with 0.1% Tween 20. Subsequently 100 ml of recombinant anti-phosphotyrosine horseradish peroxidase conjugate (1:2500) in BSA (10 mg/ml in PBS) was added. After incubation at room temperature for 1 h, the microplate was washed five times with PBS/Tween 20. After the microplate was incubated with 100 µl of TMB-ELISA (1-step Ultra TMB-ELISA, Pierce) until colour development, 100 µl of 0.5 M H$_2$SO$_4$ was added to stop the reaction, and it was read in a microplate reader at 450-655 nm.

Example C.5

Proliferation Assay on the Squamous Carcinoma Cell Line A431 Cells

The squamous carcinoma cell line (A431) was used in a cell proliferation assay, to assess the inhibitory effect of the compounds in whole cells.

In a first step the A431 cells were incubated for 24 hours in the presence of 10% FCS serum. In the second step the cells were incubated for 72 hours with the compounds to be tested at a final concentration of 100 ng/ml. The effect of the compounds on the cell proliferation was finally assessed in a standard MTT cell viability assay.

The following tables provides the IC50 values of the compounds according to the invention, obtained using the above mentioned kinase assays.

| Compound number | EGFR SPA (C1): IC50 in nM | Kinase activity.(C2): pIC50 | SKOV3 cell (C3): pIC50 | A431 cell (C5): pIC50 | EGFR ELISA (C4): IC50 in nM |
|---|---|---|---|---|---|
| 1 | >100 | <5.0 | <5.7 | <6.0 | >1000 |
| 2 | >100 | 7.0 | <5.7 | <6.0 | >1000 |
| 3 | 3.61 | 7.8 | 5.87 | <6.0 | >1000 |
| 4 | 32.58 | 7.3 | 5.54 | NT | 556 |
| 5 | 81.10 | 6.4 | 5.32 | NT | >1000 |
| 6 | 4.40 | 7.6 | 5.74 | NT | 359 |
| 7 | 6.64 | 7.1 | <5 | NT | >1000 |
| 8 | 3.97 | 7.5 | <5 | NT | 329 |
| 9 | 6.79 | 7.4 | NT | NT | >1000 |
| 16 | NT | 5.6 | NT | NT | >1000 |
| 18 | NT | 7.1 | <5 | NT | >1000 |
| 17 | NT | 7.4 | 5.08 | 5.6 | 269 |
| 10 | NT | 7.3 | <5 | <5.5 | >1000 |
| 12 | NT | <5 | <5 | <5.5 | >1000 |
| 14 | NT | <5 | <5 | <5.5 | >1000 |
| 11 | NT | <5 | <5 | <5.5 | >1000 |
| 13 | NT | 6.5 | <5 | <5.5 | >1000 |
| 20 | NT | 7.6 | 6.64 | 5.9 | NT |
| 19 | NT | 7.2 | 5.3 | <5.5 | NT |
| 21 | NT | 8.0 | 6.09 | <5.5 | 158 |
| 22 | NT | 7.8 | 6.59 | 5.8 | 38.4 |
| 23 | NT | 8.0 | 7.22 | 6.3 | NT |
| 24 | NT | 7.7 | 5.5 | <5.5 | NT |
| 25 | NT | 6.2 | <5 | <5.5 | NT |
| 26 | NT | 8.6 | 6.92 | 5.7 | NT |
| 28 | NT | 7.6 | 5.84 | 5.8 | NT |
| 29 | NT | 6.1 | <5 | <5.5 | NT |
| 30 | NT | 7.5 | 5.99 | <6.0 | NT |
| 32 | NT | 8.4 | 6.54 | NT | NT |
| 33 | NT | 7.6 | 5.76 | 5.8 | NT |
| 34 | NT | 7.2 | <5 | <5.5 | NT |
| 35 | NT | 5.4 | <5 | <5.5 | NT |
| 36 | NT | 7.8 | 6.78 | <5.5 | NT |
| 37 | NT | <5 | <5 | <5.5 | NT |
| 38 | NT | 7.7 | 6.9 | 5.9 | NT |
| 39 | NT | 7.7 | 6.7 | 5.8 | NT |
| 40 | NT | 7.5 | 7.3 | 6.2 | NT |

| Compound number | Kinase activity.(C2): pIC50 | SKOV3 cell (C3): pIC50 | Example number | Compound number | Kinase activity.(C2): pIC50 | SKOV3 cell (C3): pIC50 | Example number |
|---|---|---|---|---|---|---|---|
| 64 | 6.0 | 6.4 | B39 | 150 | 7.7 | 5.1 | B49 |
| 71 | 7.5 | 5.5 | B41 | 152 | 7.5 | 5.0 | B49 |
| 72 | 6.8 | 5.0 | B41 | 153 | 7.8 | 6.1 | B49 |
| 73 | 7.4 | 5.4 | B41 | 154 | 7.4 | 5.6 | B49 |
| 74 | 7.6 | 6.0 | B41 | 155 | 6.5 | 6.0 | B49 |
| 75 | 7.2 | 5.2 | B41 | 61 | 7.8 | 6.4 | B39 |
| 70 | 8.0 | 5.5 | B41 | 120 | 5.7 | 6.0 | B48 |
| 151 | 5.5 | 5.0 | B49 | 121 | 5.6 | 5.0 | B48 |
| 76 | 7.6 | 6.7 | B41 | 122 | 6.4 | 5.0 | B48 |
| 77 | 7.8 | 6.1 | B41 | 66 | 7.1 | 8.0 | B40 |
| 65 | 7.9 | 7.7 | B40 | 158 | 5.3 | 5.0 | B49 |
| 67 | 7.0 | 6.3 | B40 | 78 | 7.5 | 6.5 | B41 |
| 68 | 7.9 | 8.2 | B40 | 114 | 8.0 | 7.4 | B46 |
| 69 | 7.3 | 7.2 | B40 | 79 | 6.2 | 5.0 | B41 |
| 60 | 7.8 | 8.7 | B36 | 80 | 7.7 | 7.2 | B41 |
| 123 | 5.2 | 5.0 | B48 | 81 | 6.6 | 6.6 | B41 |
| 124 | 5.0 | 5.0 | B48 | 82 | 7.7 | 7.1 | B41 |
| 125 | 5.1 | 5.0 | B48 | 99 | 7.6 | 6.7 | B41 |
| 156 | 5.0 | 5.0 | B49 | 126 | 5.7 | 5.6 | B48 |
| 157 | 5.0 | 5.0 | B49 | 159 | 6.5 | 5.7 | B49 |
| 127 | 6.6 | 5.8 | B48 | 101 | 6.6 | 7.5 | B42 |

| | | | -continued | | | | |
|---|---|---|---|---|---|---|---|
| 128 | 8.0 | 6.7 | B48 | 52 | 7.1 | 7 | B34 |
| 129 | 5.8 | 5.4 | B48 | 53 | 6.7 | 6.3 | B34 |
| 130 | 7.6 | 6.9 | B48 | 54 | 6.9 | 5.9 | B34 |
| 131 | 7.6 | 7.0 | B48 | 55 | 6.3 | 6.7 | B34 |
| 160 | 7.2 | 6.2 | B49 | 56 | 5.8 | 5.0 | B34 |
| 161 | 7.2 | 5.9 | B49 | 57 | 5.2 | 6.4 | B34 |
| 83 | 6.3 | 6.1 | B41 | 58 | 5.7 | 5.7 | B34 |
| 84 | 6.2 | 6.5 | B41 | 44 | 6.2 | 5.1 | B33 |
| 103 | 7.2 | 7.3 | B43 | 45 | 6.8 | 5.0 | B33 |
| 42 | 6.3 | 7.2 | B33 | 106 | 7.0 | 7.2 | B44 |
| 43 | 7.1 | 6.3 | B33 | 105 | 6.8 | 7.6 | B44 |
| 46 | 6.7 | 5.1 | B33 | 104 | 6.0 | 6.5 | B43 |
| 47 | 6.9 | 5.8 | B33 | 115 | 8.2 | 6.9 | B46 |
| 48 | 6.5 | 5.8 | B33 | 116 | 6.7 | 7.2 | B46 |
| 49 | 6.4 | 6.1 | B33 | 132 | 5.0 | 5.0 | B48 |
| 50 | 7.1 | 6.8 | B33 | 133 | 5.8 | 5.1 | B48 |
| 51 | | 6.4 | B33 | 108 | 6.4 | 6.8 | B44 |
| 100 | 8.1 | 6.9 | B42 | 117 | 6.7 | 5.4 | B46 |
| 102 | 6.7 | 7.3 | B42 | 63 | 6.9 | 5.7 | B38 |
| 162 | 6.8 | 7.3 | B49 | 164 | 6.3 | 6.8 | B49 |
| 163 | 7.0 | 6.4 | B49 | 141 | 6.1 | 5.8 | B48 |
| 134 | 6.4 | 6.1 | B48 | 142 | 7.0 | 6.2 | B48 |
| 135 | 5.4 | 6.0 | B48 | 143 | 6.3 | 6.7 | B48 |
| 136 | 6.2 | 6.6 | B48 | 144 | 6.8 | 6.9 | B48 |
| 137 | 6.6 | 6.6 | B48 | 145 | 6.7 | 6.6 | B48 |
| 138 | 5.7 | 6.2 | B48 | 146 | 6.7 | 6.2 | B48 |
| 139 | 6.4 | 6.8 | B48 | 147 | 6.9 | 6.6 | B48 |
| 119 | 6.0 | 5.8 | B48 | 62 | 6.4 | 5.3 | B48 |
| 140 | 6.7 | 6.7 | B48 | 110 | 5.4 | 5.0 | B45 |
| 109 | 5.7 | 6.5 | B45 | 111 | 5.8 | 5.0 | B45 |
| 148 | 6.6 | 5.0 | B48 | | | | |
| 149 | 6.9 | 5.8 | B48 | | | | |

D. Composition Examples

The following formulations exemplify typical pharmaceutical compositions suitable for systemic administration to animal and human subjects in accordance with the present invention.

"Active ingredient" (A.I.) as used throughout these examples relates to a compound of formula a) of a pharmaceutically acceptable addition salt thereof.

Example D.1

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml off water. The wet powder mixture was sieved, dried and sieved again. Then there was added microcrystalline cellulose (100 g) and hydrogenated vegetable oil (15 mg). The whole was mixed well and compressed into tablets, giving 10.000 tablets, each comprising 10 mg of the active ingredient.

Coating

To a solution of methylcellulose (10 g) in denaturated ethanol (75 ml) there was added a solution of ethyl cellulose (5 g) in DCM (150 ml). Then there were added DCM (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:

1. A compound having the formula

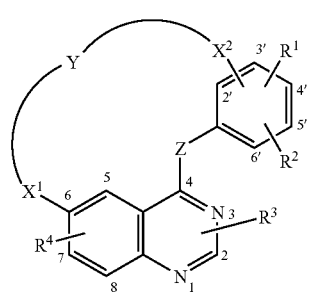

(I)

the N-oxide forms, the pharmaceutically acceptable addition salts and the stereochemically isomeric forms thereof, wherein Z represents NH;

Y represents —$C_{3-9}$alkyl-, $X^1$ represents a O;

$X^2$ represents —$NR^{12}$—$C_{1-2}$alkyl-;

$R^1$ represents hydrogen, cyano, halo, hydroxy, formyl, $C_{1-6}$alkoxy-, $C_{1-6}$alkyl-, halo-phenyl-carbonylamino-, $C_{1-4}$alkoxy- substituted with halo, $C_{1-4}$alkyl substituted with one or where possible two or more substituents selected from hydroxy or halo;

$R^2$ represents hydrogen, cyano, halo, hydroxy, hydroxycarbonyl-, $Het^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, $Het^1$, formyl; $C_{1-4}$alkyl-, $C_{2-6}$alkynyl-, $C_{3-6}$cycloalkyl-, $C_{3-6}$cycloalkyloxy-, $C_{1-6}$alkoxy-, $Ar^5$, $Ar^1$-oxy-, dihydroxyborane, $C_{1-6}$alkoxy- substituted with halo, $C_{1-4}$alkyl substituted with one or where possible two or more substituents selected from halo, hydroxy or $NR^5R^6$, $C_{1-4}$alkylcarbonyl- wherein said $C_{1-4}$alkyl is optionally substituted with one or where possible two or more substituents selected from hydroxy or $C_{1-4}$alkyl-oxy-;

$R^3$ represent hydrogen, $C_{1-4}$alkyl, or $C_{1-4}$alkyl substituted with one or more substituents selected from halo, $C_{1-4}$alkyloxy, amino-, mono- or di($C_{1-4}$alkyl)amino-, $C_{1-4}$alkyl-sulfonyl- or phenyl;

$R^4$ represents hydrogen, hydroxy, $Ar^3$-oxy, $Ar^4$—$C_{1-4}$alkyloxy, $C_{1-4}$alkyloxy-, $C_{2-4}$alkenyloxy- optionally substituted with $Het^{12}$ or $R^4$ represents $C_{1-4}$alkyloxy substituted with one or where possible two or more substituents selected from $C_{1-4}$alkyloxy-, hydroxy, halo, $Het^2$-, —$NR^7R^8$, -carbonyl-$NR^9R^{10}$ or $Het^3$-carbonyl-;

$R^5$ and $R^6$ are each independently selected from hydrogen or $C_{1-4}$alkyl;

$R^7$ and $R^8$ are each independently selected from hydrogen, $C_{1-4}$alkyl, $Het^8$, aminosulfonyl-, mono- or di ($C_{1-4}$alkyl)-aminosulfonyl, hydroxy-$C_{1-4}$alkyl-, $C_{1-4}$alkyl-oxy-$C_{1-4}$alkyl-, hydroxycarbonyl-$C_{1-4}$alkyl, $C_{3-6}$cycloalkyl, $Het^9$ carbonyl-$C_{1-4}$alkyl-, $Het^{10}$-carbonyl-, polyhydroxy-$C_{1-4}$alkyl-, $Het^{11}$-$C_{1-4}$alkyl- or $Ar^2$—$C_{1-4}$alkyl-;

$R^9$ and $R^{10}$ are each independently selected from hydrogen, $C_{1-4}$alkyl, $C_{3-6}$cycloalkyl, $Het^4$, hydroxy-$C_{1-4}$alkyl-, $C_{1-4}$alkyloxy$C_{1-4}$alkyl- or polyhydroxy-$C_{1-4}$alkyl;

$Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^2$ represents a heterocycle selected from morpholinyl, piperazinyl, piperidinyl, pyrrolidinyl, thiomorpholinyl or dithianyl wherein said $Het^2$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino-, mono- or di($C_{1-4}$alkyl)amino-$C_{1-4}$alkyl-, amino$C_{1-4}$alkyl-, mono- or di($C_{1-4}$alkyl)amino-sulfonyl-aminosulfonyl-;

$Het^3$, $Het^4$ and $Het^8$ each independently represent a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said $Het^3$, $Het^4$ or $Het^8$ is optionally substituted with one or where possible two or more substituents selected from hydroxy-, amino-, $C_{1-4}$alkyl-, $C_{3-6}$cycloalkyl-$C_{1-4}$alkyl-, aminosulfonyl-, mono- or di($C_{1-4}$alkyl)aminosulfonyl or amino-$C_{1-4}$alkyl-;

$Het^9$ and $Het^{10}$ each independently represent a heterocycle selected from furanyl, piperidinyl, morpholinyl, piperazinyl, pyrazolyl, dioxolanyl, thiazolyl, oxazolyl, imidazolyl, isoxazolyl, oxadiazolyl, pyridinyl or pyrrolidinyl wherein said $Het^9$ or $Het^{10}$ is optionally substituted $C_{1-4}$alkyl, $C_{3-6}$cycloalkyl-$C_{1-4}$alkyl- or amino-$C_{1-4}$alkyl-;

$Het^{11}$ represents a heterocycle selected from indolyl or

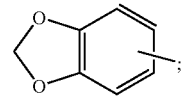

$Het^{12}$ represents a heterocycle selected from morpholinyl, piperazinyl, piperidinyl, pyrrolidinyl, thiomorpholinyl or dithianyl wherein said $Het^{12}$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino- or mono- or di($C_{1-4}$alkyl)amino-$C_{1-4}$alkyl-;

$Het^{13}$ represent a heterocycle selected from pyrrolidinyl or piperidinyl optionally substituted with one or where possible two or more substituents selected from $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-;

$Het^{14}$ represent a heterocycle selected from morpholinyl, pyrrolidinyl, piperazinyl or piperidinyl optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represent a heterocycle selected from morpholinyl, pyrrolidinyl piperazinyl or piperidinyl optionally substituted with one or where possible two or more substituents selected from $C_{1-4}$alkyl, $C_{3-4}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Ar^1$, $Ar^2$, $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl aminosulfonyl-, hydroxy-, $C_{1-4}$alkyloxy- or $C_{1-4}$alkyl.

2. A compound according to claim 1 wherein;

$R^1$ represents hydrogen, cyano, halo or hydroxy;

$R^2$ represents hydrogen, cyano, halo, hydroxy, hydroxycarbonyl-, $C_{1-4}$alkyloxycarbonyl-, $Het^{16}$-carbonyl-, $C_{1-4}$alkyl-, $C_{2-6}$alkynyl-, $Ar^5$ or $Het^1$;

$R^3$ represents hydrogen;

$R^4$ represents hydrogen, hydroxy, $C_{1-4}$alkyloxy- or $R^4$ represents $C_{1-4}$alkyloxy substituted with one or where possible two or more substituents selected from $C_{1-4}$alkyloxy- or $Het^2$-;

$Het^1$ represents thiazolyl optionally substituted with amino, $C_{1-4}$alkyl, hydroxy-$C_{1-4}$alkyl-, phenyl, phenyl-$C_{1-4}$alkyl, $C_{1-4}$alkyl-oxy-$C_{1-4}$alkyl-mono- or di($C_{1-4}$alkyl)amino- or amino-carbonyl-;

$Het^2$ represents a heterocycle selected from morpholinyl, piperazinyl, piperidinyl or pyrrolidinyl wherein said $Het^2$ is optionally substituted with one or where possible two or more substituents selected from hydroxy, amino or $C_{1-4}$alkyl-;

$Het^3$ represents a heterocycle selected from morpholinyl, piperazinyl, piperidinyl or pyrrolidinyl wherein said $Het^3$ is optionally substituted with one or where possible two or more substituents selected from hydroxy, amino or $C_{1-4}$alkyl-;

$Het^{12}$ represents a heterocycle selected from morpholinyl, piperazinyl, piperidinyl or pyrrolidinyl wherein said Het¹² is optionally substituted with one or where possible two or more substituents selected from hydroxy, amino or $C_{1-4}$alkyl-; and Het¹⁶ represents a heterocycle selected from piperidinyl or pyrrolidinyl.

3. A compound according to claim 1 wherein;

R² represents hydrogen, cyano, halo, hydroxy, hydroxycarbonyl-, $C_{1-4}$allyloxycarbonyl-, Het¹⁶-carbonyl-, $C_{2-6}$alkynyl-, Ar⁵ or Het¹;

R³ represents hydrogen;

R⁴ represents hydroxy, $C_{1-4}$alkyloxy- or R⁴ represents $C_{1-4}$alkyloxy substituted with one or where possible two or more substituents selected from $C_{1-4}$alkyloxy- or Het²-;

Het¹ represents thiazolyl optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

Het² represents a heterocycle selected from morpholinyl, piperazinyl, piperidinyl or pyrrolidinyl wherein said Het² is optionally substituted with one or where possible two or more substituents selected from hydroxy, amino or $C_{1-4}$alkyl-;

Het³ represents a heterocycle selected from morpholinyl, piperazinyl, piperidinyl or pyrrolidinyl wherein said Het³ is optionally substituted with one or where possible two or more substituents selected from hydroxy, amino or $C_{1-4}$alkyl-;

Het¹² represents a heterocycle selected from morpholinyl, piperazinyl, piperidinyl or pyrrolidinyl wherein said Het¹² is optionally substituted with one or where possible two or more substituents selected from hydroxy, amino or $C_{1-4}$alkyl-; and Het¹⁶ represents a heterocycle selected from piperidinyl or pyrrolidinyl.

4. A compound according to claim 1 wherein;

R² represents hydrogen, cyano, halo, hydroxy or $C_{2-6}$alkynyl-;

R³ represents hydrogen;

R⁴ represents $C_{1-4}$alkyloxy substituted with one or where possible two or more substituents selected from $C_{1-4}$alkyloxy- or Het²-;

Het² represents a heterocycle form morpholinyl or piperidinyl optionally substituted with $C_{1-4}$alkyl-;

Het³ represents a heterocycle selected from morpholinyl, piperazinyl, piperidinyl or pyrrolidinyl wherein said Het³ is optionally substituted with one or where possible two or more substituents selected from hydroxy, amino or $C_{1-4}$alkyl-;

Het¹² represents a heterocycle selected from morpholinyl, piperazinyl, piperidinyl or pyrrolidinyl wherein said Het² is optionally substituted with one or where possible two or more substituents selected from hydroxy, amino or $C_{1-4}$alkyl-.

5. A compound according to claim 1 wherein;

R¹ represents hydrogen or halo;

R² represents hydrogen or halo;

R³ represents hydrogen;

R⁴ represents hydrogen or $C_{1-4}$alkyloxy.

6. A compound selected from the group consisting of
4,6-ethanediylidenepyrimido[4,5-b][6,1,12]benzoxadiazacyclopentadecine, 17-bromo-8,9,10,11,12,13,14,19-octahydro-20-methoxy-13-methyl-,
4,6-ethanediylidenepyrimido[4,5-b][6,1,12]benzoxadiazacyclopentadecine, 17-bromo-8,9,10,11,12,13,14,19-octahydro-20-methoxy-,
4,6-ethanediylidenepyrimido[4,5-b][6,1,10,13]benzoxatriazacycloheptadecine-12,15-dione, 19-chloro-8,9,10,11,13,14,16,21-octahydro-22-methoxy-13-(2-methylpropyl)-,
4,6-ethanediylidenepyrimido[4,5-b][6,1,10,13]benzoxatriazacycloheptadecine-12,15-dione, 19-chloro-8,9,10,11,13,14,16,21-octahydro-22-methoxy-,
4,6-ethanediylidenepyrimido[4,5-b]pyrrolo[2,1-k][6,1,9,12]benzoxatriazacyclopentadecin-11(8H)-one, 19-chloro-[8-fluoro-9,10,11a,12,13,14,16,21-octahydro-22-methoxy-,
4,6-ethanediylidene-5H-pyrimido[4,5-b](6,1,10,13]benzoxatriazacyclohexadecine, 18-chloro-9,10,11,12,13,14,15,20-octahydro-21-methoxy-14-methyl-,
4,6-ethanediylidenepyrimido[4,5-b][6,1,11,14]benzoxatriazacycloheptadecine, 19-chloro-8,9,10,11,12,13,14,15,16,21-decahydro-22-methoxy-15-methyl-,
4,6-ethanediylidenepyrimido[4,5-b][6,1,9,12]benzoxatriazacyclopentadecine, 17-chloro-8,9,10,11,12,13,14,19-octahydro-20-methoxy-13-methyl-,
12H-4,6-ethanediylidene-13,17-methanopyrimido[4,5-b][6,1,10,16]benzoxatriazacyclononadecin-12-one, 21-chloro-8,9,10,11,13,14,15,16,18,23-decahydro-25-methoxy-,
4,6-ethanediylidene-12H-pyrimido[4,5-b][6,1,10,13]benzoxatriazacyclohexadecin-12-one, 18-chloro-8,9,10,11,13,14,15,20-octahydro-21-methoxy-13,14-dimethyl-,
4,6-ethanediylidenepyrimido[4,5-b][6,1,11,14]benzoxatriazacycloheptadecin-13(8H)-one, 19-chloro-15-ethyl-9,10,11,12,14,15,16,21-octahydro-22-methoxy-, or
4,6-ethanediylidenepyrimido[4,5-b][6,1,11,14]benzoxatriazacycloheptadecin-13(8H)-one, 19-chloro-9,10,11,12,14,15,16,21-octahydro-22-methoxy-14,15-dimethyl.

7. A compound according to claim 1—wherein the X² substituent is at position 2', the R¹ substituent is at position 4', the R² substituent is at position 5', the R³ substituent is at position 3 and the R⁴ substituent at position 7 of the structure of formula (I).

8. A pharmaceutical composition comprising a pharmaceutically acceptable carrier and, as active ingredient, an effective kinase inhibitory amount of a compound as described in claim 1.

* * * * *

UNITED STATES PATENT AND TRADEMARK OFFICE
CERTIFICATE OF CORRECTION

| | | |
|---|---|---|
| PATENT NO. | : 7,648,975 B2 | Page 1 of 1 |
| APPLICATION NO. | : 10/558007 | |
| DATED | : January 19, 2010 | |
| INVENTOR(S) | : Eddy Jean Freyne et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 578 days.

Signed and Sealed this

Twelfth Day of October, 2010

David J. Kappos
*Director of the United States Patent and Trademark Office*